(12) United States Patent
Grabstein et al.

(10) Patent No.: US 10,407,482 B2
(45) Date of Patent: Sep. 10, 2019

(54) AMINO ACID SUBSTITUTED MOLECULES

(71) Applicant: Allozyne, Inc., Seattle, WA (US)

(72) Inventors: Kenneth H. Grabstein, Mercer Island, WA (US); David A. Tirrell, Pasadena, CA (US)

(73) Assignee: ALLOZYNE, INC., Seattle, WA (US)

( * ) Notice: Subject to any disclaimer, the term of this patent is extended or adjusted under 35 U.S.C. 154(b) by 0 days.

(21) Appl. No.: 14/055,651

(22) Filed: Oct. 16, 2013

(65) Prior Publication Data

US 2014/0255345 A1   Sep. 11, 2014

Related U.S. Application Data

(63) Continuation of application No. 12/610,909, filed on Nov. 2, 2009, now Pat. No. 8,568,706, which is a continuation of application No. 12/509,213, filed on Jul. 24, 2009, now abandoned, which is a continuation of application No. 12/271,747, filed on Nov. 14, 2008, now abandoned, which is a continuation-in-part of application No. 12/105,154, filed on Apr. 17, 2008, now Pat. No. 7,829,659, which is a continuation-in-part of application No. 11/743,608, filed on May 2, 2007, now Pat. No. 7,632,492, said application No. 12/610,909 is a continuation-in-part of application No. 12/105,155, filed on Apr. 17, 2008, now abandoned, which is a continuation-in-part of application No. 11/743,608, filed on May 2, 2007, now Pat. No. 7,632,492.

(60) Provisional application No. 61/190,035, filed on Aug. 20, 2007, provisional application No. 60/796,752, filed on May 2, 2006, provisional application No. 60/796,907, filed on May 2, 2006, provisional application No. 60/796,701, filed on May 2, 2006.

(51) Int. Cl.

| C07K 14/00 | (2006.01) |
|---|---|
| C07K 14/565 | (2006.01) |
| C12P 21/00 | (2006.01) |
| A61K 38/19 | (2006.01) |
| A61K 38/21 | (2006.01) |
| C12P 21/02 | (2006.01) |
| A61K 47/60 | (2017.01) |

(52) U.S. Cl.
CPC ......... *C07K 14/565* (2013.01); *A61K 38/193* (2013.01); *A61K 38/21* (2013.01); *A61K 38/215* (2013.01); *A61K 47/60* (2017.08); *C12P 21/00* (2013.01); *C12P 21/02* (2013.01); *Y02A 50/463* (2018.01)

(58) Field of Classification Search
None
See application file for complete search history.

(56) References Cited

U.S. PATENT DOCUMENTS

| 4,609,546 A | 9/1986 | Hiratani |
|---|---|---|
| 4,717,569 A | 1/1988 | Harrison et al. |
| 4,766,106 A | 8/1988 | Katre et al. |
| 4,849,227 A | 7/1989 | Cho |
| 4,894,226 A | 1/1990 | Aldwin et al. |
| 4,902,502 A | 2/1990 | Nitecki et al. |
| 5,122,614 A | 6/1992 | Zalipsky |
| 5,281,698 A | 1/1994 | Nitecki |
| 5,340,589 A | 8/1994 | Stetsko et al. |
| 5,382,657 A | 1/1995 | Karasiewicz et al. |
| 5,428,128 A | 6/1995 | Mensi-Fattohi et al. |
| 5,573,783 A | 11/1996 | Desieno et al. |
| 5,621,039 A | 4/1997 | Hallahan et al. |
| 5,622,986 A | 4/1997 | Greenwald et al. |
| 5,643,575 A | 7/1997 | Martinez et al. |
| 5,728,560 A | 3/1998 | Shorr et al. |
| 5,730,990 A | 3/1998 | Greenwald et al. |
| 5,738,846 A | 4/1998 | Greenwald et al. |
| 5,811,076 A | 9/1998 | Brasch et al. |
| 5,824,701 A | 10/1998 | Greenwald et al. |
| 5,840,900 A | 11/1998 | Greenwald et al. |
| 5,846,917 A | 12/1998 | Oumar-Mahamat et al. |
| 5,858,660 A | 1/1999 | Eaton et al. |
| 5,880,131 A | 3/1999 | Greenwald et al. |
| 5,900,402 A | 5/1999 | Shorr |
| 5,902,588 A | 5/1999 | Greenwald et al. |
| 5,919,455 A | 7/1999 | Greenwald et al. |
| 5,951,974 A | 9/1999 | Gilbert et al. |
| 5,965,119 A | 10/1999 | Greenwald et al. |

(Continued)

FOREIGN PATENT DOCUMENTS

| JP | 6-279081 A | 10/1994 |
|---|---|---|
| JP | 11-228685 A | 8/1999 |

(Continued)

OTHER PUBLICATIONS

Bork et al., 1996, Trends in Genetics 12:425-427.*
Bork, 2000, Genome Research 10:398-400.*
Brenner, 1999, Trends in Genetics 15:132-133.*
Doerks et al., 1998, Trends in Genetics 14:248-250.*
Skolnick et al., 2000, Trends in Biotech. 18(1):34-39.*
Smith et al., 1997, Nature Biotechnology 15:1222-1223.*
Kolchanov, 1988, Journal of Molecular Evolution, vol. 27, pp. 154-162.*
Pasquo, 2012, PLoS ONE, vol. 7, Issue 2, e32555.*
Zhang et al., (2005), vol. 280, No. 21, pp. 20740-20751.*

(Continued)

*Primary Examiner* — Daniel E Kolker
*Assistant Examiner* — Jegatheesan Seharaseyon
(74) *Attorney, Agent, or Firm* — Seed IP Law Group LLP

(57) ABSTRACT

The invention provides compositions and methods of identifying, modifying and producing modified target molecules, including therapeutic molecules by modification with non-natural amino acids. Certain aspects of the invention include methods of adding a chemical moiety to a target molecule, and the compositions resulting therefrom. Certain aspects of the invention also relate to kits for identifying, modifying and producing modified target molecules described herein.

29 Claims, 10 Drawing Sheets

Specification includes a Sequence Listing.

(56) References Cited

U.S. PATENT DOCUMENTS

| | | | |
|---|---|---|---|
| 5,965,566 A | 10/1999 | Greenwald et al. | |
| 5,969,040 A | 10/1999 | Hallahan et al. | |
| 5,981,709 A | 11/1999 | Greenwald et al. | |
| 6,004,573 A | 12/1999 | Rathi et al. | |
| 6,011,042 A | 1/2000 | Greenwald et al. | |
| 6,042,822 A | 3/2000 | Gilbert et al. | |
| 6,113,906 A | 9/2000 | Greenwald et al. | |
| 6,127,355 A | 10/2000 | Greenwald et al. | |
| 6,132,713 A | 10/2000 | Fiipula et al. | |
| 6,177,087 B1 | 1/2001 | Greenwald et al. | |
| 6,180,095 B1 | 1/2001 | Greenwald et al. | |
| 6,188,965 B1 | 2/2001 | Mayo et al. | |
| 6,248,363 B1 | 6/2001 | Patel et al. | |
| 6,269,312 B1 | 7/2001 | Mayo et al. | |
| 6,586,207 B2 | 7/2003 | Tirrell et al. | |
| 6,638,500 B1 | 10/2003 | El-Tayar et al. | |
| 6,708,120 B1 | 3/2004 | Mayo et al. | |
| 6,737,236 B1 | 5/2004 | Pieken et al. | |
| 6,792,356 B2 | 9/2004 | Mayo et al. | |
| 6,801,861 B2 | 10/2004 | Mayo et al. | |
| 6,804,611 B2 | 10/2004 | Mayo et al. | |
| 6,951,939 B2 | 10/2005 | Jones | |
| 7,026,440 B2 | 4/2006 | Bentley et al. | |
| 7,045,337 B2 | 5/2006 | Schultz et al. | |
| 7,083,970 B2 | 8/2006 | Schultz et al. | |
| 7,139,665 B2 | 11/2006 | Datta et al. | |
| 7,198,915 B2 | 4/2007 | Tirrell et al. | |
| 7,354,761 B2 | 4/2008 | Schultz et al. | |
| 7,368,275 B2 | 5/2008 | Schultz et al. | |
| 7,375,234 B2 | 5/2008 | Sharpless et al. | |
| 7,449,443 B2 | 11/2008 | Tirrell et al. | |
| 7,462,463 B1 | 12/2008 | Tirrell | |
| 7,632,492 B2 | 12/2009 | Grabstein et al. | |
| 7,829,659 B2 | 11/2010 | Grabstein et al. | |
| 2002/0042097 A1* | 4/2002 | Tirrell | C12N 9/003 435/69.1 |
| 2002/0052443 A1 | 5/2002 | Greenwald et al. | |
| 2002/0061307 A1 | 5/2002 | Whitlow et al. | |
| 2002/0098192 A1 | 7/2002 | Whitlow et al. | |
| 2003/0175241 A1 | 9/2003 | Pedersen et al. | |
| 2004/0062746 A1 | 4/2004 | Martinez et al. | |
| 2004/0062748 A1 | 4/2004 | Martinez et al. | |
| 2004/0105839 A1 | 6/2004 | Park | |
| 2004/0265952 A1 | 12/2004 | Deiters et al. | |
| 2005/0032081 A1 | 2/2005 | Ju et al. | |
| 2005/0054053 A1 | 3/2005 | Aguinaldo et al. | |
| 2005/0220762 A1 | 10/2005 | Cho et al. | |
| 2005/0250183 A1 | 11/2005 | Schultz et al. | |
| 2005/0260711 A1 | 11/2005 | Datta et al. | |
| 2005/0287639 A1 | 12/2005 | Kwon et al. | |
| 2006/0246509 A1 | 11/2006 | Deiters et al. | |
| 2007/0123693 A1 | 5/2007 | Wilson | |
| 2007/0172459 A1 | 7/2007 | Gantier et al. | |
| 2007/0269369 A1 | 11/2007 | Gegg et al. | |
| 2008/0003202 A1 | 1/2008 | Guyon et al. | |
| 2008/0026422 A1 | 1/2008 | Tirrell et al. | |
| 2008/0044854 A1 | 2/2008 | Wang et al. | |
| 2008/0097083 A1 | 4/2008 | Cho et al. | |
| 2008/0108791 A1 | 5/2008 | Cho et al. | |
| 2008/0108792 A1 | 5/2008 | Hays et al. | |
| 2008/0114155 A1 | 5/2008 | Cho et al. | |
| 2008/0119640 A1 | 5/2008 | Hays et al. | |
| 2008/0132681 A1 | 6/2008 | Hays et al. | |
| 2008/0146781 A1 | 6/2008 | Cho et al. | |
| 2008/0160609 A1 | 7/2008 | Tirrell et al. | |
| 2008/0161539 A1 | 7/2008 | Cho et al. | |
| 2008/0207877 A1 | 8/2008 | Cho et al. | |
| 2008/0214439 A1 | 9/2008 | Grabstein et al. | |

FOREIGN PATENT DOCUMENTS

| | | |
|---|---|---|
| WO | WO 95/13090 A1 | 5/1995 |
| WO | WO 96/21469 A1 | 7/1996 |
| WO | WO 97/14740 A1 | 4/1997 |
| WO | WO 99/09417 A2 | 2/1999 |
| WO | WO 99/27897 A1 | 6/1999 |
| WO | WO 02/072019 A2 | 9/2002 |
| WO | WO 02/085923 A2 | 10/2002 |
| WO | WO 02/086075 A2 | 10/2002 |
| WO | WO 2004/022593 A2 | 3/2004 |
| WO | WO 2004/031352 A2 | 4/2004 |
| WO | WO 2004/035605 A2 | 4/2004 |
| WO | WO 2004/060299 A2 | 7/2004 |
| WO | WO 2004/060300 A2 | 7/2004 |
| WO | WO 2005/003157 A2 | 1/2005 |
| WO | WO 2005/003294 A2 | 1/2005 |
| WO | WO 2005/016371 A1 | 2/2005 |
| WO | WO 2005/035727 A2 | 4/2005 |
| WO | WO 2005/058346 A1 | 6/2005 |
| WO | WO 2005/074524 A2 | 8/2005 |
| WO | WO 2005/074650 A2 | 8/2005 |
| WO | WO 2005/084303 A2 | 9/2005 |
| WO | WO 2005/099769 A2 | 10/2005 |
| WO | WO 2006/122972 A1 | 11/2006 |
| WO | WO 2006/133088 A2 | 12/2006 |
| WO | WO 2006/133089 A2 | 12/2006 |
| WO | WO 2007/070672 A2 | 6/2007 |
| WO | WO 2007/130453 A2 | 11/2007 |
| WO | WO 2009/026393 A2 | 2/2009 |
| WO | 2012/032181 A2 | 3/2012 |

OTHER PUBLICATIONS

Anderson et al., "Fluorescence Resonance Energy Transfer between Unnatural Amino Acids in a Structurally Modified Dihydrofolate Reductase," *J. Am. Chem. Soc.* 124: 9674-9675, 2002.

Bain et al., "Biosynthetic Site-Specific Incorporation of a Non-Natural Amino Acid into a Polypeptide," *J. Am. Chem. Soc.* 111: 8013-8014, 1989.

Bain et al., "Ribosome-mediated incorporation of a non-standard amino acid into a peptide through expansion of the genetic code," *Nature* 356: 537-539, Apr. 9, 1992.

Baker et al., "N-Terminally PEGylated Human Interferon-β-1a with Improved Pharmacokinetic Properties and in vivo Efficacy in a Melanoma Angiogenesis Model," *Bioconjugate Chem.* 17: 179-188, 2006.

Basu et al., "Structure—Function Engineering of Interferon-β-1b for Improving Stability, Solubility, Potency, Immunogenicity, and Pharmacokinetic Properties by Site-Selective Mono-PEGylation," *Bioconjugate Chem.* 17: 618-630, 2006.

Blaskovich et al., "Polymer-Supported Acetylide Addition to Hexa-2,4-dienal," *Synthesis* 7: 965-966, Jul. 1998.

Bork et al., "Go hunting in sequence databases but watch out for the traps," *Trends in Genetics* 12(10):425-427, Oct. 1996.

Bork, "Powers and Pitfalls in Sequence Analysis: The 70% Hurdle," *Genome Res.* 10: 398-400, 2000.

Bowie et al., "Deciphering the Message in Protein Sequences: Tolerance to Amino Acid Substitutions," *Science* 247: 1306-1310, Mar. 16, 1990.

Brenner, "Errors in genome annotation," *Trends in Genetics* 15(4): 132-133, Apr. 1999.

Budisa et al., "High-level biosynthetic substitution of methionine proteins by its analogs 2-aminohexanoic acid, selenomethionine, telluromethionine and ethionine in *Escherichia coli*," *Eur. J. Biochem.* 230: 788-796, 1995.

Datta et al., "A Designed Phenylalanyl-tRNA Synthetase Variant Allows Efficient in Vivo Incorporation of Aryl Ketone Functionality into Proteins," *J. Am. Chem. Soc.* 124: 5652-5653, 2002.

Deiters et al., "Site-specific PEGylation of proteins containing unnatural amino acids," *Bioorganic & Medicinal Chemistry Letters* 14: 5743-5745, 2004.

Doerks et al., "Protein annotation: detective work for function prediction," *Trends in Genetics* 14(6): 248-250, Jun. 1998.

Döring et al., "Enlarging the Amino Acid Set of *Escherichia coli* by Infiltration of the Valine Coding Pathway," *Science* 292: 501-504, Apr. 20, 2001.

Duewel et al., "Incorporation of Trifluoromethionine into a Phage Lysozyme: Implications and a New Marker for Use in Progein $^{19}$F NMR," *Biochemistry* 36: 3404-3416, 1997.

(56) References Cited

OTHER PUBLICATIONS

Furter, "Expansion of the genetic code: Site-directed p-fluorophenylalanine incorporation in Escherichia coli," *Protein Science* 7: 419-426, 1998.
Geigert et al., "The Long-Term Stability of Recombinant (Serine-17) Human Interferon-β," *Journal of Interferon Research* 8: 539-547, 1988.
Gu et al., "tRNA$^{Ser}$(CGA) differentially regulates expression of wild-type and codon-modified papillomavirus L1 genes," *Nuc. Acids Res.* 32(15): 4448-4461, 2004.
Hinsberg et al., "Direct Studies of 1,1-Diazenes. Synthese, Infrared and Electronic Spectra, and Kinetics of the Thermal Decomposition of N-(2,2,6,6-Tetramethylpiperidyl)nitrene and N-(2,2,5,5-Tetramethylpyrrolidyl)nitrene," *J. Am. Chem. Soc.* 104: 766-773, 1982.
Hirel et al., "Extent of N-terminal methionine excision from *Escherichia coli* proteins is governed by the side-chain length of the penultimate amino acid," *Proc. Natl. Acad. Sci. USA* 86: 8247-8251, Nov. 1989.
Hohsaka et al., "Five-base codons for incorporation of nonnatural amino acids into proteins," *Nucleic Acids Res.* 29(17): 3646-3651, 2001.
Hohaska et al., "Site-specific incorporation of photofunctional nonnatural amino acids into a polypeptide through in vitro protein biosynthesis," *FEBS Lett.* 344: 171-174, 1994.
Ibba et al., "Substrate Specificity Is Determined by Amino Acid Binding Pocket Size in *Escherichia coli* Phenylalanyl-tRNA Synthetase," *Biochemistry* 33: 7107-7112, 1994.
International Search Report for PCT/US2007/010631, dated Jan. 28, 2008, 5 pages.
Invitation to Pay Additional Fees (Partial International Search Report) for PCT/US2008/073763, dated Feb. 13, 2009, 5 pages.
Kast et al., "Amino Acid Substrate Specificity of *Escherichia coli* Phenylalanyl-tRNA Synthetase Altered by District Mutations," *J. Mol. Biol.* 222:99-124, 1991.
Kiick et al., "Incorporation of azides into recombinant proteins for chemoselective modification by the Staudinger ligation," *Proc. Natl. Acad. Sci. USA* 99(1): 19-24, Jan. 8, 2002.
Kowal et al., "Exploiting unassigned codons in *Micrococcus luteus* for tRNA-based amino acid mutagenesis," *Nucleic Acids Res.* 25(22): 4685-4689, 1997.
Kwon et al., "Breaking the Degeneracy of the Genetic Code," *Journal of the American Chemical Society* 125: 7512-7513, 2003.
LaVelle et al., "Structure-activity relationships of the azide metabolite, azidoalanine, in *S. typhimurium,*" *Mutation Research* 177: 27-33, 1997.
Link et al., "Cell Surface Labeling in *Escherichia coli* via Copper(I)-Catalyzed [3+2] Cycloaddition," *J. Am. Chem. Soc.* 125(37): 11164-11165, 2003.
Monfardini et al., "A Branched Monomethoxypoly(ethylene glycol) for Protein Modification," *Bioconjugate Chemistry* 6: 62-69, 1995.
Noren et al., "A General Method for Site-Specific Incorporation of Unnatural Amino Acids into Proteins," *Science* 244: 182-188, Apr. 14, 1989.
Nowak et al., "Nicotinic Receptor Binding Site Probed with Unnatural Amino Acid Incorporation in Intact Cells," *Science* 268: 439-442, Apr. 21, 1995.
Patent Abstracts of Japan, Publication No. 06-279081. Accessed from Japan Patent Office on Apr. 13, 2009.
Patent Abstracts of Japan, Publication No. 11-228685. Accessed from Japan Patent Office on Apr. 13, 2009.
Pollack et al., "Introduction of Nucleophiles and Spectroscopic Probes into Antibody Combining Sites," *Science* 242: 1038-1040, Nov. 18, 1988.
Rostovtsev et al., "A Stepwise Huisgen Cycloaddition Process: Copper(I)-Catalyzed Regioselective 'Ligation' of Azides and Terminal Alkynes," *Angew. Chem. Int. Ed.* 41(14): 2596-2599, 2002.
Sabat et al., "Synthesis of Unnatural Amino Acids via Suzuki Cross-Coupling of Enantiopure Vinyloxazolidine Derivatives," *Organic Letters* 2(8): 1089-1092, 2000.
Schultz et al., "Photochemistry of a 1,1-Diazene, N-(2,2,5,5-Tetramethylpyrrolidinyl)nitrene," *J. Am. Chem. Soc.* 103: 1563-1564, 1981.
Sharma et al., "Efficient introduction of aryl bromide functionality into proteins in vivo," *FEBS Lett.* 467: 37-40, 2000.
Shearwater Polymers, Inc., "High Quality PEGs from NOF Corp." Jul. 1997, 1 page.
Skolnick et al., "From genes to protein structure and function: novel applications of computational approaches in the genomic era," *Trends in Biotech* 18: 34-39, Jan. 2000.
Smith et al., "The challenges of genome sequence annotation or 'The devil is in the details'," *Nature Biotechnology* 15: 1222-1223, Nov. 1997.
Speers et al., "Activity-Based Protein Profiling in Vivo Using a Copper(I)-Catalyzed Azide-Alkyne [3+2] Cycloaddition," *J. Am. Chem. Soc.* 125: 4686-4687, 2003.
Stemmer, "DNA shuffling by random fragmentation and reassembly: In vitro recombination for molecular evolution," *Proc. Nat'l. Acad. Sci. USA* 91: 10747-10751, Oct. 1994.
Stemmer, "Rapid evolution of a protein in vitro by DNA shuffling," *Nature* 370: 389-391, Aug. 4, 1994.
Tang et al., "Attenuation of the Editing Activity of the *Escherichia coli* Leucyl-tRNA Synthetase Allows Incorporation of Novel Amino Acids into Proteins in Vivo," *Biochemistry* 41: 10635-10645, 2002.
Torne et al., "Peptidotriazoles on Solid Phase: [1,2,3]-Triazoles by Regiospecific Copper(I)-Catalyzed 1,3-Dipolar Cycloadditions of Terminal Alkynes to Azides," *J. Org. Chem.* 67(9): 3057-3064, 2002.
U.S. Appl. No. 12/271,747, filed Nov. 14, 2008, "Amino Acid Substituted Molecules," 220 pages.
U.S. Appl. No. 12/509,213, filed Jul. 24, 2009, "Amino Acid Substituted Molecules," 220 pages.
U.S. Appl. No. 12/633,618, filed Dec. 8, 2009, "Amino Acid Substituted Molecules," 203 pages.
Van Hest et al., "Efficient introduction of alkene functionality into proteins in vivo," *FEBS Lett.* 428: 68-70, 1998.
Veronese, "Peptide and protein PEGylation: a review of problems and solutions," *Biomaterials* 22: 405-417, 2001.
Wan et al., "Epitope Map for a Growth Hormone Receptor Agonist Monoclonal Antibody, MAb 263," *Molecular Endocrinology* 17(11): 2240-2250, Nov. 2003.
Wang et al., "Addition of the keto functional group to the genetic code of *Escherichia coli,*" *Proc. Natl. Acad. Sci. U.S.A.* 100(1): 56-61, Jan. 7, 2003.
Wang et al., "Bioconjugation by Copper(I)-Catalyzed Azide-Alkyne [3+2] Cycloaddition," *Journal of the American Chemical Society* 125(11): 3192-3193, 2003.
Wang et al., "Expanding the Genetic Code of *Escherichia coli,*" *Science* 292: 498-500, Apr. 20, 2001.
Wang et al., "Processing of N-Terminal Unnatural Amino Acids in Recombinant Human Interferon-β in *Escherichia coli,*" *ChemBioChem* 9:324-330, 2008.
Written Opinion for PCT/US2007/010631, dated Jan. 28, 2008, 7 pages.
Wu et al., "Efficiency and Fidelity in a Click-Chemistry Route to Triazole Dendrimers by the Copper(I)-Catalyzed Ligation of Azides and Alkynes," *Angew. Chem. Int. Ed.* 43: 3928-3932, 2004.
Zalipsky "Chemistry of polyethylene glycol conjugates with biologically active molecules," *Advanced Drug Delivery Reviews* 16: 157-182, 1995.

* cited by examiner

AMINO ACID SUBSTITUTED MOLECULES

CROSS-REFERENCES TO RELATED APPLICATIONS

This application is a continuation of U.S. application Ser. No. 12/610,909, filed Nov. 2, 2009 (now U.S. Pat. No. 8,568,706 issued Oct. 29, 2013); which is a continuation of U.S. application Ser. No. 12/509,213, filed Jul. 24, 2009 (now abandoned); which is a continuation application of U.S. patent application Ser. No. 12/271,747, filed Nov. 14, 2008 (now abandoned); which is a continuation-in-part application of U.S. patent application Ser. No. 12/105,154, filed Apr. 17, 2008 (now U.S. Pat. No. 7,829,659 issued Nov. 9, 2010); which is a continuation-in-part application of U.S. patent application Ser. No. 11/743,608, filed on May 2, 2007 (now U.S. Pat. No. 7,632,492 issued Dec. 15, 2009).

U.S. application Ser. No. 12/610,909, filed Nov. 2, 2009 is also a continuation-in-part of U.S. application Ser. No. 12/105,155, filed Apr. 17, 2008 (now abandoned); which is a continuation-in-part application of U.S. patent application Ser. No. 11/743,608, filed on May 2, 2007.

U.S. application Ser. No. 12/105,154, filed Apr. 17, 2008 also claims the benefit of U.S. Provisional Application No. 61/190,035, filed Aug. 20, 2007.

U.S. application Ser. No. 11/743,608, filed May 2, 2007 also claims the benefit of U.S. Provisional Application Nos. 60/796,752, filed May 2, 2006, and 60/796,907, filed May 2, 2006, and 60/796,701, filed May 2, 2006.

All of these applications are incorporated herein by reference.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 110197_410C8_SEQUENCE_LISTING.txt. The text file is 16.1 KB, was created on Oct. 16, 2013, and is being submitted electronically via EFS-Web, concurrent with the filing of the specification.

BACKGROUND OF THE INVENTION

Field of the Invention

Molecules, including proteins, may be engineered through modification of the structural, catalytic and/or binding properties, as well as for the de novo design of artificial molecules. Molecular or protein engineering relies on an efficient recognition mechanism for incorporating desired amino acid residues in specifically chosen locations of the protein sequence or structural region. This process has been very useful for designing new macromolecules with precise control of composition and architecture; however, a major limitation exists when the mutagenesis is restricted to the 20 naturally occurring amino acids. For this reason, it is becoming increasingly clear that incorporation of non-natural amino acids can extend the scope and impact of molecular and protein engineering methods. Thus, for many applications of designed macromolecules, it would be desirable to develop methods for incorporating amino acids that have novel chemical functionality not possessed by the 20 amino acids commonly found in naturally occurring proteins, or to utilize a non-natural amino acid residue for an anchoring position for further chemical or biological modification.

For example, if certain changes in a protein or other molecule are desired (such as the size, acidity, nucleophilicity, hydrogen-bonding or hydrophobic properties, or other properties of amino acids) to fulfill a specific structural or functional property of interest, it would be advantageous to incorporate non-natural amino acid residues into the molecule. Such an advantage would greatly expand the ability to rationally and systematically manipulate the structures of proteins, in order to probe protein function, modify existing proteins, and create artificial proteins with new properties.

Description of the Related Art

Proteins are synthesized through a process beginning with RNA transcription from DNA, followed by protein translation in the cell. In order for translation to occur, a ribosome binds to a messenger RNA (mRNA) that has been transcribed from DNA. During translation, each transfer RNA (tRNA) is matched with its cognate amino acid by a collection of enzymes called aminoacyl-tRNA synthetases (AARS). The AARS charge each tRNA with the appropriate amino acid, thereby facilitating translation of the mRNA. As the process continues, the protein is elongated by the addition of the amino acids by the AARS.

Most cells make twenty different AARS, each corresponding to one of the twenty naturally occurring amino acids. The AARS enzymes function optimally with its own cognate amino acid and set of tRNA molecules appropriate to that amino acid.

Proteins may be modified or synthesized de novo through protein engineering techniques. In particular, proteins may be altered or modified to delete, substitute or add amino acids or modify existing amino acids. For example, it may be desirable to change at least one particular characteristic of a protein in order to develop a novel chemical functionality. Such characteristics may include the size, acidity, nucleophilicity, hydrogen-bonding or hydrophilic properties of certain amino acids in a protein.

Modifying molecules, including proteins, is presently largely inefficient and ineffective, with large batch-to-batch variations in quality and quantity produced. In this regard, it would be beneficial to develop an efficient method for designing molecules, including proteins, with improved properties and attached chemical moieties. The present invention provides such an advantage, as well as many others that are expressed or implied in the present disclosure.

BRIEF SUMMARY OF THE INVENTION

The present invention relates to methods, compositions (including pharmaceutical compositions) as well as kits of various embodiments disclosed herein. More specifically, the present invention relates to methods, compositions and kits relating to modified molecules comprising one or more amino acid substitutions or additions with a naturally occurring amino acid (generally, an amino acid that is different than the one occurring in the native polypeptide sequence), one or more amino acid substitutions with a non-naturally occurring amino acid, and a chemical moiety added to said non-natural amino acid residue.

Some aspects of the disclosure relate to a method for modifying a molecule comprising one or more rounds of the steps of: (a) substituting one or more amino acid residues in said molecule with a different naturally occurring amino acid residue; and (b) substituting one or more amino acid residues with a non-natural amino acid residue wherein said molecule retains a native function. Amino acid residue position or location that may be substituted with a non-natural amino acid include the amino terminus of the molecule. Other positions that may be have non-natural amino acids incorporated include surface exposed or solvent exposed locations in the target molecule's native structure which do not result in loss of function. In certain aspects, adding one or more naturally occurring amino acid residues to said molecule is conducted prior to substituting said one or more naturally occurring amino acid residues with a non-natural amino acid residue. In certain aspects, the one or more amino acid residues substituted in step (a) is located in the same amino acid position in the molecule as the one or more amino acid residues substituted in step (b). In other aspects, the one or more amino acid residues substituted in step (a) is located in a different amino acid position in the molecule as the one or more amino acid residues substituted in step (b).

In certain embodiments, a chemical moiety is added to said one or more non-natural amino acid residues. In other embodiments, the native function of the molecule is equal to or greater in magnitude compared to the function of a corresponding wild type molecule.

In certain embodiments, one or more amino acid residues substituted in step (a) comprises approximately less than or equal to fifteen, less than or equal to ten, less than or equal to eight, less than or equal to six, less than or equal to four, less than or equal to three, less than or equal to two, less than or equal to one amino acid residue(s). In certain embodiments, the one or more amino acid residues substituted in step (b) comprises approximately less than or equal to fifteen, less than or equal to ten, less than or equal to eight, less than or equal to six, less than or equal to four, less than or equal to three, less than or equal to two, less than or equal to one amino acid residue(s). In certain aspects, the one or more residues substituted in step (a) or (b) comprise amino acid residues from a single amino acid family or different amino acid families. In some embodiments, the one or more amino acid residues substituted in step (a) or (b) comprise approximately one, two, three, four, five, six, seven, eight, nine, ten, or more amino acid residues from the same amino acid family.

In certain aspects, said one or more amino acid residues is selected from the group consisting of: alanine, arginine, aspartic acid, glutamine, glutamic acid, glycine, praline, serine, leucine, cysteine, valine, lysine, methionine, tryptophan, phenylalanine, arginine, tyrosine, threonine, isoleucine, histidine, lysine and asparagine. Some aspects further comprise adding a chemical moiety to said non-natural amino acid residue. In some aspects, the chemical moiety is selected from the group consisting of: cytotoxins, pharmaceutical drugs, dyes or fluorescent labels, a nucleophilic or electrophilic group, a ketone or aldehyde, azide or alkyne compounds, photocaged groups, tags, a peptide, a polypeptide, a protein, an oligosaccharide, poly(ethylene)glycol with any molecular weight and in any geometry, polyvinyl alcohol, metals, metal complexes, polyamines, imidizoles, carbohydrates, lipids, biopolymers, particles, solid supports, a polymer, a targeting agent, an affinity group, any agent to which a complementary reactive chemical group can be attached, biophysical or biochemical probes, isotypically-labeled probes, spin-label amino acids, fluorophores, aryl iodides and bromides. In some cases, the non-natural amino acid residue is fluorinated, electroactive or unsaturated.

In some embodiments, non-natural amino acid is selected from the group consisting of: azidohomoalanine, homoproparglyglycine, p-bromophenylalanine, p-iodophenylalanine, azidophenylalanine, acetylphenylalanine and ethynylephenylalanine.

In some embodiments the molecule is selected from the group consisting of: a peptide, polypeptide, protein, carbohydrate, deoxyribonucleic acid, ribonucleic acid, lipid, biopolymer or other molecule.

In other embodiments, the molecule may be a therapeutic, diagnostic, or other molecule selected from the group consisting of: an antibody, antibody fragment, antibody derivative, Fab, Fab', F(ab)$_2$, Fd, Fv, ScFv, diabody, tribody, tetrabody, dimer, trimer or minibody, a cytokine, Factor VII, Factor VIII, Factor IX, Follitropin, G-CSF, GM-CSF, GLP-1, human growth hormone, interferon-$\alpha$, interferon-$\beta$, interferon-$\gamma$, interferon-$\Omega$, interferon-$\tau$, a transcriptional modulator that modulates cell growth, differentiation, or regulation, expression activator, inflammatory molecule, growth factor, growth factor receptor, and oncogene product.

In some aspects, one or more amino acid residues are substituted by a technique selected from the group consisting of: chemical mutagenesis, site-directed mutagenesis, error-prone PCR, homologous recombination, gene shuffling, or by computational methods or by comparison of related gene sequences. Non-natural amino acids may be incorporated in the protein using multi-site or site specific incorporation by a host cell. Further, the amino acid position at which the non-natural amino acid is incorporated may be specified by a codon that is typically used to specify a naturally occurring amino acid (such as a wobble codon, a bias codon, a sixth box codon, a 4 box codon, or any other sense codon that the host cell or in vitro translation system might be used to specify a non-natural amino acid incorporation site), or a codon which is typically a stop codon, such as amber, ochre, or opal, or a frameshift codon. In other aspects, the method may further comprise modifying a polynucleotide encoding said molecule.

In some embodiments, the method further comprises an in vivo or in vitro translational system. In some aspects, the translation system comprises a host cell selected from the group consisting of: prokaryotic, eukaryotic, and insect cells.

Some aspects further comprise using structural coordinates of said molecule to derive one or more energy calculations in order to determine which one or more amino acid residues are energetically favorable to substitution with a different amino acid residue. Some energy calculations that may be utilized include: force field calculation, original DEE or Goldstein DEE, Monte Carlo search, derived from a rotamer library, derived from a ligand or receptor binding site of the molecule, derived from one or more salvation calculations, derived from one or more binding energies, or HierDock computational screening.

In some embodiments the method further comprises using the identity of the penultimate amino acid residue in the molecule in order to determine which one or more amino acid residues may be efficiently substituted at the amino terminus. In certain embodiments, the penultimate amino acid residue is a non-natural amino acid and is either substituted or added to the target molecule in order to either retain or remove the non-natural amino acid residue at the first position of the amino terminus of the polypeptide during processing (transcription, translation, and/or post-translational modifications).

Other aspects of the disclosure relate to a composition comprising a modified molecule comprising one or more amino acid residues substituted with a different naturally occurring amino acid residue to make a sequence that differs from the native sequence of the molecule; one or more non-natural amino acid residues and a chemical moiety, wherein at least one of the non-natural amino acid residues is located at the amino terminus, and wherein said modified molecule retains a native function. Some embodiments include the composition wherein a native function is equal to or greater in magnitude compared to the function of a corresponding wild type molecule.

In some embodiments, the molecule comprises a chemical moiety selected from the group consisting of: cytotoxins, pharmaceutical drugs, dyes or fluorescent labels, a nucleophilic or electrophilic group, a ketone or aldehyde, azide or alkyne compounds, photocaged groups, tags, a peptide, a polypeptide, a protein, an oligosaccharide, polyethylene glycol with any molecular weight and in any geometry, polyvinyl alcohol, metals, metal complexes, polyamines, imidizoles, carbohydrates, lipids, biopolymers, particles, solid supports, a polymer, a targeting agent, an affinity group, any agent to which a complementary reactive chemical group can be attached, biophysical or biochemical probes, isotypically-labeled probes, spin-label amino acids, fluorophores, aryl iodides and bromides.

The modified molecule may be a therapeutic, diagnostic, or other molecule selected from the group consisting of: an antibody, antibody fragment, antibody derivative, Fab, Fab', F(ab)$_2$, Fd, Fv, ScFv, diabody, tribody, tetrabody, dimer, trimer or minibody, a cytokine, Factor VII, Factor VIII, Follitropin, G-CSF, GM-CSF, growth hormone, erythropoietin, thrombopoietin, interferon-α, interferon-β, interferon-γ, interferon-Ω, interferon-τ, GAP-1, a transcriptional modulator that modulates cell growth, differentiation, or regulation, expression activator, inflammatory molecule, growth factor, growth factor receptor, and oncogene product.

In some embodiments, the molecule comprises interferon-β. In some embodiments, the naturally occurring residues 1, 2, 36, 40, 44, 62, or 117, of the interferon-β or any combination thereof, is altered to another amino acid residue. In certain embodiments, any one or more of those residues may be replaced with azidohomoalanine, para-bromophenylalanine, homopropargylglycine, ethynylphenylalanine, azidophenylalanine, or para-iodophenylalanine. In certain embodiments, the non-natural amino acid residue is located at a terminal end of the molecule. In some cases, the terminal end comprises the amino terminus. In some cases, the terminal end comprises the carboxyl terminus.

In certain embodiments, the one or more amino acid residues substituted with another naturally occurring amino acid residue comprises substituting methionine at residue 62 of human interferon β to isoleucine, and/or isoleucine at residue 40 of human interferon β to phenylalanine, and/or isoleucine at residue position 44 of human interferon β to leucine. In some embodiments, the methionine at position 117 of human interferon β is substituted. In some cases, the methionine at position 117 is substituted with serine or threonine. In some embodiments, the methionine at position 36 is substituted with threonine, isoleucine, or alanine. In any of these embodiments, the naturally occurring amino acid residues at the aforementioned positions may be substituted with non-natural amino acids, including azidohomoalanine, homopropargylglycine, p-bromophenylalanine, azidophenylalanine, acetylphenylalanine, ethynylphenylalanine, azidophenylalanine, or p-iodophenylalanine. In addition, any of the non-natural amino acids may further comprise a chemical moiety (including polyethylene glycol).

One specific embodiment is a modified interferon-β having the following substitutions of naturally occurring residues within human interferon β: methionine 36 is substituted by isoleucine; methionine 62 is substituted by isoleucine; methionine 117 is substituted by threonine; isoleucine 40 is substituted by phenylalanine; isoleucine 44 is substituted by leucine; and serine 2 is substituted by glutamic acid. Another embodiment comprises these substitutions, as well as substitution of methionine 1 with azidohomoalanine (AHA). In particular embodiments, the present invention includes a modified human interferon-β having a sequence provided in SEQ ID NO:20 or 21, or a functional fragment thereof.

In another embodiment, the modified molecule comprises human growth hormone and one or more amino acid residues to be substituted comprise tryptophan, phenylalanine, or methionine. In another embodiment, the molecule comprises G-CSF, erthyropoietin, GLP-1, phenylalanine hydroxylase, urikase, Factor VII, or follitropin.

Still other aspects relate to a pharmaceutical composition comprising a modified molecule comprising one or more amino acid residues substituted with a naturally occurring amino acid residue; and one or more residues substituted with one or more non-natural amino acid residue; and one or more chemical moieties.

In certain embodiments, one or more properties of the molecule are altered wherein said properties are selected from the group consisting of: toxicity, biodistribution, structural properties, spectroscopic properties, chemical or photochemical properties, catalytic ability, serum half-life, shelf half-life, ability to react with other molecules covalently or non-covalently, stability, activity, conformation, substrate specificity, target binding affinity, antigen-binding ability, thermostability, resistance to at least one protease, tolerance to at least one non-aqueous environment, glycosylation pattern, phosphorylation pattern, disulfide bonding, protease cleavage site location, metal binding ability, co-factor binding ability, cross-linking ability, solubility, cysteinylation, deamidation, acetylation, biotinylation, oxidation, glutathionylation, sulphonation, immunogenicity, tissue penetration, fluorescence pegylation, multimerization ability, facility of purification, catalytic activity, vaccine stability, ability to function as a vaccine, redox potential, patient tolerance to a protein, increased efficacy of a protein in a patient, and improved delivery of a protein or protein product in a patient.

Thus, certain embodiments of the present invention relate to a method for producing a modified target polypeptide, comprising providing a host cell, the host cell comprising a vector having a polynucleotide encoding the target polypeptide, site-specifically incorporating one or more non-natural amino acid codons into the polynucleotide, wherein at least one non-natural amino acid codon corresponds to the first position of the amino terminus of the target polypeptide, (a) growing the host cell under conditions such that the host cell expresses the target polypeptide, wherein the target molecule retains the non-natural amino acid residue at the first position of the amino terminus, and wherein the non-natural amino acid residue at the first position of the amino terminus contains an azide, alkyne, vinyl, or aryl halide group, thereby producing a modified target polypeptide.

In certain embodiments, one or more non-natural amino acid codon encodes the penultimate position of the amino terminus of the target polypeptide. The methods may include one or more non-natural amino acids is selected from the group consisting of: azidonorleucine, 3-(1-naphthyl)alanine, 3-(2-naphthyl)alanine, p-ethynyl-phenylalanine, p-propargly-oxy-phenylalanine, m-ethynyl-phenylalanine, 6-ethynyl-tryptophan, 5-ethynyl-tryptophan, (R)-2-amino-3-(4-ethynyl-1H-pyrol-3-yl)propanic acid, p-bromophenylalanine, p-idiophenylalanine, p-azidophenylalanine, 3-(6-chloroindolyl)alanine, 3-(6-bromoindoyl)alanine, 3-(5-bromoindolyl)alanine, azidohomoalanine, and p-chlorophenylalanine.

In certain embodiments, the target polypeptide is selected from the group consisting of: Factor VII, Factor VIII, Factor IX, Follitropin, thrombopoeitin, erythropoietin, human growth hormone, G-CSF, GM-CSF, interferon-α, interferon-interferon-γ, interferon-Ω, interferon-τ, and GLP-1.

In certain embodiments, the site-specifically incorporating one or more amino acid codons is conducted by a technique selected from the group consisting of: site-directed mutagenesis, error-prone PCR, gene shuffling, homologous recombination, incorporation of an amber stop codon, incorporation of a wobble codon, use of an external mutant aminoacyl-tRNA synthetase, and incorporation of a bias codon.

The present invention also relates to a composition comprising a modified target polynucleotide encoding a target polypeptide, the target polynucleotide comprising one or more non-natural amino acid codons wherein at least one non-natural amino acid codon contains an azide, alkyne, vinyl, or aryl halide group and corresponds to the first position of the amino terminus of the target polypeptide. In particular embodiments, the present invention includes a modified target polynucleotide that encodes a modified interferon-beta having a sequence set forth in SEQ ID NO: 20 or 21. In related embodiments, the present invention includes a vector, e.g., an expression vector, comprising a modified target polynucleotide that encodes a modified interferon-beta having a sequence set forth in SEQ ID NO: 20 or 21.

In certain embodiments, the composition further comprises a host cell. In particular embodiments, the host cell comprises a vector comprising a modified target polynucleotide of the present invention, e.g., a modified target polynucleotide that encodes a modified interferon-beta having a sequence set forth, in SEQ ID NO: 20 or 21.

In still other embodiments, the composition comprises at least one non-natural amino acid codon corresponds to the penultimate position of the amino terminus of the target polypeptide. In still other embodiments, the composition further comprises a chemical moiety attached to one or more non-natural amino acid residues in the target polypeptide. In still other embodiments, the composition comprises a chemical moiety attached at least to the non-natural amino acid residue in the first position of the amino terminus of the target polypeptide. In some instances, the chemical moiety is covalently attached to the non-natural amino acid corresponding to the first position of the amino terminus of the target polypeptide. In other embodiments, the chemical moiety is attached to the non-natural amino acid corresponding to the first position of the amino terminus of the target polypeptide by a single carbon-carbon linkage, a double carbon-carbon linkage, a triple carbon-carbon linkage, or a triazole linkage between the chemical moiety and the non-natural amino acid. In still other embodiments, the chemical moiety is selected from the group consisting of: cytotoxins, pharmaceutical drugs, dyes or fluorescent labels, a nucleophilic or electrophilic group, a ketone or aldehyde, azide or alkyne compounds, photocaged groups, tags, a peptide, a polypeptide, a protein, an oligosaccharide, polyethylene glycol with any molecular weight and in any geometry, polyvinyl alcohol, metals, metal complexes, polyamines, imidizoles, carbohydrates, lipids, biopolymers, particles, solid supports, a polymer, a targeting agent, an affinity group, any agent to which a complementary reactive chemical group can be attached, biophysical or biochemical probes, isotypically-labeled probes, spin-label amino acids, fluorophores, aryl iodides and bromides.

The composition may include a modified target polypeptide is selected from the group consisting of: an antibody, antibody fragment, antibody derivative, Fab, Fab', F(ab)$_2$, Fd, Fv, ScFv, diabody, tribody, tetrabody, dimer, trimer or minibody, a cytokine, a transcriptional modulator that modulates cell growth, differentiation, or regulation, expression activator, inflammatory molecule, growth factor, growth factor receptor, and oncogene product. The composition may be selected from the group consisting of: Factor VII, Factor VIII, Factor IX, Follitropin, thrombopoeitin, erythropoietin, human growth hormone, G-CSF, GM-CSF, interferon-α, interferon-β, interferon-γ, interferon-Ω, interferon-τ, and GLP-1. Preferably, the composition comprises interferon-β.

In certain embodiments, at least one of the non-natural amino acid codons corresponds to positions selected from the group consisting of: 2, 17, 36, 40, 44, 62, and 117 of the modified target polypeptide.

Still other embodiments include a pharmaceutical composition comprising a modified target polypeptide comprising a target polypeptide having one or more non-natural amino acids residues incorporated, wherein at least one of the non-natural amino acid residues corresponds to the first position of the amino terminus of the target polypeptide.

Figure 1A:
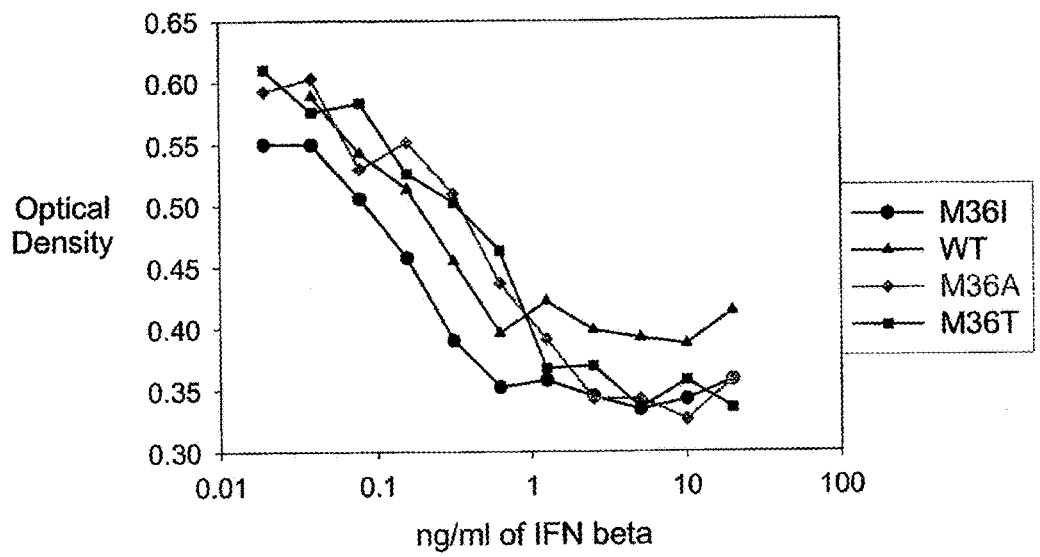
FIG. 1A illustrates in vitro biological activity of interferon-β mutants in which the methionine at position 36 is substituted with an isoleucine, arginine, or threonine residue. Biological activity was measured based on Daudi cell proliferation according to MTS metabolism after 3 days exposure to interferon-β.
Figure 1B:
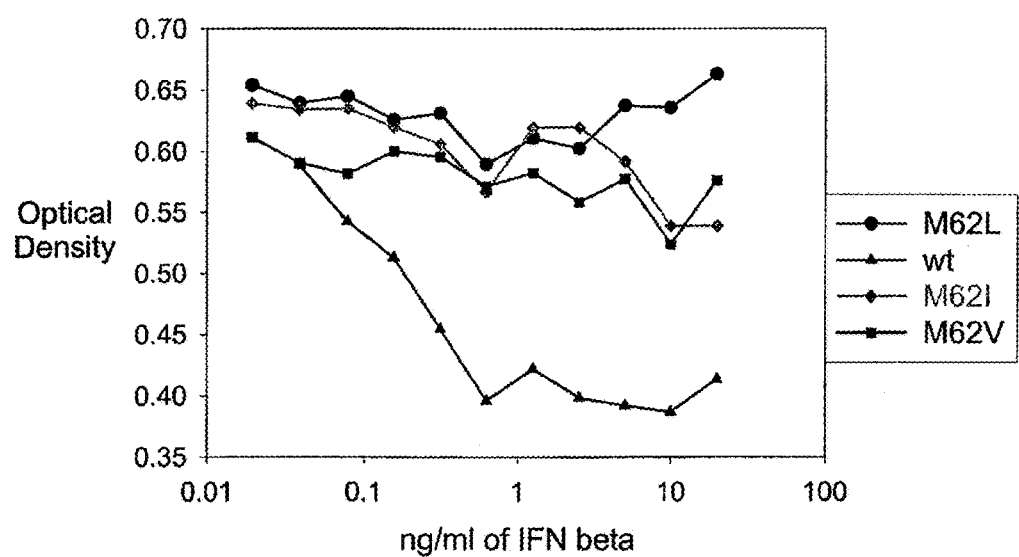
FIG. 1B illustrates in vitro biological activity of interferon-β mutants in which the methionine at position 62 is substituted with a lysine, isoleucine, or valine residue. Biological activity was measured based on Daudi cell proliferation according to MTS metabolism after 3 days exposure to interferon-β.
Figure 1C:
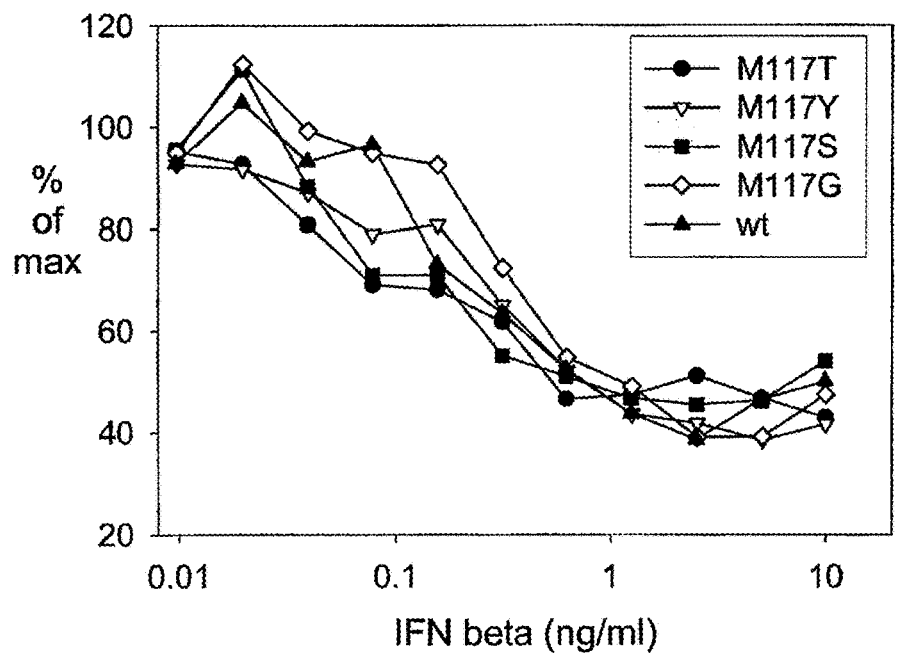
FIG. 1C illustrates the activity of interferon-β mutants in which the methionine at position 117 is substituted with threonine, tyrosine, serine, or glycine. HEK 293 cells were transfected with an interferon-β mutant, and supernatants collected at day 3. Interferon-β activity of supernatant or Avonex was measured based on inhibition of Daudi cell proliferation.
Figure 1D:
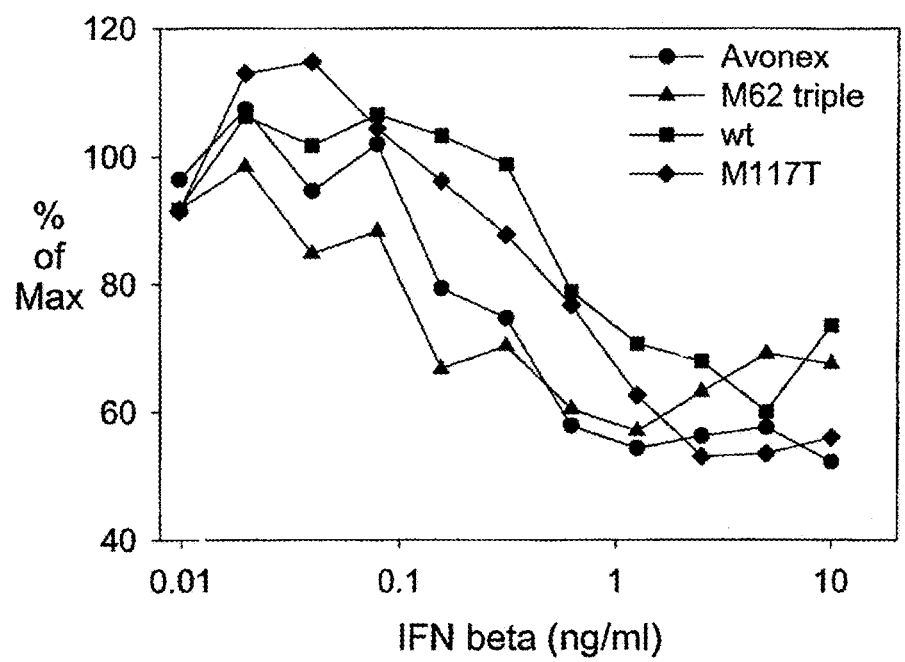
FIG. 1D illustrates the activity of interferon-β mutants in which the methionine at position 117 is substituted with a threonine, a mutant in which the methionine at position 62 is substituted with an isoleucine, the isoleucine at position 40 is substituted with phenylalanine, and the isoleucine at position 44 is substituted with leucine. AVONEX® (human interferon-β-1a) is manufactured by Biogen Idec, Inc. HEK 293 cells were transfected with an interferon-β mutant, and supernatants collected. Interferon-β activity of the supernatant or Avonex was measured based on the inhibition of Daudi cell proliferation.
Figure 2:
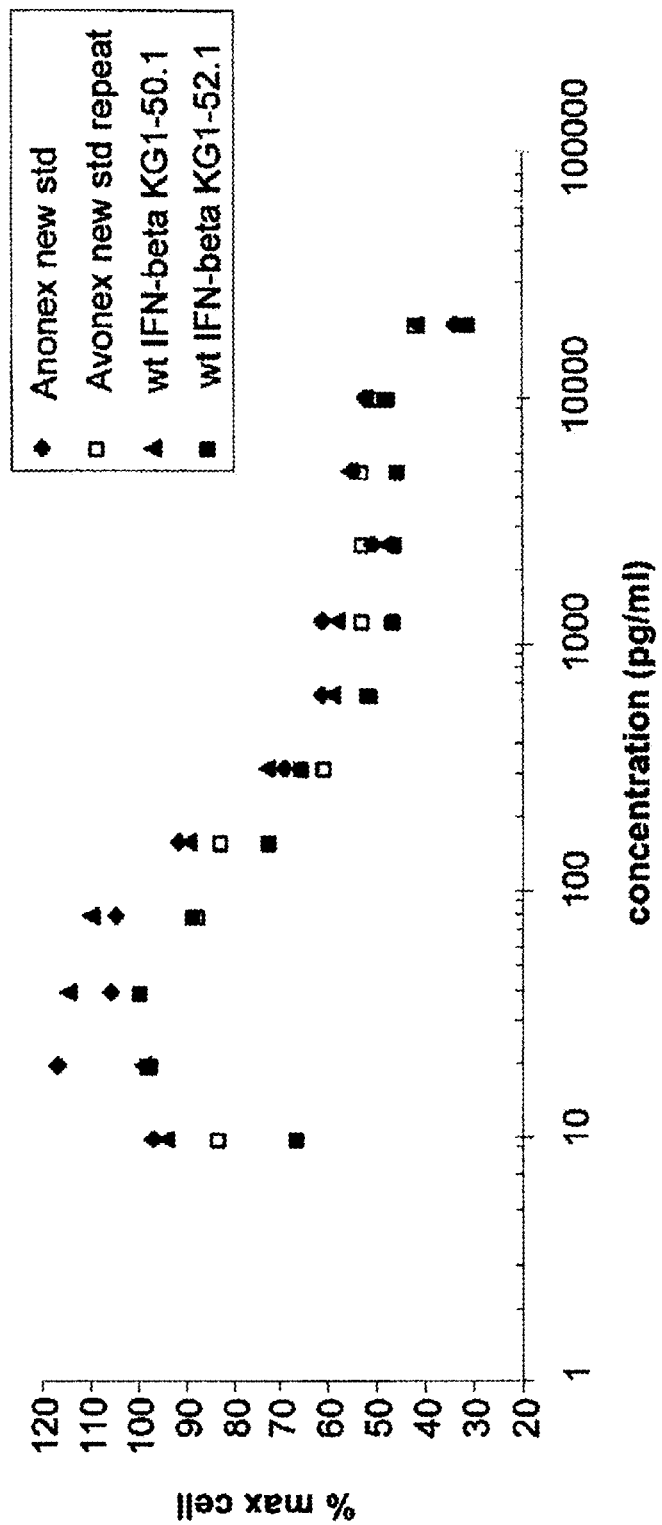
FIG. 2 illustrates the activity of interferon-β mutants. Triple: methionine at position 62 is substituted with isoleucine, isoluecine at amino acid position 40 is substituted with phenylalanine, isoleucine at amino acid position 44 is substituted with leucine. WT: wild type, no mutations. Triple-M117S: methionine at position 62 is substituted with isoleucine, isoluecine at amino acid position 40 is substituted with phenylalanine, isoleucine at amino acid position 44 is substituted with leucine, and methionine at amino acid position 117 is substituted with serine. Triple-M117T.

methionine at position 62 is substituted with isoleucine, isoluecine at amino acid position 40 is substituted with phenylalanine, isoleucine at amino acid position 44 is substituted with leucine, and methionine at position 117 is substituted with threonine. M36A-Triple: methionine at position 62 is substituted with isoleucine, isoluecine at amino acid position 40 is substituted with phenylalanine, isoleucine at amino acid position 44 is substituted with leucine, and methionine at amino acid position 36 is substituted with alanine. M36T-Triple: methionine at position 62 is substituted with isoleucine, isoluecine at amino acid position 40 is substituted with phenylalanine, isoleucine at amino acid position 44 is substituted with leucine, and methionine at position 36 is substituted with threonine. HEK 293 cells were transfected with each mutant. Activity of interferon-β mutants was measured based on inhibition of Daudi cell proliferation.

Figure 3:
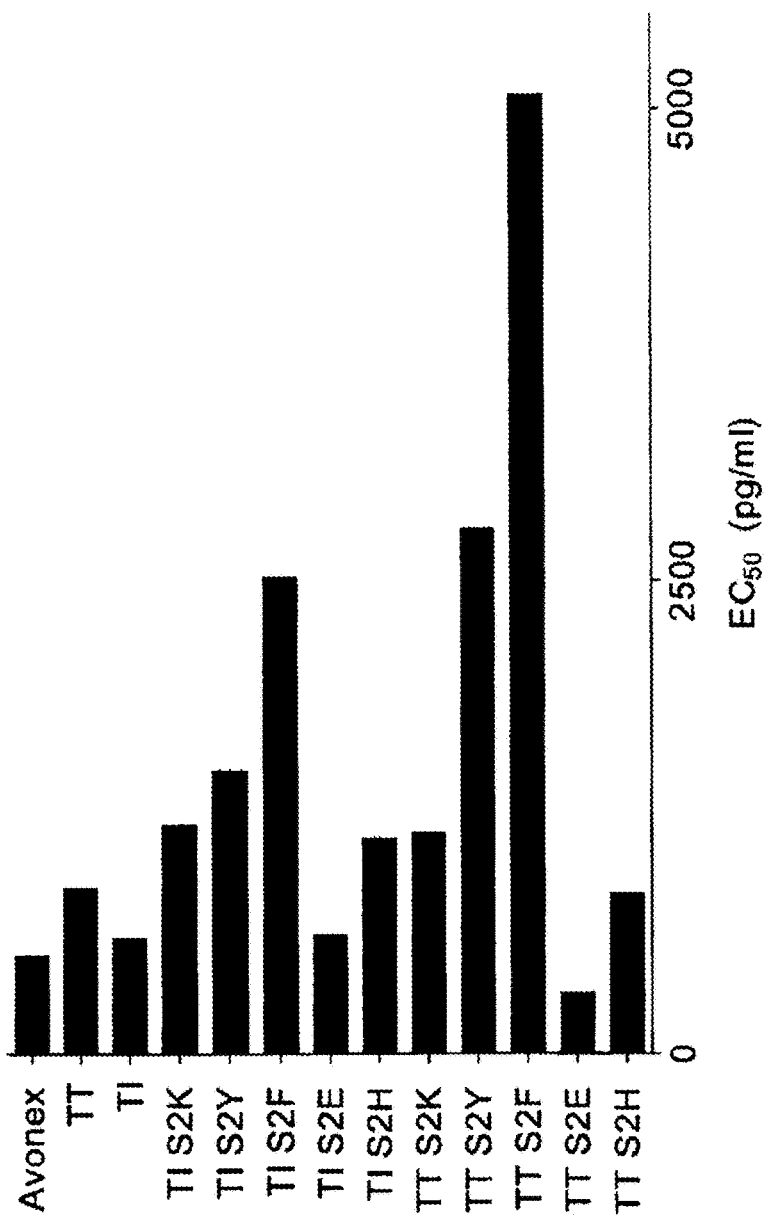

FIG. 3 illustrates the antiproliferative activity of various interferon-β mutants with a single methionine present in the molecule, and various mutations at the second amino acid position (S2). HEK 293 cells were transfected with expression plasmids encoding the mutant constructs (TT or TI), as indicated. TT indicates a mutant comprising at least an M36T-M117T mutation or substitution. TI indicates a mutant comprising at least an M36T-M117I mutation or substitution. Sandwich ELISAs were performed on supernants and biological activity was measured for rates of inhibition of proliferation.

Figure 4:
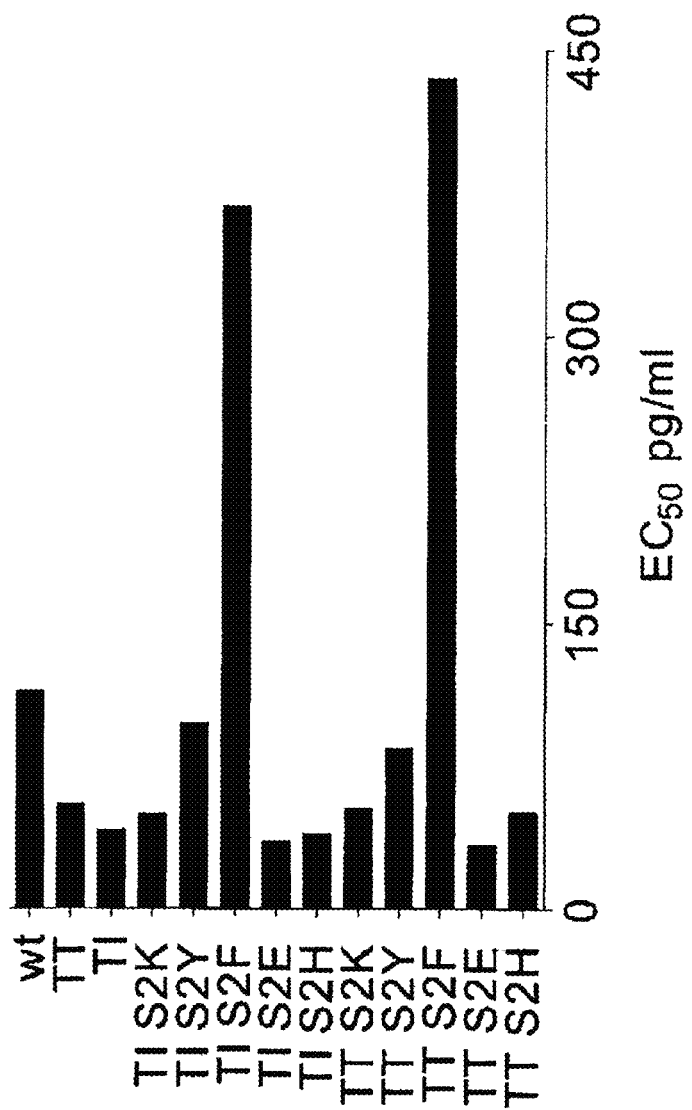

FIG. 4 illustrates the antiviral activity of various interferon-β mutants with a single methionine present in the molecule, and various mutations at the second amino acid position (S2). A549 cells were incubated with EMC virus at a titer sufficient to give complete lysis of the cells in the absence of interferon. The supernatant was removed and cells were stained in crystal violet and buffered formalin. Cell count was determined at $OD_{650}$ by a microplate reader.

Figure 5:
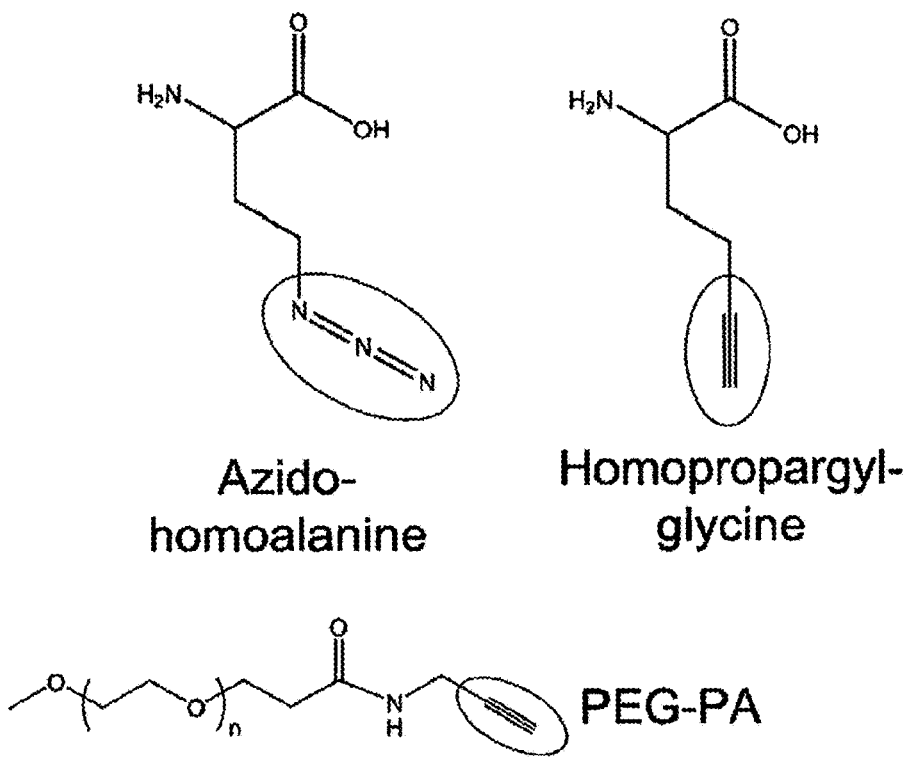

FIG. 5 depicts two methionine analogs, azidohomoalanine and homoproparglyglycine, as well as an activated poly(ethylene)glycol molecule.

Figure 6:
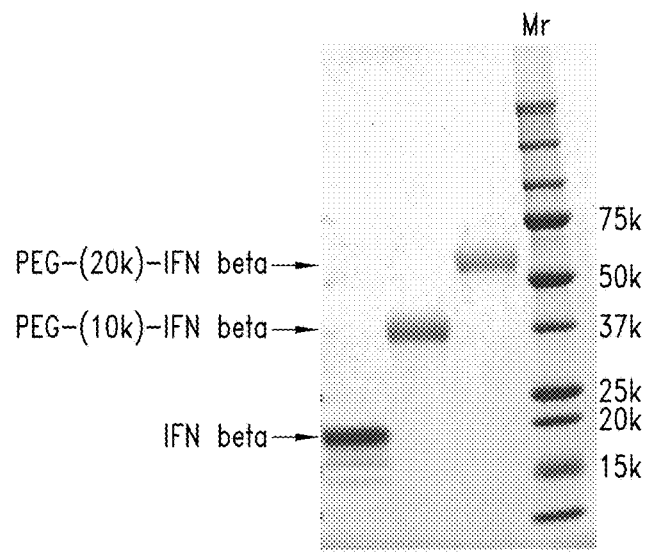

FIG. 6 illustrates an SDS-PAGE of pegylated interferon-β, with various sized PEG molecules.

Figure 7A:
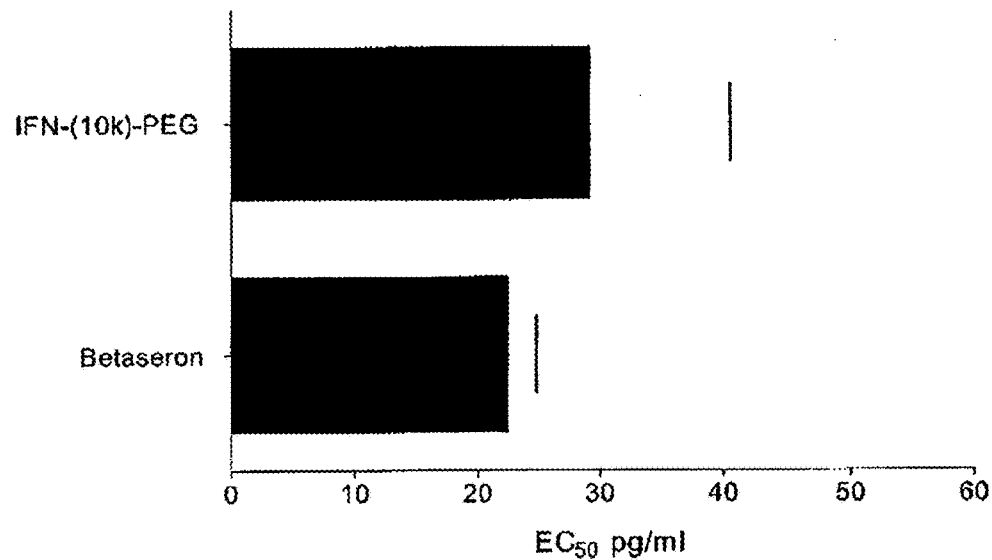

FIG. 7A illustrates antiviral activity for 10K-PEG interferon-β conjugate TIS2E. A549 cells were incubated with EMC virus at a titer sufficient to give complete lysis of the cells in the absence of interferon. The supernatant was removed and cells were stained in crystal violet and buffered formalin. Cell count was determined at $OD_{650}$ by a microplate reader.

Figure 7B:
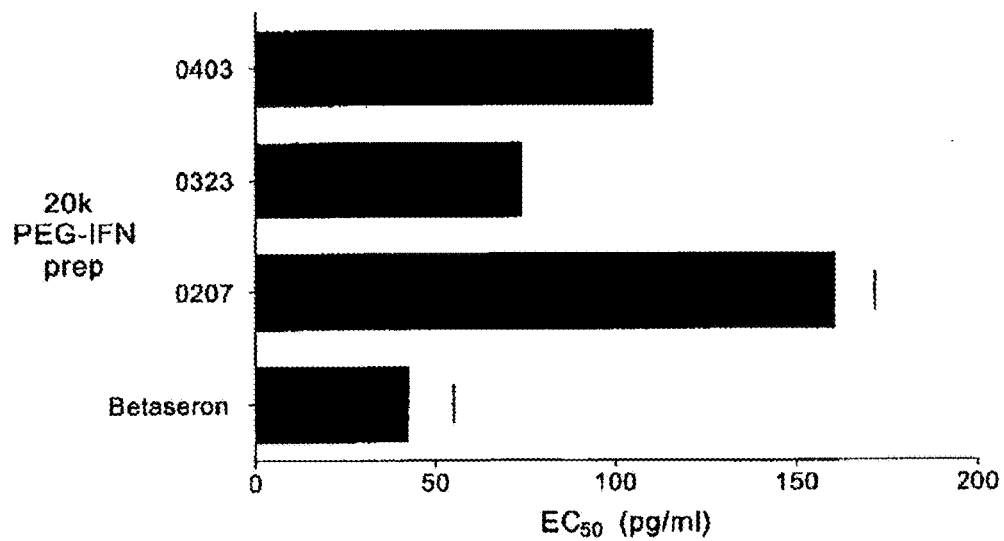

FIG. 7B illustrates antiviral activity for various 20K-PEG interferon-β conjugates (TIS2E), according to standard procedures as described for FIG. 7A.

Figure 8A:
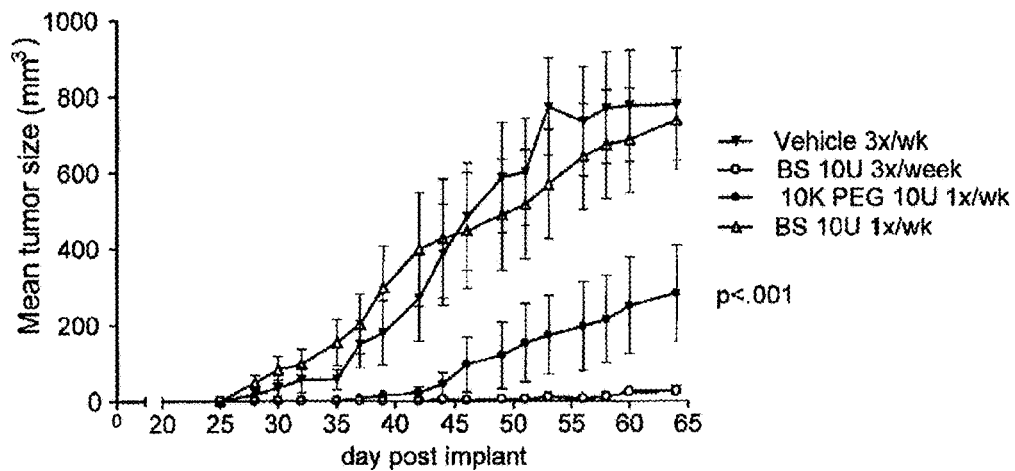

FIG. 8A illustrates ability of 10K-PEG interferon-β conjugate to inhibit tumor progression as measured by tumor size of Daudi cells implanted into SCID mice.

Figure 8B:
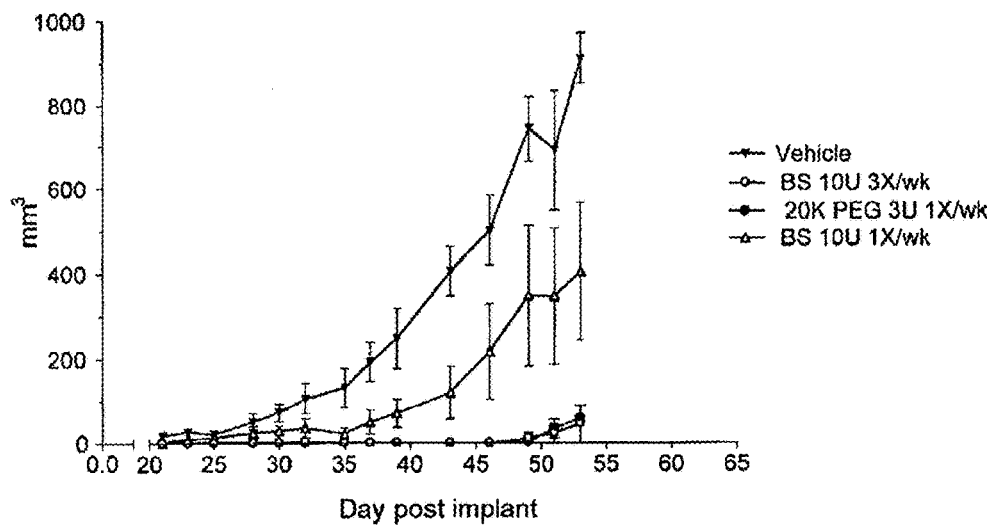

FIG. 8B illustrates ability of 20K-PEG interferon-6 conjugate to inhibit tumor progression as measured by tumor size of Daudi cells implanted into SCID mice.

Figure 9:
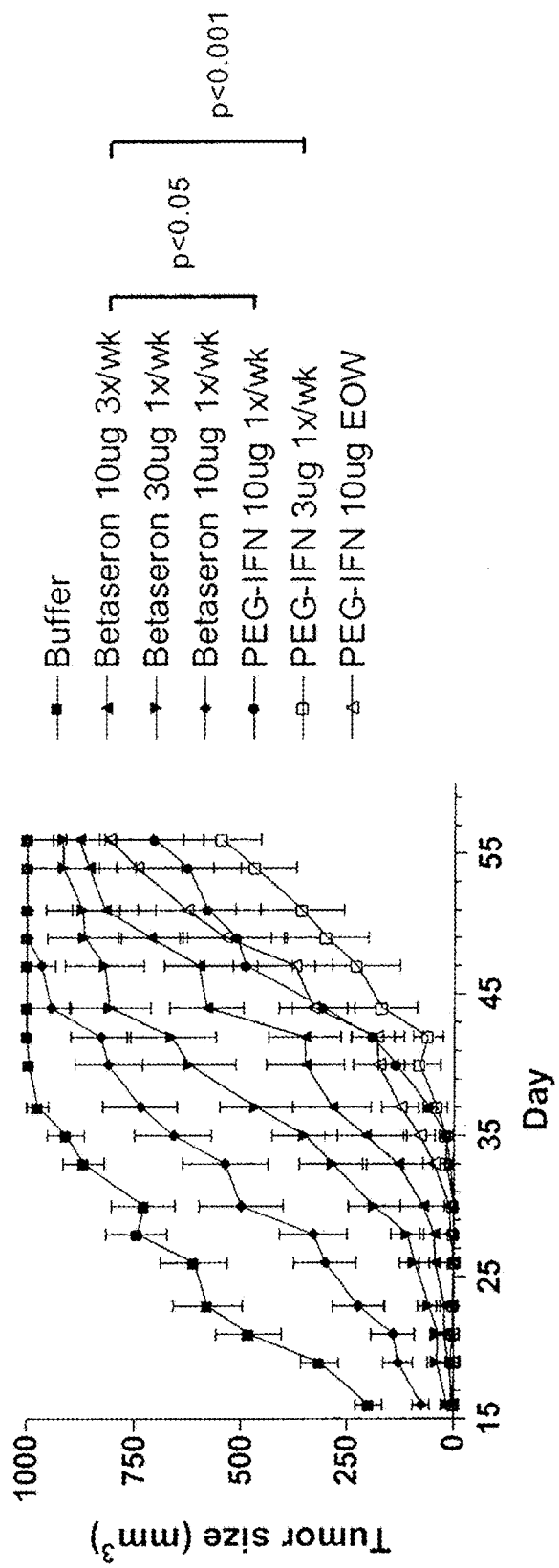

FIG. 9 illustrates in vivo potency of a representative PEG-IFNβ (at various levels to inhibit growth of Daudi cell tumors in scid mice at different levels of administration, compared to buffer and Betaseron.

Figure 10:
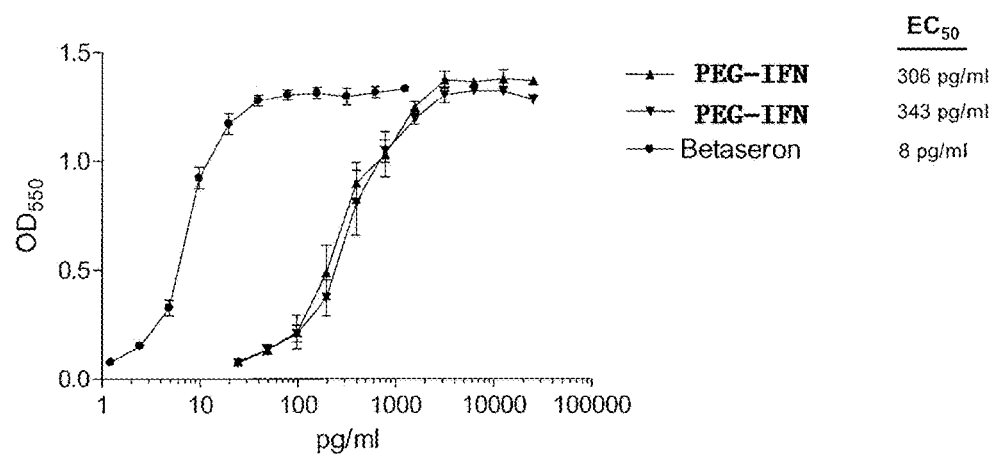

FIG. 10 illustrates antiviral activity for PEG-IFNβ. A549 cells were incubated with EMC virus at a titer sufficient to give complete lysis of the cells in the absence of interferon. The supernatant was removed and cells were stained in crystal violet and buffered formalin. Cell count was determined at $OD_{650}$ by a microplate reader.

Figure 11:
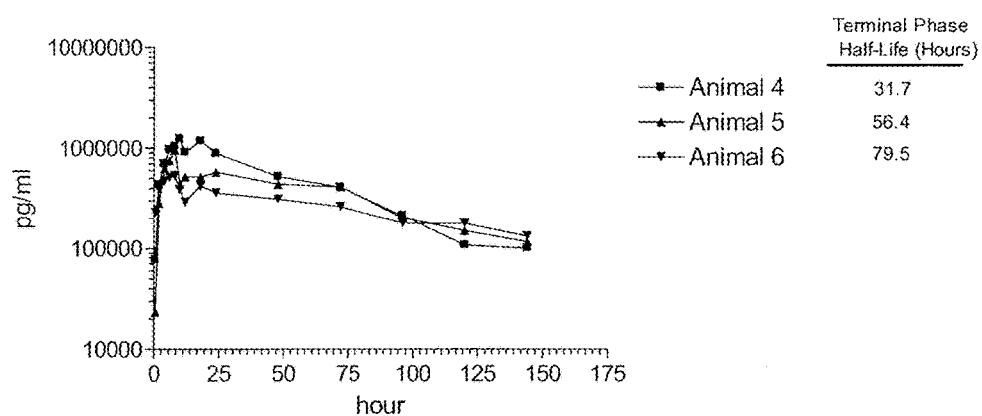

FIG. 11 provides plasma levels of PEG-IFNβ in three cynomolgus monkeys following subcutaneous administration of 0.3 mg/kg PEG-IFNβ.

DETAILED DESCRIPTION OF THE INVENTION

Overview

The present invention includes methods, compositions and kits for identifying and/or modifying molecules, optionally testing the activity of the molecule, and/or purifying the molecule.

Specifically, some embodiments provide for modifying a molecule by deletion of an amino acid and/or incorporation of one or more non-natural amino acid residues into the molecule. In certain embodiments, at least the N-terminal amino acid (typically a methionine) is replaced with a non-natural amino acid. In certain other embodiments, a non-natural amino acid is incorporated at the penultimate position, in addition to the N-terminal amino acid being replaced with a non-natural amino acid, and possibly other non-natural amino acid incorporations in the molecule. Certain embodiments utilize auxotrophic host cells for assistance in incorporating non-natural amino acids into the molecule. Certain other embodiments may utilize mutant transcription or translation machinery for assistance in incorporating non-natural amino acids, while some embodiments will utilize both auxotrophic host cells and mutant transcription or translation machinery. Exemplary means of mutant transcription machinery include mutant tRNA and/or mutant amino-acyl tRNA synthetase(s). In some embodiments, a chemical moiety is attached to one or more of the non-natural amino acids of the modified molecule.

Several detailed methods for altering molecules, including proteins, are set forth in U.S. patent application Ser. No. 09/620,691, now abandoned; Ser. No. 10/851,564, pending as U.S. Publication No. 20040219488; Ser. No. 10/612,713, pending as U.S. Publication No. 20040058415; Ser. No. 10/015,956, pending but not yet published; Ser. No. 11/094,625, pending as U.S. Publication No. 20050260711; Ser. No. 11/130,583, pending as U.S. Publication No. 20050287639; U.S. Pat. Nos. 7,139,665; and 6,586,207; all of which are hereby incorporated by reference in their entireties. Additionally, several issued U.S. patents discuss methods for calculating energy analysis for point mutations in molecules, including proteins, such as U.S. Pat. Nos. 6,188,965; 6,269,312; 6,708,120; 6,792,356; 6,801,861 and 6,804,611, all of which are hereby incorporated by reference in their entireties. Any of these referenced, or any other methods of altering, modifying or identifying molecules may be used with the present invention.

Definitions

Before describing certain embodiments in detail, it is to be understood that this invention is not limited to particular compositions or biological systems, which can, of course, vary. It is also to be understood that the terminology used herein is for the purpose of describing particular illustrative embodiments only, and is not intended to be limiting. The terms used in this specification generally have their ordinary meanings in the art, within the context of this invention and in the specific context where each term is used. Certain terms are discussed below or elsewhere in the specification, to provide additional guidance to the practitioner in describing the compositions and methods of the invention and how to make and use them. The scope and meaning of any use of a term will be apparent from the specific context in which the term is used. As such, the definitions set forth herein are intended to provide illustrative guidance in ascertaining particular embodiments of the invention, without limitation to particular compositions or biological systems. As used in the present disclosure and claims, the singular forms "a," "an," and "the" include plural forms unless the context clearly dictates otherwise.

"About" and "approximately," as used herein, generally refer to an acceptable degree of error for the quantity measured, given the nature or precision of the measurements. Typical, exemplary degrees of error may be within 20%, 10%, or 5% of a given value or range of values. Alternatively, and particularly in biological systems, the terms "about" and "approximately" may mean values that are within an order of magnitude, potentially within 5-fold or 2-fold of a given value. Numerical quantities given herein are approximate unless stated otherwise, meaning that the term "about" or "approximately" may be inferred when not expressly stated.

"Altered," as used herein may be used synonymously with "changed," "modified," and in certain embodiments, "mutated" (e.g., a mutated polynucleotide may also be referred to as altered or modified). "Mutation" or "modification" generally refers to an alteration of a target molecule, tRNA, or MRS that occurs at a nucleic acid level (i.e. altering a polynucleotide) rather than at an amino acid level (i.e. during fermentation). For example, a mutation or modification may include any physical, chemical, or biological alteration or change to the target molecule, typically at the genetic or nucleic acid level.

"Incorporation," as used herein refers to any addition, substitution, replacement, mutation or other modification in which one or more naturally occurring amino acid or non-natural amino acid is entered into the target molecule in addition to or as a substitute for another naturally occurring amino acid or non-natural amino acid. As used herein, "substitute" and any and all variations thereof, is synonomous with "replace" and any and all variations thereof.

One of skill in the art would understand that a target molecule may be altered by the addition, deletion, substitution, mutation, or chemical modification to any amino acid residue, amino acid group or component (e.g., amino acid side chain), or nucleic acid encoding an amino acid residue in the target molecule. In certain embodiments described herein, a non-natural or other amino acid residue may be incorporated into a target molecule by various methods, including but not limited to modifying a codon of the polynucleotide to alter a naturally occurring amino acid to another naturally occurring amino acid, by altering the polynucleotide from encoding a naturally occurring amino acid to a non-natural amino acid, or by adding a non-natural amino acid to the media of the host cells during protein translation (fermentation) wherein the non-natural amino acid is utilized at a position corresponding to a codon specifying a particular amino acid.

"Amino acid analog," "non-canonical amino acid," "unnatural amino acid," "modified amino acid," "unnatural AARS substrate," "non-natural AARS substrate," "non-standard amino acid," "non-natural amino acid," "unnatural amino acid," and the like may all be used interchangeably, and is meant to include all amino acid-like compounds that are similar in structure and/or overall shape to one or more of the twenty L-amino acids commonly found in naturally occurring proteins (Ala or A, Cys or C, Asp or D, Glu or E, Phe or F, Gly or G, His or H, Ile or I, Lys or K, Leu or L, Met or M, Asn or N, Pro or P, Gln or Q, Arg or R, Ser or S, Thr or T, Val or V, Trp or W, Tyr or Y, as defined and listed in WIPO Standard ST.25 (1998), Appendix 2, Table 3).

Amino acid analog can also be natural amino acids with modified side chains or backbones. Amino acids can also be naturally occurring amino acids in D-, rather than L-form. Preferably, these analogs usually are not "substrates" for the aminoacyl tRNA synthethases (AARSs) because of the normally high specificity of the AARSs. Although occasionally, certain analogs with structures or shapes sufficiently close to those of natural amino acids may be erroneously incorporated into proteins by AARSs, especially modified AARSs with relaxed substrate specificity. In a preferred embodiment, the analogs share backbone structures, and/or even the most side chain structures of one or more natural amino acids, with the only difference(s) being containing one or more modified groups in the molecule. Such modification may include, without limitation, substitution of an atom (such as N) for a related atom (such as S), addition of a group (such as methyl, or hydroxyl group, etc.) or an atom (such as Cl or Br, etc.), deletion of a group (supra), substitution of a covalent bond (single bond for double bond, etc.), or combinations thereof. Amino acid analogs may include α-hydroxy acids, and α-amino acids, and can also be referred to as "modified amino acids," or "unnatural AARS substrates."

The amino acid analogs may either be naturally occurring or non-natural (e.g., synthesized). As will be appreciated by those in the art, any structure for which a set of rotamers is known or can be generated can be used as an amino acid analog. The side chains may be in either the (R) or the (S) configuration (or D- or L-configuration). In a preferred embodiment, the amino acids are in the (S) or L-configuration.

Preferably, the overall shape and size of the amino acid analogs are such that, upon being charged to (natural or modified or re-designed) tRNAs by (natural or re-designed) AARS, the analog-tRNA is a ribosomally accepted complex, i.e., the tRNA-analog complex can be accepted by the prokaryotic or eukaryotic ribosomes in an in vivo or in vitro translation system.

"Backbone," or "template" includes the backbone atoms and any fixed side chains (such as the anchor residue side chains) of the protein (e.g., AARS).

"Protein backbone structure" or grammatical equivalents herein generally refers to the three dimensional coordinates that define the three dimensional structure of a particular protein. The structure that comprises a protein backbone structure (of a naturally occurring protein) includes the nitrogen, the carbonyl carbon, the α-carbon, and the carbonyl oxygen, along with the direction of the vector from the α-carbon to the β-carbon.

When the protein backbone structure is entered into a computer, it may either include the coordinates for both the backbone and the amino acid side chains, or just the backbone, i.e., with the coordinates for the amino acid side chains removed. If the former is done, the side chain atoms of each amino acid of the protein structure may be "stripped" or removed from the structure of a protein, as is known in the art, leaving only the coordinates for the "backbone" atoms (the nitrogen, carbonyl carbon and oxygen, and the α-carbon, and the hydrogens attached to the nitrogen and α-carbon).

Optionally, the protein backbone structure may be altered prior to the analysis outlined below. In this embodiment, the representation of the starting protein backbone structure is reduced to a description of the spatial arrangement of its secondary structural elements. The relative positions of the secondary structural elements are defined by a set of parameters called supersecondary structure parameters. These parameters are assigned values that can be systematically or randomly varied to alter the arrangement of the secondary structure elements to introduce explicit backbone flexibility. The atomic coordinates of the backbone are then changed to reflect the altered supersecondary structural parameters, and these new coordinates are input into the system for use in the subsequent protein design automation. See, for example, U.S. Pat. No. 6,269,312, hereby incorporated by reference in its entirety.

"Conformational energy" refers generally to the energy associated with a particular "conformation," or three-dimensional structure of a macromolecule, such as the energy associated with the conformation of a particular protein. Interactions that tend to stabilize a protein have energies that are represented as negative energy values, whereas interactions that destabilize a protein have positive energy values. Thus, the conformational energy for any stable protein is quantitatively represented by a negative conformational energy value. Generally, the conformational energy for a particular protein will be related to that protein's stability. In particular, molecules that have a lower (i.e., more negative) conformational energy are typically more stable, e.g., at higher temperatures (i.e., they have greater "thermal stability"). Accordingly, the conformational energy of a protein may also be referred to as the "stabilization energy."

Typically, the conformational energy is calculated using an energy "force-field" that is able to calculate or estimate the energy contribution from various interactions dependent upon the conformation of a molecule. The force-field is comprised of terms that include the conformational energy of the α-carbon backbone, side chain—backbone interactions, and side chain-side chain interactions. Typically, interactions with the backbone or side chain include terms for bond rotation, bond torsion, and bond length. The backbone-side chain and side chain-side chain interactions include van der Waals interactions, hydrogen-bonding, electrostatics and solvation terms. Electrostatic interactions may include Coulomb interactions, dipole interactions and quadrapole interactions, as well as other similar terms.

Force-fields that may be used to determine the conformational energy for a polymer are well known in the art and include the CHARMM (see, Brooks et al, *J. Comp. Chem.* 1983, 4:187-217; MacKerell et al., in *The Encyclopedia of Computational Chemistry*, Vol. 1:271-277, John Wiley & Sons, Chichester, 1998), AMBER (see, Cornell et al., *J. Amer. Chem. Soc.* 1995, 117:5179; Woods et al., *J. Phys. Chem.* 1995, 99:3832-3846; Weiner et al., *J. Comp. Chem.* 1986, 7:230; and Weiner et al., *J. Amer. Chem. Soc.* 1984, 106:765) and DREIDING (Mayo et al., *J. Phys. Chem.* 1990, 94-:8897) force-fields, as well as others, all of which are hereby incorporated by reference.

In at least one embodiment, the hydrogen bonding and electrostatics terms are as described in Dahiyat & Mayo, (*Science* 1997 278:82), hereby incorporated by reference in its entirety. The force field can also be described to include atomic conformational terms (bond angles, bond lengths, torsions), as in other references. See, e.g., Nielsen J E, Andersen K V, Honig B, Hooft R W W, Klebe G, Vriend G, & Wade R C, *Protein Engineering*, 12: 657-662 (1999); Stikoff D, Lockhart D J, Sharp K A & Honig B, *Biophys. J.*, 67: 2251-2260 (1994); Hendscb Z S, Tidor B, *Protein Science*, 3: 211-226 (1994); Schneider J P, Lear J D, DeGrado W F, *J. Am. Chem. Soc.*, 119: 5742-5743 (1997); Sidelar C V, Hendsch Z S, Tidor B, *Protein Science*, 7: 1898-1914 (1998); Jackson S E, Moracci M, Mastry N, Johnson C M, Fersht A R, *Biochem.*, 32: 11259-11269 (1993); Eisenberg, D & McLachlan A D, *Nature*, 319: 199-203 (1986); Street A G & Mayo S L, *Folding & Design*, 3: 253-258 (1998); Eisenberg D & Wesson L, *Protein Science*, 1: 227-235 (1992); all of which are hereby incorporated by reference in their entireties.

"Coupled residues" generally refers to residues in a molecule that interact through any mechanism. The interaction between the two residues is therefore referred to as a "coupling interaction." Coupled residues generally contribute to polymer fitness through the coupling interaction. Typically, the coupling interaction is a physical or chemical interaction, such as electrostatic interaction, van der Waals interaction, hydrogen bonding interaction, or a combination thereof. As a result of the coupling interaction, changing the identity of either residue will affect the "fitness" of the molecule, particularly if the change disrupts the coupling interaction between the two residues. Coupling interaction may also be described by a distance parameter between residues in a molecule. If the residues are within a certain cutoff distance, they are considered interacting.

"Fitness" is used herein to generally denote the level or degree to which a particular property or combination of properties for a molecule (such as a protein) are optimized. In certain embodiments of the invention, the fitness of a protein may be determined by particular properties that a user desires to improve. Thus, for example, the fitness of a protein may refer to the protein's thermal stability, structural stability, pharmaceutical capability, catalytic activity, ability to function as a vaccine, binding affinity, solubility (e.g., in aqueous or organic solvent), substrate specificity, resistance to at least one protease, tolerance to at least one non-aqueous environment and other activities. Other examples of fitness properties include enantioselectivity, activity towards non-natural substrates, and alternative catalytic mechanisms. Coupling interactions can be modeled as a way of evaluating or predicting fitness. Fitness can be determined or evaluated experimentally or theoretically, e.g., computationally.

Preferably, the fitness is quantitated so that each molecule, e.g., each amino acid, will have a particular "fitness value". For example, the fitness of a protein may be the rate at which the protein catalyzes a particular chemical reaction, or the fitness may be the protein's binding affinity for a ligand. In a particularly preferred embodiment, the fitness of a protein refers to the conformational energy of the polymer and is calculated, using any method known in the art. (See, e.g., Brooks B. R., Bruccoleri R E, Olafson, B D, States D J, Swaminathan S & Karplus M, *J. Comp. Chem.*, 4: 187-217 (1983); Mayo S L, Olafson B D & Goddard W A G, *J. Phys. Chem.*, 94: 8897-8909 (1990); Pabo C O & Suchanek E G, *Biochemistry*, 25: 5987-5991 (1986), Lazar G A, Desjarlais J R & Handel T M, *Protein Science*, 6: 1167-1178 (1997); Lee C & Levitt M, *Nature*, 352: 448-451 (1991); Colombo G & Merz K M, *J. Am. Chem. Soc.*, 121: 6895-6903 (1999); Weiner S J, Kollman P A, Case D A, Singh U C, Ghio C, Alagona G, Profeta S J, Weiner P, *J. Am. Chem. Soc.*, 106: 765-784 (1984), Datta, et al., *Protein Science* 13: 2693-2705 (2004), all of which are hereby incorporated by reference in their entireties).

In at least one embodiment, the fitness of a protein is quantitated so that the fitness value increases as the property or combination of properties is optimized. For example, in an embodiment where the thermal stability of a protein is to be optimized (conformational energy is preferably decreased), the fitness value may be the negative conformational energy; i.e., $F = -E$.

The "fitness contribution" of a protein residue refers to the level or extent $f(i_a)$ to which the residue $i_a$, having an identity (a), contributes to the total fitness of the protein.

Thus, for example, if changing or mutating a particular amino acid residue will greatly decrease the protein's fitness, that residue is said to have a high fitness contribution to the protein. By contrast, typically some residues $i_a$ in a protein may have a variety of possible identities (a) without affecting the protein's fitness. Such residues have a low contribution to the protein fitness.

"Dead-end elimination" (DEE) is a deterministic search algorithm that seeks to systematically eliminate bad rotamers and combinations of rotamers until a single solution remains. For example, amino acid residues can be modeled as rotamers that interact with a fixed backbone. The theoretical basis for DEE provides that, if the DEE search converges, the solution is the global minimum energy conformation (GMEC) with no uncertainty (Desmet et al., 1992).

Dead end elimination is based on the following concept. Consider two rotamers, $i_r$ and $i_t$, at residue i, and the set of all other rotamer configurations {S} at all residues excluding i (of which rotamer $j_s$ is a member). If the pairwise energy contributed between $i_r$ and $j_s$ is higher than the pairwise energy between $i_t$ and $j_s$ for all {S}, then rotamer $i_r$ cannot exist in the global minimum energy conformation, and can be eliminated. This notion is expressed mathematically by the inequality.

$$E(i_r) + \sum_{j \neq i}^{N} E(i_r, j_s) > E(i_t) + \sum_{j \neq i}^{N} E(i_t, j_s)\{S\} \quad \text{(Equation A)}$$

If this expression is true, the single rotamer $i_r$ can be eliminated (Desmet et al., 1992).

In this form, Equation A is not computationally tractable because, to make an elimination, it is required that the entire sequence (rotamer) space be enumerated. To simplify the problem, bounds implied by Equation A can be utilized:

$$E(i_r) + \sum_{j \neq i}^{N} \min(s)E(i_r, j_s) > E(i_t) + \sum_{j \neq i}^{N} \max(s)E(i_r, j_s)\{S\} \quad \text{(Equation B)}$$

Using an analogous argument, Equation B can be extended to the elimination of pairs of rotamers inconsistent with the GMEC. This is done by determining that a pair of rotamers $i_r$ at residue i and $j_s$ at residue j, always contribute higher energies than rotamers $i_u$ and $j_v$ with all possible rotamer combinations {L}. Similar to Equation B, the strict bound of this statement is given by:

$$(i_r, j_s) + \sum_{k \neq i,j}^{N} \min(t)\varepsilon(i_r, j_s, k_t) > \\ \varepsilon(i_u, j_v) + \sum_{k \neq i,j}^{N} \max(t)\varepsilon(i_u, j_v, k_i) \quad \text{(Equation C)}$$

where ε is the combined energies for rotamer pairs $$\varepsilon(i_r, j_s) = E(i_r) + E(j_s) + E(i_r, j_s) \quad \text{(Equation D),}$$

and $$\varepsilon(i_r, j_s, k_t) = E(i_r, k_t) + E(j_s, k_t) \quad \text{(Equation E).}$$

This leads to the doubles elimination of the pair of rotamers $i_r$ and $j_s$, but does not eliminate the individual rotamers completely as either could exist independently in the GMEC. The doubles elimination step reduces the number of possible pairs (reduces S) that need to be evaluated in the right-hand side of Equation 6, allowing more rotamers to be individually eliminated.

The singles and doubles criteria presented by Desmet et al. fail to discover special conditions that lead to the determination of more dead-ending rotamers. For instance, it is possible that the energy contribution of rotamer $i_t$ is always lower than $i_r$, without the maximum of $i_t$ being below the minimum of $i_r$. A modification of the criteria can be made that determines if the energy profiles of two rotamers cross. If they do not, the higher energy rotamer can be determined to be dead-ending. The doubles calculation may take significantly more computational time than the singles calculation. To accelerate the process, other computational methods have been developed to predict the doubles calculations that will be the most productive. See, for example, Gordon & Mayo, 1998, hereby incorporated by reference it its entirety. These kinds of modifications, collectively referred to as fast doubles, significantly improved the speed and effectiveness of DEE.

Several other modifications also enhance DEE. Rotamers from multiple residues can be combined into so-called super-rotamers to prompt further eliminations (Desmet et al., 1994; Goldstein, 1994).

For further discussion of these methods see, for example, Goldstein, R. F. (1994), *Biophys. J.* 66, 1335-1340; Desmet, J., De Maeyer, M., Hazes, B. & Lasters, I. (1992), *Nature* 356, 539-542; Desmet, J., De Maeyer, M. & Lasters, I. (1994), In *The Protein Folding Problem and Tertiary Structure Prediction* (Jr., K. M. & Grand, S. L., eds.), pp. 307-337 (Birkhauser, Boston); De Maeyer, M., Desmet, J. & Lasters, I. (1997), *Folding & Design* 2, 53-66, Gordon, D. B. & Mayo, S. L. (1998), *J. of Comp. Chem.* 19, 1505-1514; Pierce, N. A., Spriet, J. A., Desmet, J., Mayo, S. L., (2000), *J. of Comp. Chem.* 21, 999-1009, all of which are hereby incorporated by reference in their entireties.

"Expression system" refers to herein a host cell and compatible vector under suitable conditions, e.g., for the expression of a protein coded for by foreign DNA carried by the vector and introduced to the host cell. Common expression systems include *E. coli* host cells, *Pseudomonas*, or other bacterial cells and plasmid vectors, insect host cells such as Sf9, Hi5 or S2 cells and Baculovirus vectors, *Drosophila* cells (Schneider cells) and expression systems, and mammalian host cells, including yeast and vectors, metazoan cells may also be used. In addition to *E. coli*, other specific host cells include yeast cells, Chinese hamster ovary (CHO) cells, fibroblast cells (BHK or Vero, for example), stem cells (including embryonic stem cells), retinoblast cells (such as PerC.6 cells), hybridoma cells, neuronal cells, blood cells, bone marrow cells, liver cells, kidney cells, mammalian (including human) embryonic cells of any origin, plasmacytoma cells (such as NS1 cells), cell lines of any origin and hybrid-cross cells (including mixed mammalian cells, or cells from cross-species origin).

"Excipient," generally refers to any agent, vehicle, carrier, binder, diluent, lubricant, surfactant, buffer, anti-aggregant, coloring, stabilizer, solubilizer, preservative, etc. that may be suitable for a particular compound formulation. In certain aspects, the excipient may impart bulk to the formulation to make a tablet a practical size for administration. In other aspects, the excipient may be an agent that imparts cohesiveness to ensure the tablet remains intact after compression. In still other aspects, the excipient may be added to facilitate breakup or disintegration of the solid dosage form after administration. In certain embodiments, the excipient may impart stability, solubility, or prevent aggregation of a liquid or lyophilized formulation of a protein. Some examples of excipients include water, saline, celluloses, starches, clays, aligns, gums, talc, colloidal silicon dioxide, lactose and other sugars, polymers, as well as various combinations of these or others. The excipient may comprise active materials that do not impair the desired action, or with materials that supplement the desired action, or have another action. In addition, pharmaceutical or therapeutic carriers or vehicles may comprise an excipient.

"Host cell" means any cell of any organism that is selected, modified, transformed, grown, used or manipulated in any way for the production of a substance by the cell. A host cell may be auxotrophic, that is unable to synthesize or is deficient in at least one particular organic compound required for its maintainence or growth and must obtain the compound from another source, such as its environment or culture media. In addition, an auxotrophic host cell may have single, double, triple, quadruple, or more levels of auxotrophy such that it is unable to synthesize one, two, three, four or more organic compounds necessary for its growth or maintainence, respectively. For example, a host cell may be one that is manipulated to express a particular gene, a DNA or RNA sequence, a protein or an enzyme. Host cells may be cultured in vitro or in vivo in one or more cells in a non-human animal (e.g., a transgenic animal or a transiently transfected animal).

The methods of the invention may include steps of comparing sequences to each other, including a wild-type (also called "native") sequence to one or more mutants, or wild type sequences of the same gene from different species or related genes of the same or different species. Such comparisons typically comprise alignments of gene or polypeptide (protein) sequences, e.g., using sequence alignment programs and/or algorithms that are well known in the art (for example, BLAST, FASTA and MEGALIGN, to name a few). The skilled artisan can readily appreciate that, in such alignments, where a mutation contains a residue insertion or deletion, the sequence alignment will introduce a "gap" (typically represented by a dash, "-", or "Δ") in the polymer sequence not containing the inserted or deleted residue.

"Homologous", in all of its grammatical forms and spelling variations, refers to the relationship between two molecules (e.g., proteins, tRNAs, nucleic acids) that possess a "common evolutionary origin", including proteins from superfamilies in the same species of organism, as well as homologous proteins from different species of organism. Such proteins (and their encoding nucleic acids) have sequence and/or structural homology, as reflected by their sequence similarity, whether in terms of percent identity or by the presence of specific residues or motifs and conserved positions. Homologous molecules frequently also share similar or even identical functions.

The term "sequence similarity", in all its grammatical forms, refers to the degree of identity or correspondence between nucleic acid or amino acid sequences that may or may not share a common evolutionary origin. However, in common usage and in the instant application, the term "homologous", when modified with an adverb such as "highly", may refer to sequence similarity and may or may not relate to a common evolutionary origin.

For example, any naturally occurring nucleic acid can be modified by any available mutagenesis method to include one or more selector codon. When expressed, this mutagenized nucleic acid encodes a polypeptide comprising one or more non-natural amino acid. The mutation process can, of course, additionally alter one or more standard codon, thereby changing one or more standard amino acid in the resulting mutant protein as well. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity is routinely used to establish homology. Higher levels of sequence similarity, e.g., 30%, 40%, 50%, 60%, 70%, 80%, 90%, 95% or 99% or more can also be used to establish homology. If one or more particular amino acid or nucleic acid positions exhibit higher levels of sequence similarity than others (among a group of similar sequence(s) selected from different sources) then the positions with higher sequence similarity are considered "highly conserved." Typically, but not always, the highly conserved regions of a nucleic acid or amino acid sequence play an important role in the structure and/or function of the molecule. Methods for determining sequence similarity percentages (e.g., BLASTP and BLASTN using default parameters) are generally available.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (for example, see Sambrook et al., *Molecular Cloning: A Laboratory Manual*, Second Edition (1989) Cold Spring Harbor Laboratory Press, Cold Spring Harbor, N.Y., hereby incorporated by reference). The conditions of temperature and ionic strength determine the "stringency" of the hybridization. For preliminary screening for homologous nucleic acids, low stringency hybridization conditions, corresponding to a $T_m$ (melting temperature) of 55° C., can be used, (e.g., 5×SSC, 0.1% SDS, 0.25% milk, and no formamide; or 30% formamide, 5×SSC, 0.5% SDS). Moderate stringency hybridization conditions correspond to a higher $T_m$ (e.g., 40% formamide, with 5× or 6×SSC). High stringency hybridization conditions correspond to the highest $T_m$ (e.g., 50% formamide, 5× or 6×SSC. SSC is a 0.15M NaCl, 0.015M Na-citrate).

Hybridization requires that the two nucleic acids contain complementary sequences, although depending on the stringency of the hybridization mismatches between bases are possible. The appropriate stringency for hybridizing nucleic acids depends on the length of the nucleic acids and the degree of complementation, variables well known in the art. Thus, the greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50-9.51, hereby incorporated by reference). For hybridization with shorter nucleic acids, i.e., oligonucleotides, the position of mismatches becomes more important, and the length of the oligonucleotide determines its specificity (see Sambrook et al., supra, 11.7-11.8, hereby incorporated by reference). A minimum length for a hybridizable nucleic acid is at least about 10 nucleotides; preferably at least about 15 nucleotides; and more preferably the length is at least about 20 nucleotides.

Unless specified, the term "standard hybridization conditions" refers to a $T_m$ of about 55° C., and utilizes conditions as set forth above. In at least one embodiment, the $T_m$ is 60° C.; in at least one embodiment, the $T_m$ is 65° C. In a specific embodiment, "high stringency" refers to hybridization and/or washing conditions at 68° C. in 0.2×SSC, at 42° C. in 50% formamide, 4×SSC, or under conditions that afford levels of hybridization equivalent to those observed under either of these two conditions.

Suitable hybridization conditions for oligonucleotides (e.g., for oligonucleotide probes or primers) are typically somewhat different than for full-length nucleic acids (e.g., full-length cDNA), because of the oligonucleotides' lower melting temperature. Because the melting temperature of oligonucleotides will depend on the length of the oligonucleotide sequences involved, suitable hybridization temperatures will vary depending upon the oligonucleotide molecules used. Exemplary temperatures may be 37° C. (for 14-base oligonucleotides), 48° C. (for 17-base oligonucleotides), 55° C. (for 20-base oligonucleotides) and 60° C. (for 23-base oligonucleotides). Exemplary suitable hybridization conditions for oligonucleotides include washing in 6×SSC/0.05% sodium pyrophosphate, or other conditions that afford equivalent levels of hybridization.

"Target molecule" used herein generally refers to a chemical or biological entity which is capable of performing a chemical or biological function or activity. "Target molecule" encompasses nucleic acids (DNA, RNA, etc.), proteins, polypeptides, peptides, biopolymers, carbohydrates, glycoproteins, glycolipids, lipids and the like and any combination thereof. The methods of the present invention include modifying a single target molecule or multiple target molecules. If multiple target molecules are modified, they may be modified sequentially, simultaneously or otherwise. Furthermore, the chemical or biological function or activity herein referred to may include functions or activities similar to the corresponding native (wild type) target molecule(s) or it may include other functions, such as, for example, inhibiting the corresponding native (wild type) target molecule(s) or another target molecule, increasing or decreasing the function of the corresponding native (wild type) target molecule(s) or another target molecule, or otherwise affecting a chemical or biological mileu, cell, tissue, organ or system whether it be in vitro, in vivo, or ex vivo.

"Polypeptide," "peptide" or "protein" are used interchangably to describe a chain of amino acids that are linked together by chemical bonds. A molecule, such as a protein or polypeptide, including an enzyme, may be a "native" or "wild-type", meaning that it occurs in nature; or it may be a "mutant," "variant," "derivative," or "modification," meaning that it has been made, altered, derived, or is in some way different or changed from a native molecule or from another mutant. As used herein, "wild type" amino acid residue denotes the native amino acid residue that naturally occurs in a particular molecule, whereas "naturally occurring" amino acid residue may or may not be a wild type amino acid residue. If used in context together, a "wild type" amino acid residue may be altered to another "naturally occurring" amino acid residue. In such a context, the phrase "naturally occurring" amino acid residue refers to any of the twenty naturally occurring amino acid residues, rather than any non-natural amino acid. Thus, a "wild type" amino acid residue located in a polypeptide, may be altered to another "naturally occurring" amino acid residue different than the wild type amino acid residue, or to a "non-natural" amino acid residue.

It is recognized in the art that polypeptide transcription reads the gene or polynucleotide from the 3'→5' direction, resulting in a polypeptide generated in the 5'→3' direction. As used herein, the first position refers to the amino acid (whether naturally occurring or non-natural) at the 5', (N), or amino terminus of the polypeptide, the second position refers to the amino acid at the second or penultimate position of the polypeptide chain, the third position refers to the next position, and so on toward the 3', (C), or carboxyl terminus. It is further understood that several "proof reading" functions occur by cellular machinery during polypeptide expression (transcription, translation, etc.) that may alter the gene or polynucleotide sequence. Thus, in one embodiment herein, the modified polynucleotide is altered (either by way of substitution or addition) to include one or more non-natural amino acid codons. In certain embodiments, the polynucleotide alterations occur such that when the host cell expresses the polypeptide of interest, at least one non-natural amino acid residue retains the alterations of the gene or polynucleotide. In a preferred embodiment, the non-natural amino acid residue is at the first position (amino terminus) in the polypeptide and is retained during processing. In some embodiments, the efficiency of retention of the non-natural amino acid residue at the first position of the N-terminal of the polypeptide is increased by also altering the penultimate or second position of the polypeptide. The penultimate residue may be altered to another naturally occurring amino acid or to a non-natural amino acid. In preferred embodiments, the side chains of the non-natural amino acids incorporated into the modified polypeptide are unsaturated, thereby reducing side chain reactions or interactions with other amino acids in the polypeptide. In some embodiments, the polypeptide is generated without a host cell (in vitro, in silico, etc.) and non-natural amino acid residues are incorporated during de novo protein synthesis.

A target molecule, such as a protein or polypeptide may also be referred to as "artificial," which term includes a "mutant", "variant", "derivative" or "modification," but further contains at least one non-natural amino acid. As used herein, an "artificial polypeptide" includes, e.g., (a) a polynucleotide comprising a nucleotide sequence encoding an artificial polypeptide of the invention; (b) a polynucleotide that is complementary to or that encodes a polynucleotide sequence of (a); (c) a nucleic acid that hybridizes to a polynucleotide of (a) or (b) under stringent conditions over substantially the entire length of the nucleic acid; (d) a polynucleotide that is at least about 95%, preferably at least about 98% identical to a polynucleotide of (a), (b), or (c); and (e) a polynucleotide comprising a conservative variation of (a), (b), (c) or (d).

"Biopolymer" as used herein, refers to any natural or artificial biological or chemical molecule, such as a protein, lipid or carbohydrate that possesses additional polymeric characteristics or modifications. A biopolymer may refer to a glycosylated or pegylated, myristylated, deamidated, or otherwise modified molecule for which a polymer has been joined, conjugated or intermixed.

"Rotamer" refers to a set of possible conformers for each amino acid or analog side chain. See, for example Ponder, et al., *Acad. Press Inc.* (London) Ltd. pp. 775-791 (1987); Dunbrack, et al., *Struc. Biol.* 1(5):334-340 (1994); Desmet, et al., *Nature* 356:539-542 (1992), all of which are hereby incorporated by reference in their entireties.

A "rotamer library" is a collection of a set of possible/allowable rotametic conformations for a given set of amino acids or analogs. There are two general types of rotamer libraries: "backbone dependent" and "backbone independent." A backbone dependent rotamer library allows different rotamers depending on the position of the residue in the backbone; thus for example, certain leucine rotamers are allowed if the position is within an α helix, and different leucine rotamers are allowed if the position is not in an α-helix. A backbone independent rotamer library utilizes all rotamers of an amino acid at every position. In general, a backbone independent library is preferred in the consideration of core residues, since flexibility in the core is important. However, backbone independent libraries are computationally more expensive, and thus for surface and boundary positions, a backbone dependent library is preferred. However, either type of library can be used at any position.

"Variable residue position" herein refers to an amino acid position of the protein to be designed that is not fixed in the design method as a specific residue or rotamer, generally the wild-type residue or rotamer. It should be noted that even if a position is chosen as a variable position, it is possible that the methods of the invention will optimize the sequence in such a way as to select the wild type residue at the variable position. This generally occurs more frequently for core residues, and less regularly for surface residues. In addition, it is possible to fix residues as non-wild type amino acids as well.

"Fixed residue position" generally refers to the residue identified in the three dimensional structure as being in a set conformation. In some embodiments, a fixed position is left in its original conformation (which may or may not correlate to a specific rotamer of the rotamer library being used). Alternatively, residues may be fixed as a non-wild type residue depending on design needs; for example, when known site-directed mutagenesis techniques have shown that a particular residue is desirable, the residue may be fixed as a particular amino acid. Residues which can be fixed include, but are not limited to, structurally or biologically functional residues.

In certain embodiments, a fixed position may be "floated"; the amino acid or analog at that position is fixed, but different rotamers of that amino acid or analog are tested. In this embodiment, the variable residues may be at least one, or anywhere from 0.1% to 99.9% of the total number of residues. Thus, for example, it may be possible to change only a few (or one) residues, or most of the residues, with all possibilities in between.

As used herein, the term "mutant tRNA" or "mutant AARS" refers to a tRNA or AARs molecule that has reduced or no interaction or reaction with native amino acids or endogenous unmodified transcriptional or translational machinery, and instead is able to interact or react with non-natural amino acids and/or modified transcriptional or translational machinery, including other tRNA molecules and/or aminoacyl tRNA synthetases. In certain embodiments, the mutant molecule reacts or interacts with other mutant molecules and/or non-natural amino acids at a much greater efficiency than with naturally occurring amino acids or molecules. In certain embodiments, the mutant molecule reacts or interacts preferentially, and in certain embodiments, almost exclusively, with other mutant molecules and/or non-natural amino acids. For example, a mutant tRNA (M-tRNA) and/or a mutant aminoacyl tRNA synthetase (M-RS) may be used with reduced efficiency (as compared to wild-type or endogenous tRNA and/or AARS) by a system of interest (e.g., a translational system, e.g., a cell). The M-tRNA and/or M-RS may also be referred to as "external mutant," when the molecules are derived from a source other than the host cell in which they are being used for protein translation. In other words, in certain embodiments the M-tRNA and/or M-RS molecules may be heterologous to the translation system.

As used herein, the term "external mutant" refers to a modified molecule (e.g., an external mutant tRNA and/or an external mutant aminoacyl tRNA synthetase) that exhibits a reduced efficiency (as compared to wild-type or endogenous) for aminoacylation with the corresponding wild type amino acid. "External mutant" refers to the inability or reduced efficiency, e.g., less than 20% efficient, less than 10% efficient, less than 5% efficient, or, e.g., less than 1% efficient, of a tRNA and/or RS to function with the corresponding naturally occurring amino acid in the translation system of interest. For example, an external mutant RS in a translation system of interest aminoacylates any endogenous tRNA of a translation system of interest with the wild type amino acid at reduced or even zero efficiency, when compared to aminoacylation of an endogenous tRNA by the endogenous RS.

It should be noted, however, that an external mutant RS aminoacylates an endogenous tRNA with a replacement amino acid (whether naturally occurring or non-natural) with an increased efficiency compared with the ability of the endogenous RS to aminoacylate an endogenous tRNA with a replacement amino acid. Likewise, an external mutant tRNA functions at a higher efficiency toward the replacement amino acid codon (whether the replacement amino acid comprises a non-natural or other naturally occurring amino acid) than toward the corresponding wild type amino acid. Furthermore, an external mutant tRNA may function at an equal or higher efficiency for a particular replacement amino acid codon (whether the replacement amino acid comprises a non-natural or other naturally occurring amino acid) than an endogenous tRNA.

A mutant tRNA and/or mutant AARS that reacts with a reduced efficiency refers to the inability to react with, or reduced efficiency to interact or react with, native amino acid residues, e.g., less than 20% efficient, less than 10% efficient, less than 5% efficient, or e.g., less than 1% efficient.

In addition, "exogenous" tRNA and/or AARS molecules may be utilized in certain embodiments disclosed herein. In some embodiments, "exogenous" refers to a tRNA and/or AARS molecule that is derived from another organism and may be wild type or mutant. Thus, an exogenous tRNA or exogenous AARS may also be an external mutant tRNA, or external mutant AARS, respectively.

"Wobble degenerate codon," as used herein, refers to a codon encoding a naturally occurring amino acid, which codon, when present in mRNA, is recognized by a natural tRNA anticodon through at least one non-Watson-Crick, or wobble base-pairing (e.g., A-C or G-U base-pairing). Watson-Crick base-pairing refers to either the G-C or A-U (RNA or DNA/RNA hybrid) or A-T (DNA) base-pairing. When used in the context of mRNA codon—tRNA anticodon base-pairing, Watson-Crick base-pairing means all codon-anticodon base-pairings are mediated through either G-C or A-U. "Wobble decoding," then, generally refers to the ability of a particular tRNA to read through non-Watson-Crick base pairing.

"Bias codon," as used herein, refers to a degenerate codon that encodes a naturally occurring amino acid, which codon is one that is used by a tRNA ("bias codon tRNA") which bias codon tRNA is present in a particular host cell at a lower concentration relative to other tRNA molecules used for the same naturally occurring amino acid. In certain embodiments, the lower frequency of the bias codon tRNA may be the result of modification of the host cell in order to reduce the level or availability of the bias codon tRNA in the cell. This may be accomplished, for example, by way of deletion or inactivation of the specific bias codon tRNA gene(s) from the genome of the host cell. In certain embodiments, the bias codon tRNA is present at a frequency of less than about 25%, less than about 15%, less than about 10%, less than about 8%, less than about 5%, less than about 4%, less than about 3%, less than about 2%, less than about 1%, less than about 0.5%, less than about 0.4%, less than about 0.3%, less than about 0.2%, less than about 0.1%, less than about 0.05%, less than about 0.01%, or less than the frequency of the most common tRNA that is utilized for the same codon in the translation system.

"Sixth box codon," as used herein, refers to any one of six codons that encode the same naturally occurring or non-natural amino acid (including but not limited to arginine, leucine, or serine). For embodiments in which a sixth box codon specifies a non-natural amino acid, the sixth box codon is not recognized by at least one tRNA that decodes the other five codons encoding the same amino acid residue. This lack of recognition by the sixth box codon tRNA allows the sixth box codon to specify a position for incorporation of the non-natural amino acid that corresponds to the naturally occurring amino acid. In this case, the naturally occurring amino acid is able to incorporate in the target molecule at other positions in the same target molecule sicne it is encoded by codons that are not recognized by the sixth box codon tRNA. Examples of sixth box codons include the CGA, AGG and AGA codons for arginine, or CTA for leucine. Other degenerate codons are listed in the tables entitled, "The Genetic Code," and "The Degenerate Codons for *E. coli*" inter alia herein.

Similar to the sixth box codon is a two or four box degenerate codon for which there is a tRNA that will not wobble decode another of the degenerate codons for the same amino acid.

In still other embodiments of the present invention, artificial anticodons may be created to form Watson-Crick base pairing with wobble codons. One of skill in the art would understand that an anticodon generally refers to the nucleotide sequence (typically 3 nucleotides in length but may be 2, 3, 4, 5 nucleotides in length, or other size) that is complementary (either by Watson-Crick base pairing or wobble pairing) to the nucleotide codon present on the corresponding messenger RNA molecule. During protein translation, the anticodon on the tRNA molecule is matched to a specific amino acid that is then covalently attached to the tRNA. In certain embodiments, the anticodon matches a corresponding codon that comprises a stop codon, including a nonsense codon or missense codon. In this way, altering the anticodon may allow for specific incorporation of a non-natural amino acid in to a target molecule. An artificial anticodon, then, may be any codon that has been altered (at the nucleic acid level or amino acid level) to allow for incorporation of an amino acid (whether naturally occurring amino acid or non-natural amino acid) into a target molecule.

"Borrowed codon," as used herein, generally refers to a codon for a first naturally occurring amino acid or non-natural amino acid that is recognized by an endogenous or exogenous tRNA or M-tRNA that is capable of being aminoacylated by the corresponding AARS of the first amino acid, but which is actually aminoacylated by a chimeric M-RS. A "chimeric M-RS" refers to an AARS which contains the structures from the AARS of the first amino acid that bind to tRNA identity elements, combined with the amino acid binding domain from an AARS for a second amino acid such that the second amino acid is incorporated in the target molecule at the borrowed codon site. In certain embodiments, the chimeric M-RS may be modified to bind a non-natural amino acid, such that the non-natural amino acid is incorporated at the borrowed codon site. The borrowed codon may include codons that may be decoded by naturally occurring or artificial anticodons. In certain embodiments wherein an artificial anticodon is utilized, the anticodon may be created to form Watson-Crick base pairing with wobble codons for a particular amino acid.

The term "preferentially aminoacylates" refers to an efficiency, e.g., about 20%, about 30%, about 40%, about 50%, about 60%, about 70%, about 75%, about 85%, about 90%, about 95%, about 99% or more efficient. The efficiency may be measured by which a modified or external mutant aminoacyl tRNA synthetase aminoacylates a tRNA with a replacement amino acid, whether an unnatural amino acid or another naturally occurring amino acid when compared to the corresponding natural amino acid assigned to the particular tRNA, AARS, or both.

The term "preferentially aminoacylates" further may refer to the efficiency of the modified or external mutant aminoacyl tRNA synthetase to aminoacylate or charge a tRNA with any amino acid other than the corresponding natural amino acid assigned to the particular tRNA, AARS, or both. The term "preferentially aminoacylates" further may refer to the efficiency of the modified or external mutant aminoacyl tRNA synthetase to aminoacylate a tRNA with a non-natural amino acid compared with the non-modified or naturally occurring AARS. In certain embodiments, "preferentially aminoacylates" further relates to the efficiency as measured by the kinetics in which a modified or external mutant AARS aminoacylates a tRNA with another amino acid (as described by Km, kcat, kcat/Km, or ATP-PPi exchange rate).

It should be noted that the efficiency of aminoacylation of the tRNA by the AARS may be correlated to the efficiency of specificity, or fidelity of incorporation of the non-natural amino acid in the target polypeptide or protein. This is due to the function of the protein synthesis machinery in that once a tRNA is aminoacylated with an amino acid (whether the wild type amino acid, or a non-natural amino acid), the charged tRNA is released from the AARS enzyme and the amino acid is incorporated into the target polypeptide. When the proofreading ability of the AARS is altered, the enzyme will allow the replacement amino acid to charge the tRNA and be released for incorporation into the target protein. Thus, the efficiency of aminoacylation by the AARS directly correlates to the fidelity or specificity of incorporation of the non-natural amino acid into the target polypeptide.

The replacement (whether non-natural or naturally occurring) amino acid is then incorporated into a growing polypeptide chain with high fidelity, e.g., at greater than about 20%, 30%, 40%, 50%, 60%, 75%, 80%, 90%, 95%, or greater than about 99% efficiency for a particular codon.

The modified AARS may be altered such that the binding efficiency to the non-natural amino acid, or another selected naturally occurring amino acid, is greater than the binding efficiency of the modified AARS to the corresponding naturally occurring amino acid. In this way, a modified AARS may preferentially bind a non-natural amino acid in order to charge a tRNA even in the presence of the naturally occurring amino acid that corresponds to the AARS in its unmodified state. This "reprogramming" of an aminoacyl tRNA synthetase allows for incorporation of a non-natural amino acid into a polypeptide with lower levels of misincorporation of other amino acids into the desired site.

The "reprogramming" further may allow for use of the modified or external mutant synthetase with high levels of incorporation in standard host cells, without the need for auxotrophic host cells, and with or without depleting the media of the corresponding naturally occurring amino acid. Thus, while certain embodiments disclosed herein may be practiced by using an auxotrophic host cell, certain other embodiments may be practiced without using an auxotrophic host cell. In the event of not using an auxotrophic host cell to practice certain embodiments, another host cell may be used, cellular components may be used, or an entirely cell-free system may be used.

The term "complementary" refers to components of an external mutant pair, the external mutant tRNA and external mutant synthetase that can function together, e.g., the external mutant synthetase aminoacylates the external mutant tRNA.

The term "derived from" refers to a component that is isolated from an organism or isolated and modified, or generated, e.g., chemically synthesized, using information of the component from the organism.

The term "translation system" refers to the components necessary to incorporate a naturally occurring or non-natural amino acid into a growing polypeptide chain (protein). For example, components can include ribosomes, tRNA(s), synthetase(s), mRNA and the like. The components disclosed herein can be added to a translation system, in vivo or in vitro. An in vivo translation system may be a cell (eukaryotic or prokaryotic cell). An in vitro translation system may be a cell-free system, such as a reconstituted one with components from different organisms (purified or recombinantly produced). In certain embodiments, the translation system does not comprise a cell. In certain embodiments, the translation system does not comprise an auxotrophic cell. If the translation system does not comprise an auxotrophic cell, it may comprise another cell or cellular components.

The term "inactive RS" refers to a synthetase that has been mutated so that it no longer can aminoacylate its cognate tRNA with any amino acid, whether naturally occurring or non-natural. The term "modified RS" refers to a synthetase that has been mutated such that it no longer can aminoacylate its cognate tRNA with the corresponding naturally occurring amino acid, but may be able to aminoacylate its cognate tRNA with another amino acid, preferably a non-natural amino acid.

The term "not efficiently recognized" refers to an efficiency, e.g., less than about 10%, less than about 5%, or less than about 1%, at which a RS from one organism aminoacylates an external mutant tRNA. In certain embodiments, the RS may be from the same or a different organism than the external mutant tRNA. In some embodiments, the RS has been modified to aminoacylate a tRNA with a particular amino acid, preferably a non-natural amino acid.

The term "selection agent" refers to an agent that when present allows for a selection of certain components from a population, e.g., an antibiotic, wavelength of light, an antibody, a nutrient or the like. The selection agent can be varied, e.g., such as concentration, intensity, etc.

The term "positive selection marker" refers to a marker than when present, e.g., expressed, activated or the like, results in identification of an organism with the positive selection marker from those without the positive selection marker.

The term "negative selection marker" refers to a marker than when present, e.g., expressed, activated or the like, allows identification of an organism that does not possess the desired property (e.g., as compared to an organism which does possess the desired property).

The term "reporter" refers to a component that can be used to select components described in the present invention. For example, a reporter can include a green fluorescent protein, a firefly luciferase protein, or genes such as (β-gal/lacZ (β-galactosidase), Adh (alcohol dehydrogenase) or the like.

The term "eukaryote" refers to organisms belonging to the phylogenetic domain Eucarya such as animals (e.g., mammals, insects, reptiles, birds, etc.), ciliates, plants, fungi (e.g., yeasts, etc.), flagellates, microsporidia, protists, etc. Additionally, the term "prokaryote" refers to non-eukaryotic organisms belonging to the Eubacteria (e.g., *Escherichia coli, Thermus thermophilus*, etc.) and Archaea (e.g., *Methanococcus jannaschii, Methanobacterium thermoautotrophicum, Halobacterium* such as *Haloferax volcanii* and *Halobacterium* species NRC-1, *A. fulgidus, P. firiosus, P. horikoshii, A. pernix*, etc.) phylogenetic domains.

The term "pharmaceutical" or "pharmaceutical drug," as used herein refers to any pharmacological, therapeutic or active biological agent that may be administered to a subject. In certain embodiments the subject is an animal, including a vertebrate, and preferably a mammal, most preferably a human. In certain embodiments the animal is a vertebrate. In certain embodiments the animal is a mammal. In certain embodiments the animal is a human.

The term "pharmaceutically acceptable carrier," as used herein, refers generally to any material that may accompany the pharmaceutical drug but which does not interfere with the activity of the pharmaceutical drug and which does not cause an adverse reaction with the subject's immune system.

As used herein, the term "administering," refers to any mode of transferring, delivering, introducing or transporting a pharmaceutical drug or other agent to a subject. Such modes include oral administration, topical contact, intravenous, intraperitoneal, intramuscular, intralesional, intranasal, subcutaneous or intrathecal administration. Also contemplated by the present invention is utilization of a device or instrument in administering an agent. Such device may utilize active or passive transport and may be slow-release or fast-release delivery device.

As used herein, the term "saccharide moiety" refers to natural and non-natural sugar moieties (i.e., a non-naturally occurring sugar moiety, e.g., a sugar moiety that is modified, e.g., at one or more hydroxyl or amino positions, e.g., dehydroxylated, deaminated, esterified, etc., e.g., 2-deoxy-Gal is an example of an non-natural sugar moiety).

The term "carbohydrate" has the general formula $(CH_2O)_n$, and includes, but is not limited to, e.g., monosaccharides, disaccharides, oligosaccharides and polysaccharides. Oligosaccharides are chains composed of saccharide units, which are alternatively known as sugars. Saccharide units can be arranged in any order and the linkage between two saccharide units can occur in any of approximately ten different ways. The following abbreviations are used herein: Ara=arabinosyl; Fru=fructosyl; Fuc=fucosyl; Gal=galactosyl; GalNAc=N-acetylgalactosaminyl; Glc=glucosyl; GlcNAc=N-acetylglucosaminyl, Man=mannosyl; and NeuAc=sialyl (typically N-acetylneuraminyl).

Oligosaccharides are considered to have a reducing end and a non-reducing end, whether or not the saccharide at the reducing end is in fact a reducing sugar. In accordance with accepted nomenclature, oligosaccharides are depicted herein with the non-reducing end on the left and the reducing end on the right. All oligosaccharides described herein are described with the name or abbreviation for the non-reducing saccharide (e.g., Gal), followed by the configuration of the glycosidic bond (α or β), the ring bond, the ring position of the reducing saccharide involved in the bond, and then the name or abbreviation of the reducing saccharide (e.g., GlcNAc). The linkage between two sugars may be expressed, for example, as 2, 3; 2→3; 2-3; or (2,3). Natural and non-natural linkages (e.g., 1-2; 1-3; 1-4; 1-6; 2-3; 2-4; 2-6; etc.) between two sugars are included in the invention. Each saccharide is a pyranose.

The term "sialic acid" (abbreviated "Sia") refers to any member of a family of nine-carbon carboxylated sugars. The most common member of the sialic acid family is N-acetyl-neuraminic acid (2-keto-5-acetamindo-3,5-dideoxy-D-glycero-D-galactononulopyranos-1-onic acid) (often abbreviated as Neu5Ac, NeuAc, or NANA). A second member of the family is N-glycolyl-neuraminic acid (Neu5Gc or NeuGc), in which the N-acetyl group of NeuAc is hydroxylated. A third sialic acid family member is 2-keto-3-deoxy-nonulosonic acid (KDN) (Nadano et al., J. Biol. Chem. 261: 11550-11557, 1986; Kanamori et al., J. Biol. Chem. 265: 21811-21819, 1990). Also included are 9-substituted sialic acids such as a 9-O—C1-C6 acyl-Neu5Ac like 9-O-lactyl-Neu5Ac or 9-O-acetyl-Neu5Ac, 9-deoxy-9-fluoro-Neu5Ac and 9-azido-9-deoxy-Neu5Ac. For review of the sialic acid family, see, e.g., Varki, Glycobiology 2: 25-40, 1992; Sialic Acids: Chemistry, Metabolism and Function, R. Schauer, Ed. (Springer-Verlag, New York (1992)). The synthesis and use of sialic acid compounds in a sialylation procedure is described in, for example, international application WO 92/16640 (entire contents incorporated herein by reference).

Donor substrates for glycosyl transferases are activated nucleotide sugars. Such activated sugars generally consist of uridine and guanosine diphosphate, and cytidine monophosphate, derivatives of the sugars in which the nucleoside diphosphate or monophosphate serves as a leaving group. Bacterial, plant, and fungal systems can sometimes use other activated nucleotide sugars.

The Genetic Code and the Degenerate Codons

The standard genetic code most cells use is listed below.

The Genetic Code

Middle

| First | U | C | A | G | Last |
|-------|---|---|---|---|------|
|   | Phe | Ser | Tyr | Cys | U |
|   | Phe | Ser | Tyr | Cys | C |
| U | Leu | Ser | Stop |   |   |
| (Ochre) | Stop |   |   |   | A |
| (Umber) |   |   |   |   |   |
|   | Leu | Ser | Stop |   |   |
| (Amber) | Trp | G |   |   |   |
|   | Leu | Pro | His | Arg | U |
|   | Leu | Pro | His | Arg | C |
| C | Leu | Pro | Gln | Arg | A |
|   | Leu | Pro | Gln | Arg | G |
|   | Ile | Thr | Asn | Ser | U |
|   | Ile | Thr | Asn | Ser | C |
| A | Ile | Thr | Lys | Arg | A |
|   | Met | Thr | Lys | Arg | G |
|   | Val | Ala | Asp | Gly | U |
|   | Val | Ala | Asp | Gly | C |
| G | Val | Ala | Glu | Gly | A |
|   | Val | Ala | Glu | Gly | G |

The genetic code is degenerate, in that the protein biosynthetic machinery utilizes 61 mRNA sense codons to direct the templated polymerization of the 20 natural amino acid monomers. (See, for example, Crick et al., Nature 192: 1227, 1961, hereby incorporated by reference). Two amino acids (methionine and tryptophan), are encoded by unique mRNA triplets.

The standard genetic code applies to most, but not all, cases. Exceptions have been found in the mitochondrial DNA of many organisms and in the nuclear DNA of a few lower organisms. Some examples are given in the following table.

Examples of Non-Standard Genetic Codes

| Mitochondria | Vertebrates | UGA→ Trp; AGA, AGG → STOP |
|---|---|---|
|   | Invertebrates | UGA→ Trp; AGA, AGG → Ser |
|   | Yeasts | UGA→ Trp; CUN → Thr |
|   | Protista | UGA→ Trp; |
| Nucleus | Bacteria | GUG, UUG, AUU, CUG → initiation |
|   | Yeasts | CUG → Ser |
|   | Ciliates | UAA, UAG → Gln |

*Plant cells use the standard genetic code in both mitochondria and the nucleus.

The NCBI (National Center for Biotechnology Information) maintains a detailed list of the standard genetic code, and genetic codes used in various organisms, including the vertebrate mitochondrial code; the yeast mitochondrial code; the mold, protozoan, and coelenterate mitochondrial code and the mycoplasma/spiroplasma code; the invertebrate mitochondrial code; the ciliate, dasycladacean and hexamita nuclear code; the echinoderm and flatworm mitochondrial code; the euplotid nuclear code; the bacterial and plant plastid code; the alternative yeast nuclear code; the ascidian mitochondrial code; the alternative flatworm mitochondrial code; blepharisma nuclear code; chlorophycean mitochondrial code; trematode mitochondrial code; scenedesmus obliquus mitochondrial code; thraustochytrium mitochondrial code (all incorporated herein by reference). These are primarily based on the reviews by Osawa et al., Microbial. Rev. 56: 229-264, 1992, and Jukes and Osawa, Comp. Biochem. Physiol. 106B: 489-494, 1993, all hereby incorporated by reference in their entireties.

Degenerate Codon Selection

As described above, all amino acids, with the exception of methionine and tryptophan are encoded by more than one codon. According to the methods of the invention, a codon that is normally used to encode a natural amino acid is reprogrammed to encode an amino acid analog. An amino acid analog can be a naturally occurring or canonical amino acid analog. In a preferred embodiment, the amino acid analog is not a canonically encoded amino acid.

The following table lists some of the known anti-codon sequences for E. coli. In general, for any organism, tRNA anticodon sequence can be routinely determined using art-recognized technologies. For example, any tRNA gene can be amplified by, for example, PCR. Sequencing can be performed to determine the exact sequences of the anti-codon loop. Alternatively, biochemical binding assay may be used to determine the binding affinity of a purified tRNA to one of the 2-6 possible codons. The codon that binds the tRNA with the highest specificity/affinity presumably has pure Watson-Crick match at all three codon positions, thus determining the sequence of the anti-codon loop.

In general, the wobble base in the anti-codon loop tends to be G or U (rather than A or C), but is not limited to such.

The Degenerate Codons for E. coli

| Amino Acid | Anti-codon | Base-paring at 3rd base | Codon | Amino Acid | Anti-codon | Base-paring | Codon |
|---|---|---|---|---|---|---|---|
| Ala | GGC | W/C[1] | GCC | His | GUG | W/C | CAC |
|  |  | Wobble[2] | GCU |  |  | Wobble | CAU |
|  | UGC | W/C | GCA | Ile | GAU | W/C | AUC |
|  |  | Wobble | GCG |  |  | Wobble | AUU, AUA |
| Asp | GUC | W/C | GAC | Leu | GAG | W/C | CUC, CUA, CUG, UUC, UUG |
|  |  | Wobble | GAU |  |  | Wobble | CUU |
| Asn | GUU | W/C | AAC | Lys | UUU | W/C | AAA |
|  |  | Wobble | AAU |  |  | Wobble | AAG |
| Cys | GCA | W/C | UGC | Phe | GAA | W/C | UUC |
|  |  | Wobble | UGU |  |  | Wobble | UUU |
| Glu | UUC | W/C | GAA | Ser | GGA | W/C | UUC, AGU |
|  |  | Wobble | GAG |  |  | Wobble | UCU, AGC, UCA, UCG |
| Gly | GCC | W/C | GGC, GGA, GGG | Tyr | GUA | W/C | UAC |
|  |  | Wobble | GGU |  |  | Wobble | UAU |
| Met |  | W/C | AUG | Thr |  | W/C | ACC, ACA, ACG |
| Gln |  | W/C | CAA, CAG |  |  | Wobble | ACU |
| Arg | W/C | AGA, AGG, CGU, CGG | Pro |  |  | W/C | CCC, CCA, CCG |
|  |  | Wobble | CGC, CGA | Trp |  | Wobble | CCU |
|  |  |  |  |  |  | W/C | UGG |
| STOP | W/C | UGA, UAA | Val |  |  | W/C | GUC, GUA |
|  |  | Wobble | UAG |  |  | Wobble | GUU, GUG |

[1]Watson-Crick base pairing
[2]Wobble base pairing

When the cell has a single tRNA that recognizes a codon through a perfect complementary interaction between the anticodon of the tRNA and one codon, and recognizes a second, degenerate codon through a wobble or other non-standard base pairing interaction, a new tRNA can be constructed having an anticodon sequence that is perfectly complementary to the degenerate codon.

When the cell has multiple tRNA molecules for a particular amino acid, and one tRNA has an anticodon sequence that is perfectly complementary to the degenerate codon selected, the gene encoding the tRNA can be disabled through any means available to one of skill in the art. Such exemplary means include chemical mutagenesis, DNA shuffling or gene shuffling (including genetic recombination), randomized genetic mutagenesis, site-directed mutagenesis or deletion of either the gene or the promoter sequence of the gene. Expression of the gene also can be disabled through any antisense or RNA interference techniques.

The deletion or disablement of a tRNA will result in the disablement of the corresponding codon which may be fatal to the host cell. In order to rescue the host cell, such tRNA disablement may be accompanied by the introduction of a tRNA gene whose expression is regulated. The regulation of the tRNA expression may be accomplished by using a repressible promoter (such as copper ion inducible and repressible promoter systems in yeast). See, for example, Meth. Enzymol. 306: 145-153 (1999), hereby incorporated by reference in its entirety. The regulated tRNA will function to support host cell growth before the gene of interest in induced, and the tRNA will be repressed prior to or when the gene of interest is induced in the presence of the non-natural amino acid. The non-natural amino acid is incorporated by an exogenous tRNA or M-tRNA capable of decoding the same codon, but which only functions with its cognate M-RS and in the presence of the non-natural amino acid.

Alternatively, the disablement of the tRNA may be accomplished with an interfering RNA (iRNA), or antisense, expression of both of which may be regulated. In this case, the iRNA or antisense expression may be induced by the same agent (e.g., IPTG) as well as for inducing expression of the target molecule. The addition of the non-natural amino acid will enable the exogenous or M-tRNA and M-RS to use the same codon disabled by deletion or disablement of the endogenous tRNA.

Unnatural or Non-Natural Amino Acids

The first step in the protein engineering process is usually to select a set of non-natural amino acids that have the desired chemical properties. The selection of non-natural amino acids depends on pre-determined chemical properties and the modifications one would like to make in the target molecule or target protein. Non-natural amino acids, once selected, can either be purchased from vendors, or chemically synthesized. Any number of non-natural amino acids may be incorporated into the target molecule and may vary according to the number of desired chemical moieties that are to be attached. The chemical moieties may be attached to all or only some of the non-natural amino acids. Further, the same or different non-natural amino acids may be incorporated into the molecule, depending on the desired outcome. In certain embodiments, at least two different non-natural amino acids are incorporated into the molecule and one chemical moiety, such as PEG, is attached to one of the non-natural amino acid residues, while another chemical moiety, such as a cytotoxic agent, is attached to the other non-natural amino acid.

A wide variety of non-natural amino acids can be used in the methods of the invention. Typically, the non-natural amino acids of the invention are selected or designed to provide additional characteristics unavailable in the twenty natural amino acids. For example, non-natural amino acids are optionally designed or selected to modify the biological properties of a molecule, including a protein, e.g., into which they are incorporated. For example, the following properties are optionally modified by inclusion of an non-natural amino acid into a molecule, such as a protein: toxicity, biodistribution, solubility, stability, e.g., thermal, hydrolytic, oxidative, resistance to enzymatic degradation, and the like, facility of purification and processing, structural properties, spectroscopic properties, chemical and/or photochemical properties, catalytic activity, ability to function as a vaccine, redox potential, half-life, ability to react with other molecules, e.g., covalently or noncovalently, and the like.

As used herein an "non-natural amino acid" refers to any amino acid, modified amino acid, or amino acid analogue other than selenocysteine and the following twenty genetically encoded alpha-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine. The generic structure of an alpha-amino acid is illustrated by Formula I:

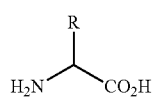

Formula I

An non-natural amino acid is typically any structure having Formula I wherein the R group is any substituent other than one used in the twenty natural amino acids. See, e.g., any biochemistry text such as Biochemistry by L. Stryer, 3rd ed. 1988, Freeman and Company, New York, for structures of the twenty natural amino acids. Note that the non-natural amino acids disclosed herein may be naturally occurring compounds other than the twenty alpha-amino acids above. Because the non-natural amino acids disclosed herein typically differ from the natural amino acids in side chain only, the non-natural amino acids form amide bonds with other amino acids, e.g., natural or non-natural, in the same manner in which they are formed in naturally occurring proteins. However, the non-natural amino acids have side chain groups that distinguish them from the natural amino acids. For example, R in Formula I optionally comprises an alkyl-, aryl-, aryl halide, vinyl halide, alkyl halide, acetyl, ketone, aziridine, nitrile, nitro, halide, acyl-, keto-, azido-, hydroxyl-, hydrazine, cyano-, halo-, hydrazide, alkenyl, alkynyl, ether, thioether, epoxide, sulfone, boronic acid, boronate ester, borane, phenylboronic acid, thiol, seleno-, sulfonyl-, borate, boronate, phospho, phosphono, phosphine, heterocyclic-, pyridyl, naphthyl, benzophenone, a constrained ring such as a cyclooctyne, thioester, enone, imine, aldehyde, ester, thioacid, hydroxylamine, amino, carboxylic acid, alpha-keto carboxylic acid, alpha or beta unsaturated acids and amides, glyoxylamide, or organosilane group, or the like or any combination thereof.

Specific examples of unnatural amino acids include, but are not limited to, p-acetyl-L-phenylalanine, O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAcβ-serine, β-O-GlcNAc-L-serine, a tri-O-acetyl-GalNAc-α-threonine, an α-GalNAc-L-threonine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, an isopropyl-L-phenylalanine, those listed below, or elsewhere herein, and the like.

Aryl substitutions may occur at various positions, e.g. ortho, meta, para, and with one or more functional groups placed on the aryl ring. Other non-natural amino acids of interest include, but are not limited to, amino acids comprising a photoactivatable cross-linker, spin-labeled amino acids, dye-labeled amino acids, fluorescent amino acids, metal binding amino acids, metal-containing amino acids, radioactive amino acids, amino acids with novel functional groups, amino acids with altered hydrophilicity, hydrophobicity, polarity, or ability to hydrogen bond, amino acids that covalently or noncovalently interact with other molecules, photocaged and/or photoisomerizable amino acids, amino acids comprising biotin or a biotin analogue, glycosylated amino acids such as a sugar substituted serine, other carbohydrate modified amino acids, keto containing amino acids, amino acids comprising polyethylene glycol or a polyether, a polyalcohol, or a polysaccharide, amino acids that can undergo metathesis, amino acids that can undergo cycloadditions, heavy atom substituted amino acids, chemically cleavable and/or photocleavable amino acids, amino acids with an elongated side chains as compared to natural amino acids, e.g., polyethers or long chain hydrocarbons, e.g., greater than about 5 or greater than about 10 carbons, carbon-linked sugar-containing amino acids, redox-active amino acids, amino thioacid containing amino acids, amino acids containing a drug moiety, and amino acids comprising one or more toxic moieties.

In addition to non-natural amino acids that contain novel side chains, non-natural amino acids also optionally comprise modified backbone structures, e.g., as illustrated by the structures of Formula II and III:

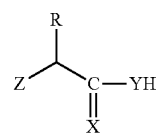

Formula II

Formula III wherein Z typically comprises OH, NH$_2$, SH, NH$_2$O—, NH—R', R'NH—, R'S—, or S—R'—; X and Y, which may be the same or different, typically comprise S, N, or O, and R and R', which are optionally the same or different, are typically selected from the same list of constituents for the R group described above for the non-natural amino acids having Formula I as well as hydrogen or (CH$_2$)$_x$ or the natural amino acid side chains. For example, non-natural amino acids disclosed herein optionally comprise substitutions in the amino or carboxyl group as illustrated by Formulas II and III. Non-natural amino acids of this type include, but are not limited to, α-hydroxy acids, α-thioacids α-aminothiocarboxylates, or α-α-disubstituted amino acids, with side chains corresponding, e.g., to the twenty natural amino acids or to non-natural side chains. They also include but are not limited to β-amino acids or γ-amino acids, such as substituted β-alanine and γ-amino butyric acid. In addition, substitutions or modifications at the α-carbon optionally include L or D isomers, such as D-glutamate, D-alanine, D-methyl-O-tyrosine, aminobutyric acid, and the like. Other structural alternatives include cyclic amino acids, such as proline analogs as well as 3-, 4-, 6-, 7-, 8-, and 9-membered ring proline analogs. Some non-natural amino acids, such as aryl halides (p-bromo-phenylalanine, p-iodophenylalanine, provide versatile palladium catalyzed cross-coupling reactions with ethyne or acetylene reactions that allow for formation of carbon-carbon, carbon-nitrogen and carbon-oxygen bonds between aryl halides and a wide variety of coupling partners.

For example, many non-natural amino acids are based on natural amino acids, such as tyrosine, glutamine, phenylalanine, and the like. Tyrosine analogs include para-substituted tyrosines, ortho-substituted tyrosines, and meta substituted tyrosines, wherein the substituted tyrosine comprises an acetyl group, a benzoyl group, an amino group, a hydrazine, an hydroxyamine, a thiol group, a carboxy group, an isopropyl group, a methyl group, a C6-C20 straight chain or branched hydrocarbon, a saturated or unsaturated hydrocarbon, an O-methyl group, a polyether group, a nitro group, or the like. In addition, multiply substituted aryl rings are also contemplated. Glutamine analogs include, but are not limited to, α-hydroxy derivatives, β-substituted derivatives, cyclic derivatives, and amide substituted glutamine derivatives. Exemplary phenylalanine analogs include, but are not limited to, meta-substituted phenylalanines, wherein the substituent comprises a hydroxy group, a methoxy group, a methyl group, an allyl group, an acetyl group, or the like.

Specific examples of non-natural amino acids include, but are not limited to, o, m and/or p forms of amino acids or amino acid analogs (non-natural amino acids), including homoallylglycine, cis- or trans-crotylglycine, 6,6,6-trifluoro-2-aminohexanoic acid, 2-aminoheptanoic acid, norvaline, norleucine, O-methyl-L-tyrosine, o-, m-, or p-methyl-phenylalanine, O-4-allyl-L-tyrosine, a 4-propyl-L-tyrosine, a tri-O-acetyl-GlcNAcβ-serine, an L-Dopa, a fluorinated phenylalanine, an isopropyl-L-phenylalanine, a p-azidophenylalanine, a p-acyl-L-phenylalanine, a p-benzoyl-L-phenylalanine, an L-phosphoserine, a phosphonoserine, a phosphonotyrosine, a p-iodo-phenylalanine, o-, m-, or p-bromophenylalanine, 2-, 3-, or 4-pyridylalanine, p-idiophenylalanine, diaminobutyric acid, aminobutyric acid, benzofuranylalanine, 3-bromo-tyrosine, 3-(6-chloroindolyl) alanine, 3-(6-bromoindolyl)alanine, 3-(5-bromonindolyl) alanine, p-chlorophenylalanine, p-ethynyl-phenylalanine, p-propargly-oxy-phenylalanine, m-ethynyl-phenylalanine, 6-ethynyl-tryptophan, 5-ethynyl-tryptophan, (R)-2-amino-3-(4-ethynyl-1H-pyrol-3-yl)propanoic acid, azidonorleucine, azidohomoalanine, p-acetylphenylalanine, p-amino-L-phenylalanine, homoproparglyglycine, p-ethyl-phenylalanine, p-ethynyl-phenylalanine, p-propargly-oxy-phenylalanine, isopropyl-L-phenylalanine, an 3-(2-naphthyl)alanine, 3-(1-naphthyl)alanine, 3-idio-tyrosine, O-propargyl-tyrosine, homoglutamine, an O-4-allyl-L-tyrosine, a 4-propyl-L-tyrosine, a 3-nitro-L-tyrosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-acetyl-L-phenylalanine, an m-acetyl-L-phenylalanine, selenomethionine, telluromethionine, selenocysteine, an alkyne phenylalanine, an O-allyl-L-tyrosine, an O-(2-propynyl)-L-tyrosine, a p-ethylthiocarbonyl-L-phenylalanine, a p-(3-oxobutanoyl)-L-phenylalanine, a p-benzoyl-L-phenylalanine, an L-phosphoserine, a phosphonoserine, a phosphonotyrosine, homoproparglyglycine, azidohomoalanine, a p-iodo-phenylalanine, a p-bromo-L-phenylalanine, dihydroxy-phenylalanine, dihydroxyl-L-phenylalanine, a p-nitro-L-phenylalanine, an m-methoxy-L-phenylalanine, a p-iodo-phenylalanine, a p-bromophenylalanine, a p-amino-L-phenylalanine, and an isopropyl-L-phenylalanine, trifluoroleucine, norleucine, 4-, 5-, or 6-fluoro-tryptophan, 4-aminotryptophan, 5-hydroxytryptophan, biocytin, aminooxyacetic acid, m-hydroxyphenylalanine, m-allyl phenylalanine, m-methoxyphenylalanine group, β-GlcNAc-serine, α-GalNAc-threonine, p-acetoacetylphenylalanine, para-halo-phenylalanine, selenomethionine, ethionine, S-nitroso-homocysteine, thia-proline, 3-thienyl-alanine, homoallyl-glycine, trifluoroisoleucine, trans and cis-2-amino-4-hexenoic acid, 2-butynyl-glycine, allyl-glycine, para-azido-phenylalanine, para-cyano-phenylalanine, para-ethynyl-phenylalanine, hexafluoroleucine, 1,2,4-triazole-3-alanine, 2-fluoro-histidine, L-methyl histidine, 3-methyl-L-histidine, β-2-thienyl-L-alanine, β-(2-thiazolyl)-DL-alanine, homoproparglyglycine (HPG) and azidohomoalanine (AHA) and the like. The structures of a variety of non-limiting non-natural amino acids are provided in the figures, e.g., FIGS. 29, 30, and 31 of US 2003/0108885 A1, the entire content of which is incorporated herein by reference.

Tyrosine analogs include para-substituted tyrosines, ortho-substituted tyrosines, and meta substituted tyrosines, wherein the substituted tyrosine comprises an acetyl group, a benzoyl group, an amino group, a hydrazine, an hydroxyamine, a thiol group, a carboxy group, an isopropyl group, a methyl group, a C6-C20 straight chain or branched hydrocarbon, a saturated or unsaturated hydrocarbon, an O-methyl group, a polyether group, a nitro group, or the like. In addition, multiply substituted aryl rings are also contemplated. Glutamine analogs of the invention include, but are not limited to, α-hydroxy derivatives, β-substituted derivatives, cyclic derivatives, and amide substituted glutamine derivatives. Example phenylalanine analogs include, but are not limited to, meta-substituted phenylalanines, wherein the substituent comprises a hydroxy group, a methoxy group, a methyl group, an allyl group, an acetyl group, or the like.

Additionally, other examples optionally include (but are not limited to) an non-natural analog of a tyrosine amino acid; an non-natural analog of a glutamine amino acid; an non-natural analog of a phenylalanine amino acid; an non-natural analog of a serine amino acid; an non-natural analog of a threonine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, phospho, phosphono, phosphine, heterocyclic, enone, imine, aldehyde, hydroxylamine, keto, or amino substituted amino acid, or any combination thereof; an amino acid with a photoactivatable cross-linker; a spin-labeled amino acid; a fluorescent amino acid; an amino acid with a novel functional group; an amino acid that covalently or noncovalently interacts with another molecule; a metal binding amino acid; a metal-containing amino acid; a radioactive amino acid; a photocaged amino acid; a photoisomerizable amino acid; a biotin or biotin-analog containing amino acid; a glycosylated or carbohydrate modified amino acid; a keto containing amino acid; an amino acid comprising polyethylene glycol; an amino acid comprising polyether; a heavy atom substituted amino acid; a chemically cleavable or photocleavable amino acid; an amino acid with an elongated side chain; an amino acid containing a toxic group; a sugar substituted amino acid, e.g., a sugar substituted serine or the like; a carbon-linked sugar-containing amino acid; a redox-active amino acid; an α-hydroxy containing acid; an amino thio acid containing amino acid; an α,α disubstituted amino acid; a β-amino acid; and a cyclic amino acid.

Typically, the non-natural amino acids utilized herein for certain embodiments may be selected or designed to provide additional characteristics unavailable in the twenty natural amino acids. For example, non-natural amino acid are optionally designed or selected to modify the biological properties of a protein, e.g., into which they are incorporated. For example, the following properties are optionally modified by inclusion of an non-natural amino acid into a protein: toxicity, biodistribution, solubility, stability, e.g., thermal, hydrolytic, oxidative, resistance to enzymatic degradation, and the like, facility of purification and processing, structural properties, spectroscopic properties, chemical and/or photochemical properties, catalytic activity, redox potential, half-life, ability to react with other molecules, e.g., covalently or noncovalently, and the like.

Other examples of amino acid analogs optionally include (but are not limited to) an non-natural analog of a tyrosine amino acid; an non-natural analog of a glutamine amino acid; an non-natural analog of a phenylalanine amino acid; an non-natural analog of a serine amino acid; an non-natural analog of a threonine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, phospho, phosphono, phosphine, heterocyclic, enone, imine, aldehyde, hydroxylamine, keto, or amino substituted amino acid, or any combination thereof; an amino acid with a photoactivatable cross-linker; a spin-labeled amino acid; a fluorescent amino acid; an amino acid with a novel functional group; an amino acid that covalently or noncovalently interacts with another molecule; a metal binding amino acid; a metal-containing amino acid; a radioactive amino acid; a photocaged amino acid; a photoisomerizable amino acid; a biotin or biotin-analogue containing amino acid; a glycosylated or carbohydrate modified amino acid; a keto containing amino acid; an amino acid comprising polyethylene glycol; an amino acid comprising polyether; a heavy atom substituted amino acid; a chemically cleavable or photocleavable amino acid; an amino acid with an elongated side chain; an amino acid containing a toxic group; a sugar substituted amino acid, e.g., a sugar substituted serine or the like; a carbon-linked sugar-containing amino acid; a redox-active amino acid; an α-hydroxy containing acid; an amino thio acid containing amino acid; an α,α disubstituted amino acid; a β-amino acid; and a cyclic amino acid other than proline.

Non-natural amino acids suitable for use in the methods of the invention also include those that have a saccharide moiety attached to the amino acid side chain. In one embodiment, an non-natural amino acid with a saccharide moiety includes a serine or threonine amino acid with a Man, GalNAc, Glc, Fuc, or Gal moiety. Examples of non-natural amino acids that include a saccharide moiety include, but are not limited to, e.g., a tri-O-acetyl-GlcNAcβ-serine, a β-O-GlcNAc-L-serine, a tri-O-acetyl-GalNAc-α-threonine, an α-GalNAc-L-threonine, an O-Man-L-serine, a tetra-acetyl-O-Man-L-serine, an O-GalNAc-L-serine, a tri-acetyl-O-GalNAc-L-serine, a Glc-L-serine, a tetraacetyl-Glc-L-serine, a fuc-L-serine, a tri-acetyl-fuc-L-serine, an O-Gal-L-serine, a tetra-acetyl-O-Gal-L-serine, a β-O-GlcNAc-L-threonine, a tri-acetyl-β-GlcNAc-L-threonine, an O-Man-L-threonine, a tetra-acetyl-O-Man-L-threonine, an O-GalNAc-L-threonine, a tri-acetyl-O-GalNAc-L-threonine, a Glc-L-threonine, a tetraacetyl-Glc-L-threonine, a fuc-L-threonine, a tri-acetyl-fuc-L-threonine, an O-Gal-L-threonine, a tetra-acetyl-O-Gal-L-serine, a β-N-acetylglucosamine-O-serine, α-N-acetylgalactosamine-O-threonine, fluorescent amino acids such as those containing naphthyl or dansyl or 7-aminocoumarin or 7-hydroxycoumarin side chains, photocleavable or photoisomerizable amino acids such as those containing azobenzene or nitrobenzyl Cys, Ser or Tyr side chains, p-carboxy-methyl-L-phenylalanine, homoglutamine, 2-aminooctanoic acid, p-azidophenylalanine, p-benzoylphenylalanine, p-acetylphenylalanine, m-acetylphenylalanine, 2,4-diaminobutyric acid (DAB) and the like. The invention includes unprotected and acetylated forms of the above. (See also, for example, WO 03/031464 A2, entitled "Remodeling and Glycoconjugation of Peptides"; and, U.S. Pat. No. 6,331,418, entitled "Saccharide Compositions, Methods and Apparatus for their synthesis;" Tang and Tirrell, *J. Am. Chem. Soc.* (2001) 123: 11089-11090; and Tang et al., *Angew. Chem. Int. Ed.*, (2001) 40:8, all of which are incorporated herein by reference in their entireties).

Many of the non-natural amino acids provided above are commercially available, e.g., from Sigma Aldrich (USA). Those that are not commercially available are optionally synthesized as provided in the examples of US 2004/138106 A1 (incorporated herein by reference) or using standard methods known to those of skill in the art. For organic synthesis techniques, see, e.g., Organic Chemistry by Fessendon and Fessendon, (1982, Second Edition, Willard Grant Press, Boston Mass.); Advanced Organic Chemistry by March (Third Edition, 1985, Wiley and Sons, New York); and Advanced Organic Chemistry by Carey and Sundberg (Third Edition, Parts A and B, 1990, Plenum Press, New York), and WO 02/085923, all of which are hereby incorporated by reference.

For example, meta-substituted phenylalanines are synthesized in a procedure as outlined in WO 02/085923 (see, e.g., FIG. 14 of the publication). Typically, NBS (N-bromosuccinimide) is added to a meta-substituted methylbenzene compound to give a meta-substituted benzyl bromide, which is then reacted with a malonate compound to give the meta substituted phenylalanine. Typical substituents used for the meta position include, but are not limited to, ketones, methoxy groups, alkyls, acetyls, and the like. For example, 3-acetyl-phenylalanine is made by reacting NBS with a solution of 3-methylacetophenone. For more details see the examples below. A similar synthesis is used to produce a 3-methoxy phenylalanine. The R group on the meta position of the benzyl bromide in that case is —OCH$_3$. (See, e.g., Matsoukas et al., *J. Med. Chem.*, 1995, 38, 4660-4669, incorporated by reference in its entirety).

In some embodiments, the design of non-natural amino acids is biased by known information about the active sites of synthetases, e.g., external mutant tRNA synthetases used to aminoacylate an external mutant tRNA. For example, three classes of glutamine analogs are provided, including derivatives substituted at the nitrogen of amide (1), a methyl group at the γ-position (2), and a N-Cγ-cyclic derivative (3). Based upon the x-ray crystal structure of *E. coli* GlnRS, in which the key binding site residues are homologous to yeast GlnRS, the analogs were designed to complement an array of side chain mutations of residues within a 10 Å shell of the side chain of glutamine, e.g., a mutation of the active site Phe233 to a small hydrophobic amino acid might be complemented by increased steric bulk at the Cγ position of Gln.

For example, N-phthaloyl-L-glutamic 1,5-anhydride (compound number 4 in FIG. 23 of WO 02/085923) is optionally used to synthesize glutamine analogs with substituents at the nitrogen of the amide. (See, e.g., King & Kidd, *J. Chem. Soc.*, 3315-3319, 1949; Friedman & Chatterrji, *J. Am. Chem. Soc.* 81, 3750-3752, 1959; Craig et al., *J. Org. Chem.* 53, 1167-1170, 1988; and Azoulay et al., *Eur. J. Med. Chem.* 26, 201-5, 1991, all of which are hereby incorporated by reference in their entireties). The anhydride is typically prepared from glutamic acid by first protection of the amine as the phthalimide followed by refluxing in acetic acid. The anhydride is then opened with a number of amines, resulting in a range of substituents at the amide. Deprotection of the phthaloyl group with hydrazine affords a free amino acid as shown in FIG. 23 of WO 2002/085923.

Substitution at the γ-position is typically accomplished via alkylation of glutamic acid. (See, e.g., Koskinen & Rapoport, *J. Org. Chem.* 54, 1859-1866, 1989, hereby incorporated by reference). A protected amino acid, e.g., as illustrated by compound number 5 in FIG. 24 of WO 02/085923, is optionally prepared by first alkylation of the amino moiety with 9-bromo-9-phenylfluorene (PhflBr) (see, e.g., Christie & Rapoport, *J. Org. Chem.* 1989, 1859-1866, 1985, hereby incorporated by reference) and then esterification of the acid moiety using O-cert-butyl-N,N'-diisopropylisourea. Addition of KN(Si(CH$_3$)$_3$)$_2$ regioselectively deprotonates at the α-position of the methyl ester to form the enolate, which is then optionally alkylated with a range of alkyl iodides. Hydrolysis of the t-butyl ester and Phfl group gave the desired γ-methyl glutamine analog (Compound number 2 in FIG. 24 of WO 02/085923, hereby incorporated by reference).

An N-Cγ cyclic analog, as illustrated by Compound number 3 in FIG. 25 of WO 02/085923, is optionally prepared in 4 steps from Boc-Asp-Ot-Bu as previously described. (See, e.g., Barton et al., *Tetrahedron Lett.* 43, 4297-4308, 1987, and Subasinghe et al., *J. Med. Chem.* 35 4602-7, 1992, each is hereby incorporated by reference). Generation of the anion of the N-t-Boc-pyrrolidinone, pyrrolidinone, or oxazolidone followed by the addition of the compound 7, as shown in FIG. 25, results in a Michael addition product. Deprotection with TFA then results in the free amino acids.

Trifluoroleucine (Tfl) and hexafluoroleucine (Hfl), may be synthesized by various methods known in the art. For example, 5',5',5'-trifluoro-DL-leucine may be synthesized in step-wise fashion by first diluting commercial trifluoromethyl crotonic acid with ethanol and hydrogenating it in the presence of a catalyst. Next, the mixture may be refluxed, and the ester distilled. Next, α-oximino-5',5',5'-trifluoroisocaproic acid may be derived by reflux and distillation, followed by recrystallization of 5',5',5'-trifluoro-DL-leucine. Likewise, (S)-5,5,5,5',5',5'-Hexafluoroleucine may be prepared from hexafluoroacetone and ethyl bromopyruvate in multiple steps, including a highly enantioselective reduction of the carbonyl group in an α-keto ester by bakers' yeast or by catecholborane utilizing an oxazaborolidine catalyst. (For more details, see for example, Rennert, Anker, *Biochem.* 1963, 2, 471; Zhang, et al., *Helv. Chim. Acta* 1998, 81, 174-181, R., *Prot. Sci.* 7: 419-426 (1998); Hendrickson, et al., *Annual Rev. Biochem.* 73: 147-176 (2004); U.S. Patent Application Nos. 20030108885 and 20030082575, as well as U.S. Provisional Application No. 60/571,810, all of which are hereby incorporated by reference in their entireties). One point of novelty of the present disclosure relates to increased thermal and chemical stability of leucine-zipper domain-rich molecules for which a fluorinated non-natural amino acid(s) has been incorporated.

Likewise, homopropargylyglycine (HPG) and azidohomoalanine (AHA) may be synthesized by published methods. For example, according to Mangold, et al., *Mutat. Res.*, 1989, 216, 27, which is hereby incorporated by reference in its entirety.

In addition to the above non-natural amino acids, a library of tyrosine analogs has also been designed. Based upon the crystal structure of *B. stearothermophilus* TyrRS, whose active site is highly homologous to that of the *M. jannashii* synthetase, residues within a 10 Å shell of the aromatic side chain of tyrosine were mutated (Y32, G34, L65, Q155, D158, A167, Y32 and D158). The library of tyrosine analogs, as shown in FIG. 26 of WO 02/085923, has been designed to complement an array of substitutions to these active site amino acids. These include a variety of phenyl substitution patterns, which offer different hydrophobic and hydrogen-bonding properties. Tyrosine analogs are optionally prepared using the general strategy illustrated by WO 02/085923 (see, e.g., FIG. 27 of the publication). For example, an enolate of diethyl acetamidomalonate is optionally generated using sodium ethoxide. A desired tyrosine analog can then be prepared by adding an appropriate benzyl bromide followed by hydrolysis.

Exemplary Molecules

Essentially any protein (or portion thereof) that includes an non-natural amino acid, e.g., an non-natural amino acid comprising a moiety where a chemical moiety is attached, such as an aldehyde- or keto-derivatized amino acid, or an non-natural amino acid that includes a chemical moiety (and any corresponding coding nucleic acid, e.g., which includes one or more selector codons) can be produced using the compositions and methods herein. No attempt is made to identify the hundreds of thousands of known proteins, any of which can be modified to include one or more non-natural amino acid, e.g., by tailoring any available mutation methods to include one or more appropriate degenerate codons in a relevant translation system. Common sequence repositories for known proteins include GenBank EMBL, DDBJ and the NCBI. Other repositories can easily be identified by searching on the internet.

Typically, the proteins are, e.g., at least about 60%, 70%, 75%, 80%, 90%, 95%, or at least about 99% or more identical to any available protein (e.g., a therapeutic protein, a diagnostic protein, an industrial enzyme, or portion thereof, and the like), and they comprise one or more non-natural amino acid.

In one aspect, a composition includes at least one protein with at least one, e.g., at least about two, three, four, five, six, seven, eight, nine, or at least about ten or more unnatural amino acids, e.g., an unnatural amino acid comprising a moiety where a saccharide moiety can be attached, or an unnatural amino acid that includes a saccharide moiety, and/or which include another unnatural amino acid. The unnatural amino acids can be the same or different, e.g., there can be 1, 2, 3, 4, 5, 6, 7, 8, 9, or 10 or more different sites in the protein that comprise 1, 2, 3, 4, 5, 6, 7, 8, 9, or 10 or more different unnatural amino acids. In another aspect, a composition includes a protein with at least one, but fewer than all, of a particular amino acid present in the protein substituted with the unnatural amino acid, e.g., an unnatural amino acid comprising a moiety where a saccharide moiety can be attached, or an unnatural amino acid that includes a saccharide moiety. For a given protein with more than one unnatural amino acids, the unnatural amino acids can be identical or different (e.g., the protein can include two or more different types of unnatural amino acids, or can include two of the same unnatural amino acid). For a given protein with more than two unnatural amino acids, the unnatural amino acids can be the same, different, or a combination of multiple unnatural amino acids of the same kind with at least one different unnatural amino acid.

A "target molecule," "target protein," or "target polypeptide," and the like as used herein generally refer to any naturally occurring or synthetic (artificial) therapeutic, diagnostic, bio-molecule, peptides, polypeptides, or proteins that can be modified as discussed by the present invention. Some examples of target molecules include, but are not limited to, e.g., α-1 antitrypsin, Angiostatin, Antihemolytic factor, antibodies (including an antibody or a functional fragment or derivative thereof selected from: Fab, Fab', F(ab)$_2$, Fd, Fv, ScFv, diabody, tribody, tetrabody, dimer, trimer or minibody), angiogenic molecules, angiostatic molecules, Apolipoprotein, Apoprotein, Asparaginase, Adenosine deaminase, Atrial natriuretic factor, Atrial natriuretic polypeptide, Atrial peptides, Angiotensin family members, Bone Morphogenic Protein (BMP-1, BMP-2, BMP-3, BMP-4, BMP-5, BMP-6, BMP-7, BMP-8a, BMP-8b, BMP-10, BMP-15, etc.); C-X-C chemokines (e.g., T39765, NAP-2, ENA-78, Gro-a, Gro-b, Gro-c, IP-10, GCP-2, NAP-4, SDF-1, PF4, MIG), Calcitonin, CC chemokines (e.g., Monocyte chemoattractant protein-1, Monocyte chemoattractant protein-2, Monocyte chemoattractant protein-3, Monocyte inflammatory protein-1 α, Monocyte inflammatory protein-1 β, RANTES, I309, R83915, R91733, HCC1, T58847, D31065, T64262), CD40 ligand, C-kit Ligand, Ciliary Neurotrophic Factor, Collagen, Colony stimulating factor (CSF), Complement factor 5a, Complement inhibitor, Complement receptor 1, cytokines, (e.g., epithelial Neutrophil Activating Peptide-78, GROα/MGSA, GROβ, GROγ, MIP-1α, MIP-1δ, MCP-1), deoxyribonucleic acids, Epidermal Growth Factor (EGF), Erythropoietin ("EPO", representing a preferred target for modification by the incorporation of one or more nonnatural amino acid), Exfoliating toxins A and B, Factor IX, Factor VII, Factor VIII, Factor X, Fibroblast Growth Factor (FGF), Fibrinogen, Fibronectin, G-CSF, GM-CSF, Glucocerebrosidase, Gonadotropin, growth factors, Hedgehog proteins (e.g., Sonic, Indian, Desert), Hemoglobin, Hepatocyte Growth Factor (HGF), Hepatitis viruses, Hirudin, Human serum albumin, Hyalurin-CD44, Insulin, Insulin-like Growth Factor (IGF-I, IGF-II), interferons (e.g., interferon-α, interferon-β, interferon-γ, interferon-ε, interferon-ζ, interferon-η, interferon-κ, interferon-λ, interferon-τ, interferon-ς, interferon-ω), glucagon-like peptide (GLP-1), GLP-2, GLP receptors, glucagon, other agonists of the GLP-1R, natriuretic peptides (ANP, BNP, and CNP), Fuzeon and other inhibitors of HIV fusion, Hurudin and related anticoagulant peptides, Prokineticins and related agonists including analogs of black mamba snake venom, TRAIL, RANK ligand and its antagonists, calcitonin, amylin and other glucoregulatory peptide hormones, and Fc fragments, exendins (including exendin-4), exendin receptors interleukins (e.g., IL-1, IL-2, IL-3, IL-4, IL-5, IL-6, IL-7, IL-8, IL-9, IL-10, IL-11, IL-12, etc.), I-CAM-1/LFA-1, Keratinocyte Growth Factor (KGF), Lactoferrin, leukemia inhibitory factor, Luciferase, Neurturin, Neutrophil inhibitory factor (NIF), oncostatin M, Osteogenic protein, Parathyroid hormone, PD-ECSF, PDGF, peptide hormones (e.g., Human Growth Hormone), Oncogene products (Mos, Rel, Ras, Raf, Met, etc.), Pleiotropin, Protein A, Protein G, Pyrogenic exotoxins A, B, and C, Relaxin, Renin, ribonucleic acids, SCF/c-kit, Signal transcriptional activators and suppressors (p53, Tat, Fos, Myc, Jun, Myb, etc.), Soluble complement receptor I, Soluble I-CAM 1, Soluble interleukin receptors (IL-1, 2, 3, 4, 5, 6, 7, 9, 10, 11, 12, 13, 14, 15), soluble adhesion molecules, Soluble TNF receptor, Somatomedin, Somatostatin, Somatotropin, Streptokinase, Superantigens, i.e., Staphylococcal enterotoxins (SEA, SEB, SEC1, SEC2, SEC3, SED, SEE), Steroid hormone recetors (such as those for estrogen, progesterone, testosterone, aldosterone, LDL receptor ligand and corticosterone), Superoxide dismutase (SOD), Toll-like receptors (such as Flagellin), Toxic shock syndrome toxin (TSST-1), Thymosin α 1, Tissue plasminogen activator, transforming growth factor (TGF-α, TGF-β), Tumor necrosis factor β (TNF β), Tumor necrosis factor receptor (TNFR), Tumor necrosis factor-α (TNF α), tranScriptional modulators (for example, genes and transcriptional modular proteins that regulate cell growth, differentiation and/or cell regulation), Vascular Endothelial Growth Factor (VEGF), virus-like particle, VLA-4/VCAM-1, Urokinase, signal transduction molecules, estrogen, progesterone, testosterone, aldosterone, LDL, corticosterone amidase, amino acid racemase, acylase, dehalogenase, dioxygenase, CD40L/CD40, diarylpropane peroxidase, epimerase, epoxide hydrolase, esterase, isomerase, kinase, glucose isomerase, glycosidase, glycosyl transferase, haloperoxidase, monooxygenase, lipase, lignin peroxidase, nitrile hydratase, nitrilase, protease, phosphatase, subtilisin, transaminase, nuclease, and many others.

Target molecules include transcriptional modulators, signal transduction molecules and oncogene products, which may be found in prokaryotes, viruses, and eukaryotes, including fungi, plants, yeasts, insects, and animals, including mammals, providing a wide range of therapeutic targets. It will be appreciated that expression and transcriptional activators regulate transcription by many mechanisms, e.g., by binding to receptors, stimulating a signal transduction cascade, regulating expression of transcription factors, binding to promoters and enhancers, binding to proteins that bind to promoters and enhancers, unwinding DNA, splicing pre-mRNA, polyadenylating RNA, and degrading RNA.

Some examples of transcriptional modulators or expression activators include but are not limited to: cytokines, inflammatory molecules, growth factors, their receptors, and oncogene products, e.g., interleukins (e.g., IL-1, IL-2, IL-8, etc.), interferons, FGF, IGF-I, IGF-II, FGF, PDGF, TNF, TGF-α, TGF-β, EGF, KGF, SCF/c-Kit, CD40L/CD40, VLA-4/VCAM-1, ICAM-1/LFA-1, and hyalurin/CD44; signal transduction molecules and corresponding oncogene products, e.g., Mos, Ras, Raf, and Met; and transcriptional activators and suppressors, e.g., p53, Tat, Fos, Myc, Jun, Myb, Rel, and steroid hormone receptors such as those for estrogen, progesterone, testosterone, aldosterone, the LDL receptor ligand and corticosterone.

For modification of antibodies, the non-natural amino acid residue(s) may be placed at any location or position in the antibody structure, depending on the desired goal. For example, the non-natural amino acid residue may be placed in the Fab variable region, the Fc region, or in another location that interacts with the Fc region of the antibody. In other embodiments, the non-natural amino acid residue may be placed in the binding interface of the antibody, or the $V_H$ region. In certain embodiments, the modified antibody exhibits an increase or decrease in its ability to kill one or more targets. In particular, an antibody with increased ability to kill one or more targets, or with reduced side effects may be desired.

In other embodiments, the non-natural amino acid(s) confer enhanced binding affinity to an Fc-receptor and/or to C1q of the complement system. In particular, a modified antibody may have an altered (e.g., enhanced) affinity and/or specificity for an antigen or a protein binding partner (e.g., C1q of the complement and/or the Fc receptor on macrophages, etc.). For example, modification of a molecule may increase or decrease its antibody-dependent cell-mediated cytotoxicty (ADCC) function, or complement fixation activity. In other examples, modification of a particular molecule may increase or decrease its ability to bind another molecule of natural counter structure (such as an antibody).

Another class of proteins able to be modified as disclosed herein include enzymes (e.g., industrial enzymes) or portions thereof. Examples of enzymes include, but are not limited to, e.g., amidases, amino acid racemases, acylases, dehalogenases, dioxygenases, diarylpropane peroxidases, epimerases, epoxide hydrolases, esterases, isomerases, kinases, glucose isomerases, glycosidases, glycosyl transferases, haloperoxidases, monooxygenases (e.g., p450s), lipases, lignin peroxidases, nitrile hydratases, nitrilases, proteases, phosphatases, subtilisins, transaminase, and nucleases.

Still another class of proteins that may be modified as disclosed herein include vaccine proteins e.g., in proteins from infectious fungi, e.g., *Aspergillus, Candida* species; bacteria, particularly *E. coli*, which serves a model for pathogenic bacteria, as well as medically important bacteria such as Staphylococci (e.g., *aureus*), or Streptococci (e.g., *pneumoniae*); protozoa such as sporozoa (e.g., *Plasmodia*), rhizopods (e.g., *Entamoeba*) and flagellates (*Trypanosome, Leishmania, Trichomonas, Giardia*, etc.); viruses such as (+) RNA viruses (examples include Poxviruses e.g., vaccinia; Picornaviruses, e.g., polio; Togaviruses, e.g., rubella; Flaviviruses, e.g., HCV; and Coronaviruses), (−) RNA viruses (e.g., Rhabdoviruses, e.g., VSV; Paramyxovimses, e.g., RSV; Orthomyxovimses, e.g., influenza; Bunyaviruses; and Arenaviruses), dsDNA viruses (Reoviruses, for example), RNA to DNA viruses, i.e., Retroviruses, e.g., HIV and HTLV, and certain DNA to RNA viruses such as Hepatitis B.

Agriculturally related proteins such as insect resistance proteins (e.g., the Cry proteins), starch and lipid production enzymes, plant and insect toxins, toxin-resistance proteins, Mycotoxin detoxification proteins, plant growth enzymes (e.g., Ribulose 1,5-Bisphosphate Carboxylase/Oxygenase, "RUBISCO"), lipoxygenase (LOX), and Phosphoenolpyruvate (PEP) carboxylase are also suitable target molecules.

Some target molecules that can be modified as disclosed herein are commercially available (see, e.g., the Sigma BioSciences catalogue and price list), and the corresponding protein sequences and genes and, typically, many variants thereof, are well-known (see, e.g., Genbank).

Typically, the target molecules are proteins that are, e.g., at least about 60%, 70%, 75%, 80%, 90%, 95%, or at least about 99% or more identical to any available protein (e.g., a therapeutic protein, a diagnostic protein, an industrial enzyme, or portion thereof, and the like), and they comprise one or more non-natural amino acid.

Any of the exemplary target molecules disclosed herein or otherwise can be modified according to methods described herein and may result in altering one or more therapeutic, diagnositic, or enzymatic properties of the target protein. Examples of therapeutically relevant properties include serum half-life, shelf half-life, stability, immunogenicity, therapeutic activity, detectability (e.g., by the inclusion of reporter groups (e.g., labels or label binding sites)) in the non-natural amino acids, specificity, reduction of LD50 or other side effects, ability to enter the body through the gastric tract (e.g., oral availability), or the like. Examples of relevant diagnostic properties include shelf half-life, stability (including thermostability), diagnostic activity, detectability, specificity, or the like. Examples of relevant enzymatic properties include shelf half-life, stability, specificity, enzymatic activity, production capability, resistance to at least one protease, tolerance to at least one non-aqueous solvent, or the like.

Multiprotein Complexes

Another aspect of the invention provides a method for generating an immunoconjugate target molecule comprising an antibody (or functional fragment/derivative thereof) and one or more therapeutic moieties, the method comprising: (1) incorporating one or more non-natural amino acid(s) at specified position(s) of the antibody using any of the suitable subject methods; (2) contacting the antibody with the one or more therapeutic moieties to form a conjugate that attaches the one or more therapeutic moieties to the non-natural amino acid(s) of the antibody.

The therapeutic moieties may be the same or different, may be conjugated to the same or different non-natural amino acids, and may be cleaveable under one or more conditions selected from: mild or weak acidic conditions (e.g. about pH 4-6, including about pH 5), reductive environment (e.g. the presence of a reducing agent), divalent cations, or optionally, heat. Additional aspects of the invention provide for an immunoconjugate target molecule produced by any of the suitable subject methods. Non-natural amino acids can also be used to join two or more target molecules or target molecule sub-units with unique functionalities. For example, bispecific antibodies may be generated by linking two target molecule antibodies (or functional parts thereof or derivatives thereof, such as Fab, Fab', Fd, Fv, ScFv fragments, etc.) through non-natural amino acids incorporated therein.

Although the electrophilic moiety (e.g., a keto moiety, an aldehyde moiety, and/or the like) and nucleophilic moiety described herein in the context of attaching sugar or other chemical moieties to proteins, the same set of electrophilic and nucleophilic moieties may be used to join two protein molecules, such as two antibody molecules.

Thus the instant invention provides methods for synthesis of multiprotein conjugates comprising target molecules. These methods involve, in some embodiments, incorporating into a first target protein (e.g., a first antibody) a first non-natural amino acid that comprises a first reactive group; and contacting the first target protein with a second target protein (e.g., a second antibody) comprising a second non-natural amino acid that comprises a second reactive group, wherein the first reactive group reacts with the second reactive group, thereby forming a covalent bond that attaches the second target protein to the first target protein.

The first reactive group comprises, in some embodiments, an electrophilic moiety (e.g., a keto moiety, an aldehyde moiety, and/or the like), and the second reactive group comprises a nucleophilic moiety. In some embodiments, the first reactive group comprises a nucleophilic moiety and the second reactive group comprises an electrophilic moiety (e.g., a keto moiety, an aldehyde moiety, and/or the like). For example, an electrophilic moiety is attached to the non-natural amino acid of the first antibody, and the nucleophilic moiety is attached to the non-natural amino acid of the second antibody.

Different functional domains of different target proteins may be linked together through similar fashion to create novel proteins with novel functions (e.g., novel transcription factors with unique combination of DNA binding and transcription activation domains; novel enzymes with novel regulatory domains, etc.).

Exemplary Methods of Altering Molecules

The following means for deleting, substituting, adding or otherwise incorporating amino acid residues may be used with non-natural amino acid residues or naturally occurring amino acid residues, depending on the desired outcome of each round of mutation or modification, as well as the overall goal relating to modifying the target molecule. Non-natural amino acids may be incorporated according to specific amino acid residue (e.g., by replacing all or nearly all positions of a particular amino acid in the polypeptide), or site-specifically at a desired amino acid position.

With regard to amino acid residue specific incorporation, one general approach to modifying the target molecule comprises replacing several or all but one of a particular selected amino acid residue in the target molecule. In certain embodiments, the selected amino acid residue is methionine. In at least one embodiment, every methionine amino acid residue in a target molecule is replaced by gene mutation with another naturally occurring or non-natural amino acid residue. Thus, in certain embodiments, the polynucleotide is altered or modified in order to change the nucleic acid sequence of a particular naturally occurring amino acid codon to a non-natural amino acid codon or a stop codon (or other nonsense codon) in order to allow incorporation of a non-natural amino acid at a selected location in the target molecule. Next, the remaining amino acid residue(s) is/are replaced with a non-natural amino acid during fermentation. Fermentation allows for reduced manufacturing costs, compared with chemical synthesis of molecules.

In certain embodiments, the non-natural amino acid corresponds to the naturally occurring amino acid that it is replacing in the target molecule. In other embodiments, the non-natural amino acid codon does not correspond in chemical structure to the naturally occurring amino acid codon that is being replaced in the target molecule. In certain embodiments, particularly where the non-natural amino acid does correspond to the naturally occurring amino acid that it is replacing in the target molecule, the endogenous tRNA and/or aminoacyl tRNA synthetase machinery may be used for incorporation of the non-natural amino acid into the target molecule. In some embodiments, this method would rely on manufacturing in cells (such as auxotrophic host cells) that are unable or deficient in the naturally occurring amino acid that is being replaced. Thus, during protein translation, the corresponding non-natural amino acid is present in the culture medium (with or without the corresponding naturally occurring amino acid selected to be replaced) and the non-natural amino acid is incorporated at the naturally occurring amino acid position that is the intended target for replacement.

In certain other methods, non-natural amino acids may be incorporated as additional amino acids, rather than as replacement amino acids, in the target molecule.

In certain embodiments where the selected amino acid residue is methionine, azidohomoalanine or homopropargylglycine, or other non-natural amino acids may be substituted for the remaining methionine in the target molecule. Preferably, the target molecule retains the ability to properly fold.

Using this particular method of residue-specific incorporation, the multiple different target molecules may be utilized with success. Since ultimately, every specific naturally occurring amino acid residue in a particular amino acid family or type will be substituted or replaced with another amino acid (whether naturally occurring or non-natural), preferable amino acid residue families to select for substitution include those in which few naturally occurring amino acids are present in the target molecule. For example, most preferred target molecules have few methionine or tryptophan residues present and such amino acid types may be easily substituted or replaced with a non-natural amino acid or other naturally occurring amino acid with a lower likelihood for disruption of the structure or function of the target molecule.

In one exemplary embodiment, a target molecule may have up to about 10, about 9, about 8 about 7, about 6, about 5, about 4, about 3, about 2 or about 1 substitution(s) without disrupting the structure or function of the target molecule. In certain embodiments, the location of these substitutions may also be considered. For instance, the substitution(s) should preferably not occupy a position in the active site for receptor binding or other intermolecular action for the target molecule. Likewise, the substitution(s) should preferably not occupy a key structural position unless the non-natural amino acid or naturally occurring replacement amino acid is chemically or structurally compatible with those functional properties. In the event that the non-natural or replacement naturally occurring amino acid is not compatible, a codon of the target molecule may be modified at the polynucleotide level in order to encode for another amino acid (either naturally occurring or non-natural). Preferably, the substitution is conservative, i.e. retains the proper structure and function of the target molecule. Thus, methionine residues may be preferably replaced with threonine, isoleucine, or leucine prior to replacing any remaining methionine residues with a non-natural amino acid.

In certain embodiments in which only a single non-natural amino acid is desired in a target molecule, then all of the methionine (or other selected amino acid type) are substituted with other naturally occurring amino acids and one methionine amino acid residue is retained (or introduced, if it doesn't already exist) at the desired non-natural position in the target molecule. Subsequently, a non-natural or other replacement amino acid is incorporated at the single methionine amino acid residue position. As one of skill in the art would appreciate, this method may be employed for any particular amino acid type other than methionine.

The location of the one remaining natural amino acid residue that is replaced by the non-natural amino acid may be any desired location for which the properties of the non-natural amino acid are beneficial (for example, at the amino terminus).

In certain embodiments, in order to maintain the proper structure and/or function of the target molecule, the substitution of specific amino acid types (such as methionine) may also be accompanied by the substitution of other amino acids that interact with the substituted amino acids, particularly for folding.

Following incorporation of the non-natural amino acid into the target molecule, a chemical moiety may be attached to the molecule, thereby forming a conjugate. Such methods of modifying target molecules with non-natural amino acids enables highly specific incorporation, highly efficient incorporation, and results in high yields if modified target molecules.

With regard to site-specific incorporation of non-natural amino acids, manipulation of transcriptional and/or translational machinery may be required for increased efficiency of incorporation of a non-natural amino acid. For example, manipulation of an aminoacyl-tRNA synthetase and/or an aminoacyl-tRNA may be necessary in order to achieve site-specific incorporation of an non-natural amino acid. In addition, modifying the editing function of an aminoacyl tRNA synthetase may also provide for increased efficiency and/or increased specificity for incorporation of a particular non-natural amino acid.

Thus, the promiscuity of some aminoacyl-tRNA synthetases (whether wild type or mutant) may be exploited toward certain non-natural amino acids that bear structural resemblance to the specific natural amino acid counterpart(s).

Furthermore, auxotrophic host cells may be utilized in order to increase the efficiency of incorporation of the non-natural amino acid, whether by site-specific or residue-specific incorporation. Auxotrophic host cells are mutant cells that are unable to synthesize a particular organic compound required for its growth and can only grow if the compound is taken up from the growth media. When the media contains a non-natural amino acid (instead of or in addition to the naturally occurring amino acid counterpart), the auxotrophic host cell utilizes the non-natural amino acid and incorporates it into the polypeptide chain. Auxotrophic host cells may be used in concert with manipulated machinery (such as mutant aminoacyl tRNAs and/or mutant aminoacyl tRNA synthetases) for increased efficiency of incorporation of non-natural amino acids.

Well over 100 non-coded amino acids (all ribosomally acceptable) have been reportedly introduced into proteins using other methods (see, for example, Schultz et al., *J. Am. Chem. Soc.*, 103: 1563-1567, 1981; Hinsberg et al., *J. Am. Chem. Soc.*, 104: 766-773, 1982; Pollack et al., *Science*, 242: 1038-1040, 1988; Nowak et al., *Science*, 268: 439-442, 1995, all of which are hereby incorporated by reference in their entireties) any or all of these referenced analogs may be used in the subject methods for efficient incorporation of the analogs into protein products. In general, the method of the instant invention can be used to incorporate amino acid analogs into protein products either in vitro or in vivo.

Furthermore, the target molecule can have one or more non-natural amino acid residues at any particular position in the protein, and the non-natural amino acid residues may be the same or different from each other. In certain aspects, a composition of the present invention includes at least one protein with one or more non-natural amino acids, including at least one, at least two, at least three, at least four, at least five, at least six, at least seven, at least eight, at least nine, or at least ten or more non-natural amino acid residues that may be any combination of the same or different from each other. Typically, the target molecules (e.g., proteins) may be at least 60%, at least 70%, at least 75%, at least 80%, at least 85%, at least 90%, at least 95%, or at least 99% or more identical to any available target protein (e.g., a therapeutic protein, a diagnostic protein, etc.).

One of the surprising results of the present invention includes the finding that different penultimate N-terminal (amino terminal) non-natural amino acid residues affect cellular processing of a molecule in which the N-terminal amino acid is a non-natural amino acid. Examples of this effect are demonstrated herein. For example, in one embodiment, the non-natural amino acid codon encoding the amino acid located at the amino terminus of the polypeptide is cleaved during translational processing, likely due to peptidase activity. Thus, in certain embodiments, the amino terminal non-natural amino acid codon will be retained at a greater efficiency when the second position, or penultimate amino acid residue position, is also altered to a codon that encodes a non-natural amino acid. These changes may be conducted in any manner outlined herein, whether at a nucleic acid level or amino acid level.

The N-terminus (amino terminus) may be altered by adding a non-natural amino acid, or by replacing the native amino acid residue (typically a methionine) with a non-natural amino acid. In particular, as described in the Figures inter alis, specific amino acid residues at the penultimate N-terminal position can support efficient retention or removal of the N-terminal non-natural amino acid residue. Furthermore, unsaturated side chains found on some non-natural amino acids (such as azidohomoalanine and homopropargylglycine) may be incorporated with little or no side reactions with the natural amino acids. (Kiick et al., *PNAS USA* 99: 19-24 (2002); Wu, et al., *Angew. Chem. Int. Ed. Eng.* 43: 3928-3932 (2004)).

In one exemplary embodiment, using the methods disclosed herein, a mutant interferon-β conjugate was generated with azidohomoalanine (AHA) or homopropargylglycine (HPG) incorporated at the amino terminus, as well as the following amino acid mutations or substitutions: S2E, C17S, M36I, I40F, I44L, M62I, M117T. Thus, the target molecule interferon-β had every methionine amino acid residue altered to another naturally occurring amino acid residue, with the exception of the initiator methionine residue, which was altered to AHA. In addition, other amino acid positions were altered to other naturally occurring amino acids. Multiple naturally occurring amino acid residues were selected for altering the wild type sequence of the interferon-β target molecule.

In another exemplary embodiment, using the methods disclosed herein, a mutant interferon-β conjugate was generated with azidohomoalanine (AHA) or homopropargylglycine (HPG) incorporated at the amino terminus, as well as the following amino acid mutations or substitutions: S2E, M36I, I40F, I44L, M62I, M117T. Thus, the target molecule interferon-β had every methionine amino acid residue altered to another naturally occurring amino acid residue, with the exception of the initiator methionine residue, which was altered to AHA. In addition, other amino acid positions were altered to other naturally occurring amino acids. I40 and I44 were altered to maintain bioactivity, since these residues interact with the internal methionine. The penultimate S2 residue was altered to eliminate methionine aminopeptidase cleave of the N-terminal AHA.

Other amino acid mutations or substitutions for the target interferon-β molecule were conducted individually and/or combinatorially based on sequence comparisons of various species of interferon-β and/or interferon-α molecules. Since the human interferon-β molecule contained only 4 methionine residues in the wild type sequence (at positions 1, 36, 62, and 117), and since it was desired that the chemical moiety (PEG) would be attached at the amino terminus of the molecule, methionine was selected as the amino acid to be replaced. Studying sequences of the interferon molecules, the methionine at position 36 in human interferon-β was isoleucine in the corresponding dog sequence; alanine in the corresponding mouse sequence; threonine in the corresponding rat sequence; and histidine in the human interferon-α sequence. Likewise, for the methionine located at amino acid position 62 in the human interferon-β sequence, isoleucine was present in the corresponding chicken sequence at position 62, leucine was present in the corresponding Australian echidna sequence at position 62, leucine was present in the corresponding human interferon-α-1 sequence (13), and valine was present in the corresponding human interferon-α-1 sequence (6). Finally, for the methionine located at amino acid position 117 of the human interferon-β molecule, valine was present in the corresponding monkey sequence at position 117, threonine and serine were present in other species at position 117, and aspartic acid, asparagines, and serine were present at position 117 in other human interferon sequences. Thus, these amino acids were first selected as the first candidates for mutation and/or substitution at the corresponding methionine residues in the human interferon-β molecule.

Additionally, once certain desired amino acid residues or amino acid positions were identified based on the sequence comparisons, the energy calculations were conducted for various amino acid alterations to those sites. In light of these analyses, multiple interferon-β mutations and/or substitutions were conducted at the following amino acid positions (amino terminus is position 1, such that M1AHA indicates that the methionine at position 1 is altered to AHA or azidohomoalanine, all others follow the same format): M1AHA, M1 HPG, S2H, S2E, S2Q, S2Y, S2F, S2K, M36T, M36A, M36I, M36V, M62Q, M62S, M62T, M62H, M62N, M62Y, M62F, M62I, M62A, M62L, M62G, M117 any, M117S, M117T, M117Y, M117G, M62L-I40L, M62I-I40F-I44L ("Chicken triple" or "triple"), M62I-I40F-I44L-M117T, M62I-I40F-I44L-M117S, M36A-M62I-I40F-I44L, M36T-M62I-I40F-I44L, M36T-M62I-I40F-I44L-M117T, M36T-M62I-I40F-I44L-M117S, M62L-I40L, M36T-M117I ("TI," wherein TI may comprise further mutations and/or substitutions), M36T-M117T ("TT," wherein TT may comprise further mutations and/or substitutions), TI-S2K, TI-S2Q, TI-S2Y, TI-S2F, TI-S2E, TI-S2H, TT-S2K, TT-S2Y, TT-S2F, TT-S2E, TT-S2H, TT-S2Q.

The M1AHA, S2E, C17S, M36I, I40F, I44L, M62I, M117T mutant interferon-β molecule containing these amino acid substitutions retained the amino terminal AHA, was easily purified and refolded properly (including disulfide bond formation). Additionally, the mutant interferon-β molecule was efficiently PEGylated with poly(ethylene) glycol (10K) and poly(ethylene)glycol (20K), and will be PEGylated with poly(ethylene)glycol (40K) using a [3+2] copper catalyzed cycloaddition between the azide moiety and the alkyne moiety. The mutant interferon-β PEGylated conjugate was structurally stable and retained full biological functional activity both in vitro and in vivo. Details of the mutant interferon-β conjugate are set forth in the Examples herein.

In Vitro Incorporation

In general, any means known in the art for generating transcripts can be employed to synthesize proteins with amino acid analogs or naturally occurring amino acid residues. For example, any in vitro transcription system or coupled transcription/translation systems can be used to generate a transcript of interest, which then serves as a template for protein synthesis. Alternatively, any cell, engineered cell/cell line, or functional components (lysates, membrane fractions, etc.) that is capable of expressing proteins from nucleic acid materials can be used to generate a transcript. These means for generating a transcript will typically include such components as RNA polymerase (T7, SP6, etc.) and co-factors, nucleotides (ATP, CTP, GTP, UTP), necessary transcription factors, and appropriate buffer conditions, as well as at least one suitable DNA template, but other components may also be added for optimized reaction conditions.

In certain aspects of the present invention, target molecules may be identified and/or modified by "DNA shuffling, " or "gene shuffling," which may comprise point mutations, gene duplications and/or genetic recombination. Gene shuffling may occur to some degree in nature, and is a successful laboratory procedure used in vitro or in vivo, that may mimic the natural evolutionary processes of mutation and recombination on an accelerated scale. The technique may be used to evolve target molecules, including proteins and in particular enzymes or antibodies, to possess novel specificities, characteristics or activities.

For example, gene shuffling may occur by a first round of error-prone PCR, by generating an expression library or by introducing a particular non-natural or naturally occurring amino acid residue in a host cell line, which results in random or selected mutations. The pool or library of mutated variants may then be submitted to random fragmentation and PCR-based reassembly to generate a population of full-length recombined variants. In addition to or alternatively to, the pool or library of mutated PCR products may be expressed in a host cell that incorporates a particular amino acid residue either randomly or selectively at particular locations, thereby generating a round of modification for the target molecule of interest. Next, screening or testing the population of variants leads to identification and isolation of particular mutant clones with improved functions or characteristics. The selected clones may subsequently be submitted for any number of additional rounds of "gene shuffling." In at least certain cases, multiple rounds are sufficient to obtain optimal variants, as the particular selected characteristics may be enhanced upon each successive round. In at least some instances, both coding and non-coding genes or gene fragments are responsible for the enhanced characteristics or activities.

In other instances, a bacteriophage may be created for expression of a library containing a non-natural amino acid, where the bacteriophage genome has been codon optimized to eliminate a particular codon that will be used for the incorporation of a non-natural amino acid in the bacterial host cell in which the phage library will be expressed. In at least one embodiment, a library of mutant or variant molecules can be expressed in a host cell line in which a codon has been introduced that encodes a non-natural amino acid. For additional details, see for example, Stemmer, *Proc. Nat'l. Acad. Sci. USA,* 91: 10747-10751 (1994), hereby incorporated by reference in its entirety.

In another exemplary embodiment, a bacteriophage is created for expressing a library containing a non-natural amino acid, in which the bacteriophage genome has been optimized to eliminate a particular codon that will be used for the incorporation of a non-natural amino acid in the bacterial host cell expressing the phage.

In another exemplary embodiment, a library of a target molecule, such as ScFv, such as any combinatorial library of heavy and light immunoglobulin chains, or such as a randomized antigen binding library (including a phage library) may be expressed in a host cell that incorporates a non-natural amino acid at a particular codon and subsequently introduce that codon either randomly or at particular locations in the library of molecules. Thus, expressing the library in the host cell would incorporate the non-natural amino acid. Next, the library may be subjected to antigen binding selection to identify or isolate a particular target molecule.

In certain aspects of the invention, a target molecule may be altered or modified for selection of a particular characteristic by chemical and/or site-directed mutagenesis and/or multi-site incorporation. Chemical mutagenesis may include subjecting or treating a target molecule with a mutagenic agent. Mutagenic agents may function in a variety of ways, including increasing the "mispairing" ability, increasing frameshift mutations, or damaging or altering a base. Mutagenic agents are well known in the art and may include base analog mutagens (such as 5-bromo-deoxyuridine), alkylators (such as ethyl methane sulfonate, methyl methane sulfonate, diethylsulfate and nitrosoguanidine), chemicals causing oxidative deamination (such as nitrous acid), as well as ultraviolet (UV) light.

Site-directed mutagenesis may involve PCR or non-PCR based modifications. Site-directed mutagenesis may allow for mutations of a specific amino acid residue with a specific codon substitution, deletion or addition. In addition, a set of random mutations over a gene region or entire gene may be accomplished by random and extensive mutagenesis (also called targeted random, region-specific, or library mutagenesis). Site-directed mutagenesis may be in vitro or in vivo.

Site-directed mutagenesis may be accomplished by a number of approaches. In particular, one approach involves using an oligonucleotide complementary to part of a single-stranded DNA template but containing an internal mismatch to direct the mutation. This approach may be used for single as well as multi-site mutations, insertions and deletions. Another approach involves replacing the region to be mutated in the target molecule previously obtained by ligation of a number of synthetic oligonucleotides. Following either of these approaches, the mutant or modified target molecules may undergo sequencing to verify the desired mutations have occurred.

Site-directed mutagenesis may be accomplished by using a single mutagenic primer, or multiple mutagenic primers that are annealed to the single-stranded template, extended briefly with Klenow fragment, and used to transfect a host (such as a bacterial or yeast cell). In one particular method, the mutagenic primer or primers may extend around the entire plasmid containing the desired sequence to be mutated. Following this "all the way around" technique, the new strand may be ligated. If multiple primers are used, at least one primer typically is used to protect the mismatch mutation after extension and ligation. Another technique involving a single primer is the "gapped duplex" technique, which utilizes a single-stranded region formed by annealing the template with a restriction fragment from the vector itself. This allows the 5' end of the oligonucleotide to be protected after extension and ligation. The template used for site-directed mutagenesis may be double-stranded or single-stranded, circular or linear, or any combination of these. For more details for particular techniques, see for example, Carter, *Biochem. J.*, 237:1-7 (1986); Bain, et al. *J. Am. Chem. Soc.* 111: 8013-8014 (1989); Wang et al, *Proc. Nat'l. Acad. Sci. USA* 100:1 (2003); Ling and Robinson, *Analy. Biochem.* 254: 157-178 (1997), all of which are hereby incorporated by reference in their entireties.

In addition, point mismatch repair, or mutagenesis using repair-deficient host strains is further embodied by the present invention. Deletion mutagenesis, restriction-selection and restriction-purification, mutagenesis by total gene synthesis, double-strand break repair, and other methods known in the art may be employed.

As further described herein, error-prone PCR may be used to alter or modify a target molecule, including a protein, at the genetic level. For example, PCR may be performed under conditions that allow for low copying fidelity of the DNA polymerase, and a high rate of point mutations results in the entire PCR product. Further, recursive ensemble mutagenesis may be used in which an algorithm for protein mutagenesis is used to produce diverse populations of phenotypically related mutants whose members differ in amino acid sequence.

In one of the embodiments, a target molecule such as an antibody and/or antibody fragment containing non-natural amino acids can be directly synthesized chemically using solid phase synthesis and ligation technologies, or using in vitro translation I expression. For example the intact antibody or its fragments can also be expressed using a variety of well-established protein expression systems including *E. coli*, yeasts, insect (e.g., baculo-virus system), and mammalian cells.

In another preferred embodiment, two or more analogs may be used in the same in vitro or in vivo translation system, with or without utilizing O-tRNA/O-RS pairs. Utilizing O-tRNA/O-RS pairs may be more easily accomplished when a natural amino acid is encoded by four or more codons. However, for amino acids encoded by only two codons, one can be reserved for the natural amino acid, while the other is "shared" by one or more amino acid analog(s). These analogs may resemble only one natural amino acid (for example, different phenylalanine analogs), or resemble different amino acids (for example, analogs of phenylalanine and tyrosine).

For in vitro use, one or more O-RSs of the instant invention can be recombinantly produced and supplied to any available in vitro translation systems (such as the commercially available Wheat Germ Lysate-based PROTEINSCRIPT-PRO™, Ambion's *E. coli* system for coupled in vitro transcription/translation; or the rabbit reticulocyte lysate-based RETIC LYSATE IVT™ Kit from Ambion). Optionally, the in vitro translation system can be selectively depleted of one or more natural AARSs (by, for example, immunodepletion using immobilized antibodies against natural AARS) and/or natural amino acids so that enhanced incorporation of the analog can be achieved. Alternatively, nucleic acids encoding the re-designed M-RSs may be supplied in place of recombinantly produced AARSs. The in vitro translation system may also be supplied with the analogs to be incorporated into mature protein products.

Although in vitro protein synthesis usually cannot be carried out on the same scale as in vivo synthesis, in vitro methods can yield hundreds of micrograms of purified protein containing amino acid analogs. Such proteins have been produced in quantities sufficient for their characterization using circular dichroism (CD), nuclear magnetic resonance (NMR) spectrometry, and X-ray crystallography. This methodology can also be used to investigate the role of hydrophobicity, packing, side chain entropy and hydrogen bonding in determining protein stability and folding. It can also be used to probe catalytic mechanism, signal transduction and electron transfer in proteins. In addition, the properties of target molecules can be modified using this methodology. For example, photocaged proteins can be generated that can be activated by photolysis, and novel chemical handles have been introduced into target molecules for the site specific incorporation of optical and other spectroscopic probes.

In Vivo Incorporation

The development of a general approach for the incorporation of non-natural amino acids into target molecules in vivo, directly from the growth media, would greatly enhance the power of non-natural amino acid mutagenesis. For example, the ability to synthesize large quantities of proteins containing heavy atoms would facilitate protein structure determination, and the ability to site-specifically substitute fluorophores or photocleavable groups into proteins in living cells would provide powerful tools for studying protein function in vivo. Alternatively, one might be able to enhance the properties of proteins by providing building blocks with new functional groups, such as a keto-containing amino acid.

In certain embodiments herein, one or more AARS of the instant invention can be supplied to a host cell (prokaryotic or eukaryotic) as nucleic acid material, such as coding sequences on plasmids or viral vectors, which may optionally integrate into the host genome and constitutively or inducibly express the re-designed AARSs. A heterologous or endogenous target molecule can be expressed in such a host cell, at the presence of supplied non-natural amino acids. The protein products can then be purified using any art-recognized protein purification techniques, or techniques specially designed for the target molecule.

In one particular embodiment, for site-specific and/or multisite incorporation of non-natural amino acids, a procedure described in U.S. Pat. No. 6,586,207 may be used, the entire content of which is incorporated herein by reference. Briefly, U.S. Pat. No. 6,586,207 provides general methods for producing a modified target molecule, wherein the target molecule is modified by replacing a selected amino acid with a desired non-natural amino acid. In certain embodiments, the method relates to producing a modified polypeptide, comprising:

a. providing a host cell in a medium, the host cell comprising:
  i. a vector having a polynucleotide sequence encoding an aminoacyl-tRNA synthetase for an amino acid analogue; and
  ii. a vector having a polynucleotide sequence encoding a polypeptide molecule of interest so as to produce a host vector system; wherein the vectors of (i) and (ii) may be the same or different, b. replacing the medium with a medium which has the desired amino acid analogue or adding the desired amino acid analogue to the medium, wherein the desired amino acid analogue is selected from the group consisting of an analogue that comprises side chain functionalities different from its corresponding natural amino acid, an analogue that is an optical isomer of the corresponding natural amino acid, an analogue that is a hydrophobic amino acid analogue, and an analogue that comprises fluorinated, electroactive, conjugated, azido, carbonyl, alkyl, or unsaturated side chain functionalities; and any amino acid that may be utilized efficiently by the AARS encoded on the polynucleotide c. growing the host cell in the medium which has the desired amino acid analogue under conditions so that the host cell expresses the polypeptide molecule of interest and the desired amino acid analogue is incorporated into the polypeptide molecule of interest thereby producing the modified polypeptide.

According to this method, expression of an aminoacyl-tRNA synthetase results in an increase in the activity of the aminoacyl-tRNA synthetase. This method is partially based on the discovery that incorporation of non-natural non-natural amino acids into polypeptides can be improved in cells that express or overexpress aminoacyl-tRNA synthetases (AARSs) that recognize such non-natural amino acids as substrates. "Improvement" as referred to herein, includes either increasing the scope of non-natural amino acids (i.e., kinds of non-natural amino acids) that can be incorporated, or by increasing, the yield of the modified target molecule. Expression of the aminoacyl-tRNA synthetase increases the level of aminoacyl-tRNA synthetase activity in the cell. The increased activity leads to an increased rate of incorporation of non-natural amino acids into the growing peptide, thereby increasing the rate of synthesis of the target molecule, and thereby increasing the quantity of polypeptides containing such non-natural amino acids.

The nucleic acids encoding the aminoacyl-tRNA synthetase, and/or the nucleic acids encoding the tRNA molecule, and/or the nucleic acids encoding the polypeptide of interest (antibody or its fragment), may be located in the same or different vectors. The vectors may include expression control elements which direct the production of the AARS, the tRNA, and the target molecule. The expression control elements (i.e., regulatory sequences) can include inducible promoters, constitutive promoters, secretion signals, enhancers, transcription terminators, and other transcriptional regulatory elements.

For both in vivo as well as in vitro incorporation of non-natural amino acids into a target molecule, any combination of multisite and/or site-specific incorporation (including addition or substitution) may be utilized in making a modified target molecule. In one particular method, multiple amino acid residues or positions of a particular amino acid family are selected and replaced with alternative naturally occurring amino acids, which preferably allow for retention of function of the target molecule. Next, some or all of these selected amino acid residues are replaced with one or more non-natural amino acid(s). In another particular method, a naturally occurring amino acid residue may be added to a particular protein such that it is the sole amino acid residue of that particular family, or only one of a few in the target molecule. Subsequently, the added amino acid residue is replaced with one or more non-natural amino acid residues. In certain embodiments, the non-natural amino acid corresponds to or is in the same amino acid family as the naturally occurring amino acid it replaced.

Host Cells and Translation Systems

Certain embodiments disclosed herein can be practiced within a cell, which enables production levels of target molecules to be made for practical purposes. In preferred embodiments, the cells used are culturable cells (i.e., cells that can be grown under laboratory conditions). Suitable cells include mammalian cells (human or non-human mammals), bacterial cells, and insect cells, etc.

One example includes PFENEX™ technology, which is a cell line using *Pseudomonas fluorescens*-based cell lines that increase cellular expression while maintaining certain solubility and activity characteristics due to its use of different pathways in the metabolism of certain sugars compared to *E. coli*.

In addition, other auxotrophic host cell lines include K10 based Phe auxotrophic strain (AF), DH10B based Phe auxotrophic strain (AF), Phe/Trp double auxotrophic strains (AFW), Phe/Trp/Lys triple auxotrophic strains (AFWK), and a Met auxotroph (M15MA on M15 background).

Cells that may be used to practice certain embodiments disclosed herein include auxotrophic host cells (whether prokaryotic or eukaryotic). Auxotrophic cells may exhibit single, double, triple, quadruple, or greater levels of auxotrophy (each level of auxotrophy indicates a particular organic compound that the organism is unable to synthesize or otherwise lacks and must be supplied to the cell). Certain embodiments disclosed herein expressly do not utilize an auxotrophic host cell. Insofar as an auxotrophic host cell is not used, another cell or cell components may be used to practice certain embodiments disclosed herein. Other embodiments may use one, two, three, or more different auxotrophic host cells that may be from the same or different strains or organisms.

Host cells may be genetically engineered (e.g., transformed, transduced or transfected) with the vectors of this disclosure, which can be, for example, a cloning vector or an expression vector. The vector can be, for example, in the form of a plasmid, a bacterium, a virus, a naked polynucleotide, or a conjugated polynucleotide. The vectors are introduced into cells and/or microorganisms by standard methods including electroporation (From et al., *PNAS. USA* 82, 5824 (1985)), infection by viral vectors, high velocity ballistic penetration by small particles with the nucleic acid either within the matrix of small beads or particles, or on the surface (Klein et al., *Nature* 327, 70-73 (1987)). Berger, Sambrook, and Ausubel provide a variety of appropriate transformation methods.

The engineered host cells can be cultured in conventional nutrient media modified as appropriate for such activities as, for example, screening steps, activating promoters or selecting transformants. These cells can optionally be cultured into transgenic organisms.

Some examples of host cells that may be useful include but are not limited to (e.g., mammalian cells, yeast cells, bacterial cells, plant cells, fungal cells, archaebacterial cells, insect cells, and/or the like). Some examples of specific host cells include *E. coli, Pseudomonas, S. cerivisiae*, etc.

In certain embodiments, the non-natural amino acid is provided by introducing additional nucleic acid construct(s) into the translation system, wherein the additional nucleic acid construct(s) encode one or more proteins required for biosynthesis of the non-natural amino acid.

In one embodiment, the translation system is a cell, and the method further comprises disabling one or more genes encoding any endogenous tRNA that forms Watson-Crick base-pairing with the codon(s) at the specified position(s). In one embodiment, the translation system is a cell, and the method further comprises inhibiting one or more endogenous AARS that charges tRNAs that form Watson-Crick base-pairing with the codon(s) at the specified position(s).

Also provided by the invention are compositions that include a translation system. The translation systems may include one or both of an external mutant or modified tRNA (M-tRNA) and/or an external mutant or modified aminoacyl tRNA synthetase (M-RS). In embodiments that utilize M-tRNA and/or M-RS, may be derived from a species different from that of the cell.

In certain embodiments, the translation system comprises more than two different subject polynucleotides or nucleic acid constructs. Each of the polynucleotides, or nucleic acid constructs is capable of carrying a different non-natural amino acid. In certain embodiments, the first polynucleotide further comprises a first promoter sequence controlling the expression of the M-tRNA. In certain embodiments, the second polynucleotide further comprises a second promoter sequence controlling the expression of the modified AARS. The M-RS may have a relaxed substrate specificity, or the M-RS may be capable of charging the M-tRNA with an non-natural amino acid.

In certain embodiments, the M-tRNA is from a yeast, and the cell is an *E. coli* bacterium. In certain embodiments, the M-RS and the M-tRNA are from the same organism, and the organism is different from that of the cell. In certain embodiments, the M-RS and the M-tRNA are from a yeast, and cell is an *E. coli* bacterium.

In certain embodiments, the expression and/or function of an endogenous tRNA homologous to the tRNA is impaired or abolished. In certain embodiments, the expression of the endogenous tRNA is impaired/abolished by inhibiting the function of the endogenous tRNA's cognate AARS, thereby impairing/abolishing the charging of the endogenous tRNA. In certain embodiments, the expression of the endogenous tRNA is abolished by deleting the gene encoding the endogenous tRNA.

Under certain circumstances, the modified tRNA interacts with the wobble degenerate codon with an affinity at 37° C. of at least about 1.0 kcal/mole, or 1.5 kcal/mole, or even 2.0 kcal/mole more favorably than the interaction between its unmodified version and the wobble degenerate codon.

In enzyme kinetics, $k_{cat}$ is a first-order rate constant corresponding to the slowest step or steps in the overall catalytic pathway. The $k_{cat}$ represents the maximum number of target molecules of substrate which can be converted into product per enzyme target molecule per unit time (which occurs if the enzyme is "saturated" with substrate), and thus is often referred to as the turnover number. The $K_m$ is an apparent dissociation constant and is related to the enzyme's affinity for the substrate; it is the product of all the dissociation and equilibrium constants prior to the first irreversible step in the pathway. Often, it is a close measure of the enzyme-substrate dissociation constant. The $k_{cat}/K_m$ is a second-order rate constant which refers to the free enzyme (not enzyme-substrate complex) and is also a measure of the overall efficiency of the enzyme catalysis and is also referred to as the specificity constant.

In certain embodiments, the external mutant synthetase has improved or enhanced enzymatic properties, e.g., the $K_m$ is higher or lower, the $k_{cat}$ is higher or lower, the value of $k_{cat}/K_m$ is higher or lower or the like, for the non-natural amino acid compared to a naturally occurring amino acid, e.g., one of the 20 known amino acids. The Km of the M-RS is preferably equal to or lower for the non-natural amino acid than for the corresponding wild type natural amino acid.

In certain embodiments, the $k_{cat}/K_m$ values of the M-RS, or exogenous AARS, may range from 3-fold, 5-fold, 10-fold, 25-fold, 50-fold, 100-fold, 150-fold, 200-fold, 250-fold, 300-fold, 350-fold, 385-fold, 400-fold higher than for the naturally occurring amino acid.

In some exemplary embodiments, typical Km values for different amino acids with M-RS may range from approximately 15 microM, 20 microM, 30 microM, 50 microM, 75 microM, 100 microM, 150 microM, 200 microM, 300 microM, 400 microM, 440 microM, 500 microM, 1000 microM, 1500 microM, 2000 microM, 3000 microM, 4000 microM, 5000 microM, 6000 microM, or greater or any value therebetween.

Likewise, the $k_{cat}$ values of the M-RS or exogenous AARS, is preferably equal to or higher for the non-natural amino acid than for the natural amino acid. For example, kcat values for different amino acids with the corresponding M-RS may range from approximately 0.002 sec$^{-1}$, 0.0018 sec$^{-1}$, 0.0015 sec$^{-1}$, 0.014 sec$^{-1}$, 0.1 sec$^{-1}$, 0.3 sec$^{-1}$, 1 sec$^{-1}$, 3 sec$^{-1}$, 5 sec$^{-1}$, 8 sec$^{-1}$, 10 sec$^{-1}$, 13.3 sec$^{-1}$, 15 sec$^{-1}$, or higher.

Thus, the $k_{cat}$/Km of the M-RS or exogenous AARS, is optimally equal to or higher for the non-natural amino acid than for the natural wild type amino acid. Typical $k_{cat}$/Km values may range from approximately 0.0001 M$^{-1}$ s$^{-1}$, 0.0003 M$^{-1}$ s$^{-1}$, 0.005 M$^{-1}$ s$^{-1}$, 0.05 M$^{-1}$ s$^{-1}$, 0.5 M$^{-1}$ s$^{-1}$, 0.547 M$^{-1}$ s$^{-1}$, 1 M$^{-1}$ s$^{-1}$, 5 M$^{-1}$ s$^{-1}$, 10 M$^{-1}$ s$^{-1}$, 20 M$^{-1}$ s$^{-1}$, 30 M$^{-1}$ s$^{-1}$, 32 M$^{-1}$ s$^{-1}$, 500 M$^{-1}$ s$^{-1}$, 600 M$^{-1}$ s$^{-1}$, 1000 M$^{-1}$ s$^{-1}$, 5000 M$^{-1}$ s$^{-1}$, 1100 M$^{-1}$ s$^{-1}$.

In certain embodiments, the rate of the ATP-PPi exchange reaction catalyzed by AARSs in the presence of amino acids can be measured for the molecules of the present invention. It is generally considered that the aminoacyl-tRNA is formed through a two step process. In the first step, the amino acid is accepted by the synthetase and is adenylated, which results in a release of pyrophosphate (PPi). In the second step, the proper tRNA is accepbed by the synthetase, and the amino acid residue is transferred to the 2' or 3' OH of the 3'-terminal residue of the tRNA. Thus, measurement of the ATP-PPi exchange rate will indicate the formation of the aminoacyl-tRNA for a particular amino acid, a particular tRNA, or a particular AARS, depending on the desired goal.

In certain embodiments, the M-tRNA interacts with the wobble degenerate codon with an affinity at 37° C. of at least about 1.0 kcal/mole, 1.5 kcal/mole, 2.0 kcal/mole, 2.5 kcal/mole, 3.0 kcal/mole, 3.5 kcal/mole, 4.0 kcal/mole, 4.5 kcal/mole, 5.0 kcal/mole or greater (or any value therebetween) favorably than the interaction between its unmodified version and the wobble degenerate codon.

The methods of the invention can be practiced within a cell, which enables production levels of proteins to be made for practical purposes. Because of the high degree of conservation of the genetic code and the surrounding molecular machinery, method of the invention can be used in most cells. In at least one embodiment, the cells used are culturable cells (i.e., cells that can be grown under laboratory conditions).

The present invention includes host cells and cell lines already generated (including auxotropic prokaryotic strains and/or eukaryotic strains). In one embodiment, the host cell is generally capable of incorporating a non-natural amino acid into a peptide or polypeptide chain. In at least one embodiment, the host cell is capable of selectively or preferentially incorporating a non-natural amino acid into a peptide or polypeptide chain. In at least one embodiment, the host cell is capable of exclusively incorporating a non-natural amino acid into a peptide or polypeptide chain.

In the host-vector system, the production of an aminoacyl-tRNA synthetase can be controlled by a vector which comprises expression control elements that direct the production of the aminoacyl-tRNA synthetase. Preferably, the production of aminoacyl-tRNA synthetase is in an amount that enables efficient incorporation of the specified non-natural amino acid into the target molecule.

In the host-vector system, the production of an aminoacyl-tRNA synthetase can be controlled by a vector which comprises expression control elements that direct the production of the aminoacyl-tRNA synthetase. Preferably, the production of aminoacyl-tRNA synthetase is in an amount in excess of the level of naturally occurring aminoacyl-tRNA synthetase, such that the activity of the aminoacyl-tRNA synthetase is greater than naturally occurring levels.

In the host-vector system, the production of an antibody, fragment, or other target molecule can be controlled by a vector that comprises expression control elements for producing the modified target molecule. In certain aspects, the target molecule so produced is in an amount in excess of the level produced by a naturally occurring gene encoding the target molecule.

The host-vector system can constitutively express the AARS and induce to express the target molecule (e.g., antibody) by contacting the host-vector system with an inducer, such as isopropyl-β-D-thiogalactopyranoside (IPTG). The host-vector system can also be induced to express the aminoacyl-tRNA synthetase and/or the protein of interest by contacting the host-vector system with an inducer, such as IPTG. Other inducers include stimulation by an external stimulation such as heat shock.

In one embodiment, the host-vector system is grown in media lacking the natural amino acid and supplemented with a non-natural non-natural amino acid. It is in this media that the target polypeptide is induced for expression, thereby producing a modified target molecule that has incorporated at least one non-natural amino acid. This method is superior to existing methods as it improves the efficiency of incorporating non-natural amino acids into target molecules, and it increases the quantity of the modified target molecules so produced.

In another embodiment, the host-vector system may be used to regulate or induce the expression of a target molecule in host cells where such induction is desirable. In particular, the target molecule may be under control of an inducible promoter, or alternatively, under the control of a strong promoter when the polynucleotide contains one or more stop codon, frameshift codon, or bias codon at a specific position that prevents the target molecule from being efficiently translated.

The translational machinery of the host cell will read through the specified codon, effectively inducing expression of the target molecule, in the presence of the host-vector system and upon addition of the non-natural amino acid. This type of inducible expression may increase the ability to manufacture high levels of toxic proteins, and may be particularly useful in mammalian cells wherein inducible protein synthesis is limited. Thus, protein products, such as monoclonal antibodies, are expressed constitutively. In this manner, an inducible system of protein synthesis enables increased expression of molecules that would otherwise be toxic to the host cells. Moreover, it facilitates incorporation of non-natural amino acids in mammalian cells when the non-natural amino acid itself is toxic.

Other methods for modifying target molecules include constructing expression libraries (e.g., U.S. Pat. Nos. 5,783, 431; 5,824,485, hereby incorporated by reference in their entireties). Libraries may be composed of cDNA or genomic sequences from a single organism or species, or multiple organisms or species. The sequences are operably linked to proper regulatory sequences in an expression cassette. The sequences may also be generally optionally randomly concatenated to further enhance diversity. Expression libraries may be preselected or prescreened for a particular sequence that encodes a functional product. Libraries may also be generated that are biased towards particular sequences that encode target molecules with particularly desired activities.

Another method of incorporating one or more non-natural amino acid residues is by utilizing bias codons for which there is a low abundance of corresponding tRNA such that the presence of a bias codon significantly slows translation of the protein. The bias codon specifies the non-natural amino acid through the introduction of a tRNA that decodes the bias codon in the host cell. The tRNA is subsequently aminoacylated by an aminoacyl-tRNA synthetase specific for the non-natural amino acid.

In one embodiment, the codon that specifies a non-natural amino acid is a codon that is decoded by a two box set of tRNAs, a four box set of tRNAs, or a six box set of tRNAs. This includes, but is not limited to, serine, arginine, and leucine. The specified codon may be selected from one box that will not base pair by Watson and Crick or Wobble with tRNAs for the same amino acids. For example, serine tRNAs that decode UCU, UCC, UCA, and UCG codons, will not base pair with the serine AGU or AGC codons. Thus, the non natural amino acid, used by a modified SerRS, may be specified by the AGU (Wobble) codon. All other serine residues in the protein of interest would be specified by UCU, UCC, UCA, and UCG. In this way, the non natural amino acid would be specifically incorporated at the AGU codon.

In one embodiment, the tRNA may be one that is normally used by a different amino acyl tRNA synthetase, but whose aminoacylation been changed due to modification or mutation of the tRNA at a critical identity determining position.

For example, the Gln tRNA, with certain modification including a change to the opal anticodon, is aminoacylated by the TrpRS. Conversely, the Trp tRNA may be used by the GlnRS to decode an Amber stop codon.

In one embodiment, the AARS is a chimeric fusion of 2 different synthetases such that the aminoacylation function of one synthetase is fused to the tRNA binding and identity elements of another. This will result in the aminoacylation of a tRNA with an incorrect amino acid, and the incorporation of that amino acid at the codon normally reserved for another amino acid. The chimeric AARS may be further modified to incorporate a non natural amino acid. The derivation of the chimeric AARS may utilize computational biology, gene shuffling, or other domain shuffling strategies.

In the case of using an amber or wobble stop codon, such codon may be placed anywhere in the target molecule, depending on the desired goal. For example, such codon may be placed at the preferred site for attaching a chemical moiety, such as polyethylene glycol. Following insertion of the stop codon, a non-natural amino acid residue (such as p-bromo-phenylalanine) is incorporated at the codon site by any process described herein or known in the art. For instance, the non-natural amino acid may be incorporated via an auxotrophic host cell, by M-RS, by M-tRNA molecules, or any combination thereof. If utilizing an auxotrophic host cell, the host cell may be a single auxotroph (i.e. deficient in or unable to synthesize a single particular amino acid, therefore able to incorporate the single corresponding non-natural amino acid from the culture media) or a multiple auxotroph (i.e. incapable of synthesizing more than one amino acid, thereby capable of incorporating more than one non-natural amino acid from the culture media). Thus, the non-natural amino acid is specifically incorporated without disrupting other residues, and without the need to screen large numbers of mutants.

As one of skill in the art would appreciate that any of the aforementioned methods to modify or alter a target molecule may incorporate radioactive, doped or other tags or markers in the process of modification.

Generation of AARS by Mutagenesis and Selection/Screening

In certain embodiments, the AARS capable of charging a particular M-tRNA with a particular non-natural amino acid can be obtained by mutagenesis of the AARS to generate a library of candidates, followed by screening and/or selection of the candidate AARS's capable of their desired function. Such M-RS and M-tRNA molecules may be used for in vitro or in vivo production of desired target molecule with modified non-natural amino acids.

Libraries of M-RSs can be generated using various mutagenesis techniques known in the art. For example, the M-RSs can be generated by site-specific mutations, random mutations, diversity generating recombination mutations, chimeric constructs, and by other methods described herein or known in the art.

In one embodiment, selecting (and/or screening) the library of RSs (optionally mutant RSs) for members that are active, e.g., that aminoacylate a mutant tRNA (M-tRNA) in the presence of an non-natural amino acid and a natural amino acid, includes: introducing a positive selection or screening marker, e.g., an antibiotic resistance gene, or the like, and the library of (optionally mutant) RSs into a plurality of cells, wherein the positive selection and/or screening marker comprises at least one codon, whose translation (optionally conditionally) depends on the ability of a candidate M-RS to charge the M-tRNA (with either a natural and/or a non-natural amino acid); growing the plurality of cells in the presence of a selection agent; identifying cells that survive (or show a specific response) in the presence of the selection and/or screening agent by successfully translating the codon in the positive selection or screening marker, thereby providing a subset of positively selected cells that contains the pool of active (optionally mutant) RSs. Optionally, the selection and/or screening agent concentration can be varied. Preferably, the cells do not contain any functional endogenous tRNA/RS pair that can help to translate the codon. The endogenous tRNA/RS pair may be disabled by gene deletion and/or RS inhibitors.

Since many essential genes of the cell likely also contain codons that rely on the ability of the M-RS to charge the M-tRNA at the absence of functional endogenous translational machinery, in certain embodiments no extra positive selection markers are needed for the positive selection process—the survival of the cell can be used as a confirmation of positive selection.

In other embodiments, positive selection markers may be used; such as a chloramphenicol acetyltransferase (CAT) gene. Optionally, the positive selection marker is a β-lactamase gene. In another aspect the positive screening marker comprises a fluorescent or luminescent screening marker or an affinity based screening marker (e.g., a cell surface marker).

In a similar embodiment, a cell-free in vitro system may be used to test the ability of M-RS to charge M-tRNA in a positive screening. In one embodiment, negatively selecting or screening the pool for active RSs (optionally mutants) that preferentially aminoacylate the M-tRNA in the absence of the non-natural amino acid includes: introducing a negative selection or screening marker with the pool of active (optionally mutant) RSs from the positive selection or screening into a plurality of translational systems, wherein the negative selection or screening marker comprises at least one codon (e.g., codon for a toxic marker gene, e.g., a ribonuclease barnase gene), whose translation depends on the ability of a candidate M-RS to charge the M-tRNA; and identifying the translation system that shows a specific screening response in a first media supplemented with the non-natural amino acid and a screening or selection agent, but fails to show the specific response in a second media supplemented with the natural amino acid and the selection or screening agent, thereby providing surviving cells or screened cells with the at least one recombinant M-RS.

In one aspect, the concentration of the selection (and/or screening) agent is varied. In some aspects the first and second organisms are different. Thus, the first and/or second organism optionally comprises: a prokaryote, a eukaryote, a mammal, an *Escherichia coli*, a fungi, a yeast, an archaebacterium, a *eubacterium*, a plant, an insect, a protist, etc. In other embodiments, the screening marker comprises a fluorescent or luminescent screening marker or an affinity based screening marker.

In a related aspect, methods for producing a recombinant mutant tRNA (M-tRNA) include: (a) generating a library of mutant tRNAs derived from at least one tRNA, from a first organism; (b) selecting (e.g., negatively selecting) or screening the library for (optionally mutant) tRNAs that are aminoacylated by an aminoacyl-tRNA synthetase (RS) from a second organism in the absence of a RS from the first organism, thereby providing a pool of tRNAs (optionally mutant); and, (c) selecting or screening the pool of tRNAs (optionally mutant) for members that are aminoacylated by an introduced mutant RS (M-RS), thereby providing at least one recombinant M-tRNA; wherein the at least one recombinant M-tRNA recognizes a degenerate codon and is not efficiency recognized by the RS from the second organism and is preferentially aminoacylated by the M-RS.

Methods for generating specific M-tRNA/M-RS pairs are provided. Methods include: (a) generating a library of mutant tRNAs derived from at least one tRNA from a first organism; (b) negatively selecting or screening the library for (optionally mutant) tRNAs that are aminoacylated by an aminoacyl-tRNA synthetase (RS) from a second organism in the absence of a RS from the first organism, thereby providing a pool of (optionally mutant) tRNAs; (c) selecting or screening the pool of (optionally mutant) tRNAs for members that are aminoacylated by an introduced mutant RS (M-RS), thereby providing at least one recombinant M-tRNA. The at least one recombinant M-tRNA preferentially recognizes a degenerate codon and is not efficiently recognized by the RS from the second organism and is preferentially aminoacylated by the M-RS. The method also includes (d) generating a library of (optionally mutant) RSs derived from at least one aminoacyl-tRNA synthetase (RS) from a third organism; (e) selecting or screening the library of mutant RSs for members that preferentially aminoacylate the at least one recombinant M-tRNA in the presence of an non-natural amino acid and a natural amino acid, thereby providing a pool of active (optionally mutant) RSs; and, (f) negatively selecting or screening the pool for active (optionally mutant) RSs that preferentially aminoacylate the at least one recombinant M-tRNA in the absence of the non-natural amino acid, thereby providing the at least one specific M-tRNA/M-RS pair, wherein the at least one specific M-tRNA/M-RS pair comprises at least one recombinant M-RS that is specific for the non-natural amino acid and the at least one recombinant M-tRNA. Specific M-tRNA/M-RS pairs produced by the methods are included. Additionally, such methods include wherein the first and third organism are the same (e.g., *Methanococcus jannaschii*).

The various methods of the invention (above) optionally comprise wherein selecting or screening comprises one or more positive or negative selection or screening, e.g., a change in amino acid permeability, a change in translation efficiency, and a change in translational fidelity. Additionally, the one or more change is optionally based upon a mutation in one or more gene in an organism in which an external mutant tRNA-tRNA synthetase pair are used to produce such protein. Selecting and/or screening herein optionally comprises wherein at least 2 codons within one or more selection gene or within one or more screening gene are used. Such multiple codons are optionally within the same gene or within different screening/selection genes. Additionally, the optional multiple codons are optionally different codons or comprise the same type of codons.

Aminoacyl-tRNA Synthetases

The aminoacyl-tRNA synthetase (used interchangeably herein with AARS or "synthetase") used in the methods of the invention can be a naturally occurring synthetase derived from a different organism, a mutated or modified synthetase or a wholly de novo designed synthetase.

The synthetase used can recognize the desired non-natural amino acid selectively over other amino acids available to the cell. For example, when the non-natural amino acid to be used is structurally related to a naturally occurring amino acid in the cell, the synthetase should charge the M-tRNA target molecule with the desired non-natural amino acid with an efficiency at least substantially equivalent to that of, and more preferably at least about twice, 3 times, 4 times, 5 times or more than that of the naturally occurring amino acid. However, in cases in which a well-defined protein product is not necessary, the synthetase can have relaxed specificity for charging amino acids. In such an embodiment, a mixture of external mutant tRNAs could be produced, with various amino acids or analogs.

Preferably, the modified AARS specifically or preferentially charges the non-natural amino acid to the modified tRNA over any natural amino acid. In a preferred embodiment, the specificity constant for activation of the analog by the modified AARS (defined as $k_{cat}/K_M$) is equal to or greater than at least about 2-fold larger than that for the natural amino acid, preferably about 3-fold, 4-fold, 5-fold, 6 fold, 7 fold, 8 fold, 9 fold, 10 fold or more than that for the natural amino acid.

In certain embodiments, the synthetase can be designed using computational techniques such as those described in Datta of al., *J. Am. Chem. Soc.* 124: 5652-5653, 2002, and in copending U.S. patent application Ser. No. 10/375,298 (or US patent application publication US20040053390A1, all of which are hereby incorporated by reference in their entireties).

Domain Shuffling Design of an AARS

For an M-RS or exogenous AARS that is utilized for incorporation of a non-natural amino acid by way of a borrowed codon, the M-RS or exogenous AARS may be designed rationally by identifying the amino acid binding domains and tRNA identity determining domains of the first and second AARS. In the preferred embodiment, the first and second AARS are of related or homologous structure. The domains responsible may be defined and redistributed to create M-RS molecules that contain the amino acid binding domains of one MRS and the tRNA identity elements of the other.

The shuffling of domains of the two AARS molecules of the borrowed codon may be accomplished by using directed gene shuffling in which several related AARS molecules of at least two different specificities are subjected to PCR mediated recombination in order to generate a library. The library may subsequently be screened by methods known in the art in order to select the M-RS or exogenous AARS of the preferred specificity. In certain embodiments, the M-RS may be generated from within the same amino acid family, from across different amino acid families, and/or from different source organisms.

Computational Design of a Molecule

Specifically, in one embodiment, the subject method partly depends on the design and engineering of a wild type molecule to a modified form. One particular method is described in more detail in US patent application publication US20040053390A1, the entire contents of which are incorporated herein by reference.

Briefly, the methods described therein relate to computational tools for modifying a particular target molecule through mutation or modification.

According to the method, a rotamer library for the non-natural amino acid is built by varying its torsional angles to create rotamers that might be incorporated into the target molecule of interest. The geometric orientation of the backbone of the non-natural amino acid is specified by the crystallographic orientation of the backbone of the natural substrate in the crystal structure.

The protocol may also employ a computational method to enhance the interactions between the ligand or receptor binding site of the target molecule of interest. Enhancing these interactions may occur by scaling up the pair-wise energies in the energy calculations between the ligand or receptor and the amino acids allowed at the design positions on the target molecule. In an optimization calculation where the protein-ligand/receptor interactions are scaled up compared to the intra-protein interactions, sequence selection is biased toward selecting amino acids to be those that have favorable interaction with the ligand/receptor.

Available Sequence and Structural Information for Non-Natural Amino Acids

In the method of the present invention, an accurate description of the target molecule is important for the computational design approach, since the energy calculations depend on the crystal structure for the protein backbone descriptions. However, in many cases it may be perfectly acceptable to use a known crystal structure of a homologous protein (for example, a homolog from a related species) or even a conserved domain to substitute for an unknown crystal structure of the target molecule to be modified and/or the non-natural amino acid to be incorporated. It may be preferred that the modified target molecule binds to its corresponding ligand/receptor in the same orientation as the unmodified target molecule, since this orientation may be important for the structure and/or function of the target molecule and/or its ligand/receptor.

The target molecule to be modified may be from any organism, including prokaryotes and eukaryotes, such as bacteria, fungi, extremeophiles such as the archebacteria, worms, insects, fish, amphibian, birds, animals (particularly mammals and particularly human) and plants.

The crystal structures of the target molecule to be modified may be derived anew or provided by known structure databases, such as the Brookhaven Protein Data Bank (PDB, see Bernstein et al., *J. Mol. Biol.* 112: 535-542, 1977). A structure database or Molecular Modeling DataBase (MMDB) contains experimental data from crystallographic and NMR structure determinations. The data for MMDB are obtained from the Protein Data Bank (PDB). The NCBI (National Center for Biotechnology Information) has cross-linked structural data to bibliographic information, to the sequence databases and to the NCBI taxonomy. Cn3D, the NCBI 3D structure viewer, can be used for easy interactive visualization of molecular structures from Entrez.

The Entrez 3D Domains database contains protein domains from the NCBI Conserved Domain Database (CDD). Computational biologists define conserved domains based on recurring sequence patterns or motifs. CDD currently contains domains derived from two popular collections, Smart and Pfam, plus contributions from colleagues at NCBI, such as COG. The source databases also provide descriptions and links to citations. Since conserved domains correspond to compact structural units, CDs contain links to 3D-structure via Cn3D whenever possible.

To identify conserved domains in a protein sequence, the CD-Search service employs the reverse position-specific BLAST algorithm. The query sequence is compared to a position-specific score matrix prepared from the underlying conserved domain alignment. Hits may be displayed as a pairwise alignment of the query sequence with a representative domain sequence, or as a multiple alignment. CD-Search now is run by default in parallel with protein BLAST searches. While the user waits for the BLAST queue to further process the request, the domain architecture of the query may already be studied. In addition, CDART, the Conserved Domain Architecture Retrieval Tool allows user to search for proteins with similar domain architectures. CDART uses precomputed CD-search results to quickly identify proteins with a set of domains similar to that of the query. (For more details, see Marchler-Bauer et al., *Nucleic Acids Res.* 31: 383-387, 2003; and Marchler-Bauer et al., *Nucleic Acids Res.* 30: 281-283, 2002, both of which are hereby incorporated by reference in their entireties).

Alternatively, in certain embodiments, the exact crystal structure of a particular target molecule is not known but its protein sequence is similar or homologous to a known sequence with a known crystal structure. In such instances, it is expected that the conformation of the target molecule will be similar to the known crystal structure of the homologous sequence. The known structure may, therefore, be used as the structure for the target molecule, or may be used to predict the structure of the target molecule (i.e., in "homology modeling" or "molecular modeling"). As a particular example, the Molecular Modeling Database (MMDB) described above (see, Wang et al., *Nucl. Acids Res.* 2000, 28:243-245; Marchler-Bauer et al., *Nucl. Acids Res.* 1999, 27: 240-243, which are hereby incorporated by reference in their entireties) provides search engines that may be used to identify proteins and/or nucleic acids that are similar or homologous to a protein sequence (referred to as "neighboring" sequences in the MMDB), including neighboring sequences whose three-dimensional structures are known. The database further provides links to the known structures along with alignment and visualization tools, such as Cn3D (developed by NCBI), RasMol, etc., whereby the homologous and parent sequences may be compared and a structure may be obtained for the parent sequence based on such sequence alignments and known structures.

The homologous sequence with known 3D-structure may be at least about 60%, or at least about 70%, or at least about 80%, or at least about 90%, or at least about 95% identical to the target molecule of interest. In the few cases where the structure for a particular target molecule's gene or protein sequence may not be known or available, it is typically possible to determine the structure using routine experimental techniques (for example, X-ray crystallography and Nuclear Magnetic Resonance (NMR) spectroscopy) and without undue experimentation. (See, e.g., *NMR of Macromolecules: A Practical Approach*, G. C. K. Roberts, Ed., Oxford University Press Inc., New York (1993); Ishima and Torchia, *Nat. Struct. Biol.* 7: 740-743, 2000; Gardner and Kay, *Annu. Rev. Bioph. Biom.* 27: 357-406, 1998; Kay, *Biochem. Cell. Biol.* 75: 1-15, 1997; Dayie et al., *Annu. Rev. Phys. Chem.* 47: 243-282, 1996; Wuthrich, *Acta Cyrstallogr. D* 51: 249-270, 1995; Kahn et al., *J. Synchrotron Radiat.* 7: 131-138, 2000; Oakley and Wilce, *Clin. Exp. Pharmacol. P.* 27: 145-151, 2000; Fourme et al., *J. Synchrotron Radiat.* 6: 834-844, 1999, all of which are hereby incorporated by reference in their entireties).

Alternatively, in other embodiments, the three-dimensional structure of a target molecule's nucleic acid or amino acid sequence may be calculated from the sequence itself and using ab initio molecular modeling techniques already known in the art. (See e.g., Smith et al., *J. Comput. Biol.* 4: 217-225, 1997; Eisenhaber et al., *Proteins* 24: 169-179, 1996; Bohm, *Biophys Chem.* 59: 1-32, 1996; Fetrow and Bryant, *BioTechnol.* 11: 479-484, 1993; Swindells and Thornton, *Curr. Opin. Biotech.* 2: 512-519, 1991; Levitt et al., *Annu. Rev. Biochem.* 66: 549-579, 1997; Eisenhaber et al., *Crit. Rev. Biochem. Mol.* 30:1-94, 1995; Xia et al., *J. Mol. Biol.* 300: 171-185, 2000; Jones, *Curr. Opin. Struc. Biol.* 10: 371-379, 2000 all of which are hereby incorporated by reference in their entireties). Three-dimensional structures obtained from ab initio modeling are typically less reliable than structures obtained using empirical (e.g., NMR spectroscopy or X-ray crystallography) or semi-empirical (e.g., homology modeling) techniques. However, such structures will generally be of sufficient quality, although less preferred, for use in the methods of this invention.

Methods for Predicting 3D Structure Based on Sequence Homology

For target molecules to be modified that have not been crystallized or been the focus of other structural determinations, a computer-generated molecular model of the target molecule and its ligand/receptor binding site can nevertheless be generated using any of a number of techniques available in the art.

Computer programs for performing energy minimization routines are commonly used to generate molecular models. For example, both the CHARMM (Brooks et al, (1983) *J Comput Chem* 4:187-217) and AMBER (Weiner et al (1981) *J. Comput. Chem.* 106: 765) algorithms handle all of the molecular system setup, force field calculation, and analysis (see also, Eisenfield et al. (1991) *Am J Physiol* 261:C376-386; Lybrand (1991) *J Pharm Belg* 46:49-54; Froimowitz (1990) *Biotechniques* 8:640-644; Burbam et al. (1990) *Proteins* 7:99-111; Pedersen (1985) *Environ Health Perspect* 61:185-190; and Kini et al. (1991) *J Biomol Struct Dyn* 9:475-488). In addition, Hier Dock or Monte Carlo calculations may be employed (Datta, et al., *Protein Science*, 13:2693-2705 (2004). All of these cited references are hereby incorporated by reference in their entireties.

At the heart of these programs is a set of subroutines that, given the position of every atom in the model, calculate the total potential energy of the system and the force on each atom. These programs may utilize a starting set of atomic coordinates, the parameters for the various terms of the potential energy function, and a description of the molecular topology (the covalent structure). Common features of such molecular modeling methods include: provisions for handling hydrogen bonds and other constraint forces; the use of periodic boundary conditions; and provisions for occasionally adjusting positions, velocities, or other parameters in order to maintain or change temperature, pressure, volume, forces of constraint, or other externally controlled conditions.

Most conventional energy minimization methods use the input coordinate data and the fact that the potential energy function is an explicit, differentiable function of Cartesian coordinates, to calculate the potential energy and its gradient (which gives the force on each atom) for any set of atomic positions. This information can be used to generate a new set of coordinates in an effort to reduce the total potential energy and, by repeating this process over and over, to optimize the molecular structure under a given set of external conditions.

In general, energy minimization methods can be carried out for a given temperature, Ti, which may be different than the docking simulation temperature, To. Upon energy minimization of the target molecule at Ti, coordinates and velocities of all the atoms in the system are computed. Additionally, the normal modes of the system are calculated. It will be appreciated by those skilled in the art that each normal mode is a collective, periodic motion with all parts of the system moving in phase with each other and that the motion of the target molecule is the superposition of all normal modes. For a given temperature, the mean square amplitude of motion in a particular mode is inversely proportional to the effective force constant for that mode, so that the motion of the target molecule will often be dominated by the low frequency vibrations.

After the molecular model has been energy minimized at Ti, the system is "heated" or "cooled" to the simulation temperature, To, by carrying out an equilibration run where the velocities of the atoms are scaled in a step-wise manner until the desired temperature, To, is reached. The system is further equilibrated for a specified period of time until certain properties of the system, such as average kinetic energy, remain constant. The coordinates and velocities of each atom are then obtained from the equilibrated system.

Further energy minimization routines can also be carried out. For example, a second class of methods involves calculating approximate solutions to the constrained EOM for the protein. These methods use an iterative approach to solve for the Lagrange multipliers and, typically, only need a few iterations if the corrections required are small. The most popular method of this type, SHAKE (Ryckaert et al. (1977) *J. Comput. Phys.* 23:327; and Van Gunsteren et al. (1977) *Mol. Phys.* 34:1311, both of which are hereby incorporated by reference in their entireties) is easy to implement and scales as O(N) as the number of constraints increases. An alternative method, RATTLE (Anderson (1983) *J. Comput. Phys.* 52:24, hereby incorporated by reference) is based on the velocity version of the Verlet algorithm.

In other embodiments, rather than holding the identity of the non-natural amino acid constant and varying the molecule's structure (by modeling several different mutant structures), the subject method is carried out using the molecular model(s) for a single modified target molecule (e.g., in which one more non-anchor amino acid residues are changed) and sampling a variety of different non-natural amino acids or potential fragments thereof, to identify analogs which are likely to support the molecule's structure and/or function. This approach can make use of coordinate libraries for non-natural amino acids (including rotamer variants) or libraries of functional groups and spacers that can be joined to form the side-chain of an non-natural amino acid.

There are a variety of computational methods that can be readily adapted for identifying the structure of non-natural amino acids that would have appropriate steric and electronic properties to incorporate in the target molecule to be modified. (See, for example, Cohen et al. (1990) *J. Med. Cam.* 33: 883-894; Kuntz et al., (1982) *J. Mol. Biol* 161: 269-288; DesJarlais (1988) *J. Med. Cam.* 31: 722-729; Bartlett et al. (1989) (*Spec. Publ., Roy. Soc. Chem.*) 78: 182-196; Goodford et al. (1985) *J. Med. Cam.* 28: 849-857; DesJarlais et al. *J. Med. Cam,* 29: 2149-2153 all of which are hereby incorporated by reference in their entireties). Directed methods generally fall into two categories: (1) design by analogy in which 3-D structures of known molecules (such as from a crystallographic database) are docked to the modified target molecule structure and scored for goodness-of-fit; and (2) de novo design, in which the non-natural amino acid model is constructed piece-wise in the modified target molecule.

In an illustrative embodiment, the design of potential non-natural amino acids that may function with a particular modified target molecule begins from the general perspective of shape complimentary for the target molecule's structure, and a search algorithm is employed which is capable of scanning a database of small target molecules of known three-dimensional structure for candidates which fit geometrically into the substrate binding site. Such libraries can be general small target molecule libraries, or can be libraries directed to non-natural amino acids or small target molecules that can be used to create non-natural amino acids. It is not expected that the target molecules found in the shape search will necessarily be leads themselves, since no evaluation of chemical interaction necessarily be made during the initial search. Rather, it is anticipated that such candidates might act as the framework for further design, providing molecular skeletons to which appropriate atomic replacements can be made. Of course, the chemical complimentary of these target molecules can be evaluated, but it is expected that atom types will be changed to maximize the electrostatic, hydrogen bonding, and hydrophobic interactions with the ligand—receptor binding site. Most algorithms of this type provide a method for finding a wide assortment of chemical structures that may be complementary to the shape of the target molecule's ligand/receptor binding site.

For instance, each of a set of small target molecules from a particular database, such as the Cambridge Crystallographic Data Bank (CCDB) (Allen et al. (1973) *J. Chem. Doc.* 13: 119), is individually docked to the modified target molecule in a number of geometrically permissible orientations with use of a docking algorithm. In a preferred embodiment, a set of computer algorithms called DOCK, can be used to characterize the shape of invaginations and grooves that form the binding site. See, for example, Kuntz et al. (1982) *J. Mol. Biol* 161: 269-288.

The orientations are evaluated for goodness-of-fit and the best are kept for further examination using molecular mechanics programs, such as AMBER or CHARMM. Such algorithms may provide several advantages. First, such algorithms can retrieve a remarkable diversity of molecular architectures. Second, the best structures have, in previous applications to other proteins, demonstrated impressive shape complementarity over an extended surface area. Third, the overall approach appears to be quite robust with respect to small uncertainties in positioning of the candidate atoms.

In certain embodiments, the subject method can utilize an algorithm described by Goodford (1985, *J. Med. Chem.* 28:849-857) and Boobbyer et al. (1989, *J. Med. Chem.* 32:1083-1094), both of which are hereby incorporated by reference. Those papers describe a computer program (GRID) which seeks to determine regions of high affinity for different chemical groups (termed probes) on a molecular surface. GRID provides a tool for suggesting modifications to known ligands that might enhance binding. It may be anticipated that some of the sites discerned by GRID as regions of high affinity correspond to "pharmacophoric patterns" determined inferentially from a series of known ligands. As used herein, a pharmacophoric pattern is a geometric arrangement of features of the anticipated non-natural amino acid that is believed to be important for binding. Goodsell and Olson (1990, *Proteins: Struct Funct Genet.* 8:195-202) have used the Metropolis (simulated annealing) algorithm to dock a single known ligand into a target protein, and their approach can be adapted for identifying suitable non-natural amino acids for docking with the target molecule. This algorithm can allow torsional flexibility in the amino acid side-chain and use GRID interaction energy maps as rapid lookup tables for computing approximate interaction energies.

Yet a further embodiment of the present invention utilizes a computer algorithm such as CLIX which searches such databases as CCDB for small target molecules which can be oriented in the ligand/receptor binding site of the target molecule in a way that is both sterically acceptable and has a high likelihood of achieving favorable chemical interactions between the candidate target molecule and the surrounding amino acid residues. The method is based on characterizing the substrate binding site in terms of an ensemble of favorable binding positions for different chemical groups and then searching for orientations of the candidate target molecules that cause maximum spatial coincidence of individual candidate chemical groups with members of the ensemble. The current availability of computer power dictates that a computer-based search for novel ligands follows a breadth-first strategy. A breadth-first strategy aims to reduce progressively the size of the potential candidate search space by the application of increasingly stringent criteria, as opposed to a depth-first strategy wherein a maximally detailed analysis of one candidate is performed before proceeding to the next. CLIX conforms to this strategy in that its analysis of binding is rudimentary and seeks to satisfy the necessary conditions of steric fit by having individual groups in "correct" places for bonding, without imposing the sufficient condition that favorable bonding interactions actually occur. A ranked "shortlist" of target molecules, in their favored orientations, is produced which can then be examined on a target molecule-by-target molecule basis, using computer graphics and more sophisticated molecular modeling techniques. CLIX is also capable of suggesting changes to the substituent chemical groups of the candidate target molecules that might enhance binding. Again, the starting library can be of non-natural amino acids or of target molecules which can be used to generate the side-chain of an non-natural amino acid. The algorithmic details of CLIX is described in Lawerence et al. (1992) *Proteins* 12:31-41, hereby incorporated by reference in its entirety.

Yet another embodiment of a computer-assisted molecular design method for identifying non-natural amino acids that may be utilized by a predetermined modified target molecule comprises the de novo synthesis of potential inhibitors by algorithmic connection of small molecular fragments that will exhibit the desired structural and electrostatic complementarity with the ligand/receptor binding site of the target molecule.

In yet another embodiment, potential non-natural amino acids can be determined using a method based on an energy minimization-quenched molecular dynamics algorithm for determining energetically favorable positions of functional groups in the target molecule to be modified. The method can aid in the design of target molecules that incorporate such functional groups by modification of known amino acid and non-natural amino acids or through de novo synthesis.

For example, the multiple copy simultaneous search method (MCSS) described by Miranker et al. (1991) *Proteins* 11: 29-34, herein incorporated by reference, can be adapted for use in the subject method. To determine and characterize a local minima of a functional group in the force field of the protein, multiple copies of selected functional groups are first distributed in an amino acid position of interest on the target molecule to be modified. Energy minimization of these copies by molecular mechanics or quenched dynamics yields the distinct local minima. The neighborhood of these minima can then be explored by a grid search or by constrained minimization. In one embodiment, the MCSS method uses the classical time dependent Hartee (TDH) approximation to simultaneously minimize or quench many identical groups in the force field of the protein.

Implementation of the MCSS algorithm requires a choice of functional groups and a molecular mechanics model for each of them. Groups must be simple enough to be easily characterized and manipulated (3-6 atoms, few or no dihedral degrees of freedom), yet complex enough to approximate the steric and electrostatic interactions that the functional group would have in the selected position in the target molecule to be modified. A preferred set is, for example, one in which most organic target molecules can be described as a collection of such groups (*Patai's Guide to the Chemistry of Functional Groups*, ed. S. Patai (New York: John Wiley, and Sons, (1989), hereby incorporated by reference). This includes fragments such as acetonitrile, methanol, acetate, methyl ammonium, dimethyl ether, methane, and acetaldehyde.

Determination of the local energy minima in the binding site requires that many starting positions be sampled. This can be achieved by distributing, for example, 1,000-5,000 groups at random inside a sphere centered on the binding site; only the space not occupied by the protein needs to be considered. If the interaction energy of a particular group at a certain location with the protein is more positive than a given cut-off (e.g., 5.0 kcal/mole) the group is discarded from that site. Given the set of starting positions, all the fragments are minimized simultaneously by use of the TDH approximation (Elber et al. (1990) *J. Am. Chem. Soc.* 112: 9161-9175), hereby incorporated by reference. In this method, the forces on each fragment consist of its internal forces and those due to the protein. The essential element of this method is that the interactions between the fragments are omitted and the forces on the protein are normalized to those due to a single fragment. In this way simultaneous minimization or dynamics of any number of functional groups in the field of a single protein can be performed.

Minimization is performed successively on subsets of, e.g., 100, of the randomly placed groups. After a certain number of step intervals, such as 1,000 intervals, the results can be examined to eliminate groups converging to the same minimum. This process is repeated until minimization is complete (e.g., RMS gradient of 0.01 kcal/mole/Å). Thus the resulting energy minimized set of target molecules comprises what amounts to a set of disconnected fragments in three dimensions representing potential side-chains for non-natural amino acids.

The next step then is to connect the pieces with spacers assembled from small chemical entities (atoms, chains, or ring moieties) to form non-natural amino acids, e.g., each of the disconnected can be linked in space to generate a single target molecule using such computer programs as, for example, NEWLEAD (Tschinke et al. (1993) *J. Med. Chem.* 36: 3863, 3870), herein incorporated by reference. The procedure adopted by NEWLEAD executes the following sequence of commands (1) connect two isolated moieties, (2) retain the intermediate solutions for further processing, (3) repeat the above steps for each of the intermediate solutions until no disconnected units are found, and (4) output the final solutions, each of which is a single molecule. Such a program can use for example, three types of spacers: library spacers, single-atom spacers, and fuse-ringspacers. The library spacers are optimized structures of small molecules such as ethylene, benzene and methylamide. The output produced by programs such as NEWLEAD consist of a set of molecules containing the original fragments now connected by spacers. The atoms belonging to the input fragments maintain their original orientations in space. The molecules are chemically plausible because of the simple makeup of the spacers and functional groups, and energetically acceptable because of the rejection of solutions with van-der Waals radii violations.

In addition, the order in which the steps of the present method are performed is purely illustrative in nature. In fact, the steps can be performed in any order or in parallel, unless otherwise indicated by the present disclosure.

Furthermore, the method of the present invention may be performed in either hardware, software, or any combination thereof, as those terms are currently known in the art. In particular, the present method may be carried out by software, firmware, or microcode operating on a computer or computers of any type. Additionally, software embodying the present invention may comprise computer instructions in any form (e.g., source code, object code, interpreted code, etc.) stored in any computer-readable medium (e.g., ROM, RAM, magnetic media, punched tape or card, compact disc (CD) in any form, DVD, etc.). Furthermore, such software may also be in the form of a computer data signal embodied in a carrier wave, such as that found within the well-known Web pages transferred among devices connected to the Internet. Accordingly, the present invention is not limited to any particular platform, unless specifically stated otherwise in the present disclosure.

Exemplary computer hardware means suitable for carrying out the invention can be a Silicon Graphics Power Challenge server with 10 R10000 processors, for example, running in parallel. Suitable software development environment includes, for example, CERIUS2 by Biosym/Molecular Simulations (San Diego, Calif.), or other equivalents.

The computational method described above has been effectively used in modifying enzymes of the protein synthesis machinery (e.g., AARS) to allow incorporation of unnatural amino acids. The same suite of computational tools can also be leveraged to design the final products (e.g., monoclonal antibodies or other therapeutics) in which the unnatural amino acids would be incorporated so as to enhance or modify their structural or functional properties.

Testing for Incorporation

It is further recognized that if one desired goal for modifying the molecule is to retain at least one native function, then testing of its function may be conducted following each round of amino acid modification (including substitution of one or more particular amino acid residues). Methods of identifying incorporation of non-natural amino acids and/or chemical moieties are well known in the art. For example, flow cytommetry, Northern blots, Western blots, PCR, RNA microsequencing, reporter assays, FLAG epitopes, binding to other molecules (such as streptavidin), radio-label detection, colorimetric assays, RNAse protection assays, mass spectrometry (including MALDI and MALDI-TOF), chromatography (such as HPLC), NMR, IR, ELISA, fluorescent microscopy and any combination of these or other techniques known in the art may be implemented.

In addition to incorporating one or more members of a particular amino acid family into the modified target molecule, it is recognized that other amino acid residues may be physically or chemically altered (including substituted) in order to promote or retain proper molecular structure (i.e. folding) and/or at least one native function. For example, it may be necessary to alter certain specific amino acid residues that interact with residues already substituted or selected for substitution in the target molecule. As another example, it may be necessary to alter certain specific amino acid residues that interact with the selected target molecule's corresponding binding partner (e.g., receptor-ligand binding site) in addition to the other amino acid residues chosen for substitution. Therefore, multiple amino acid residues from multiple amino acid families may be substituted (to naturally occurring or non-natural amino acid residues) in the selected target molecule, depending on the goal of modification, as well as the native structure of the selected target molecule.

In one of the embodiments, a protein such as an antibody and/or antibody fragment containing non-natural amino acids can be directly synthesized chemically using solid phase synthesis and ligation technologies, or using in vitro translation/expression. For example the intact antibody or its fragments can also be expressed using a variety of well-established protein expression systems including *E. coli*, yeasts, insect (e.g., baculo-virus system), and mammalian cells.

In certain embodiments, the method of site specific incorporation of non natural amino acids includes inducing the translation of a protein such that the mature, functional protein product is not expressed unless the non natural amino acid is added to the growth medium of the cell. In some embodiments, "mature, functional protein product" includes a gene product that is translated from a start codon to a stop codon. In some embodiments, "mature, functional protein product" includes a protein product that is modified post-translationally, such as by glycosylation, phosphorylation, or other modification. In some embodiments, "mature, functional protein product" includes a protein that is folded in a configuration that allows for at least one function, including by interaction with other target molecules (including engaging with one or more receptors, playing a role in one or more enzymatic activities, or pairing with one or more ligands). In some embodiments, a "mature functional protein product" may include a precursor protein product such as, for example, a member of the angiotensin peptide family, or the insulin peptide family.

Nucleic Acid Constructs

In certain embodiments, the target molecule (or portion or fragment thereof) in the methods and/or compositions of the invention is encoded by a nucleic acid. Typically, the nucleic acid comprises at least one degenerate codon, at least about two, three, four, five, six, seven, eight, nine, or at least about ten or more degenerate codons.

In one embodiment, at least one of the modified nucleic acid construct(s) is operably linked to and subject to the control of a promoter, preferably an inducible promoter. In one embodiment, multiple polynucleotides are encoded by a plasmid or plasmids. In one embodiment, a first polynucleotide further comprises a first promoter sequence controlling the expression of the modified tRNA. In one embodiment, the first promoter is an inducible promoter. In one embodiment, a second polynucleotide further comprises a second promoter sequence controlling the expression of the modified AARS. In certain embodiments, the first and second polynucleotides are present on the same target molecule.

As described herein, the invention provides for nucleic acid polynucleotide sequences and polypeptide amino acid sequences. However, one of skill in the art will appreciate that the invention is not limited to those sequences disclosed herein. One of skill will appreciate that the present invention also provides many related and unrelated sequences with the functions described herein.

One of skill will also appreciate that many variants of the disclosed sequences are included in the invention. For example, conservative variations of the disclosed sequences that yield a functionally identical sequence are included in the invention. Variants of the nucleic acid polynucleotide sequences wherein the variants hybridize to at least one disclosed sequence are considered to be included in the invention. Unique subsequences of the sequences disclosed herein, as determined by, e.g., standard sequence comparison techniques are also included in the invention.

Many biosynthetic pathways already exist in cells for the production of amino acids and other compounds. While a biosynthetic method for a particular non-natural amino acid may not exist in nature, e.g., in *E. coli*, the invention provides such methods. For example, biosynthetic pathways for non-natural amino acids are optionally generated in *E. coli* by adding new enzymes or modifying existing *E. coli* pathways. Additional new enzymes are optionally naturally occurring enzymes or artificially evolved enzymes. For example, the biosynthesis of p-aminophenylalanine (as presented, e.g., in WO 02/085923, hereby incorporated by reference) relies on the addition of a combination of known enzymes from other organisms. The genes for these enzymes can be introduced into a cell, e.g., an *E. coli* cell, by transforming the cell with a plasmid comprising the genes. The genes, when expressed in the cell, provide an enzymatic pathway to synthesize the desired compound. Examples of the types of enzymes that are optionally added are provided in the examples below. Additional enzyme sequences are found, e.g., in Genbank. Artificially evolved enzymes are also optionally added into a cell in the same manner. In this manner, the cellular machinery and resources of a cell are manipulated to produce non-natural amino acids.

A variety of methods are available for producing novel enzymes for use in biosynthetic pathways or for evolution of existing pathways. For example, recursive recombination, e.g., as developed by Maxygen, Inc., is optionally used to develop novel enzymes and pathways. (See, e.g., Stemmer 1994, *Nature* 370(4): 389-391; and Stemmer, 1994, *Proc. Natl. Acad. Sci. USA*. 91: 10747-10751, which are hereby incorporated by reference in their entireties). Similarly DesignPath™ developed by Genencor is optionally used for metabolic pathway engineering, e.g., to engineer a pathway to create a non-natural amino acid in *E coli*. This technology reconstructs existing pathways in host organisms using a combination of new genes, e.g., identified through functional genomics, and molecular evolution and design. Diversa Corporation also provides technology for rapidly screening libraries of genes and gene pathways, e.g., to create new pathways. One of the biosynthetic pathways may include the editing function of protein translation, such that the efficiency of an AARS disclosed herein is increased by a mutant editing function.

Typically the non-natural amino acid produced with an engineered biosynthetic pathway of the invention is produced in a concentration sufficient for efficient protein biosynthesis, e.g., a natural cellular amount, but not to such a degree as to affect the concentration of the other amino acids or exhaust cellular resources. Typical concentrations produced in vivo in this manner are about 10 mM to about 0.05 mM. Once a bacterium is transformed with a plasmid comprising the genes used to produce enzymes desired for a specific pathway and a twenty-first amino acid, e.g., pAF, dopa, O-methyl-L-tyrosine, or the like, is generated, in vivo selections are optionally used to further optimize the production of the non-natural amino acid for both ribosomal protein synthesis and cell growth.

In some embodiments, the incorporation rates of a non-natural amino acid were approximately 65% or greater, 70% or greater, 75% or greater, 80% or greater, 85% or greater, 90% or greater, 91% or greater, 92% or greater, 93% or greater, 94% or greater, 95% or greater, 96% or greater, 97% or greater, 98% or greater, or 99% or greater utilizing a modified RS.

Adding Chemical Moieties to Molecules

The addition of one or more chemical moieties to a target molecule, including a protein, can modulate protein folding, secretion, biological activity, serum half-life, localization, and other properties. The incorporation of a non-natural amino acid, e.g., a non-natural amino acid comprising a moiety at which place a chemical moiety can be attached, or a non-natural amino acid that includes an attached chemical moiety, can be done to, e.g., tailor changes in protein structure and/or function, e.g., to change size, acidity, nucleophilicity, hydrogen bonding, hydrophobicity, accessibility of protease target sites, target access to a protein moiety, etc. Proteins that include a non-natural amino acid, e.g., a non-natural amino acid comprising a moiety where a chemical moiety can be attached, or a non-natural amino acid that includes a chemical moiety, can have enhanced, or even entirely new, catalytic or physical properties.

For example, the following properties are optionally modified by inclusion of a non-natural amino acid joined to a chemical moiety: toxicity, biodistribution, structural properties, spectroscopic properties, chemical and/or photochemical properties, catalytic ability, half-life (e.g., serum half-life), ability to react with other molecules, e.g., covalently or noncovalently, protein stability, protein activity, protein conformation, protein substrate specificity, protein-target binding affinity, antigen-binding ability, thermostability, protein resistance to at least one protease, protein tolerance to at least one non-aqueous environment, glycosylation pattern, phosphorylation pattern, disulfide bonding, protease cleavage site location, metal binding ability, co-factor binding ability, cross-linking ability, solubility, cysteinylation, deamidation, acetylation, biotinylation, oxidation, glutathionylation, sulphanation, half-life in serum, immunogenicity, tissue penetration, fluorescence pegylation, multimerization ability, toxicity, biodistribution, facility of purification, processing structural properties, spectroscopic properties, chemical and/or photochemical properties, catalytic activity, ability to function as a vaccine, retard excretion from subject's or patient's body, redox potential, ability to react with other molecules either covalently or noncovalently, patient tolerance to said protein, increased efficacy of said protein in a patient, improved delivery of said protein or protein product in a patient, increased resistance to peptidase, and any combination thereof.

Besides clearance through kidneys and the liver, a significant proportion of biotherapeutics are cleared through receptor-mediated degradation. Cytokines and growth factors, when bound to their receptors, are internalized into cellular compartments called endosomes where the receptor-ligand complexes are degraded. However, those ligands that dissociate rapidly from their receptors in the endosome are recycled back to the cell surface and avoid depletion, thereby eliciting increased half-life.

Several chemical moieties, including poly(ethylene)glycol, react with functional groups present in the twenty naturally occurring amino acids, such as, for example, the epsilon amino group in lysine amino acid residues, the thiol present in cysteine amino acid residues, or other nucleophilic amino acid side chains. When multiple naturally occurring amino acids react in the protein, these non-specific chemical reactions result in a final protein product that contains many isomers of proteins conjugated to one or more poly(ethylene)glycol strands at different locations within the protein.

One advantage of certain embodiments of the present invention includes the ability to add one or more chemical moiety (such as poly(ethylene)glycol) by incorporating non-natural amino acids that possess unique functional groups that react with an activated poly(ethylene)glycol strand by way of chemistry that is unreactive with the naturally occurring amino acids present in the target molecule. For example, azide and alkyne groups are unreactive with all naturally occurring functional groups in a protein. Thus, the non-natural amino acid may be incorporated in one or more specific sites in a target molecule where poly(ethylene) glycol or other modification is desired without the undesirable non-specific reactions. In certain embodiments, the particular chemistry involved in the reaction results in a stable, covalent link between the poly(ethylene)glycol strand and the target molecule. In addition, such reactions may be performed in mild aqueous conditions that are not damaging to most target molecules. Thus, unlike reactions with standard polypeptides that contain highly reactive naturally occurring amino acid residues, the reactions disclosed herein that utilize non-natural amino acid residues can be performed in vivo or on unpurified preparations of the target molecule due to the lack of undesirable non-specific reactions with the biological functional groups.

Chemical moieties attached to natural amino acids are limited in number and scope. By contrast, chemical moieties attached to non-natural amino acids can utilize a significantly greater spectrum of useful chemistries by which to attach the chemical moiety to the target molecule.

Essentially any target molecule, including any protein (or portion thereof) that includes a non-natural amino acid, e.g., a non-natural amino acid containing a reactive site or side chain where a chemical moiety may attach, such as an aldehyde- or keto-derivatized amino acid, can serve as a substrate for attaching a chemical moiety. Some examples of specific proteins are described herein inter alia, and no attempt is made to identify every known protein which can be modified to include one or more non-natural amino acid, e.g., by tailoring any available mutation methods to include one or more appropriate degenerate codons in a relevant translation system. Common sequence repositories for known proteins include GenBank EMB, DDBJ and the NCBI.

A target molecule with an added chemical moiety is herein referred to as a "conjugate." "Chemical moiety," as referred to herein, may include any biological or chemical addition or modification, or any combination thereof, to an amino acid residue of the target molecule. Chemical moieties may be conjugated directly or indirectly (by way of a linker) to a non-natural amino acid or a naturally occurring amino acid in the target molecule.

Some examples of chemical moieties that are included in the present invention include but are not limited to, cytotoxins, pharmaceutical drugs, dyes or fluorescent labels (e.g., green-fluorescent protein or red-fluorescent protein), a nucleophilic or electrophilic group, a ketone or aldehyde, azide or alkyne compounds, photocaged groups (e.g., nitrobenzyl ethers and esters), tags (e.g., biotin), a peptide, polypeptide or protein, a glycosylation group (such as an oligosaccharide), poly(ethylene)glycol (PEG) with any molecular weight (e.g., PEG2000, PEG3350, PEG3500, PEG8000) and in any geometry (linear, branched, star, dendrimer, etc.), other poly(alkylene)glycols, poly(propylene)glycol, polyoxyethylated glycerol, polyoxyethylated sorbitol, polyoxyethylated glucose, poly(vinyl)alcohol, metals or metal complexes, polyamines, imidizoles, carbohydrates (including dextran or chitosan), peptides, polypeptides, proteins, lipids, biopolymers, particles, solid supports (e.g., resin), any polymer that alters the pharmacodynamics of a target molecule, a targeting agent, an affinity group (such as biotin or streptavidin), any agent to which a complementary reactive chemical group can be attached, biophysical or biochemical probes (such as isotpically labeled amino acids, spin-label amino acids and fluorophores, aryl iodides and bromides and any combination of these or others. For further examples see Magliery, *Med. Chem. Rev.* 2005, 2, 303-323, hereby incorporated by reference in its entirety.

The moiety may be strongly electrophilic or nucleophilic and thereby be available for reacting directly with the therapeutic target molecule or the antibody or fragment thereof. Alternatively, the moiety may be a weaker electrophile or nucleophile and therefore require activation prior to the conjugation with the therapeutic molecule or the antibody or fragment thereof. This alternative would be desirable where it is necessary to delay activation of the chemically reactive moiety until an agent is added to the target molecule in order to prevent the reaction of the agent with the moiety. In either scenario, the moiety is chemically reactive, the scenarios differ (in the reacting with antibody scenario) by whether following addition of an agent, the moiety is reacted directly with an antibody or fragment thereof or is reacted first with one or more chemicals to render the moiety capable of reacting with an antibody or fragment thereof. In certain embodiments, the chemically reactive moiety includes an amino group, a sulfhydryl group, a hydroxyl group, a carbonyl-containing group, or an alkyl leaving group.

Polyalkylene glycols that are particularly suitable for use in preparing the conjugates of the invention include, but are not limited to, poly(ethylene glycols), and copolymers of ethylene oxide and propylene oxide; particularly preferred are PEGs, and more particularly preferred are monofunctionally activated hydroxyPEGs (e.g., hydroxyPEGs activated at a single terminus, including reactive esters of hydroxyPEG-monocarboxylic acids, hydroxyPEG-monoaldehydes, hydroxyPEG-monoamines, hydroxyPEG-monohydrazides, hydroxyPEG-monocarbazat-es, hydroxyPEG-monoiodoacetamides, hydroxyPEG-monomaleimides, hydroxyPEG-monoorthopyridyl disulfides, hydroxyPEG-monooximes, hydroxyPEG-monophenyl carbonates, hydroxyPEG-monophenyl glyoxals, hydroxyPEG-monothiazolidine-2-thiones, hydroxyPEG-monothioesters, hydroxyPEG-monothiols, hydroxyPEG-monotriazines and hydroxyPEG-monovinylsulfones).

In certain embodiments, it may be necessary or desirable to minimize the formation of intramolecular and intermolecular crosslinking by polymers, such as PEG, during the reaction in which the polymer is attached or coupled to the modified target molecule to form the conjugates of the invention. Minimizing cross-linking, including intramolecular cross links with individual protein molecules, "dumbbell" structures, in which one strand of polymer connects two protein molecules, and larger aggregates or gels. Minimizing these and other crosslinking reactions may be accomplished by using polymers that are activated at only one end (monofuncationally activated, as described above) or polymer preparations in which the percentage of bifunctionally active (referred to as "bis-activated PEG diols" in the case of linear PEGs) or multi-functionally activated polymers is less than about 50%, 40%, 35%, 25%, 15%, 10%, 5%, or 2% (w/w). In certain embodiments, the overall PEGylation rate (that is, for at least one strand of PEG attached to the target molecule) is approximately 50%, 60%, 70%, 80%, 90%, 95%, 96%, 97%, 98%, 99%, or greater.

Particularly preferred polymers for use in preparing the conjugates of the present invention, which have reduced antigenicity, substantially reduced antigenicity, or no detectable antigenicity, are monofunctionally activated PEGs that do not contain methoxyl groups, other alkoxyl groups or aryloxyl groups. The substitution of such monofunctionally activated PEGs in place of monofunctionally activated mPEG in the synthesis of conjugates of the invention confers on the resulting conjugates an unexpectedly decreased antigenicity, i.e., a decreased ability to interact with antibodies developed against mPEG conjugates of the same bioactive component. The resultant conjugates also have decreased immunogenicity, i.e., decreased ability to evoke an immune response.

In certain such embodiments, the polyalkylene glycol has a molecular weight of from about 1,000 Daltons to about 100 kDa, preferably about 2 kDa to about 60 kDa; about 2 kDa to about 30 kDa, about 5 kDa to about 20 kDa; about 10 kDa to about 40 kDa; about 10 kDa to about 20 kDa; two branches each with a molecular weight of about 2 kDa to about 30 kDa; and more preferably two branches, each of about 18 kDa to about 22 kDa. In one particular embodiment, the polyalkylene glycol is poly(ethylene)glycol and has a molecular weight of about 10 kDa; about 20 kDa, about 30 kDa, or about 40 kDa. In specific embodiments, the PEG is a PEG 10 kDa (linear or branched), a PEG 20 kDa (linear or branched), a PEG 30 kDa (linear or branched), or a PEG 40 kDa (linear or branched).

Conjugates according to this aspect of the invention may comprise one or more strands of polyalkylene glycol, in certain embodiments preferably from about one to about 10 strands, from about one to about five strands, more preferably from about one to about three strands, and most preferably from about one to about two strands; in other embodiments preferably from about five to about 100 strands, from about 10 to about 50 strands and more preferably from about six to about 20 strands per subunit of high molecular weight enzyme proteins. In a particularly preferred such embodiment, the polyalkylene glycol used in the conjugate comprises one or two strands of a monofunctionally activated poly(ethylene glycol) (e.g., a reactive ester of a hydroxyPEG-monoacid, a hydroxyPEG-monoaldehyde, a hydroxyPEG-monovinylsulfone or a hydroxyPEG-monophenyl carbonate derivative) having a molecular weight of from about 18 kDa to about 22 kDa or about 27 kDa to about 33 kDa.

A number of investigators have disclosed the preparation of linear or branched "non-antigenic" PEG polymers and derivatives or conjugates thereof (see, e.g., U.S. Pat. Nos. 5,428,128; 5,621,039; 5,622,986; 5,643,575; 5,728,560; 5,730,990; 5,738,846; 5,811,076; 5,824,701; 5,840,900; 5,880,131; 5,900,402; 5,902,588; 5,919,455; 5,951,974; 5,965,119; 5,965,566; 5,969,040; 5,981,709; 6,011,042; 6,042,822; 6,113,906; 6,127,355; 6,132,713; 6,177,087, and 6,180,095; see also PCT publication WO 95/13090 and published U.S. patent application nos. 2002/0052443, 2002/0061307 and 2002/0098192).

Any water-soluble mono- or bifunctional poly(alkylene oxide) having a linear or branched chain may be utilized in certain embodiments. Typically, the polyol is a poly(alkylene glycol) such as poly(ethylene)glycol (PEG). Those of skill in the art will recognize that other polyols, such as poly(propylene glycol) and copolymers of polyethylene glycol and polypropylene glycol can be suitably used.

Alternatively, the chemical moiety may be joined, fused, or otherwise attached to a target molecule by way of a naturally occurring amino acid (whether it originated in the native target molecule or was added through modification).

The location of the chemical moiety in a particular target molecule may affect the structure and/or function of the target molecule. For example, if the chemical moiety is near an active binding site, the moiety may sterically block desired interactions of the protein in vivo. However, if the chemical moiety is located far away from the active sites, it can sterically protect the target molecule from renal uptake, etc. without significantly reducing the activity of the target molecule. Likewise, if the chemical moiety is located near an antigenic epitope, it can reduce antigenicity of the target molecule in vivo. Thus, it is important to be able to control the location(s) at which the chemical moiety is joined to the target target molecule.

In certain embodiments, the non-natural amino acid does not contain primary amine or thiol side-chain groups. In some embodiments, the non-natural amino acid is linked to a chemical moiety (such as PEG) via a triazole linkage. The triazole linkage may be formed, for example, by copper-mediated Huisgen [3+2] cycloaddition of an azide and an alkyne. The azide group may be provided, for example, by para-azidophenylalanine, and the alkyne group may be provided, for example, by an alkyne derivatized PEG reagent. In other embodiments, the alkyne may be provided by ethynyl Phenylalanine or ethynyl Trp, or homopropargyl glycine. In still other embodiments, the azide may be provided by azide derivatized PEG. In other embodiments, the azide may be provided by azidohomoalanine, and the alkyne may be provided by alkyne derivatized PEG.

Historically, common chemical moieties, such as polyethylene glycol (PEG), also react with functional groups present in naturally occurring amino acids (such as the epsilon amino group in lysine or the thiol group in cysteine residues). Thus, these non-specific reactions result in a final protein preparation that contains many isomers of proteins conjugated to one or more chemical moieties at various locations within the protein, depending on the amino acid content of the protein. This range of isomers affects the overall therapeutic effectiveness of the protein, due to the variation of isomers contained within the final preparation, or requires extensive purification to obtain a single desired isomer or isomer range. All of these requirements lead to increased cost and effort in manufacturing proteins. While putting protecting groups on some amino acid residues (and subsequently removing them) has provided some benefit, this technique also requires significant complications to the protein production and is largely impractical for manufacturing large quantities of modified proteins.

The present invention has the advantage of joining chemical moieties, including PEG, to target molecules, such as proteins, by utilizing unique functional groups in a nonnatural amino acid that can react with an activated PEG or other chemical moiety using chemical reactions that do not react with naturally occurring amino acids. Therefore, the methods used in the present invention provide for an efficient mode of incorporating chemical moieties into proteins or other target molecules at the non-natural amino acid location, which may be any desired location in a protein or other target molecule. These reactions may also be performed in mild aqueous solutions that are not damaging to proteins and the linkages to the chemical moieties for a stable covalent bond. These reactions may also be performed in vivo or on unpurified preparations of protein, due to the lack of side reactions with biological functional groups.

Thus, several advantages of the present methods include the ability to add chemical moieties to the modified target molecules described herein which can be conducted in aqueous buffers, in a wide range of pH, at room temperature, and in a very short period of time.

In addition to attaching a chemical moiety, the atoms in proximity to the functional groups could be altered, such as by adding electron withdrawing or donating groups, or adding methyl or other groups that add steric hindrance to the target molecule. This can alter the reactivity of the functional groups or alter the stability of the starting groups or the linkage formed. For example, an electron withdrawing group such as a nitro group can be added to the phenyl ring of bromophenylalanine to increase reactivity. A cleavable linkage could also be placed in proximity, such as an ester or disulfide group between the chemical moiety and the active group (e.g. alkyne), so that the chemical moiety could be removed from the protein slowly by hydrolysis of the ester or quickly by disulfide reduction. If necessary, interactions between sulfur atoms and the catalyst may be prevented or reduced by using excess catalyst or reversibly protecting cysteinyl thiols.

Without wishing to be bound by any particular theory, PEGylation is a process by which oligosaccharides and synthetic polymers such as polyethylene glycol (PEG) are site-specifically and covalently attached to therapeutic protein target molecules. PEGylation can significantly enhance protein half-life by shielding the polypeptide from proteolytic enzymes and increasing the apparent size of the protein, thus reducing clearance rates. Moreover, PEG conjugates can enhance protein solubility and have beneficial effects on biodistribution. The physical and pharmacological properties of PEGylated proteins are affected by the number and the size of PEG chains attached to the polypeptide, the location of the PEG sites, and the chemistry used for PEGylation. Examples of PEG conjugation to proteins include reactions of N-hydroxysuccinimidyl ester derivatized PEGs with lysine, 1,4-addition reactions of maleimide and vinylsulfone derivatized PEGs with cysteine, and condensation of hydrazide containing PEGs with aldehydes generated by oxidation of glycoproteins.

PEGylation can significantly enhance protein half-life by shielding the polypeptide from proteolytic enzymes and increasing the apparent size of the protein, thus reducing clearance rates. Moreover, PEG conjugates can enhance protein solubility and have beneficial effects on biodistribution. The physical and pharmacological properties of PEGylated proteins are affected by the number and the size of PEG chains attached to the polypeptide, the location of the PEG sites, and the chemistry used for PEGylation. "PEG" may include target molecules of the general formula $CH_2CH_2O(CH_2CH_2O)_nCH_2CH_2$. PEG includes linear polymers having hydroxyl groups at each end other terminus, such as HO-PEG-OH. Examples of PEG conjugation to proteins include reactions of N-hydroxysuccinimidyl ester derivatized PEGs with lysine, 1,4-addition reactions of maleimide and vinylsulfone derivatized PEGs with cysteine, and condensation of hydrazide containing PEGs with aldehydes generated by oxidation of glycoproteins.

Some examples of PEG polymers include methoxy-PEG-OH (m-PEG), wherein one terminus is relatively inert while the other terminus is a hydroxyl group that is subject to chemical modification. Branched PEGs may also be used $(R-PEG-OH)_n$ in which R represents a central core moiety, including pentaerythritol, glycerol, or lysine and n represents the number of branching arms, which can range from three to a hundred or more. The hydroxyl groups are further subject to chemical modification. Another branched form has a single terminus and is subject to chemical modification (see, for example, PCT patent application WO 96/21469). This type of PEG can be represented as $(CH_3O-PEG)$-$_p$R—X) where p equals 2 or 3, and R represents a central core such that lysine or glycerol and X represents a functional group such as carboxyl that is subject to chemical activation. Another branched form "pendent PEG" has reactive groups, such as carboxyl, along the PEG backbone rather than at the end of PEG chains. PEG-methyl maleimide, which may be used, for example, in thiol-specific pegylation of antibodies, viruses, peptides, and proteins, aldehyde derivatives of PEG (PEG-butyraldehyde, PEG-pentaldehyde, PEG-amido-propionaldehyde, PEG-urethano-propioaldehyde) which may be used, for example, in N-terminal specific pegylation of proteins, and multi-arm PEG which are used, for example, as reactive components in hydrogel formulations.

Many PEG reagents have been developed for modifying proteins which involve the covalent attachment of a PEG target molecule via the formation of a linking group between the PEG polymer and the protein. Some such reagents are unstable in the aqueous medium in which the PEGylation reaction occurs. Also, some proteins may lose in vitro biological activity due to steric interaction with the protein's active sites upon addition of PEG.

A primary method by which site-specific pegylation of a protein may be conducted is the pegylation of a free cysteine moiety with a PEG-maleimide reagent. A PEG-sulfhydryl reactive derivative may react with a cysteine via a Michael addition to form a stable 3-thiosuccidimidyl ether linkage. The maleimide specific sulfhydryl reagent can form a covalent bond with a cysteine residue about 1000-fold faster than a corresponding amine, thereby selectively derivatizing the cysteine moiety. The resulting compound is very stable and cannot be reversed under physiological conditions.

Another method of enhancing protein stabilization via pegylation occurs using PEG aldehyde derivatives. This may be carried out, for example, by reacting the PEG aldehyde with a protein amine at a single site at the N-terminus of the protein, at a pH of from 5.5 to 7.5, which forms an intermediate Schiff base. If the amination process is desired at more than one amino site on the protein, the reaction may be executed at a pH of 8.0 and above, preferably from 8.0 to 10.0. Such PEG aldehydes are typically very stable in an aqueous medium but may be somewhat less reactive for Schiff base formation. These reagents may be used for a greater overall selectivity for the reductive amination reaction and choice of which protein amine is utilized for pegylation of the protein.

Copolymers of ethylene oxide and propylene oxide are closely related to PEG in their chemistry, and can be used instead of PEG in many applications. They have the following general formula: $HO-CH_2CHRO(CH_2CHRO)_nCH_2CHR-OH$ where R is H or $CH_3$, $CH_2CH_3$, $(CH_2)mCH_3$.

Since PEG is water-soluble as well as soluble in many organic solvents, PEG is a useful polymer. PEG is generally non-toxic and non-immunogenic. When PEG is chemically attached to a water insoluble compound, the resulting conjugate generally becomes water soluble as well as soluble in many organic solvents. Thus, as used herein, the "PEG moiety" is intended to include but not be limited to, linear and branched PEG, methoxy PEG, hydrolytically or enzymatically degradable PEG, pendent PEG, dendrimer PEG, copolymers of PEG and one or more polyols, and copolymers of PEG and PLGA (poly(lactic/glycolic acid) of any weight and/or size.

When more than one reactive site is present in a protein (e.g., multiple amino or thiol groups) or reactive electrophiles are used, nonselective attachment of one or multiple PEG molecules can occur, leading to the generation of a heterogeneous mixture that is difficult to separate. The lack of selectivity and positional control in the attachment of PEG chains can lead to significant losses in biological activity and possibly enhanced immunogenicity of the conjugated protein. Modification of proteins with amine-reactive PEGs typically results in drastic loss of biological activity due to modification of lysine residues located in regions of the protein important for biological activity. In certain situations, bioactivity of growth hormones may be reduced 400-fold or more. For example, bioactivity of GCSF is reduced 1,000-fold when the proteins are modified using conventional amine-PEGylation technologies (Clark et al., *J. Biol. Chem.* 271: 21969, 1996; Bowen et al., *Exp. Hematol.* 27, 425, 1999). Thus there is a need for a method that allows for the completely site-specific and irreversible attachment of PEG chains to molecules, including proteins.

The compositions, including proteins, comprise at least one non-natural amino acid, e.g., a non-natural amino acid comprising a moiety where a chemical moiety can be attached, or a non-natural amino acid that includes a chemical moiety are useful for, e.g., novel therapeutics, diagnostics, catalytic enzymes, industrial enzymes, binding proteins (e.g., antibodies), and e.g., the study of protein structure and function. (See, e.g., Dougherty, (2000) *Curr. Opin. in Chem. Biol.*, 4:645-652, hereby incorporated by reference.)

In addition, PEG molecules (or other chemical moieties) may be attached to non-natural amino acids through techniques other than amine-PEGylation, thus sparing the primary amine groups of lysines from undesirable PEGylation. The major advantages of such molecular or protein engineering technologies include the creation of next-generation, proprietary pharmaceuticals that are homogeneously modified; retain high biological activity and remain longer in the body; have increased potency and stability and decreased immunogenicity; are consistent lot to lot in biological activities. These techniques may be used to enhance the half-life, efficacy, and/or safety of bio-pharmaceuticals in all areas, including the specific field of cancer, endocrinology, infectious disease, immunology, systems medicine and inflammation, etc.

Methods of identifying incorporation of non-natural amino acids and/or chemical moieties into a target molecule are well known in the art and have been described herein inter alia. For example some modes of testing for incorporation of one or more chemical moiety include flow cytommetry, Northern blots, Western blots, PCR, RNA microsequencing, reporter assays, FLAG epitopes, binding to conjugate molecules (such as streptavidin), radio-label detection, colorimetric assays, RNAse protection assays, mass spectrometry (including MALDI and MALDI-TOF), NMR, IR, ELISA, fluorescent microscopy and any combination of these or other techniques known in the art.

Glycosylating Molecules

The invention also provides glycoproteins that comprise a saccharide moiety and a polypeptide. In certain embodiments in the glycoproteins of the invention, the saccharide moiety is attached to the polypeptide by a reaction product of a nucleophilic reaction between a first reactive group attached to an non-natural amino acid present in the polypeptide and a second reactive group attached to the saccharide moiety. In certain embodiments, the first reactive group is an electrophilic moiety (e.g., keto moiety, aldehyde moiety, and/or the like) and the second reactive group is a nucleophilic moiety.

A wide variety of suitable reactive groups are known to those of skill in the art. Such suitable reactive groups can include, for example, amino, hydroxyl, carboxyl, carboxylate, carbonyl, alkenyl, alkynyl, aldehyde, ester, ether (e.g., thioether), amide, amine, nitrile, vinyl, sulfide, sulfonyl, phosphoryl, or similarly chemically reactive groups. Additional suitable reactive groups include, but are not limited to, maleimide, N hydroxysuccinimide, sulfo-N-hydroxysuccinimide, nitrilotriacetic acid, activated hydroxyl, haloacetyl (e.g., bromoacetyl, iodoacetyl), activated carboxyl, hydrazide, epoxy, aziridine, sulfonylchloride, trifluoromethyldiaziridine, pyridyldisulfide, N-acyl-imidazole, imidazolecarbamate, vinylsulfone, succinimidylcarbonate, arylazide, anhydride, diazoacetate, benzophenone, isothiocyanate, isocyanate, imidoester, fluorobenzene, biotin and avidin.

In some embodiments, one of the reactive groups is an electrophilic moiety, and the second reactive group is a nucleophilic moiety. Either the nucleophilic moiety or the electrophilic moiety can be attached to the side-chain of the non-natural amino acid; the corresponding group is then attached to the saccharide moiety.

Suitable electrophilic moieties that react with nucleophilic moieties to form a covalent bond are known to those of skill in the art. In certain embodiments, such electrophilic moieties include, but are not limited to, e.g., carbonyl group, a sulfonyl group, an aldehyde group, a ketone group, a hindered ester group, a thioester group, a stable imine group, an epoxide group, an aziridine group, etc.

Suitable nucleophilic moieties that can react with electrophilic moiety are known to those of skill in the art. In certain embodiments, such nucleophiles include, for example, aliphatic or aromatic amines, such as ethylenediamine. In certain embodiments, the nucleophilic moieties include, but are not limited to, e.g., —NR1-NH$_2$ (hydrazide), —NR1(C=O)NR2NH$_2$ (semicarbazide), —NR1(C=S)NR2NH$_2$ (thiosemicarbazide), —(C=O)NR1NH$_2$ (carbonylhydrazide), —(C=S)NR1NH$_2$ (thiocarbonylhydrazide), —(SO$_2$)NR1NH$_2$ (sulfonylhydrazide), —NR1NR2(C=O)NR3NH$_2$ (carbazide), NR1NR2(C=S)NR3NH$_2$ (thiocarbazide), —O—NH$_2$ (hydroxylamine), and the like, where each R1, R2, and R3 is independently H, or alkyl having 1-6 carbons, preferably H. In certain embodiments, the reactive group is a hydrazide, hydroxylamine, semicarbazide, carbohydrazide, a sulfonylhydrazide, or the like.

The product of the reaction between the nucleophile and the electrophilic moiety typically incorporates the atoms originally present in the nucleophilic moiety. Typical linkages obtained by reacting the aldehydes or ketones with the nucleophilic moieties include reaction products such as an oxime, an amide, a hydrazone, a reduced hydrazone, a carbohydrazone, a thiocarbohydrazone, a sulfonylhydrazone, a semicarbazone, a thiosemicarbazone, or similar functionality, depending on the nucleophilic moiety used and the electrophilic moiety (e.g., aldehyde, ketone, and/or the like) that is reacted with the nucleophilic moiety. Linkages with carboxylic acids are typically referred to as carbohydrazides or as hydroxamic acids. Linkages with sulfonic acids are typically referred to as sulfonylhydrazides or N-sulfonylhydroxylamines. The resulting linkage can be subsequently stabilized by chemical reduction.

Suitable electrophilic moieties that react with nucleophilic moieties to form a covalent bond are known to those of skill in the art. In certain embodiments, such electrophilic moieties include, but are not limited to, e.g., carbonyl group, a sulfonyl group, an aldehyde group, a ketone group, a hindered ester group, a thioester group, a stable imine group, an epoxide group, an aziridine group, etc.

Suitable nucleophilic moieties that can react with electrophilic moiety are known to those of skill in the art. In certain embodiments, such nucleophiles include, for example, aliphatic or aromatic amines, such as ethylenediamine. In certain embodiments, the nucleophilic moieties include, but are not limited to, e.g., —NR1-NH$_2$ (hydrazide), —NR1(C=O)NR2NH$_2$ (semicarbazide), —NR1(C=S)NR2NH$_2$ (thiosemicarbazide), —(C=O)NR1NH$_2$ (carbonylhydrazide), —(C=S)NR1NH$_2$ (thiocarbonylhydrazide), —(SO$_2$)NR1NH$_2$ (sulfonylhydrazide), —NR1NR2(C=O)NR3NH$_2$ (carbazide), NR1NR2(C=S)NR3NH$_2$ (thiocarbazide), —O—NH$_2$ (hydroxylamine), and the like, where each R1, R2, and R3 is independently H, or alkyl having 1-6 carbons, preferably H. In certain embodiments, the reactive group is a hydrazide, hydroxylamine, semicarbazide, carbohydrazide, a sulfonylhydrazide, or the like.

The product of the reaction between the nucleophile and the electrophilic moiety typically incorporates the atoms originally present in the nucleophilic moiety. Typical linkages obtained by reacting the aldehydes or ketones with the nucleophilic moieties include reaction products such as an oxime, an amide, a hydrazone, a reduced hydrazone, a carbohydrazone, a thiocarbohydrazone, a sulfonylhydrazone, a semicarbazone, a thiosemicarbazone, or similar functionality, depending on the nucleophilic moiety used and the electrophilic moiety (e.g., aldehyde, ketone, and/or the like) that is reacted with the nucleophilic moiety. Linkages with carboxylic acids are typically referred to as carbohydrazides or as hydroxamic acids. Linkages with sulfonic acids are typically referred to as sulfonylhydrazides or N-sulfonylhydroxylamines. The resulting linkage can be subsequently stabilized by chemical reduction.

Other aspects of the invention include methods for synthesis of a glycoprotein by incorporating into a protein an non-natural amino acid that comprises a saccharide moiety. A glycoprotein produced by the method is also a feature of the invention. In certain embodiments, the incorporating step comprises using an mutant tRNA/mutant aminoacyl-tRNA synthetase (M-tRNA/M-RS) pair, wherein the M-tRNA recognizes a degenerate codon and incorporates the non-natural amino acid that comprises a saccharide moiety (e.g., a β-O-GlcNAc-L-serine, a tri-acetyl-β-GlcNAc-serine, a tri-O-acetyl-GalNAc-α-threonine, an α-GalNAc-L-threonine, and/or the like) into the protein in response to the degenerate codon, and wherein the M-RS preferentially aminoacylates the M-tRNA with the non-natural amino acid. In one embodiment, the incorporating step is performed in vivo.

These methods can further involve contacting the saccharide moiety with a glycosyl transferase, a sugar donor moiety, and other reactants required for glycosyl transferase activity for a sufficient time and under appropriate conditions to transfer a sugar from the sugar donor moiety to the saccharide moiety. In certain embodiments, the method further comprises contacting the product of the glycosyl transferase reaction with at least a second glycosyl transferase and a second sugar donor moiety. In other words, the invention provides methods in which an amino acid-linked saccharide moiety or an non-natural amino acid that includes a saccharide moiety is further glycosylated. These glycosylation steps are preferably (though not necessarily) carried out enzymatically using, for example, a glycosyltransferase, glycosidase, or other enzyme known to those of skill in the art. In some embodiments, a plurality of enzymatic steps are carried out in a single reaction mixture that contains two or more different glycosyl transferases. For example, one can conduct a galactosylating and a sialylating step simultaneously by including both sialyl transferase and galactosyl transferase in the reaction mixture.

For enzymatic saccharide syntheses that involve glycosyl transferase reactions, the recombinant cells of the invention optionally contain at least one heterologous gene that encodes a glycosyl transferase. Many glycosyl transferases are known, as are their polynucleotide sequences. See, e.g., "The WWW Guide To Cloned Glycosyl transferases," (available on the World Wide Web). Glycosyl transferase amino acid sequences and nucleotide sequences encoding glycosyl transferases from which the amino acid sequences can be deduced are also found in various publicly available databases, including GenBank, Swiss-Prot, EMB, and others.

In certain embodiments, a glycosyl transferase of the invention includes, but is not limited to, e.g., a galactosyl transferase, a fucosyl transferase, a glucosyl transferase, an N-acetylgalactosaminyl transferase, an N-acetylglucosaminyl transferase, a glucuronyl transferase, a sialyl transferase, a mannosyl transferase, a glucuronic acid transferase, a galacturonic acid transferase, an oligosaccharyl transferase, and the like. Suitable glycosyl transferases include those obtained from eukaryotes or prokaryotes.

An acceptor for the glycosyl transferases will be present on the glycoprotein to be modified by the methods of the invention. Suitable acceptors, include, for example, galactosyl acceptors such as Galβ1,4GalNAc-; Galβ1,3GalNAc-; lacto-N-tetraose-; Galβ1,3GlcNAc-; Galβ1,4GlcNAc-, Galβ1,3Ara-; Galβ1,6GlcNAc-; and Galβ1,4Glc-(lactose). Other acceptors known to those of skill in the art (see, e.g., Paulson et al., *J. Biol. Chem.* 253: 5617-5624, 1978). Typically, the acceptors form part of a saccharide moiety chain that is attached to the glycoprotein.

In one embodiment, the saccharide moiety comprises a terminal GlcNAc, the sugar donor moiety is UDP-GlcNAc and the glycosyl transferase is a β1-4N-acetylglucosaminyl transferase. In another embodiment, the saccharide moiety comprises a terminal GlcNAc, the sugar donor moiety is UDP-Gal and the glycosyl transferase is a β1-4-galactosyl transferase. Additional sugars can be added.

In one embodiment, the saccharide moiety comprises a terminal GlcNAc, the sugar donor moiety is UDP-GlcNAc and the glycosyl transferase is a β1-4N-acetylglucosaminyl transferase. In another embodiment, the saccharide moiety comprises a terminal GlcNAc, the sugar donor moiety is UDP-Gal and the glycosyl transferase is a β1-4-galactosyl transferase. Additional sugars can be added.

In one embodiment, the saccharide moiety comprises a terminal GlcNAc, the sugar donor moiety is UDP-Gal and the glycosyl transferase is a β-1,4-galactosyl transferase.

In one embodiment, the saccharide moiety comprises a terminal GlcNAc, the sugar donor moiety is UDP-GlcNAc and the glycosyl transferase is a β1-4N-acetylglucosaminyl transferase.

Optionally, the method further comprises contacting the product of the N-acetylglucosaminyl transferase reaction with a β1-4-mannosyl transferase and GDP-mannose to form a saccharide moiety that comprises Manβ1-4GlcNAcβ1-4GlcNAc-. Optionally, the method further comprises contacting the Manβ1-4GlcNAcβ1-4GlcNAc-moiety with an α1-3mannosyl transferase and GDP-mannose to form a saccharide moiety that comprises Manα1-3Manβ1-4GlcNAcβ1-4GlcNAc-. Optionally, the method further comprises contacting the Manα1-3Manβ1-4GlcNAcβ1-4GlcNAc-moiety with an α1-6 mannosyl transferase and GDP-mannose to form a saccharide moiety that comprises Manα1-6(Manα1-3)Manβ1-4GlcNAcβ1-4GlcNAc-. Optionally, the method further comprises contacting the Manα1-6(Manα1-3)Manβ1-4GlcNAcβ1-4GlcNAc-moiety with a β1-2N-acetylglucosaminyl transferase and UDP-GlcNAc to form a saccharide moiety that comprises Manα1-6(GlcNAcβ1-2Manα1-3)Manβ1-4GlcNAcβ1-4GlcNAc-. Optionally, the method further comprises contacting the Manα1-6(GlcNAcβ1-2Manα1-3)Manβ1-4GlcNAcβ1-4GlcNAc-moiety with a β1-2N-acetylglucosaminyl transferase and UDP-GlcNAc to form a saccharide moiety that comprises GlcNAcβ1-2Manα1-6(GlcNAcβ1-2Manα1-3)Manβ1-4GlcNAcβ1-4GlcNAc-.

The step of incorporating into a protein an non-natural amino acid that comprises a first reactive group, in some embodiments, comprises using an mutant tRNA/mutant aminoacyl-tRNA synthetase (M-tRNA/M-RS) pair, where the M-tRNA preferentially recognizes a degenerate codon for wild-type tRNA, and incorporates the non-natural amino acid into the protein in response to the degenerate codon, and wherein the M-RS preferentially aminoacylates the M-tRNA with the non-natural amino acid. In some embodiments, the non-natural amino acid is incorporated into the polypeptide in vivo.

The invention also provides glycoproteins that comprise a saccharide moiety and a polypeptide. In certain embodiments in the glycoproteins of the invention, the saccharide moiety is attached to the polypeptide by a reaction product of a nucleophilic reaction between a first reactive group attached to an non-natural amino acid present in the polypeptide and a second reactive group attached to the saccharide moiety. In certain embodiments, the first reactive group is an electrophilic moiety (e.g., keto moiety, aldehyde moiety, and/or the like) and the second reactive group is a nucleophilic moiety.

A wide variety of suitable reactive groups are known to those of skill in the art. Such suitable reactive groups can include, for example, amino, hydroxyl, carboxyl, carboxylate, carbonyl, alkenyl, alkynyl, aldehyde, ester, ether (e.g., thioether), amide, amine, nitrile, vinyl, sulfide, sulfonyl, phosphoryl, or similarly chemically reactive groups. Additional suitable reactive groups include, but are not limited to, maleimide, N hydroxysuccinimide, sulfo-N-hydroxysuccinimide, nitrilotriacetic acid, activated hydroxyl, haloacetyl (e.g., bromoacetyl, iodoacetyl), activated carboxyl, hydrazide, epoxy, aziridine, sulfonylchloride, trifluoromethyldiaziridine, pyridyldisulfide, N-acyl-imidazole, imidazolecarbamate, vinylsulfone, succinimidylcarbonate, arylazide, anhydride, diazoacetate, benzophenone, isothiocyanate, isocyanate, imidoester, fluorobenzene, biotin and avidin.

The glycosylation reactions include, in addition to the appropriate glycosyl transferase and acceptor, an activated nucleotide sugar that acts as a sugar donor for the glycosyl transferase. The reactions can also include other ingredients that facilitate glycosyl transferase activity. These ingredients can include a divalent cation (e.g., $Mg^{2+}$ or $Mn^{2+}$), materials necessary for ATP regeneration, phosphate ions, and organic solvents. The concentrations or amounts of the various reactants used in the processes depend upon numerous factors including reaction conditions such as temperature and pH value, and the choice and amount of acceptor saccharides to be glycosylated. The reaction medium may also comprise solubilizing detergents (e.g., Triton or SDS) and organic solvents such as methanol or ethanol, if necessary.

Because the glycopolypeptides or pegylated molecules of the invention provide a variety of new polypeptide sequences (e.g., comprising an non-natural amino acid that comprises an amino acid, where a saccharide or PEG moiety can be linked, or an non-natural amino acid that includes a saccharide or PEG moiety, respectively in the case of proteins synthesized in the translation systems herein, or, e.g., in the case of the novel synthetases, novel sequences of standard amino acids), the glycopolypeptides also provide new structural features which can be recognized, e.g., in immunological assays. Thus antibodies and antisera that are specifically immunoreactive with an artificial polypeptide of the invention are also provided. In other words, the generation of antisera, which specifically bind the polypeptides of the invention, as well as the polypeptides which are bound by such antisera, are a feature of the invention.

The post-translational modification of proteins by glycosylation can affect protein folding and stability, modify the intrinsic activity of proteins, and modulate their interactions with other biomolecules. See, e.g., Varki, *Glycobiology* 3: 97-130, 1993. Natural glycoproteins are often present as a population of many different glycoforms, which makes analysis of glycan structure and the study of glycosylation effects on protein structure and function difficult. Therefore, methods for the synthesis of natural and non-natural homogeneously glycosylated proteins are needed for the systematic understanding of glycan function, and for the development of improved glycoprotein therapeutics.

Exemplary Chemistry for Addition of Chemical Moieties to Molecules

Numerous chemical moieties may be joined or linked to a particular molecule through various known methods in the art. As an illustrative example, azide moieties may be useful in conjugating chemical moieties such as PEG or others described herein. The azide moiety serves as a reactive functional group, and is absent in most naturally occurring compounds (thus it is unreactive with the native amino acids of naturally occurring compounds). Azides also undergo a selective ligation with a limited number of reaction partners, and azides are small and can be introduced to biological samples without altering the molecular size of significantly.

One reaction that allows incorporation or introduction of azides to molecules is the copper-mediated Huisgen [3+2] cycloaddition of an azide. This reaction can be used for the selective PEGylation of proteins. (Tornoe et al., *J. Org. Chem.* 67: 3057, 2002; Rostovtsev et al., *Angew. Chem., Int. Ed.* 41: 596, 2002; and Wang et al., *J. Am. Chem. Soc.* 125: 3192, 2003, Speers et al., *J. Am. Chem. Soc.*, 2003, 125, 4686; all of which are hereby incorporated by reference). The copper catalyst may be provided by ultrapure CuBr, $CuSO_4$ combined with tris(2-carboxyethyl)phosphine or ascorbate, by copper wire with exposure to air, or any other source. The reaction may be accelerated by addition of a ligand such as bathophenanthrolinedisulfonic acid, tris-(triazolyl)amine, or other triazole or phosphine ligands, or by the addition of palladium catalyst. Optionally, oxygen may be excluded from the reaction to improve yields. For example, Deiters et al, (*Bioorg. Med. Chem. Lett.* 14(23): 5743-5745, 2004) report a generally applicable PEGylation methodology based on the site-specific incorporation of para-azidophenylalanine into proteins in yeast. The azido group was used in a mild [3+2] cycloaddition reaction with an alkyne derivatized PEG reagent to afford selectively PEGylated protein. Also, Kiick, et al., report incorporation of azides into recombinant proteins for chemoselective modification by the Staudinger ligation, which does not require a copper catalyst but instead exploits the reaction between an azide and a phosphane to form a phospha-azaylide, which is then trapped by an acyl group with formation of a stable amide bond.

Reaction conditions may be varied to optimize PEGylation of any particular protein, such as, e.g., a modified IFNβ protein. For example, OEGylation may be performed under denaturing and/or reducing conditions. Thus, in particular embodiments, the reaction may be performed in the presence of DTT and/or SDS. Suitable concentrations of DTT include, e.g., ranges of 0-10 mM, 0.1-10 mM, 0.1-5 mM, and 1-5 mM. In one embodiment, the concentration of DTT is approximately 2 mM. Suitable concentrations of SDS include, e.g., ranges of 0-6%. In one embodiments, the concentration of SDS is approximately 2%. In other embodiments, specific concentration of PEG and/or protein are utilized in the PEGylation reaction. For example, suitable concentration ranges of PEG include 0.1-5.0 wt % PEG, 1.0-5.0 wt % PEG, and 2.0-3.0 wt % PEG, and in one embodiment, PEG is present at approximately 2.0 wt %. Suitable concentration of IFNβ or modified IFNβ include, e.g., 0.1-5 mg/ml and 1.0-5 mg/ml. In particular embodiments, triazole is present at a concentration of approximate 0-3-fold the Cu concentration. In further embodiments, a 1:1-2:1 molar ration of triazole ligand to copper catalyst is used. In another embodiment, CuBr or CuSO4 is present at a concentration in the range of 0.1-5.0 mM. In one specific embodiment, PEGylation of IFNβ or modified IFNβ is performed in the presence of 2 mM DTT, 3 mM triazole, 1.5 mM $CuSO_4$, 2% SDS, 2 wt % PEG, and 1-2 mg/ml IFN.

In other aspects of the invention, the non-natural amino acid may contain a halogenated aryl or vinyl group (for example, para-bromophenylalanine or para-iodophenylalanine). A cross-coupling reaction may be conducted, such as a palladium-catalyzed Suzuki reaction with PEG-phenylboronic acid, or other reaction described herein to yield a carbon-carbon linkage between the chemical moiety (such as PEG) and the molecule. Several common procedures used historically to conjugate chemical moieties to molecules (including proteins) also react with functional groups present in naturally occurring amino acids, such as the epsilon amino group in lysine or the thiol group in cysteine residues. Thus, the non-specific reactions result in the final protein preparation containing many isomers of proteins conjugated to one or more chemical moieties at different locations within the protein, depending on the amino acid sequence of the target protein.

The use of a non-natural amino acid at a particular location in a target molecule allows for chemical modification, such as PEGylation, to occur at that specific site. As disclosed herein, typically molecule modification schemes utilize the chemistry of amino acid side chains to add chemical moieties to the target molecule. In one particular example, pegylated human interferon-α-2B protein product (PEG-Intron) produces up to 14 different positions of modification, including molecules with multiple PEGs attached. For example, the PEG-Intron results in monopegylated positional isomers, with the PEG moiety occurring at lysine, tyrosine, histidine, serine and cysteine residues. Protein products that are mixed isomers have lower activity due to the myriad of locations where the chemical moiety is attached and since not all positional isomers are active, or may have reduced activity.

For example, PEG-Intron has an antiviral activity of 28% of the unmodified interferon-α protein, with a range of 6-37% for individual isomer species. In addition, manufacturing costs are increased due to the need to separate out the fraction of undesired species and additional processing of the variable modified protein batches. Thus, there is a need in the art for production of proteins with chemical moieties (including PEG) that are consistently modified.

While some techniques for controlling the location of the chemical moiety attachment are known in the art, such as adjusting the pH of the reaction mixture, using protecting groups for some amino acid residues during chemical moiety conjugation, altering the folding state of the protein to allow for better structural access to specific protein regions, and altering the chemistry of the activated chemical moiety species so it is less likely to react with other nondesired functional groups, none of these techniques eliminates side reactions with undesired amino acid residues. One known technique avoids side reactions with undesired amino acid residues by using protecting groups for some amino acid residues during chemical moiety conjugation, followed by removing the protecting groups from the modified protein. However, this technique is cumbersome, expensive and impractical for manufacturing a modified protein product.

It is desirable to synthesize molecules, including therapeutic molecules, in which the added chemical moiety may be specifically directed to a target location in the molecule in order to reduce variability of the overall modified protein product and increase activity or other desired goal. For example, if the chemical moiety is near an active binding site of the protein, it can sterically block desired interactions of the protein in vivo, if the chemical moiety is located near an antigenic epitope, it may reduce the antigenicity of the molecule in vivo. Likewise, if the chemical moiety is located away from active sites, it may sterically protect the molecule from renal uptake or clearance in vivo without reducing the activity of the molecule.

One of the advantages of certain embodiments of the present invention includes utilizing non-natural amino acids at specific positions where PEGylation is desired. In certain embodiments, PEGylation chemistry can be used that is specific to the non-natural amino acid side chain, which results in the PEG being added only at the desired location in the target molecule. The efficiency of this chemical reaction is much higher than traditional PEGylation methods due to the absence of the cross-reactivity or other undesirable side-reactions. For example, copper catalyzed cycloaddition between an azide and an alkyne may be up to 80% efficient or greater. Such chemistry is not reactive with other components of the molecule. Other, non-reactive chemistry PEGylation schemes may be utilized as well.

Since certain embodiments of the chemical reactions described herein provide for reactions that solely react with unique functional groups in non-natural amino acid residues, the reactions allow for naturally occurring amino acids to remain unmodified. For instance, palladium-catalyzed cross coupling reactions are largely unreactive with naturally occurring amino acid residues, thus allowing for site specific, covalent linkage of a chemical moiety with the molecule without undesired conjugation elsewhere in the molecule. Another advantage is that these specifically disclosed chemical reactions may be performed in mild aqueous conditions that are not damaging to proteins. In addition, the conjugation chemistry may be reversed, such that the reactive group is present on an activated chemical moiety, rather than the target non-natural amino acid. Under these circumstances, the activated chemical moiety could be reacted with nonnatural amino acids such as homoproparglyglycine or homoallylglycine.

In certain other embodiments, multiple different non-natural amino acid residues may be incorporated into a target molecule and one or more of the non-natural amino acid residues could be conjugated to a chemical moiety by any of the techniques described herein.

A number of other well-known chemical reactions may be utilized to attach a chemical moiety to a protein or other molecule, some of which are described herein. The reactive group may be either located on the target molecule, or on the chemical moiety selected for conjugation to the target molecule. The Suzuki Coupling is a palladium-catalyzed cross coupling between organobornic acid and aryl or vinyl halides, pseudo-halides (including triflates), alkyls, alkenyls and/or alkynyls. In addition, potassium trifluoroborates and organoboranes or boronate esters may be used instead of boronic salts. For more details, see for example, Baxter, et al., *J. Am. Chem. Soc.*, 2003, 125, 7198-7199; Wu, et al., *J. Org. Chem.*, 2003, 68, 670-673 and Molander, et al., *J. Org. Chem.*, 2002, 67, 8424-8429.

The Hiyama Coupling reaction may also be used to join chemical moieties to molecules, including proteins. The Hiyama Coupling is well known in the art and involves a palladium-catalyzed C—C bond formation between aryl, alkenyl, or alkyl halides or pseudohalides and organosilanes. The success of this reaction depends on the polarization of the Si—C bond, thus activation of silane with base or fluoride ions (TASF, TBAF) results in a pentavlant silicon compound. Another approach includes using silacyclobutanes. For more details, see for example, Lee et al., *J. Am. Chem. Soc.*, 2003, 125, 5616-5617; Denmark, et al., *J. Am. Chem. Soc.*, 1999, 121, 5821-5822; Li, et al., *Synthesis*, 2005, 3039-3044; Murata, et al., *Synthesis*, 2001, 2231-2233; Lee, *Org. Lett.*, 2000, 2053-2055.

The Kumada Coupling reaction may also be used to join chemical moieties to molecules, including proteins. The Kumada Coupling reaction is a palladium or nickel catalyzed cross coupling reaction of Grignard reagents with alkyl, vinyl or aryl halides. For more details, see for example, Frisch, et al., *Angew. Chem.*, 2002, 114, 4218-4221. The Negishi Coupling reaction may also be used to join chemical moieties to molecules, including proteins. The Negishi Coupling is a nickel or palladium catalyzed coupling of organozinc compounds with various halides (aryl, vinyl, benzyl or allyl). For further details, see for example, Hadei, et al., *Org. Lett.*, 2005, 7, 3805-3807; Hua, et al., *Org. Lett.*, 2003, 5, 423-425; Lutzen, et al., *Eur. J. Org. Chem.*, 2002, 2292-2297. The Stille Coupling may also be used to join chemical moieties to molecules, including proteins. The Stille Coupling reaction forms a C—C bond between stannanes and halides or pseudohalides. For further details, see for example, Mee, et al., *Angew. Chem.*, 2004, 116, 1152-1156; Huang, et al., *Tetrahedron*, 2003, 59, 3635-3641; Del Valle, et al., *J. Org. Chem.*, 1990, 55, 3019-3023; Lerebours, et al., *J. Org. Chem.* 2005, 70, 8601-8604.

The Heck Reaction may also be used to join chemical moieties to molecules, including proteins. The Heck Reaction is a palladium-catalyzed C—C coupling between aryl halides or vinyl halides and activated alkenes in the presence of a base. For further details see, for example, Chandrasekhar, et al., *Org. Lett.*, 2002, 4, 4399-4401; Masllorens, et al., *Org. Lett.*, 2003, 5, 1559-1561; Battistuzzi, et al., *Org. Lett.*, 2003, 5, 777-780; Mo, et al., *J. Am. Chem. Soc.*, 2005, 127, 751-760; Hansen, et al., *Org. Lett.*, 2005, 7, 5585-5587. The Fukuyama Coupling is another reaction that may be used to join chemical moieties to molecules, including proteins. The Fukuyama Coupling is a palladium-catalyzed coupling of organozinc compounds with thioesters to form ketones. The oxidateive addition of a thioester is followed by transmetallation from the zinc compound. Reductive elimination leads to the coupled product. For more details, see for example, Tokuyama, et al., *J. Braz. Chem. Soc.*, 1998, 9, 381-387. Another reaction that may be used to join chemical moieties to molecules, including proteins, is the Sonogashira Coupling. The Sonogashira Coupling reaction couples terminal alkynes with aryl or vinyl halides using a palladium catalyst, a copper(I) cocatalyst, and an amine base. For more details see, for example, Liang, et al., *J. Org. Chem.*, 2006, 71, 379-381; Gholap, et al., *J. Org. Chem.*, 2005, 70, 4869-4872; Liang, et al., *J. Org. Chem.* 2005, 70, 391-393; Elangovan, et al., *Org. Lett.*, 2003, 5, 1841-1844; Batey, et al., *Org. Lett.*, 2002, 1411-1414.

The Cadiot-Chodkiewicz Coupling may also be used to join chemical moieties to proteins or other molecules. This reaction is a copper(I) catalyzed coupling of a terminal alkyne and an alkynl halide offers access to unsymmetrical bisacetylenes. Further details may be found, for example, at Marino, et al., *J. Org. Chem.*, 2002, 67, 6841-6844. Another reaction that may be used to join chemical moieties to proteins or other molecules includes the Eglinton Reaction. This reaction is an oxidative coupling of terminal alkynes, and allows the synthesis of symmetric or cyclic bisacetylenes via reaction of the terminal alkyne with a stoichiometric amount of a copper(I) salt in pyridine. In addition, the Glaser Coupling is a synthesis of symmetric or cyclic bisacetylenes via a coupling reaction of terminal alkynes. The reaction is mechanically similar to the Eglinton Reaction; the difference being the use of catalytic copper(I) which is reoxidized in the catalytic cycle by oxygen in the reaction medium. The Hay Coupling is a copper-catalyzed reaction that utilizes copper-TMEDA complex. For more details on the Eglinton, Glaser, or Hay reactions, see for example, Gibtner, et al., *Chem. Euro. J.*, 2002, 68, 408-432. Each of these references cited are hereby incorporated by reference in their entireties.

Pharmaceutical Compositions

The present invention further relates to pharmaceutical compositions and methods of use. The pharmaceutical compositions of the present invention include modified target molecules in pharmaceutical form, i.e. pharmaceutical salts, derivatives, carriers, and the like. Pharmaceutical compositions of the present disclosure may be made by methods described herein, or other methods known in the art. In at least one embodiment, the pharmaceutical composition exhibits at least one improved property selected from the group consisting of: protein stability, protein activity, protein conformation, protein substrate specificity, protein-target binding affinity, antigen-binding ability, thermostability, protein resistance to at least one protease, protein tolerance to at least one non-aqueous environment, patient tolerance to said protein, increased efficacy of said protein in a patient, improved delivery of said protein or protein product in a patient and any combination thereof.

The present invention also relates to methods of therapeutically or prophylactically treating or diagnosing a disease or disorder by administering a composition or agent of the present invention by any mode described herein. Such composition may be administered in vitro, in vivo, ex vivo or any combination thereof.

For example, if the composition is administered ex vivo, a cell or population of cells (including tissues or organs) may be obtained from a subject and contacted with an amount of a composition of the invention that is effective in prophylactically or therapeutically or diagnostically effective in treating the disease, disorder or condition. Following contact with a composition of the present invention, the cells, tissues or organs may then be returned to the subject in the same or another site.

If the composition is administered in vivo, it may be directly or indirectly administered to the cells, tissues and/or organs of a subject. For example, a particular cell or group of cells may be targeted for administration of a pharmaceutical agent or drug. Any such mode of administration herein described may be utilized in such in vivo delivery.

Most administered protein pharmaceuticals are cleared rapidly from the body, necessitating frequent, often daily injections. Thus, there is considerable interest in developing long-acting protein therapeutics that are able to maintain efficacious levels in the body for long periods of time, providing patients with greater therapeutic benefits. For example, PEGylation-based drug delivery technology is a method for increasing protein half-life.

When more than one reactive site is present in a protein (e.g., multiple amino or thiol groups) or reactive electrophiles are used, nonselective attachment of one or multiple PEG molecules can occur, leading to the generation of a heterogeneous mixture that is difficult to separate. The lack of selectivity and positional control in the attachment of PEG chains can lead to significant losses in biological activity and possibly enhanced immunogenicity of the conjugated protein. Modification of proteins with amine-reactive PEGs typically results in drastic loss of biological activity due to modification of lysine residues located in regions of the protein important for biological activity. In certain situations, bioactivity of growth hormones may be reduced 400-fold or more. For example, bioactivity of GCSF is reduced 1,000-fold when the proteins are modified using conventional amine-PEGylation technologies (Clark et al., *J. Biol. Chem.* 271: 21969, 1996; Bowen et al., *Exp. Hematol.* 27, 425, 1999). Thus there is a need for a method that allows for the completely site-specific and irreversible attachment of PEG chains to molecules, including proteins.

It would be advantageous to use advanced protein engineering technologies to create long-acting, "patient friendly" human protein pharmaceuticals, by, for example, incorporating non-natural amino acids and/or chemical moieties into a pharmaceutical drug, such that the engineered pharmaceutical may achieve longer half life and/or sustained or even enhanced biological activity.

Multi-Drug Immunoconjugates

Immunoconjugation may be used to increase the therapeutic efficacies of antibodies. However, current technologies allow attachment of only a single type of drug to an antibody. This is primarily due to the limitations in the scope of chemistries available in the set of natural amino acids, which do not allow precise control over the immunoconjugation processes.

Attempts to attach multiple drugs on an antibody using current technologies lead to significant heterogeneity from molecule to molecule, and inconsistencies from lot to lot. Non-natural amino acids can be used to provide a wide variety of new chemistries to attach drugs site-specifically, thus enabling the provision of tumor-targeted, multi-drug regimens to cancer patients. For example, the instant methods can be used to produce immunoconjugates either by attaching a single type of drug site-specifically on to antibodies and/or antibody fragments to overcome issues related to heterogeneity, or by attaching multiple drug-types site-specifically on to antibodies and/or antibody fragments in a stoichiometrically controlled manner. In other words, the methods of the instant invention can be used to design a novel class of immunoconjugates that carry a combination of drugs that can be delivered simultaneously and specifically to a particular target site, where the therapeutic molecules in the medicament are highly homogeneous, with lot-to-lot consistency. The major advantages of such immunoconjugates include: simultaneous targeted delivery of multiple drugs that act synergistically in treating and/or killing target cells (including tumor cells); combining drugs that act in different phases of the cell cycle to increase the number of target cells exposed to a particular pharmaceutical drug or effect; focused delivery of the pharmacological agent to target cells, thus maximizing the pharmaceutical benefit or effect; minimized exposure to non-target cells, tissues or organs; precise control over drug payloads and drug ratios leading to homogenous final products.

In one specific example, particular cytokines (such as interferon-β) may inhibit tumor formation, cause regression of established tumors, and/or prevent recurrence of certain cancers. See, for example, Qin, et al. *P.N.A.S.*, V. 95, No. 24, pp. 14411-14416, (1998); Ikeda, et al., *Hepatology*, 32 (2): 228-32, (2000), both of which are hereby incorporated by reference. As disclosed in the cited references, interferon β has potent antiproliferative activity against most human tumor cells in vitro, but relies on high concentrations of cytokine in order to achieve the anti-tumor effect. Such high concentrations cannot be utilized by parenteral protein administration because of rapid protein clearance and systemic toxicities. Thus, a novel modified interferon β that exhibits higher potentcy and sustained in vivo retention in the subject or patient, is needed in the art. In one embodiment of the present invention, a novel, modified interferon β is provided that fills this need.

Thus the invention provides an immunoconjugate comprising an antibody (or its functional fragment) specific for a target (e.g., a target cell), the antibody (or fragment or functional equivalent thereof) conjugated, at specific, predetermined positions, with two or more therapeutic molecules, wherein each of the positions comprise an non-natural amino acid. In certain embodiments, the antibody fragments are F(ab')$_2$, Fab', Fab, ScFv or Fv fragments.

Immobilization of Molecules on a Solid Support

Another aspect of the invention provides a method for immobilizing one or more target molecules, including proteins, peptides, polypeptides, biopolymers or other target molecules to a solid support including an array, a purification column, microscopic slides, tubes, microfluidic devices, chromatography columns or any other surface, the method comprising: (1) incorporating one or more non-natural amino acid(s) at specified position(s) of the polypeptide(s) using any of the suitable methods; (2) contacting the polypeptide(s) with a solid support to conjugate the polypeptide(s) through the non-natural amino acid(s).

In certain embodiments, the one or more target molecules are attached to the solid support in a consistent orientation. In certain embodiments, the active site(s) of each target molecule are accessible to potentially interacting target molecules. In certain embodiments, the target molecule of interest (or library of target molecules) is attached to a solid support through a biological or chemical linker (including any of the chemical moieties disclosed herein).

The solid support may comprise any known solid or semi-solid substance, including resins, glass, metals, silicon, plastics, wood, minerals, fabrics or spun fibers and any combination of these. In addition, the solid or semi-solid support may be coated with another biological or chemical to facilitate adherence of the target molecule(s) to the solid support. Alternatively, such coating may be for selective adherence of specific target molecules or for disallowing specific target molecules from adhering to the solid support.

Another aspect of the invention provides a molecular array produced by any of the suitable subject methods.

In at least one embodiment, a target molecule of the present invention is immobilized by use of a column that has a biological or chemical agent attached (such as a complementary amino acid tag) that selects for the target target molecule(s). Thus, the column will selectively immobilize the target molecules containing the marker through chemical reaction. In at least one embodiment, the biological or chemical marker may be cleaved or separated from the remaining target molecule through chemical or biological cleavage (for example, by use of enzymatic or proteolytic cleaving site).

In at least one embodiment, the one or more non-natural amino acid residues in the modified target molecule may be used to capture the protein on a matrix or solid support for the purpose of immobilizing the target molecule and/or purifying it from other proteins. In at least one embodiment, the other proteins comprise contaminating proteins. In at least one embodiment, the method for immobilizing a modified target molecule from a sample of mixed target molecules (which may contain contaminating target molecules) that includes reversibly binding the modified target molecule comprising one or more non-natural amino acid residue to a matrix and subsequently releasing the target molecule from the matrix once the other target molecules in the sample have been removed.

Kits

The present invention further provides kits relating to any of the compositions and/or methods described herein. Kits of the present invention may include methods of identifying, modifying or altering a target molecule, as well as assays to test at least one property of the modified or altered target molecule.

For example, the kits can include one or more translation system as described herein (e.g., a cell), one or more non-natural amino acid, e.g., with appropriate packaging material, containers for holding the components of the kit, instructional materials for practicing the methods herein and/or the like. Similarly, products of the translation systems (e.g., proteins such as EPO analogs comprising non-natural amino acids) can be provided in kit form, e.g., with containers for holding the components of the kit, instructional materials for practicing the methods herein and/or the like.

A kit of the present invention may include devices, reagents, one or more containers, or other components. A kit of the present invention may also require the use of an apparatus, instrument or device, including a computer.

In one exemplary embodiment, naturally occurring methionine amino acid residues are replaced by non-natural amino acids, such as azido-methionine. Since azide is a versatile functional group and is abiotic in animals as well as being resistant to oxidation and relatively non-reactive with water. Although kinetically stable, azides are predisposed to unique modes of reactivity owing to their large intrinsic energy content, which has been exploited for development of reactions, including the Staudinger ligation of azides with functionalized phosphines and the [3+2] cycloaddition of azides with activated alkynes. Utilizing an auxotrophic host cell that is capable of incorporating azidomethionine highly efficiently, the target molecule will undergo incorporation of the non-natural amino acid azidomethionine.

For example, using an auxotrophic host cell in which phenylalanine non-natural amino acids may be incorporated site specifically at the TTT codon, then the target gene sequence for the target molecule will be designed using only a single codon of phenylalanine (TTC).

For ease in purification, the target molecule may have a poly-azidomethionine tag that would increase the rate at which the target molecule is able to covalently bind to the column. The tag can be linked directly to the target sequence or it may be separated from the target gene with a protease site, thereby enabling the user to purify the target molecule without an azide tag.

All embodiments described herein are intended to be able to be combined with one or more other embodiments, even for those described under different aspects of the invention.

General Techniques

General texts which describe molecular biological techniques, which are applicable to the present invention, such as cloning, mutation, cell culture and the like, include Berger and Kimmel, Guide to Molecular Cloning Techniques, Methods in Enzymology volume 152 Academic Press, Inc., San Diego, Calif. (Berger); Sambrook et al., Molecular Cloning—A Laboratory Manual (3rd Ed.), Vol. 1-3, Cold Spring Harbor Laboratory, Cold Spring Harbor, N.Y., 2000 ("Sambrook") and Current Protocols in Molecular Biology, F. M. Ausubel et al., eds., Current Protocols, a joint venture between Greene Publishing Associates, Inc. and John Wiley & Sons, Inc., (supplemented through 2002) ("Ausubel"), all of which are hereby incorporated by reference in their entireties). These texts describe mutagenesis, the use of vectors, promoters and many other relevant topics related to, e.g., the generation of external mutant tRNA, external mutant synthetases, and pairs thereof.

Various types of mutagenesis are used in the present invention, e.g., to produce novel sythetases or tRNAs. They include but are not limited to site-directed, random point mutagenesis, homologous recombination (DNA shuffling), mutagenesis using uracil containing templates, oligonucleotide-directed mutagenesis, phosphorothioate-modified DNA mutagenesis, mutagenesis using gapped duplex DNA or the like. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, whether chemical or involving chimeric constructs, is also included in the present invention. In one embodiment, mutagenesis can be guided by known information of the naturally occurring target molecule or altered or mutated naturally occurring target molecule, e.g., sequence, sequence comparisons, physical properties, crystal structure or the like.

The above texts and examples found herein describe these procedures as well as the following publications and references cited within: Sieber, et al., *Nature Biotech.*, 19:456-460 (2001); Ling et al., *Anal Biochem.* 254(2): 157-178 (1997); Dale et al., *Methods Mol. Biol.* 57:369-374 (1996); I. A. Lorimer, I. Pastan, *Nucleic Acids Res.* 23, 3067-8 (1995); W. P. C. Stemmer, *Nature* 370, 389-91 (1994); Arnold, *Curr. Opin. in Biotech.* 4:450-455 (1993); Bass et al., *Science* 242:240-245 (1988); Fritz et al., *Nucl. Acids Res.* 16: 6987-6999 (1988); Kramer et al., *Nucl. Acids Res.* 16: 7207 (1988); Sakamar and Khorana, *Nucl. Acids Res.* 14: 6361-6372 (1988); Sayers et al., *Nucl. Acids Res.* 16:791-802 (1988); Sayers et al., *Nucl. Acids Res.* 16: 803-814 (1988); Carter, *Methods in Enzymol.* 154: 382-403 (1987); Kramer & Fritz *Methods in Enzymol.* 154:350-367 (1987); Kunkel, The efficiency of oligonucleotide directed mutagenesis, in Nucleic Acids & Molecular Biology (Eckstein, F. and Lilley, D. M. J. eds., Springer Verlag, Berlin)) (1987); Kunkel et al., *Methods in Enzymol.* 154, 367-382 (1987); Zoller & Smith, *Methods in Enzymol.* 154:329-350 (1987); Carter, *Biochem. J.* 237:1-7 (1986); Eghtedarzadeh & Henikoff, *Nucl. Acids Res.* 14: 5115 (1986); Mandecki, *Proc. Natl. Acad. Sci. USA*, 83:7177-7181 (1986); Nakamaye & Eckstein, *Nucl. Acids Res.* 14: 9679-9698 (1986); Wells et al., *Phil. Trans. R. Soc. Lond.* A 317: 415-423 (1986); Botstein & Shortie, *Science* 229:1193-1201 (1985); Carter et al., *Nucl. Acids Res.* 13: 4431-4443 (1985); Grundström et al., *Nucl. Acids Res.* 13: 3305-3316 (1985); Kunkel, *Proc. Natl. Acad. Sci. USA* 82:488-492 (1985); Smith, *Ann. Rev. Genet.* 19:423-462 (1985); Taylor et al., *Nucl. Acids Res.* 13: 8749-8764 (1985); Taylor et al., *Nucl. Acids Res.* 13: 8765-8787 (1985); Wells et al., *Gene* 34:315-323 (1985); Kramer et al., *Nucl. Acids Res.* 12: 9441-9456 (1984); Kramer et al., *Cell* 38:879-887 (1984); Nambiar et al., *Science* 223: 1299-1301 (1984); Zoller & Smith, *Methods in Enzymol.* 100:468-500 (1983); and Zoller & Smith, *Nucl. Acids Res.* 10:6487-6500 (1982), all of which are incorporated herein by reference. Additional details on many of the above methods can be found in Methods in Enzymology Volume 154, which also describes useful controls for trouble-shooting problems with various mutagenesis methods.

Oligonucleotides, e.g., for use in mutagenesis of the present invention, e.g., mutating libraries of synthetases, or altering tRNAs, are typically synthesized chemically, for example, according to the solid phase phosphoramidite triester method described by Beaucage and Caruthers, *Tetrahedron Letts.* 22(20):1859-1862, (1981) e.g., using an automated synthesizer, as described in Needham-VanDevanter et al., *Nucleic Acids Res.*, 12:6159-6168 (1984), or as described by Tang and Tirrell *J. Am. Chem. Soc.* (2001) 123: 11089-11090 and Tang, et al. *Angew. Chem. Int. Ed.* (2001) 40:8, all of which are hereby incorporated by reference in their entireties.

In addition, essentially any nucleic acid can be custom or standard ordered from any of a variety of commercial sources, such as The Midland Certified Reagent Company, The Great American Gene Company, ExpressGen Inc., Operon Technologies Inc. (Alameda, Calif.) and many others.

The present invention also relates to host cells and organisms for the in vivo incorporation of an non-natural amino acid via external mutant tRNA/RS pairs. Host cells are genetically engineered (e.g., transformed, transduced or transfected) with the vectors of this invention, which can be, for example, a cloning vector or an expression vector. The vector can be, for example, in the form of a plasmid, a bacterium, a virus, a naked polynucleotide, or a conjugated polynucleotide. The vectors are introduced into cells and/or microorganisms by standard methods including electroporation, infection by viral vectors, high velocity ballistic penetration by small particles with the nucleic acid either within the matrix of small beads or particles, or on the surface.

The engineered host cells can be cultured in conventional nutrient media modified as appropriate for such activities as, for example, screening steps, activating promoters or selecting transformants. These cells can optionally be cultured into transgenic organisms.

Other useful references, e.g., for cell isolation and culture (e.g., for subsequent nucleic acid isolation) include Freshney (1994) Culture of Animal Cells, a Manual of Basic Technique, third edition, Wiley-Liss, New York and the references cited therein; Payne et al. (1992) Plant Cell and Tissue Culture in Liquid Systems John Wiley & Sons, Inc. New York, N.Y.; Gamborg and Phillips (eds.) (1995) Plant Cell, Tissue and Organ Culture; Fundamental Methods Springer Lab Manual, Springer-Verlag (Berlin Heidelberg New York) and Atlas and Parks (eds.) The Handbook of Microbiological Media (1993) CRC Press, Boca Raton, Fla., all of which are hereby incorporated by reference in their entireties.

Several well-known methods of introducing target nucleic acids into bacterial cells are available, any of which can be used in the present invention. These include: fusion of the recipient cells with bacterial protoplasts containing the DNA, electroporation, projectile bombardment, and infection with viral vectors, etc. Bacterial cells can be used to amplify the number of plasmids containing DNA constructs of this invention. For example, the bacteria are grown to log phase and the plasmids within the bacteria may be isolated by a variety of methods known in the art (see, for instance, Sambrook). In addition, a plethora of kits are commercially available for the purification of plasmids from bacteria, (see, e.g., EasyPrep™, FlexiPrep™, both from Pharmacia Biotech; StrataClean™, from Stratagene; and, QIAprep™ from Qiagen). The isolated and purified plasmids are then further manipulated to produce other plasmids, used to transfect cells or incorporated into related vectors to infect organisms.

Typical vectors contain transcription and translation terminators, transcription and translation initiation sequences, and promoters useful for regulation of the expression of the particular target nucleic acid. The vectors optionally comprise generic expression cassettes containing at least one independent terminator sequence; sequences permitting replication of the cassette in eukaryotes, prokaryotes or both (e.g., shuttle vectors) and selection markers for both prokaryotic and eukaryotic systems. Vectors are suitable for replication and integration in prokaryotes, eukaryotes or both. (See, for example, Giliman & Smith, *Gene* 8:81 (1979); Roberts, et al., *Nature*, 328:731 (1987); Schneider, B., et al., *Protein Expr. Purif.* 6435: 10 (1995), all of which are hereby incorporated by reference). Additionally, a catalogue of Bacteria and Bacteriophages useful for cloning is provided, e.g., by the ATCC, e.g., The ATCC Catalogue of Bacteria and Bacteriophage (1992) Gherna et al. (eds.) published by the ATCC. Additional basic procedures for sequencing, cloning and other aspects of molecular biology and underlying theoretical considerations are also found in Watson et al. (1992) Recombinant DNA Second Edition Scientific American Books, NY.

Non-natural amino acids may be incorporated into protein using various methods. For example, in one embodiment, if the non-natural amino acid is structurally/sterically similar to one of the twenty natural amino acids, the non-natural amino acid may be incorporated into a target protein by way of competitive biosynthetic assimilation (see, for example, Budisa 1995, *Eur. J. Biochem* 230: 788-796; Deming 1997, *J. Macromol. Sci. Pure Appl. Chem.* A34; 2143-2150; Duewel 1997, *Biochemistry* 36: 3404-3416; van Hest and Tirrell 1998, *FEBS Lett* 428(1-2): 68-70; Sharma et al., 2000, *FEBS Lett* 467(1): 37-40, all of which are incorporated herein by reference).

In certain embodiments, the competing natural amino acids might be selectively depleted to enhance the incorporation of non-natural amino acids.

In another embodiment, non-natural amino acids may be incorporated into a target molecule, including a protein, by using either a nonsense suppressor or a frame-shift suppressor tRNA in response to amber or four-base codons, respectively (See Bain et al., *J. Am. Chem. Soc.* 111: 8013, 1989; Noren et al., *Science* 244: 182, 1989; Furter, *Protein Sci.* 7: 419, 1998; Wang et al., *Proc. Natl. Acad. Sci, U.S.A.*, 100: 56, 2003; Hohsaka et al., *FEBS Lett.* 344: 171: 1994; Kowal and Oliver, *Nucleic Acids Res.* 25: 4685, 1997, all of which are incorporated herein by reference) Such methods insert non-canonical amino acids at codon positions that will normally terminate wild-type peptide synthesis (e.g., a stop codon or a frame-shift mutation). These methods have worked well for single-site insertion of novel amino acids. These methods may work modestly well for multisite incorporation, if modest (20-60%) suppression efficiencies are acceptable (See Anderson et al., *J. Am. Chem. Soc.* 124: 9674, 2002; Bain et al., *Nature* 356: 537, 1992; Hohsaka et al., *Nucleic Acids Res.* 29: 3646, 2001, all of which are incorporated herein by reference).

In yet another embodiment, efficient multisite incorporation may be accomplished by replacement of natural amino acids in auxotrophic *Escherichia coli* strains, and by using aminoacyl-tRNA synthetases with relaxed substrate specificity or attenuated editing activity (See, for example, Wilson and Hatfield, *Biochem. Biophys. Acta* 781: 205, 1984; Kast and Hennecke, *J. Mol. Biol.* 222: 99, 1991; Ibba et al., *Biochemistry* 33: 7107, 1994; Sharma et al., *FEBS Lett.* 467: 37, 2000; Tang and Tirrell, *Biochemistry* 41: 10635, 2002; Datta et al., *J. Am. Chem. Soc.* 124: 5652, 2002; Doring et al., *Science* 292: 501, 2001, all of which are incorporated herein by reference). This method may be useful, particularly when it is acceptable to allow non-natural amino acids to "share" codons with one of the natural amino acids, and when incorporation at an unintended site does not substantially compromise the function of the target molecule.

EXAMPLES

The following examples are provided as further illustrations and not limitations of the present invention. The teachings of all references, patents and published patent applications cited throughout this application, as well as the Figures are hereby incorporated by reference.

Example 1 (Prophetic)

Design of Site-Specific PEGylated Proteins

The design of a pegylated GM-CSF, Erythropoietin (EPO), Human Growth Hormone, Phenylalanine hydroxylase, urikase, Factor VII, follitropin, G-CSF, or other target molecule may comprise a multi-step process. In the case of EPO, which wild type sequence contains two methionine amino acids—including one at the amino terminus, only one methionine would require substitution. In the case of G-CSF, the wild type sequence does not contain any arginine residues. Thus, an arginine residue could be introduced at any desirable location in the molecule and subsequently substituted or replaced with a non-natural amino acid. Likewise, for Human Growth Hormone, the wild type sequence only contains a single tryptophan residue, phenylalanine hydroxylase contains only 3 methionine residues and 3 tryptophan residues, and follitropin contains only 5 methionine residues.

In an optional first step, existing specific target wild type amino acids (for example, methionine residues) will be designed to other naturally occurring amino acid residues. The amino acid residues that replace the target wild type amino acids would likely support the molecule's native structural stability and/or activity. Next, specific amino acid residue positions will be selected for incorporation of one or more non-natural amino acid. The selected amino acid residue positions for incorporation of the non-natural amino acids may be the same amino acid residues that were replaced by other naturally occurring amino acid residues in the optional first step, or may be naturally occurring amino acid residues that were not changed, or may be still other positions corresponding to codons in the nucleotide sequence not effectively encoding any natural amino acid including, for example, stop codons, 4 or 5 base codons, or bias codons. The non-natural amino acid residues may or may not be a corresponding analog to the specific amino acid being replaced in the optional first step.

Replacement of amino acid residues with other naturally occurring amino acid residues and/or incorporation of non-natural amino acid residues may be accomplished by any methods known or as-yet unknown in the art. For example, amino acid specific external mutant tRNA synthetase-tRNA pairs may be employed to increase the yield and efficiency of the substitution (including, for example, stop codons such as amber codon, ochre codon, or opal codon; degenerate codons such as wobble codons, bias codons, 4 or 5 base pair codons, sixth box codons, or other means) or other codons which typically specify a naturally occurring amino acid but is distinct from the other codons used in the protein to encode that particular naturally occurring amino acid. Host cell lines that have been engineered to preferentially incorporate a particular amino acid (or amino acids) may be utilized, including but not limited to auxotrophic host cell lines. The host cell line may be modified by site directed mutagenesis (including, for example, by PCR, restriction digests and re-ligation, chemical mutagenesis, or other means). Other methods of altering a particular amino acid residue may be used, such as engineering host cells with exogenous or external mutant AARS with or without a cognate tRNA, to facilitate incorporation of a particular non-natural amino acid.

In the next step, a chemical moiety (such as polyethylene glycol) is added to the non-natural amino acid residue in the molecule, thereby forming a pegylated GM-CSF molecule.

The amino acid residues selected for replacement by naturally occurring amino acid residues and/or non-natural amino acid residues may be determined, in part, by evaluating energy calculations and/or three-dimensional structural location of the residues. Additionally, replacement amino acids may be selected by alignment of nucleic acid or amino acid sequences of related genes or proteins, respectively. Such sequences may be from the same species or different species.

Optionally, rather than replacing all specific target wild type amino acid residues with other naturally occurring amino acid residues, as described in the optional first step, an alternative approach may be used. For example, one or more specific target wild type amino acid residue(s) may be retained in the molecule, which may then be substituted with a non-naturally occurring amino acid residue and the subsequent addition of a chemical moiety made to the non-naturally occurring amino acid.

Example 2 (Prophetic)

Site-Specific PEGylation of GM-CSF

A GM-CSF molecule contains four wild type methionine amino acid residues at positions 36, 46, 79 and 80. There are at least two possibilities for inserting a site-specific methionine analog into GM-CSF for use as an anchoring residue for pegylation.

One option would be to retain one of the four methionine residues in the GM-CSF molecule and replace the three other methionine residues with other naturally occurring amino acid residues. Selecting which three methionine residues will be replaced and/or selecting which naturally occurring amino acid residues shall replace the three wild type methionine residues may be determined, in part, by evaluating energy calculations as described herein. Additionally, replacement amino acids may be selected by alignment of nucleic acid or amino acid sequences of related genes or proteins, respectively. The sequences may be from the same species or different species.

A second option would be to replace all four methionine residues in the GM-CSF molecule and add a methionine residue at another specific location on the molecule. Next, the added or retained methionine residue will be replaced with a non-natural amino acid residue. Again, selecting whether three or four methionine residues are replaced, as well as selecting the specific location of the newly added methionine residue may be determined, in part, by evaluating energy calculations and alignments of related sequences.

Example 3 (Prophetic)

Energy Calculations for Site-Specific PEGylated GM-CSF

Energy calculations for the target molecule discussed in the previous Example may be conducted by any known method, some of which are described herein. The sequence and number of energy calculations may be performed in a number of ways. For example, a point mutation calculation may be performed for each selected methionine position (which include positions 36, 46, 79 and 80). Alternatively or additionally, combination mutation calculations may be performed for all four methionines such that one methionine is retained in its wild type position, while the other three methionine residues will be varied simultaneously to other naturally occurring amino acids. In this manner, it may be determined whether all four methionine residues will be replaced with other amino acid residues, or if one methionine residue will be retained while the other three are replaced with other naturally occurring amino acid residues.

In order to limit energy calculations, the structural architecture of the molecule may be considered. For example, replacing the wild type methionine residues in the core of the GM-CSF molecule may be restricted to only hydrophobic amino acids, in order to maintain the structural integrity of the molecule. Whereas methionine residues that are located at positions that are partially or completely solvent exposed may be replaced with a broader selection of amino acid residues.

Once energy calculations for replacing the wild type target amino acid residue(s) (e.g. methionine residues) have been conducted, the most energetically favorable model GM-CSF molecule(s) will be generated and tested for stability and function. Modified GM-CSF molecules that test successfully for stability and function may be used for further design of insertion and/or replacement of methionine residues with non-natural amino acid residues.

In addition to energy calculations, determining the positions for incorporating non-natural amino acid residues (e.g. methionine analogs) will be based on the overall structure and architecture of the GM-CSF molecule. For example, favorable positions for inserting or replacing a methionine residue with a non-natural amino acid residue may include surface-exposed positions, preferably distal from the receptor-binding site. Positions to avoid may possibly include core amino acid residues and/or residue positions at the dimer interface or that are unsymmetrical with regard to the dimer, as well as amino acid positions that are highly conserved (such as surface amino acids) residues.

Example 4 (Prophetic)

Selection of Non-Natural Amino Acids

The selection of non-natural amino acid residues for replacement of the target amino acid residue (whether retained in the wild type position or added after replacement of all specific target amino acid residues) may include choosing any known or newly generated non-natural amino acid that is capable of retaining the protein's structure and/or function or capable of being utilized by the endogenous protein translational apparatus of the host cell. In order to preserve the structural integrity of the GM-CSF molecule, the non-natural amino acid residue may be an analog of the target wild type amino acid residue. For example, a methionine residue may be replaced in the GM-CSF molecule with a methionine analog, such as homoproparglyglycine (HPG) or azidohomoalanine (AHA). Such a substitution may occur in a methionine auxotrophic cell line, or may utilize an overexpressed methionyl-tRNA synthetase, or a mutant aminoacyl-tRNA synthetase capable of incorporating the non-natural amino acid at the methionine position.

Determining which non-natural amino acid residues to incorporate into the GM-CSF molecule may be conducted, in part, by evaluating energy calculations. For example, using an existing (or synthesizing a new) rotamer library for the non-natural amino acids may be used. The rotamer library may be based on the torsional angles of other known methionine analogs, if exact rotamers of HPG and/or AHA are not known. Once the rotamer library is obtained, point mutation calculations may be performed as described herein, in order to determine which non-natural amino acid replacement is most energetically favorable.

Example 5 (Prophetic)

Site-Specific Modification of Other Proteins

The aforementioned steps and Examples may also apply to other molecules, such as interferon-α, interferon-β, Factor VII, hematopoietic growth factors, monoclonal antibodies (including bispecific antibodies and toxins), insulin-like growth factor I, insulin, human Growth Hormone, IL-2, erythropoietin, G-CSF, GM-CSF, Phenylalanine hydroxylase, prolactin, luteinizing hormone, follitropin, parathyroid hormone, proglucagon, glucagon, GLP-1, GLP-2, GLP receptors, exendins (including exendin-4), exendin receptors, or thrombolytics. Additionally, the specific target wild type amino acid may vary and may include any naturally occurring amino acid, including alanine, arginine, asparagines, aspartic acid, glutamine, glutamic acid, glycine, methionine, proline, serine, leucine, cysteine, tryptophan, isoleucine, phenylalanine, tyrosine, threonine, histidine, valine, and lysine. The non-natural amino acids may contain functionally important side chains, such as alkyne and azide derivatives of the particular amino acids.

Example 6 (Prophetic)

Methods of Site-Specific PEGylation

Proteins or other molecules may have a chemical moiety, including polyethylene glycol, attached or fushed to a particular amino acid, and especially a non-natural amino acid residue as described here in other areas of the application. The protein containing the non-natural amino acid (which may include a halogenated aryl or vinyl group, such as para-bromophenylalanine or para-iodophenylalanine) may then be pegylated via a conjugation reaction that is otherwise unreactive with the endogenous and naturally occurring amino acids of the proteins. Such conjugation reactions are known in the art and include palladium-catalyzed Suzuki reaction with PEG-phenylboronic acid, palladium-catalyzed Sonogashira coupling with PEG-alkyne, palladium-catalyzed Heck coupling with PEG-alkene or palladium-catalyzed Hiyama reaction with PEG-silane. These palladium-catalyzed reactions, as well as others, are described in detail in other areas of the application. These reactions result in a carbon-carbon linkage between the PEG and the target protein.

In other aspects of the invention, the non-natural amino acid may contain a halogenated aryl or vinyl group (for example, para-bromophenylalanine or para-iodophenylalanine). A cross-coupling reaction may be conducted, such as a palladium-catalyzed Suzuki reaction with PEG-phenylboronic acid, or other reaction described herein to yield a carbon-carbon linkage between the chemical moiety (such as PEG) and the molecule. Several common procedures used historically to conjugate chemical moieties to molecules (including proteins) also react with functional groups present in naturally occurring amino acids, such as the epsilon amino group in lysine or the thiol group in cysteine residues. Thus, these non-specific reactions result in the final protein preparation containing many isomers of proteins conjugated to one or more chemical moieties at different locations within the protein, depending on the amino acid sequence of the target protein.

In one particular example, pegylated human interferon-α-2B protein product (PEG-Intron) includes up to 14 monopegylated and multipegylated positional isomers, with the PEG moiety occurring at lysine, tyrosine, histidine, serine and cysteine residues. Protein products that are mixed isomers may have lower activity due to the myriad of locations where the chemical moiety is attached. For example, PEG-Intron has an antiviral activity of 28% of the unmodified interferon-α protein, with a range of 6-37% for individual isomer species. In addition, manufacturing costs are increased due to the need to separate out the fraction of undesired species and additional processing of the variable modified protein batches. Thus, there is a need in the art for production of proteins with chemical moieties (including PEG) that are consistently modified at specific preferred sites.

While some techniques for biasing the location of the chemical moiety attachment are known in the art, such as adjusting the pH of the reaction mixture, using protecting groups for some amino acid residues during chemical moiety conjugation, altering the folding state of the protein to allow for better structural access to specific protein regions, and altering the chemistry of the activated chemical moiety species so it is less likely to react with other nondesired functional groups, none of these techniques eliminates side reactions with undesired amino acid residues. One known technique avoids side reactions with undesired amino acid residues by using protecting groups for some amino acid residues during chemical moiety conjugation, followed by removing the protecting groups from the modified protein. However, this technique is cumbersome, expensive and impractical for manufacturing a modified protein product, and requires that the protein be synthesized by chemical means rather than by fermentation.

It is desirable to synthesize molecules, including therapeutic molecules, in which the added chemical moiety may be specifically directed to a target location in the molecule in order to reduce variability of the final modified protein product and increase activity or other desired goal. For example, if the chemical moiety is near an active binding site of the protein, it can sterically block desired interactions of the protein in vivo, if the chemical moiety is located near an antigenic epitope, it may reduce the antigenicity of the molecule in vivo. Likewise, if the chemical moiety is located away from active sites, it may sterically protect the molecule from renal uptake or clearance in vivo without reducing the activity of the molecule.

Since certain embodiments of the chemical reactions described herein provide for reactions that solely react with unique functional groups in non-natural amino acid residues, the reactions allow for naturally occurring amino acids to remain unmodified. For instance, palladium-catalyzed cross coupling reactions are largely unreactive with naturally occurring amino acid residues, thus allowing for site specific, covalent linkage of a chemical moiety with the molecule without undesired conjugation elsewhere in the molecule. Another advantage is that these specifically disclosed chemical reactions may be performed in mild aqueous conditions that are not damaging to proteins. In addition, the conjugation chemistry may be reversed. For example, homoproparglyglycine could be coupled with a bromophenyl-PEG by a Sonogashira coupling. Thus, in some embodiments, the reactive group is present on an activated chemical moiety, rather than the target non-natural amino acid.

In certain other embodiments, multiple different non-natural amino acid residues may be incorporated into a target molecule and one or more of the non-natural amino acid residues could be conjugated to a chemical moiety by any of the techniques described herein.

A number of other well-known chemical reactions may be utilized to attach a chemical moiety to a protein or other molecule, some of which are described herein. The reactive group may be either located on the target molecule, or in a bifunctional linker group that reacts with the non-natural amino acid and with the chemical moiety to be attached. The Suzuki Coupling is a palladium-catalyzed cross coupling between organobornic acid and aryl or vinyl halides, pseudo-halides (including triflates), alkyls, alkenyls and/or alkynyls. In addition, potassium trifluoroborates and organoboranes or boronate esters may be used instead of boronic salts. For more details, see for example, Baxter, et al., *J. Am. Chem. Soc.*, 2003, 125, 7198-7199; Wu, et al., *J. Org. Chem.*, 2003, 68, 670-673 and Molander, et al., *J. Org. Chem.*, 2002, 67, 8424-8429.

For a Sonogashira Coupling, PEG-alkyne can be synthesized by reacting propargylamine with monomethoxy-poly (ethylene glycol)-NHS, where NHS is any N-Hydroxysuccinimidyl ester of PEG designed for reaction with amines. PEG-alkyne can also be synthesized by reductive amination between monomethoxy-poly (ethylene glycol)-aldehyde and propargylamine with a reducing agent, such as sodium cyanoborohydride. The PEG-alkyne can then be conjugated to the protein containing p-bromophenylalanine in its sequence.

For a Heck Coupling, PEG-alkene can be synthesized by reacting allylamine with an activated PEG as described above for a Sonogashira Coupling.

A general palladium catalyzed reaction may use Pd(Oac)$_2$, Na$_2$DCl$_4$ or PdCl$_2$, for example. A ligand, such as tris(3-sulfonato-phenyl)phosphine trisodium, 2-(di-tert-butylphosphino) ethyltrimethylammonium chloride, or phenylbis(3-(N,N-Dimethylguanidino)phenyl)phosphine dihydrochloride may be added to accelerate the reaction. A base such as triethylamine, pyrrolidine, Na$_2$CO$_3$, diisopropylamine or tetrabutylammonium acetate may be added to accelerate the reaction, although it may also occur in aqueous buffer solutions with acidic pH. In the case of a Sonogashira reaction, a copper co-catalyst such as Cu (I) is added. The activated PEG species and the aryl halide-containing non-natural amino acid species are combined with the above reagents in water to couple the two species together.

These reactions may proceed in aqueous solutions at a lower temperature such as 4° C., room temperature, 37° C., or elevated temperatures. Exclusion of oxygen may aid the kinetics but is not necessary. Iodinated aryl groups are more active but brominated aryl groups may also be used. The addition of an electron-withdrawing group to the phenyl ring, such as a nitro or acetyl group, may improve reactivity, especially for the brominated species. This reaction is beneficial in that the reactants and catalysts undergo few, if any, side reactions with naturally occurring amino acids. These reactions also provide site-specific conjugation of PEG to non-natural amino acid residues incorporated into the molecule. The C—C bond (single, double or triple bond) formed in this conjugation reaction between PEG and the non-natural amino acid is stable, both in storage conditions and in vivo.

Example 7 (Prophetic)

Copper Catalyzed Site-Specific PEGylation

In another example, a PEG-alkyne may be conjugated to azidohomoalanine via a [3+2] copper catalyzed cycloaddition to yield a triazole linkage between the PEG and the protein. In this reaction, the copper catalyst may be provided by ultrapure CuBr, by CuSO$_4$ combined with a reducing agent such as tris(2-carboxyethyl)phosphine, ascorbate, or dithiothreitol, by copper wire with exposure to air, or other sources. In addition, the reaction may be further accelerated by adding a ligand, such as bathophenanthrolinedisulfonic acid, tris-(triazolyl)amine, or other triazole or phosphine ligands, or by adding palladium catalysts. Furthermore, the degree of exposure to oxygen or the redox state of the reaction may be controlled to improve reaction yields.

Example 8 (Prophetic)

Codon-Modified Genes

In another example, a gene for a target molecule (such as a protein) will be designed using only a single codon of a target amino acid, such as phenylalanine (TTC), and a tag will be added to the target molecule containing the TTT wobble phenylalanine codon. The non-natural amino acid joined with the reactive chemical moiety (the non-natural phenylalanine, in this case), will be incorporated only at the tag region using a tRNA-Phe (outfitted with the AAA anticodon) designed to incorporate the non-natural phenylalanine analog at the wobble TTT codon. The molecule or protein may be bound to a column containing a chemical group reactive with the side chain of the non-natural phenylalanine analog contained specifically in the protein tag region, and may optionally contain a protease or other enzymatic cleavage site. The amino acid tag and/or cleavage site may be located on either end of the molecule (i.e. the N-terminal or C-terminal end). The amino acid tag may be linked directly to the molecule or protein sequence, and the tag may be separated from the rest of the molecule by a protease or other cleavage site.

For example, any of the following molecules may be constructed by methods known in the art, including mutating tRNA from eukaryotic or prokaryotic sources to be outfitted with the AAA anticodon (tRNA$^{Phe}_{AAA}$) which reads UUU codons faster than wild-type tRNA$^{Phe}_{GAA}$. The tRNA$^{Phe}_{AAA}$ is then selectively charged with an non-natural amino acid and multiple site-specific incorporation of the analog in the protein tag results. (For more details see, for example, Kwon, et al., *J. Am. Chem. Soc.* 2003, 125, 7512-7513):

1. START codon—(TTT)$_N$—Protease Site—Target Protein/Molecule
2. START codon—(TTT)$_N$—Target Protein/Molecule
3. START codon—Target Protein/Molecule—(TTT)$_N$
4. START codon—Target Protein/Molecule—Protease Site—(TTT)$_N$ Example 9 (Prophetic)

Expression of Site-Specific Modified Proteins

While any phenylalanine analog may be used in this Example, an *E. coli* auxotrophic strain with a mutant yeast phenylalanine tRNA synthetase and/or modified yeast tRNA is capable of incorporating phenylalanine analogs (such as azido-phenylalanine, alkyne phenylalanine or acetyl-phenylalanine) at specific wobble codons with little misincorporation of the analog in the target protein/molecule at other phenylalanine positions.

Misincorporation of natural phenylalanine into the tag region (if a tag is included) may be controlled by providing the cells with a significantly higher concentration of the phenylalanine analog compared to naturally occurring phenylalanine residues in the medium. Since a lower concentration of phenylalanine may limit the overall protein yield, the poly(TTT) tag may also be increased in length.

Finally, the poly(TTT) tagged molecules may be immobilized on a solid support surface by preparation of a column or other surface containing the corresponding amino acid.

Example 10

Expression Vector for Modified IFNβ

An *E. coli* synthetic gene encoding a 20 kDa modified human interferon-β protein with a single methionine codon (at the amino terminus) was amplified by polymerase chain reaction (PCR) using overlapping oligonucleotides (kit from OPERON®). The synthetic gene was cloned into the pQE30 expression vector (available from QIAGEN®) under the control of a T5-lac-lac promoter/regulator using standard molecular biology techniques, thus forming an interferon-β mutein.

Example 11

Modified IFNβ

Different penultimate amino acid residues were introduced into the mutein by standard molecular biology site-directed mutagenesis. The oligonucleotide sequences encoding the N-terminal tryptic peptide of 11 amino acids are listed in the Table 1 below. The sequences of all of the cloned genes were confirmed by DNA sequencing, using standard methods.

TABLE 1

NUCLEIC ACID AND AMINO ACID SEQUENCES

| Name | N-terminal oligonucleotide sequence | Peptide Sequence |
|---|---|---|
| IFNβ-2A | Atggcgtataatctgttaggctttctgcaacgt (SEQ ID NO: 7) | XQYNLLGFLQR (SEQ ID NO: 8) |
| IFNβ-2S | Atgagctataatctgttaggctttctgcaacgt (SEQ ID NO: 9) | XSYNLLGFLQR (SEQ ID NO: 10) |
| IFNβ-2G | Atgggctataatctgttaggctttctgcaacgt (SEQ ID NO: 11) | XGYNLLGFLQR (SEQ ID NO: 12) |
| IFNβ-2H | Atgcactataatctgttaggctttctgcaacgt (SEQ ID NO: 13) | XHYNLLGFLQR (SEQ ID NO: 14) |
| IFNβ-2Q | Atgcagtataatctgttaggctttctgcaacgt (SEQ ID NO: 15) | XQYNLLGFLQR (SEQ ID NO: 16) |
| IFNβ-2E | Atggagtataatctgttaggctttctgcaacgt (SEQ ID NO: 17) | XEYNLLGFLQR (SEQ ID NO: 18) |

CALCULATED PEPTIDE MOLECULAR WEIGHT (Daltons)

| Name | X = Met | X = AHA | X = HPG | X Cleaved |
|---|---|---|---|---|
| IFNβ-2A | 1324.70 | 1319.62 | 1302.63 | 1193.66 |
| IFNβ-2S | 1340.69 | 1335.61 | 1318.62 | 1209.65 |
| IFNβ-2G | 1340.68 | 1305.60 | 1288.61 | 1179.64 |
| IFNβ-2H | 1390.72 | 1385.64 | 1368.65 | 1259.68 |
| IFNβ-2Q | 1381.72 | 1376.64 | 1359.65 | 1259.68 |
| IFNβ-2E | 1382.70 | 1377.62 | 1360.63 | 1251.66 |

Example 12

Expression of Modified IFNβ

The pQE30 expression vector containing the synthetic interferon-β gene was transformed with a helper plasmid (pREP4 from QIAGEN®) into a methionine auxotrophic host cell (M15MA) (Link, Tirrell, *J. Am. Chem. Soc.* 125: 11164-11165 (2003)). Two antibiotics (100 mg/L carbenicillin and 50 mg/L kanamycin) were used in all culture media for selection of both pQE30 and pREP4 plasmids.

A single colony was selected and used to inoculate LB broth for overnight growth at 37° C. The overnight culture was diluted 50 fold the next morning into fresh LB media, and the cells were allowed to grow at 37° C. until the concentration was approximately 1 (OD=600). The culture was then centrifuged to obtain a cell pellet and remove the LB media. Cells were resuspended in M9 minimal media and grown at 37° C. for half an hour. Cells were centrifuged again, and resuspended in M9 minimal media supplemented with 19 amino acids (no methionine). The cell culture was supplemented with 50 mg/L of L-azidohomoalanine (AHA) (MEDCHEM®, WA) or L-homopropargylglycine (HPG) (Tirrell Lab, CalTech). Parallel cultures with and without 25 mg/L methionine were grown as controls. A final concentration of 1 mM IPTG was added last to induce recombinant protein expression (via inducible promoter). Cells were harvested 2 hours post induction.

Example 13

Analysis of Recombinant Proteins

Recombinant proteins were analyzed by matrix assisted laser desorption/ionization mass spectrometry (MALDI-MS). First, recombinant muteins were separated from endogenous *E. coli* proteins by 4-20% SDS-PAGE under reducing conditions, using standard techniques. The interferon-β mutein band was visualized by Coomassie blue stain or SureBlue Safestain (INVITROGEN®), and was excised from the gel and subjected to overnight trypsin digestion at 37° C. after destaining and modification with iodoacetamide. Following sample drying, it was re-dissolved in 0.1% trifluoroacetic acid (TFA) containing 2% acetonitrile. The same was then desalted by using wall-coated C18 micropipette tips (NEW OBJECTIVE®) and eluted in 10-20 microliters of 60% acetonitrile with 0.1% TEA. The eluted sample was mixed sith an equal volume of 10 mg/mL alpha-cyano-4-hydroxycinnamic acid in 70% acetonitrile containing 0.1% TFA plus 5 mM ammonium dihyrogen phosphate (ALDRICH®). One microliter was spotted on an OPTI-TOF® 96 well insert (APPLIED BIOSYSTEMS®) and analyzed using a 4800 MALDI TOF/TOF analyzer calibrated for a mass range of 900 to 4000 Da with "4700 calibration mix" (APPLIED BIOSYSTEMS®).

For mass spectrometry data acquisition, 100 laser shots were fired at 20 different random locations on the sample spot (total of 2000 laser shots per sample). For tandem mass spectrometry (MSMS) data acquisition, up to 3000 laser shots were accumulated per precursor ion. The N-terminal amino acid residues were confirmed by the presence of anticipated fragment ions in their respective tandem mass spectra.

Example 14

Processing of N-Terminal Unnatural Amino Acids in Recombinant Proteins in *E. coli*

We demonstrate the effects of the penultimate amino acid residue (the amino acid residue directly following the initiator methionine) on the processing of two non-natural amino acids, L-azidohomoalanine (AHA) and L-homopropargylglycine (HPG) at the amino terminus of proteins in *E. coli*. We have identified several specific amino acids at the penultimate position that can be used to efficiently retain or remove the amino terminal AHA or HPG.

Recombinant interferon-β mutein was isolated by washing the host cell inclusion bodies, followed by separation via 4-20% SDS-PAGE. After transferring the product to a PVDF membrane, the interferon-β band was cut and analyzed with five cycles of Edman degradation on a sequencer machine equipped with on-line HPLC system. Routinely, 1.0 pmol PTH-standards were used for calibration. S4 solvent, which transfers the PTH-derivatives to HPLC, contains 1.2 pmol PTH-norvaline thus acting as an internal calibrant to independently monitor transfer to the HPLC.

Free non-natural amino acids (HPG, AHA, 2,4-diaminobutyric acid) were subjected to N-terminal sequencing to establish their elution time and stability to the sequencing conditions. A synthetic peptide containing AHA at the N-terminus (X-SYNLLG, where X=AHA) (SEQ ID NO: 22) was custom synthesized by MEDCHEM® (Federal Way, Wash.). X-SYNLLG (SEQ ID NO: 22) was used as a standard to generate a correlation factor to convert the AHA peak area to its molar amount. The percentage of cleaved product was calculated by dividing the amount of protein initiated at the second position by the sum amount of protein initiated at both the first and second positions. The efficiency of cleavage is reported as the mean values of 2-4 sequence cycles. Percentage of amino-terminal processed proteins based on amino-terminal sequencing analysis are presented in TABLE 2 below.

TABLE 2

| Name | Percentage Cleaved Product | |
|---|---|---|
| | with AHA | with HPG |
| IFNβ-2A | 96 | 91 |
| IFNβ-2S | 80 | 80 |
| IFNβ-2G | 52 | 33 |
| IFNβ-2H | 8 | 0 |
| IFNβ-2Q | 0 | 0 |
| IFNβ-2E | 0 | 0 |

Thus, the extent of processing of AHA or HPG at the N-terminus depends on the identity of the penulatimate amino acid residue. Of the three amino acids that favor the removal of N-terminal methionine (alanine, glycine and serine), alanine is most efficient (90-100%). Therefore, potentially all penulatimate residues that are inactive for methinonine AP cleavage of N-terminal methionine will also retain N-terminal AHA or HPG, as shown for histidine, glutamine, and glutamic acid. Furthermore, manipulating MetAP expression levels or substrate binding site may represent another strategy for desired processing of N-terminal UAAs.

Example 15

Modification of Human IFNβ

A human interferon-β molecule was modified according to the methods described herein. The amino acid residues at positions 1 (methionine), 2 (serine), 17 (cysteine), 36 (methionine), 40 (isoluecine), 44 (isoleucine), 62 (methionine), and 117 (methionine) were substituted to other natural or non-natural amino acids. In particular, the amino acid at residue position 1 (methionine) was substituted to either azidohomoalanine or homopropargylcine. The amino acid at position 2 (serine) was substituted to alanine, glycine, histidine, glutamine, or glutamic acid. The amino acid residue at position 36 (methionine) was substituted to threonine, alanine or isoleucine. The amino acid residue at position 40 (isoleucine) was substituted to phenylananine or leucine. The amino acid residue at position 44 (isoleucine) was substituted to leucine. The amino acid residue at position 62 (methionine) was substituted to leucine, isoleucine, valine, glutamine, serine, threonine, histidine, asparagines, tyrosine, phenylalanine, alanine, or glycine. The amino acid residue at position 117 (methionine) was substituted to threonine, tyrosine, serine or glycine. The resulting modified human interferon beta molecule produced a stably folded protein with functional activity.

The particular amino acid incorporated was chosen based on a number of criteria, including sequence comparison of the human interferon-β gene with those from other species. A mutant interferon-β retained gene and protein function when the methionine residue at amino acid position 36 was replaced with threonine, alanine, or isoleucine, as well as when the serine at position 2 was replaced with either serine, alanine, histidine, glycine, glutamine (preferred) or glutamic acid. Other interferon-β mutants were synthesized with retained gene and protein function when the methionine residue at amino acid position 117 was replaced with threonine, tyrosine, serine, or glycine.

Example 16

Analysis of IFNβ Muteins

When the methionine residue at amino acid position 62 of the human interferon-β sequence was replaced with any single naturally occurring amino acid residue, including leucine, isoleucine, valine, glutamine, serine, threonine, histidine, asparagines, tyrosine, phenylalanine, alanine, or glycine, further mutations were needed for function and/or stability.

Thus, the isoleucine residue at amino acid position 40 and/or the isoleucine residue at amino acid position 44 were also substituted with other amino acid residues, since residues at these positions were predicted to interact with the residue at amino acid position 62.

Sequence analysis indicated the sequence of *Gallus gallus* interferon-β contained an isoleucine residue at amino acid position 62, a phenylalanine residue at amino acid position 40, combined with a leucine residue at amino acid position 44 ("chicken triple"). According to the crystal structure and as predicted by the computational modeling, the amino acid residues at positions 40 and 44 form a non-covalent bond or otherwise interact with the amino acid at position 62 of the interferon-β molecule (See Tables 3-5). The corresponding substitutions were made in the human interferon-β mutants and the resulting multi-substituted mutant exhibited increased activity (see Figures).

By comparison, substituting the methionine residue at position 62 with a leucine residue, combined with substituting the isoluecine residue at position 40 with a leucine residue, corresponding to the Australian echidna species sequence, failed to produce a stably folded or functional protein.

TABLE 3

COMPUTATIONAL PREDICTIONS OF Met62 WITH ASSOCIATED RESIDUES, 40 AND 44

| 62 | 40 | 44 | Total Energy | |
|---|---|---|---|---|
| M | I | I | −22.91406 | Human |
| T | I | I | −15.94224 | |
| I | I | I | −10.97000 | |
| F | I | I | −17.28953 | |
| L | I | I | −9.61812 | |
| I | F | L | −22.81071 | Chicken |
| L | L | I | −5.78861 | |

TABLE 4

REPEAT BIOASSAY OF Met SUBSTITUTIONS APPROXIMATE VALUE

| | Arbitrary Units of Biological Activity (units/100 pg) |
|---|---|
| Chicken triple (M62I, I40F, I44L) | ~9.9 |
| M117any* | ~1 |
| M36T | ~0.75 |
| M36A | ~0.75 |
| M36I | ~2.5 |
| Avonex | ~5.3 |
| Wt IFN beta | ~1.2 |

HEK 293 transfection supernatants were retested, and repeat transfections were tested.
IFN beta activity of supernatant or Avonex was measured as inhibition of Daudi cell proliferation.
Units/100 pg are expressed as relative to wt IFN beta (1 unit/100 pg).
*any naturally occurring amino acid.

TABLE 5

BIOASSAY OF MET SUBSTITUTIONS AND monoMET IFN BETA APPROXIMATE VALUE

| | Concentration (pg/ml) | | | | | | | | | | |
|---|---|---|---|---|---|---|---|---|---|---|---|
| | 10 | ~45 | ~65 | ~90 | ~200 | ~500 | ~800 | ~2000 | ~6000 | ~8000 | 10000 | ~40000 |
| Anonex new std | 96 | 115 | 105 | 104 | 103 | 91 | 69 | 61 | 61 | 50 | 55 | 35 |
| Avonex new std repeat | 92 | 92 | 100 | 111 | 98 | 81 | 61 | 52 | 51 | 51 | 54 | 41 |
| wt IFN-beta KG1-50.1 | 83 | 92 | 115 | 101 | 105 | 90 | 70 | 59 | 52 | 48 | 55 | 41 |

TABLE 5-continued

BIOASSAY OF MET SUBSTITUTIONS AND monoMET IFN BETA APPROXIMATE VALUE

| | Concentration (pg/ml) | | | | | | | | | | |
|---|---|---|---|---|---|---|---|---|---|---|---|
| | 10 | ~45 | ~65 | ~90 | ~200 | ~500 | ~800 | ~2000 | ~6000 | ~8000 | 10000 | ~40000 |
| wt IFN-beta KG1-52.1 | 65 | 92 | 100 | 101 | 99 | 89 | 65 | 52 | 47 | 45 | 48 | 31 |
| Triple | 60 | 79 | 71 | 52 | 51 | 58 | 51 | 50 | 49 | 53 | 53 | 39 |
| Wt | 66 | 97 | 99 | 62 | 71 | 50 | 50 | 42 | 43 | 43 | 48 | 30 |
| triple-M117S | 51 | 71 | 61 | 50 | 36 | 41 | 42 | 43 | 40 | 43 | 46 | 25 |
| triple-M117T | 48 | 56 | 39 | 33 | 36 | 38 | 41 | 43 | 43 | 42 | 45 | 26 |
| M36A-triple | 58 | 69 | 51 | 56 | 35 | 33 | 41 | 31 | 30 | 39 | 47 | 26 |
| M36T-triple | 68 | 72 | 71 | 59 | 51 | 48 | 48 | 43 | 43 | 49 | 50 | 34 |
| Triple | 59 | 80 | 70 | 56 | 55 | 51 | 59 | 55 | 50 | 54 | 54 | 39 |
| M36T-triple-M117T | 62 | 90 | 68 | 57 | 54 | 43 | 42 | 53 | 49 | 47 | 48 | 30 |
| M36T-triple-M117S | 78 | 99 | 101 | 74 | 64 | 56 | 58 | 55 | 50 | 41 | 40 | 32 |
| Wt | 68 | 99 | 102 | 86 | 71 | 65 | 49 | 47 | 46 | 45 | 47 | 29 |

Example 17

Additional IFNβ Muteins

In addition or instead of the previously disclosed peptide mutations, human interferon-β was modified by substituting glutamate for the serine at amino acid position 2, and serine for the cysteine at amino acid position 17 of the naturally occurring peptide. The substitution at amino acid position 2 provided, among other advantages, increased retention of the amino terminal amino acid substitution (methionine analog) which, in some cases was azidohomoalanine. The substitution at amino acid position 17 provided, among other advantages, improved purification of protein produced in host cells, in particular E. coli.

Example 18

Substitution of N-Terminal Methionine in IFNβ

The sole remaining methionine in the mutant interferon-β molecules of the previous Example is the methionine at amino acid position 1. This methionine residue was replaced with a non-natural amino acid residue (azidohomoalanine or homoproparglyglycine). One method of replacing or substituting the methionine is by a fermentation process wherein the non-natural amino acid is supplied in place of or at much higher concentrations than the corresponding natural amino acid residue (in this case, methionine) and using endogenous tRNA machinery. Another method of substituting the methionine is by using an external mutant amino acid tRNA synthetase, and/or an external mutant tRNA molecule. Other methods may be used. The methionine substitution may be conducted in a host cell, such as E. coli, Pseudomonas, or mammalian cells. The mutant interferon-β molecule was expressed in an E. coli host cell.

In other instances, a host cell with a mutant amino terminal methionine aminopeptidase may be used to process or retain a non-natural amino acid. In this fashion, a host cell harborning a mutant methionine aminopeptidase whose specificity has been altered with respect to the penultimate amino acid residue is used for expression of the protein. Use of a secretion system in the host cell (such as E. coli) may use signal peptidases and/or proteases that are present in the periplasm to control the expression and processing of the amino terminal amino acid.

Example 19

PEGylation of Modified IFNβ

Upon substitution of a non-natural amino acid residue with the methionine at position 1, a chemical moiety (polyethylene glycol) was conjugated to the residue. Since the amino acid position 1 is at the terminus, the attached chemical moiety had minimal interference with the protein folding, overall structure and/or function. The chemical moiety was attached by way of a copper-catalyzed cycloaddition between an azide and an alkyne, but may be attached by other methods known in the art and/or described in other Examples (such as Example 6 or Example 7), or other areas of the present application.

Interferon-β constructs with specific methionine substitutions were screened using transient transfections in mammalian cells (HEK 293 T cells) and the supernatants analyzed as measured by, for example, anti-viral activity, antiproliferative activity, and/or ELISA.

Example 20

Stabilization of Modified IFNβ

In addition to or instead of other amino acid substitutions disclosed herein, the serine amino acid at position 2 of the naturally occurring human interferon-β was modified to glutamate, and the cysteine at amino acid position 17 was modified to serine. These substitutions surprisingly provide increased stabilization and/or production of the modified proteins in the host cell.

Retention of the non-natural amino acid residue (such as azidohomoalanine or homoproparglycine) at the amino terminus during protein processing is necessary for addition of the chemical moiety (such as pegylation), and depends on the identity of the amino acid residue at the penultimate residue position.

In other instances, it may be desirable for the non-natural amino acid residue to be removed during protein processing, such as for allowing regulation of the location of amino acid substitutions. For example, efficient removal of the substitution of the amino terminal methionine of human interferon β with a non-natural amino acid residue (such as azidohomoalanine or homoproparglycine) allows for the introduction of a methionine analog in positions other than the amino terminus of the molecule, while retaining at least one non-natural amino acid residue in the molecule.

In this regard, we found the highest retention of the non-natural amino acid residue (such as azidohomoalanine or homoproparglycine) at the amino terminus of human interferon β when the penultimate amino acid residue is selected from the following: glutamine, glutamic acid, or histidine. We would also expect high retention when the penultimate amino acid residue of any protein is phenylalanine, methionine, lysine, tyrosine, tryptophan, or arginine. We found some retention of the non-natural amino acid residue (such as azidohomoalanine or homoproparglycine) when the penultimate amino acid residue is glycine or serine, and a low level of retention (high level of removal) of the non-natural amino acid residue when the penultimate amino acid is alanine.

Example 21

MonoMet IFNβ

In one particular mutant of human interferon-β, MonoMet (which included a single methionine replaced at the amino terminus during fermentation with AHA, and with all other methionines replaced genetically), the mutant protein was expressed in *E. coli* with either serine, alanine, glycine, glutamine, histidine or glutamic acid at amino acid position number 2. When the amino acid at position 2 was serine, and the amino terminal methionine was substituted with a non-natural amino acid (azidohomoalanine or homoproparglycine), the non-natural amino acid is not efficiently retained and is partially processed, resulting in heterogenous protein products. Such products included proteins with uncleaved non-natural amino acids at the amino terminus, proteins with cleaved non-natural amino acids at the amino terminus, and proteins with formylated non-natural amino acids at the amino terminus. When the amino acid at position 2 is histidine, glutamine or glutamic acid, the amino terminal non-natural amino acid is highly retained.

When azidohomoalanine is used as the non-natural amino acid at the amino terminus and the amino acid at position 2 of the human interferon β is histidine, glutamine or glutamic acid, the azide moiety of the azidohomoalanine is retained and the N formyl group is removed.

When the amino acid at position 2 of the human interferon β is alanine, and the amino terminus methionine is substituted with a non-natural amino acid (azidohomoalanine or homoproparglycine), the non-natural amino acid is removed.

In addition to the non-natural amino acids used, other non-natural amino acids may be incorporated instead, such as azidonorleucine.

A mutant interferon-β product was thus generated with AHA incorporated at the amino terminus, and the other mutations are S2E, C17S, M36I, I40F, I44L, M62I, M117T. The mutant interferon-β containing these amino acid substitutions retained the amino terminal AHA, was easily purified and refolded properly (including disulfide bond formation). Additionally, the interferon-β mutant was efficiently PEGylated and the final formulation was stable and retained full biological activity both in vitro and in vivo.

Example 22

Purification and PEGylation of Proteins and Interferon-B by Copper-Catalyzed Azide-Alkyne Cycloaddition We demonstrate a modified copper-catalyzed cycloaddition method for pegylation of a target molecule, such as a protein or peptide that contains a non-natural amino acid residue. The modified method allows for efficient purification, folding and oxidation of the target molecule. Typically, other methods of copper-catalyzed cycloaddition require the presence of Cu(I) by using ultrapure CuBr or $CuSO_4$ and a reducing agent, such as TCEP or Cu(0). Our modified method is conducted in the presence of DTT. Without wishing to be bound to any particular theory, the DTT may act either as a reducing agent for a biomolecule and/or for the copper species, and may act as a ligand for copper in the modified cycloaddition reaction.

Oxygen may be required for the modified cycloaddition reaction, especially in the presence of reducing agents, and can be provided either by introducing air into the reaction vessel or by allowing the reaction vessel to remain open to the ambient air, or by otherwise adding oxidants and/or reductants to control the overall redox state of the reaction mixture. The modified cycloaddition reaction may be performed by using non-natural amino acid-containing biomolecules, including reactions with or without a triazole linkage, and various concentrations of several copper species, SDS (which is desirable in certain embodiments), DTT, TCEP, and PEG-alkyne.

The reaction may occur in mixed micelle "microreactors" containing the target molecule and other reactants. The reaction may be sonicated, which may improve mass transport between different mixed micelles for improved mixing, and/or affect the introduction of oxygen to the reaction mixture, as well as the mixture of copper oxidation states. In some instances, subjecting the solubilized target molecule to a freeze/thaw cycle prior to beginning the reaction improves the CuBr catalyzed reaction. The freeze/thaw cycle may affect mixed micelles of the target molecule, or otherwise affect solubility of the molecule. In our modified method, the cycloaddition reaction is performed preferentially using $CuSO_4$, rather than CuBr. Alkyne-PEGs may be manufactured from PEG-NHS esters, either in organic or aqueous solution.

Modified interferon-β and PEG-interferon-β were purified by first refolding the interferon-β by dilution into a buffer containing zwittergent with no additional SDS, which allows for subsequent ion exchange chromatography analysis of the solution. Anion exchange chromatography and size exclusion chromatography may be used for purifying pegylated and unpegylated interferon-β. The zwittergent may be removed from the pegylated interferon-β while also removing unpegylated interferon-β. This allows for production of a pure pegylated interferon-β suitable for in vitro or in vivo assays or for clinical administration.

Example 23

PEG-Interferon-Beta Inhibits Tumor Progression in Murine Xenograft Model

We tested the efficacy of PEG-(20K) interferon beta and its ability to inhibit the growth of a tumor grown subcutaneously in immunocompromised (SCID) mice compared to BETASERON®. PEG-(20K) interferon beta inhibits tumor progression in vivo more efficiently than BETASERON®.
Animal Studies The mice used in these studies were female C.B-17 SCID mice 6-8 weeks. (Charles River Laboratories, Wilmington, Mass.). Food and water were provided ad libitum. Test animals were housed in a specific pathogen-free environment and allowed to acclimate in a temperature and humidity controlled environment prior to the commencement of experimental procedures.

Daudi cells, a human B lymphoblastoid cell ine (ATCC, Manassas, Va.), were injected subcutaneously in the abdominal midline. Mice were treated either with PEG-(20K)-interferon (IFN) (3 U), BETASERON® (human interferon-β-1b) (10 U) or vehicle either once per week or three times per week, following tumor implantation. After tumors became palpable (about 3 weeks) tumor measurements were made in two dimensions three times a week using digital calipers. Tumor volume was determined using the formula for a prolate spheroid. Tumor progression was measured for 65 days.
Activity Studies IFN beta was PEGylated and purified. The PEG IFN beta was compared to commercial BETASERON® (Bayer Corp.) for antiviral activity using $EC_{50}$ as a measure of drug potency. The results are shown in FIGS. 8A and 8B. The data were analyzed using one way repeated measures ANOVA with a Tukey-Kramer multiple comparison post test.

Example 24 (Prophetic)

Exogenous tRNA Expression Produces Differential Regulation of Genes Due to Codon Bias It has previously been shown in eukaryotic cells that levels of translation of specific target genes can be altered by providing a single tRNA expression construct. The authors suggested that the levels or amount of tRNAs in cells is related to the levels of gene expression at translation levels, and suggested that low levels of specific tRNAs lead to low levels of translation potentially due to problems in decoding the mRNA in host cells containing large numbers of the specified codons. See Gu, et al. Nuc. Acids Res. 32:4448 (2004), hereby incorporated by reference in its entirety. For example, if a particular host cell contained high levels of a specific tRNA species, this high level of tRNA may result in codon bias of mRNA molecules for the major protein products of the cell. Thus, how a codon is used is approximately equal to the ability of the tRNA to regulate expression of the target genes in both differentiated and non-differentiated epithelium.

Considering this, using methods described herein, inter alia, it may be desirable to use the cell's tendency for codon bias (i.e. "bias codon") to specify an incorporation of a non-natural amino acid by introducing an exogenous or external mutant tRNA that decodes the bias codon and is aminoacylated by an exogenous or external mutant M-RS.

Example 25

Site-Specific PEGylation of Interferonβ by Cu(I)-Catalyzed Cycloaddition

The present example demonstrates improved methods for site-specific PEGylation of proteins. In this study, nonnatural amino acids(s) were used with a recombinant protein to produce site-specific conjugation. Site-specific PEGylation enhanced pharmacokinetic and pharmacodynamic properties of the therapeutic protein including an increase in serum half-life and a decrease in bioactivity. In contrast, methods that randomly PEGylate proteins may yield a product protein that does not contain the PEG in a specific location or site. Randomly PEGylated protein may have reduced bioactivity and/or produce a nonhomogeneous product and/or produce a product that varies from batch to batch.

mPEG-NHS 10 kDa linear, 20 kDa linear, and 40 kDa branched were purchased from Nektar, San Francisco, Calif. and NOF, Tokyo Japan. PEG-alkyne were obtained from NOF, Tokyo Japan. Both AHA and triazole ligand were custom synthesized by MedChem Source, Federal Way, Wash. Copper sulfate and copper bromide (ultrapure) were obtained from Sigma Aldrich, USA.

Methods to Produce IFNβ-AHA

Human IFNβ was mutated to remove 3 of 4 natural Met residues (M36I, M62I, M117T) (see: Ser. No. 11/743,608), to maintain bioactivity by modifying two other residues that interact with the internal Met (I40F, I44L), and to eliminate methionine aminopeptidase cleavage of the N-terminal AHA by modifying the penultimate residue (S2E). The N-terminal codon for Met in the mature protein was left intact.

Methionine auxotrophic host E. coli cells were used for protein expression. An auxotrophic host cell refers to a cell that is unable to synthesize one or more natural amino acids. The cells were expanded in media containing all 20 natural amino acids, then washed and resuspended in media containing 19 natural amino acids, AHA, and no Met. Following induction, the resulting recombinant protein contained AHA at the N-terminus instead of Met.

PEGylation was conducted according to the scheme diagrammed below. PEG-alkyne was reacted with IFNβ-AHA while the protein was denatured and reduced.

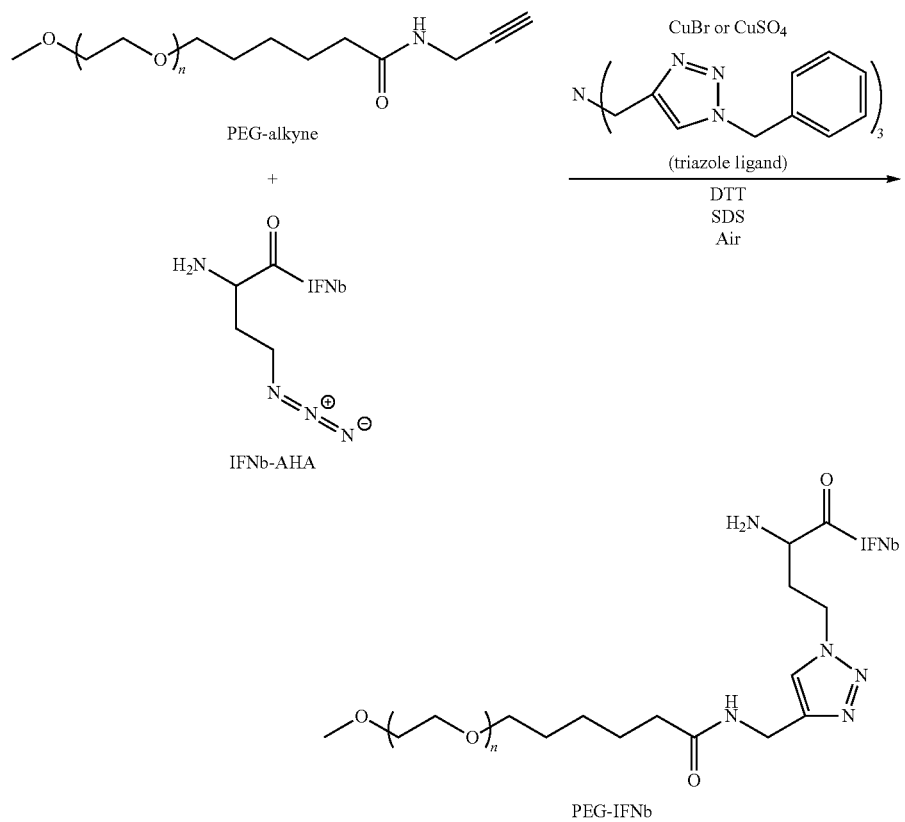

Three different mPEGs (either 10 kDa, 20 kDa or 40 kDa) were functionalized with an alkyne group by nucleophilic addition of propargylamine. NHS esters of PEG 10 kDa linear or 20 kDa linear PEG, or 40 kDa branched were reacted with propargylamine in dioxane, as shown below.

mPEG-C2-NHS (10 kDa linear)+propargylamine→PEG-alkyne 10 k Linear mPEG-C5-NHS (20 kDa linear)+propargylamine→PEG-alkyne 20 k Linear mPEG$_2$-C3-NHS (40 kDa branched)+propargylamine→PEG-alkyne 40 k Branched

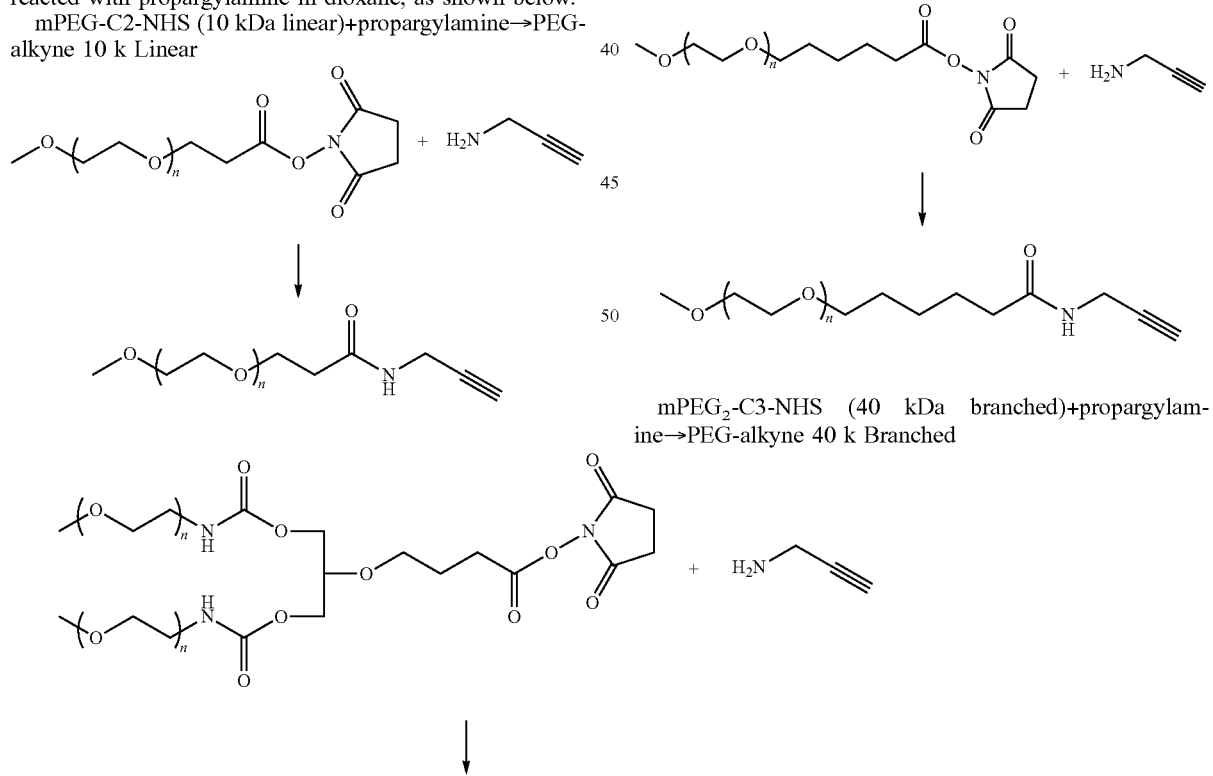

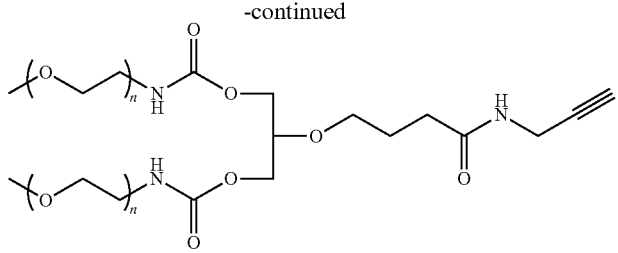

Each PEG-NHS ester was dissolved in dioxane at 2.5 wt %, under argon. The reaction flasks were briefly placed in a warm water bath to dissolve the PEG, with stirring. 50 molar excess (10K or 20K) or 100 molar excess (40 kDa PEG,) of propargylamine was added to each reaction. The mixtures were allowed to react for at least 1.5 h at room temperature under argon. The functionalized PEG was isolated by dripping into 5-10× cold hexane, with stirring for 15 min, and then filtering through a 0.2 um nylon membrane. The crude precipitate was then dissolved in water with 0.5-1 mL 1M NaOH to hydrolyze any remaining NHS ester (10 min) and then neutralized with an equal volume of 1M HCl. The product was then dialyzed against 0.1M NaCl, 0.05M NaCl, and then water three times, followed by filtration and lyophilization. The product structure was confirmed by $^1$H NMR.

A schematic diagram of the procedure used for 10 kDa PEGylation of IFNβ is provided below.

IFNAHA was reacted with mPEG-alkyne 10 kDa linear with varying concentrations of PEG, copper, and triazole ligand, and for various times. The reaction occurred in 100 mM phosphate, 10 mM dithiothreitol, 2% SDS, pH 7.55 buffer in an air atmosphere. The triazole ligand was prepared as a stock in DMSO and the CuBr was prepared as a stock in H2O. The default reaction conditions were 0.5 mg/mL IFNAHA, 2 wt % PEG, 2 mM triazole ligand, 1 mM CuBr, reacting for 24 h at room temperature. Increasing the PEG concentration to 2 mM and using a triazole ligand to copper ratio of 1 or 2 produced the most PEG-IFN. Increasing concentrations of copper (holding the triazole to copper ratio at 2) caused loss of protein from the reaction mixtures, especially at 2 mM or higher.

Schematic diagrams of the procedures used for PEGylation of IFNβ with 20 kDa and 40 kDa PEG are shown below.

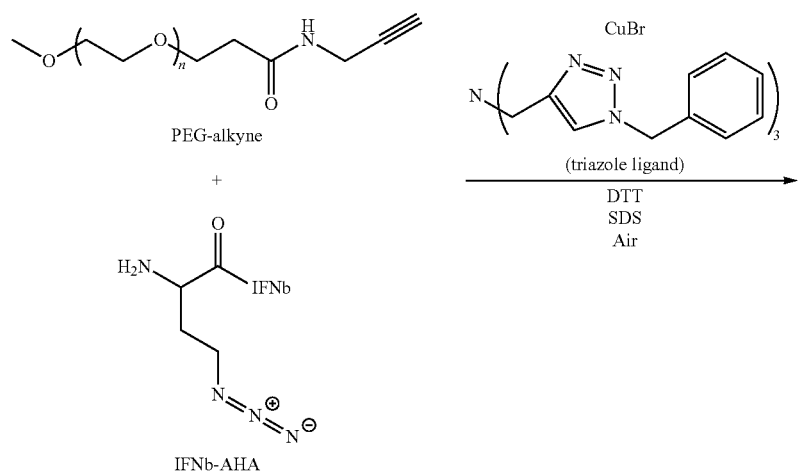

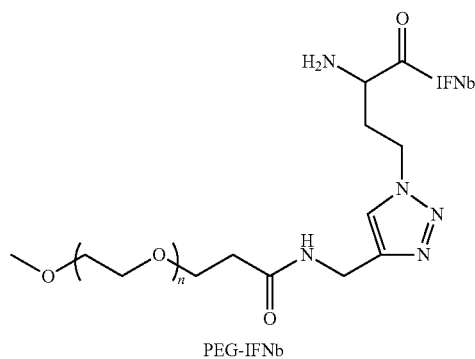

20 kDa Example
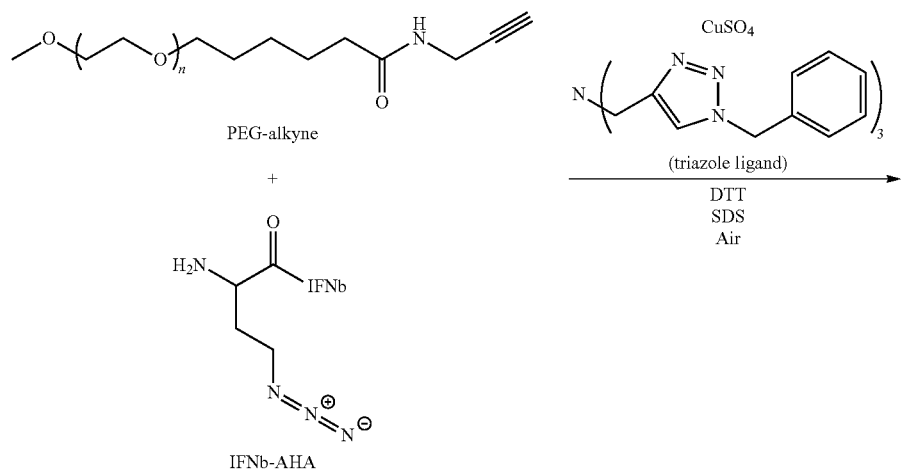
40 kDa Example
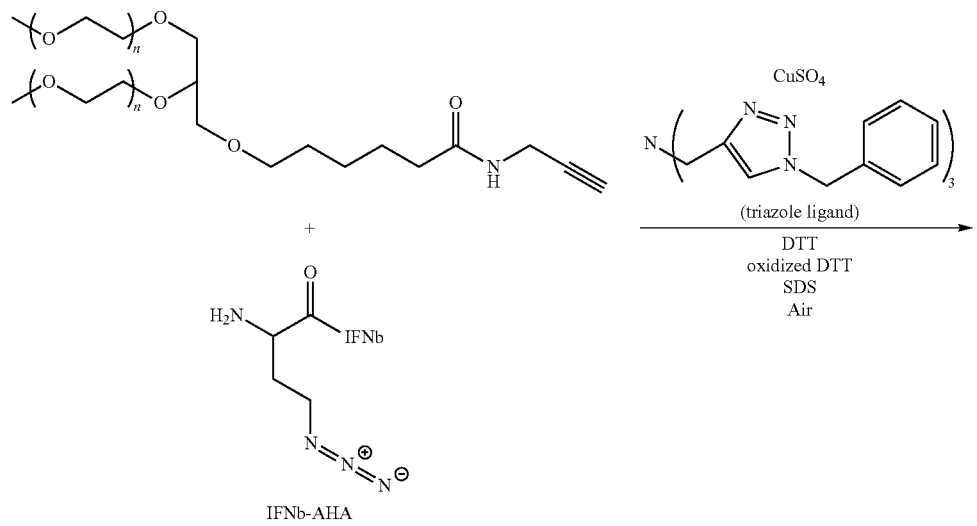

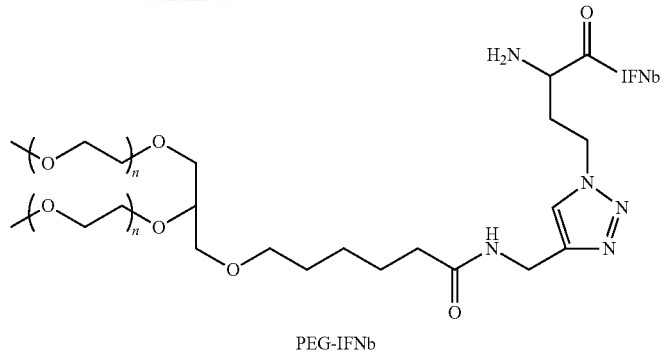

PEG-IFNb

IFNAHA was reacted with mPEG-alkyne 20 kDa linear and 40 kDa branched using similar methods as those for the 10 kDa reaction. However, the kDa reaction occurred in 0.5% SDS, with 2 mg/mL IFNAHA, and 1 mM CuSO4 (rather than CuBr), for 25 hours. The 40 kDa reaction occurred with 2 mM DTT and 8 mM oxidized DTT, with 1 mg/mL IFNAHA, and 1 mM CuSO4 (rather than CuBr), for 22 hours.

The reaction was optimized by weight-percent PEG-alkyne, concentration of copper catalyst, and the molar ratio of triazole ligand to copper catalyst. Soluble fractions of the reaction mixtures were separated by SDS-PAGE and the resulting PEG-IFNβ bands were quantified by densitometry. PEGylation was most efficient around 2-3 wt % PEG-alkyne. We noted that higher concentrations were less efficient and hypothesize that efficiency of pegylation may be limited by viscosity. We noted that a 1:1 or 2:1 molar ratio of triazole ligand to copper catalyst was most efficient.

Higher concentrations of CuBr caused the protein (primarily the unPEGylated protein) to precipitate, perhaps by copper-induced oxidation reactions. Optimal conditions resulted in >90% of IFNβ-AHA being PEGylated.

The PEG20k-IFNβ ran around 60 k Mr and the PEG40k-IFNβ ran around 140 k Mr on SDS-PAGE. 50% of the IFNAHA reacted with PEG20 kDa and 57% of the IFNAHA reacted with PEG40 kDa.

Utilizing the procedures described above, site-specific PEGylation of IFNAHA was achieved. This PEGylation was specific to the AHA residue at position 1, with no side reaction to other residues.

Bioactivities of the various PEGylated IFNAHAs and Betaseron® (a commercially available IFNβ-1β; Bayer HealthCare Pharmaceuticals) were assessed in vitro as the ability to prevent lysis of A549 cells exposed to EMC virus (lower EC50=more potent in vitro). The results are shown below.

Betaseron®: $EC_{50}$=17 pg/mL
PEG10-IFNβ: $EC_{50}$=11 pg/mL
PEG20-IFNβ: $EC_{50}$=48 pg/mL
PEG40-IFNβ: $EC_{50}$=1249 pg/mL In vitro bioactivity of the PEG-IFNβs was a function of the MW of the conjugated PEG.

This study demonstrates that site-specific PEGylated IFNβ produced by the methods described herein retains biological activity. These methods allow PEGylation of recombinant proteins at a single pre-determined site, without side reactions to other residues within the protein. The resulting PEGylated proteins retain biological activity and are expected to have enhanced pharmacokinetic properties, including increased serum half-life.

Example 26

Refolding of Expressed Proteins

This example provides methods for obtaining refolded, soluble forms of proteins, and in this particular example, to refold a PEGylated protein. We describe a method for increasing the yield of a PEGylated protein by using the methods described herein to refold PEG-beta interferon.

The methods are generally accomplished by preparing a refolded, soluble form of an insoluble or aggregated PEG interferon beta protein which contains one or more free cysteine residues. The methods include the steps of: a) causing a host cell to express a interferon beta protein in an insoluble or aggregated form; b) lysing the cells by chemical, enzymatic or physical means; c) solubilizing the insoluble or aggregated protein by exposing the insoluble or aggregated protein to a denaturing agent, a reducing agent and a cysteine blocking agent; and d) PEGylating the reduced, denatured protein, and e) refolding the PEGylated protein by reducing the concentrations of the denaturing agent and reducing agents to levels sufficient to allow the PEG interferon beta protein to refold into a soluble, biologically active form.

Exemplary procedures and reagents are described below.
Protein Solution
    0.1-0.5 mg/ml IFN-PEG
    20 mM NaPhosphate pH7.5
    150 mM NaCl
    10 mM DTT
    1 mM EDTA
    0.02% SDS
Refolding Buffer
    10 mM Tris pH10
    10 mM NaCl
    1 mM EDTA
    6 µM CuSO4
    0.3% Zwittergent 3-14

The Protein Solution and Refolding Buffer are used in a range of concentrations in relation to one another. For example, the protein concentration in the Protein Solution is effective in a wide range of concentrations, e.g., between 0.001-20 mg/ml or, preferably, 0.1-0.5 mg/ml in a preferred range. In addition, any buffer, e.g., Tris, Hepes, Acetate, citrate, etc. may be used at a pH range 2-12. In this example, the preferred pH is 7.5 or in a range of pH 6.0-9.0. The NaCl concentration in the protein solution may range between 0 to 2 M or preferably 150 mM. DTT is added in a concentration range between 0 to 200 mM between 100 µM and 20 mM (preferably 10 mM). The concentration of DTT must be adjusted depending on the concentration of $CuSO_4$ used during refolding using a stoichiometric ratio between 100-250 fold excess DTT to $CuSO_4$. The EDTA concentration can range between 0 and 50 mM or 100 µM and 1 mM. As with the concentration of DTT, the concentration of EDTA is adjusted depending on the concentration of $CuSO_4$ during refolding using a stoichiometric ratio between 100-250 fold excess EDTA to $CuSO_4$ as previously described. In addition, the concentration of SDS may range between 0 and 1% or in the range of 0.01 and 0.1%.

With respect to the Refolding Buffer, Tris buffer provided the most efficient protein refolding, with a pH of at least 10 is required for certain proteins. NaCl concentration can range between 0 and 2M with a preferred concentration of 1-50 mM. The EDTA concentration can range between 0 and 50 mM or between 100 µM and 2 mM; with a preferred concentration of EDTA of 1 mM. As previously described, the stoichometric ratio of 100-250 fold excess EDTA to $CuSO_4$ are required during refolding.

Other salts of Cu can be used and other metals beside Cu can be used, i.e., Pd, Pt, Au, Ag, etc.

$CuSO_4$ (6 µM) or in the range of 4-10 µM was found to be the optimal concentration when used with 1 mM EDTA. However, as previously described the appropriate concentration is dependent on the DTT and EDTA concentrations, and will generally be in the range of 0.1-100 µM or 4-10 µM in a preferred range.

Zwittergent 3-14 surfactant can range between 0.1 and 1.0% and can be substituted by other non-denaturing surfactants such as Tween-80, octylglucoside, etc. or by denaturing surfactants at concentrations low enough to allow refolding such as SDS.

Protocol:

Protein refolding is performed at room temperature by following the following steps:

1) Drip Protein Solution into rapidly mixing (>200 rpm) 10-fold (or in the range of 5-20 fold) volume of Refolding Buffer. The Refolding Buffer volume can range between 0.5-500-fold or in the range of 1-20-fold or preferably 5-10 fold dilution of the Protein Solution volume. Protein Solution may be provided to the refolding buffer in pulses with refolding time between pulses.

2) Adjust pH to 10.0 with 5M NaOH (several drops are required). Other buffers or bases may be used for pH adjustment.

3) Mix for 2.5 hours, 22° C., 150 rpm. In some instances, mixing at pH 10 may range between 10 minutes to 48 hours with a preferred time of 2-3 hours.

4) Adjust pH to 5.0 by adding 1M Acetic Acid to a final concentration of 20 mM. Other buffers or acids besides acetic acid can be used to reduce the pH to 5.0. pH can range between 2 to 12, These methods may be utilized to achieve proper folding of recombinant produced proteins, including the site-specific mutants described herein. Accordingly, these methods provide bioactive proteins.

Example 27

Site-Specific PEGylation of Interferonβ by Cu(I)-Catalyzed Cycloaddition

The present example demonstrates additional compounds and methods for site-specific PEGylation of proteins. A branched PEG-alkyne (40 kDa) was obtained from NOF, Tokyo Japan (NOF Product No. GL2-400PP2). Each branch of the PEG-portion of the PEG-alkyne was 20 kDa. Both AHA and triazole ligand were custom synthesized by MedChem Source (Federal Way, Wash.). Copper sulfate and copper bromide (ultrapure) were obtained from Sigma Aldrich, USA. A modified human interferon-β polypeptide (IFNβ-AHA) was prepared according the procedures disclosed above comprising the following amino acid alterations: methionine at position 1 to azidohomoalanine, serine at position 2 to glutamic acid, cysteine at position 17 to serine, methionine at position 36 to isoleucine, isoleucine at position 40 to phenylalanine, isoleucine at position 44 to leucine, methionine at position 62 to isoleucine, and methionine at position 117 to threonine.

PEGylation at position 1 the modified human interferon-β polypeptide (IFNβ-AHA) was conducted according to the scheme diagrammed below. PEG-alkyne was reacted with IFNβ-AHA while the protein was denatured and reduced.

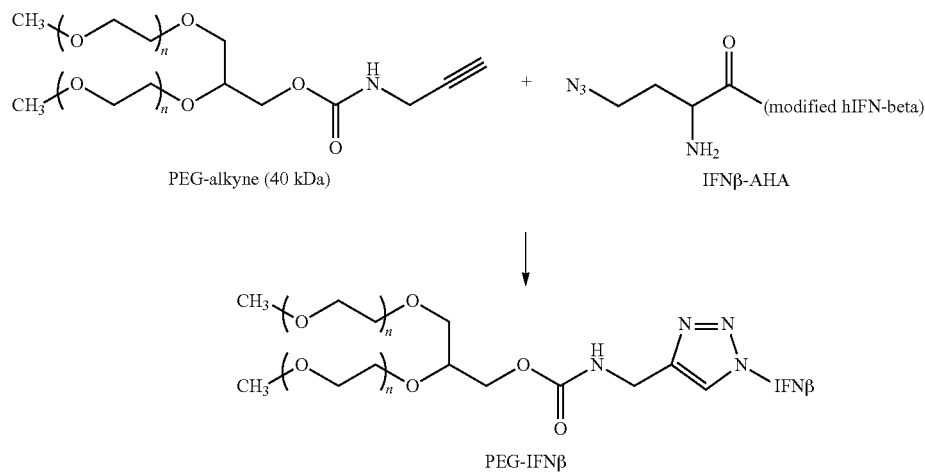

In the above reaction, PEG-alkyne was reacted with IFNβ-AHA by Cu(I)-catalyzed azide and alkyne cycloaddition. The reactants were combined at the final concentrations shown below, with the triazole added second to last and the copper added last. The triazole ligand was added as a solid to the reaction.

| | |
|---|---|
| IFNb-AHA | 1 mg/mL |
| PEG-Alkyne | 0.6 wt % |
| PEG diol (30 kDa) | 1.4 wt % |
| SDS | 2% |
| DTT | 2 mM |
| Phosphate (pH 7.55) | 80 mM |
| Triazole ligand | 3 mM |
| $CuSO_4$ | 1.5 mM |

The PEG diol and triazole ligand had the following structures. The reaction was prepared at 1 L scale in a 2 L beaker. The reaction proceeded overnight with mixing at room temperature. The PEGylation efficiency was assessed by SDS-PAGE. The reaction proceeded to 71% PEG-IFNβ.

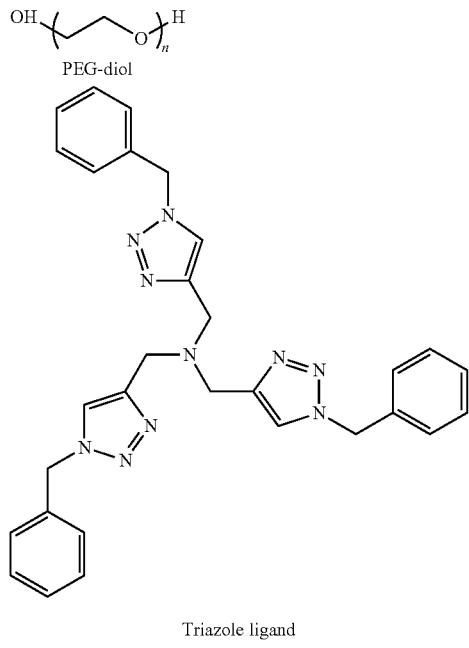

After the above PEGylation reaction PEG-IFNβ was captured on ceramic hydroxyapatite (CHT), eluted and folded, captured on cation ion exchange (IEX) and the eluant concentrated for polish step on size exclusion chromatography (SEC). The CHT column separated PEGylated IFNb from the pegylation reaction mix components and from the residual unpegylated IFNβ. Protein from the CHT column was rapidly diluted into a 4 C buffer containing 1% Tween-80 and trace amounts of $CuSO_4$ balanced with DTT and EDTA. The pH was adjusted to 10.2 and the protein allowed to fold overnight at 4 C. After folding the pH was reduced to 4.0 and the sample was applied to an IEX column. The IEX column served to exchange the surfactant from SDS to Tween-80 and to concentrate protein for subsequent SEC polish step. Eluant from the IEX column was concentrated by ultrafiltration prior to application to the SEC column. The SEC column separated aggregate from monomer and exchanged buffer into final formulation buffer. The eluted target protein was concentrated, sterile filtered and packaged to provide PEG-IFNβ.

In vivo potency of the above PEG-IFNβ was demonstrated by its ability to inhibit growth of Daudi cell tumors in scid mice, generally according to procedures described in Example 23. $10^7$ Daudi cells were implanted subcutaneously in scid mice. Treatments were begun on the day of implantation and terminated after 4 weeks of treatment. Animals were sacrificed when tumors reached 1000 $mm^3$. The results of this assay are presented in FIG. 9 at different levels of administration, along with comparative data against buffer and Betaseron.

The in vitro efficacy of the above PEG-IFNβ as compared to Betaseron was demonstrated by assaying their ability to inhibit the cytopathic effect of EMC virus on A549 cells, according to procedures described in Example 23. The results of this assay are presented in FIG. 10, which shows that two different preparations of PEG-IFNb were capable of inhibiting EMC virus.

Example 28

In Vivo Pharmacokinetic Profile of PEG-IFNβ

The pharmacokinetic characteristics of the PEG-IFNβ of Example 27 were examined in cynomolgus monkeys in comparison to Avonex®, a recombinant Interferon beta-1a.

PEG-IFNβ was administered to male cynomolgus monkeys via a single intravenous injection (0.06 mg/kg) in a saphenous vein or a subcutaneous injection (0.3 mg/kg) in the mid-scapular region. Avonex® was administered via intravenous injection or intramuscular injection. Three animals were used for each treatment group. Plasma was collected from each animal via a femoral vein at the following time points: pre-dose and at 0.17 (intravenous groups only), 0.5, 2, 4, 6, 8, 10, 12, 18, 24, 48, 72, 96, 120, and 144 hours post-dose. PEG-IFNβ and Avonex® levels were measured using an A549 antiviral assay, as shown in FIG. 11 for a single subcutaneous administration of PEG-IFNβ. During the study, animals were observed twice daily for mortality and signs of pain and distress. In addition, cage side observations for general health and appearance were done once daily.

The pharmacokinetic parameters of PEG-IFNβ and Avonex® following subcutaneous, intramuscular or intravenous dosing including $AUC_{all}$, AUCINF, $t_{1/2}$, Cl, $V_c$, Vss, Tmax, and Cmax were obtained from the non-compartmental analysis of the plasma data using WinNonlin and is provided in Tables 6 and 7. The calculated bioavailability was determined by calculating the ratio of the area under the curve from the time of dosing extrapolated to infinity ($AUC_{(0-\infty)}$) to compare parameters between intravenous and subcutaneous injection. After intravenous injection, the mean serum PEG-IFNβ concentration declined over time in a biphasic manner with a terminal elimination half-life (t½) of 29.77 hours. The volume of distribution ($V_z$) was 73.81 ml/kg, indicating that the drug was in the more accessible compartment.

TABLE 6

Pharmacokinetic Profiles of PEG-IFNβ in Cynomolgus Monkeys

| Route of Delivery | Animal # | Cmax (ng/mL) | Tmax (h) | $t_{1/2}$ (h) | AUC$_{(all)}$ (h*ng/mL) | AUC$_{(0-\infty)}$ (h*ng/mL) | $V_z$ (mL/kg) | Cl (mL/kg/h) | Calc. Bioavailability (%) |
|---|---|---|---|---|---|---|---|---|---|
| IV | C20091 | NA | NA | 28.86 | 35,725 | 37,861 | 65.99 | 1.58 | |
| | A01567 | NA | NA | 25.60 | 32,064 | 34,033 | 65.11 | 1.76 | |
| | C21561 | NA | NA | 34.84 | 30,562 | 33,392 | 90.32 | 1.80 | |
| | Average | NA | NA | 29.77 | 32,783 | 35,095 | 73.81 | 1.71 | |
| SC | C20089 | 1,241.07 | 10.00 | 34.52 | 63,240 | 68,276 | NA | NA | |
| | C22405 | 954.86 | 8.00 | 56.40 | 49,654 | 59,111 | NA | NA | |
| | C22354 | 537.18 | 8.00 | 79.47 | 37,591 | 52,877 | NA | NA | |
| | Average | 911.04 | 8.67 | 56.80 | 50,162 | 60,088 | NA | NA | 34.2 |

TABLE 7

Pharmacokinetic Profiles of Avonex ® in Cynomolgus Monkeys

| Route of Delivery | Animal # | Cmax (ng/mL) | Tmax (h) | $t_{1/2}$ (h) | AUC$_{(all)}$ (h*ng/mL) | AUC$_{(0-\infty)}$ (h*ng/mL) | $V_z$ (mL/kg) | Cl (mL/kg/h) | Calc. Bioavailability (%) |
|---|---|---|---|---|---|---|---|---|---|
| IV | C20637 | NA | NA | 4.0 | 91.28 | 91.7 | 473.04 | 81.8 | |
| | C20076 | NA | NA | 4.9 | 119.1 | 120.7 | 440.24 | 62.1 | |
| | C21597 | NA | NA | 4.0 | 218.9 | 220.4 | 199.49 | 34.0 | |
| | Average | NA | NA | 4.3 | 143.1 | 144.3 | 370.9 | 59.3 | |
| IM | C20637 | 34.2 | 2 | 3.8 | 190.0 | 194.3 | NA | NA | |
| | C20076 | 47.3 | 2 | 4.9 | 307.5 | 307.8 | NA | NA | |
| | C21597 | 15.9 | 2 | 5.8 | 346.6 | 348.2 | NA | NA | |
| | Average | 34.5 | 2 | 4.8 | 281.4 | 283.4 | NA | NA | 98.2 |

Following subcutaneous injection of PEG-IFNβ, a longer absorption phase and a lower level of peak concentration was achieved, as compared to intravenous injection. The average half-life (t½) □ of 57 hours was greater in comparison to intravenous injection, indicating that the rate of clearance was substantially decreased. The average bioavailability of PEG-IFNβ was approximately 34%. No adverse clinical observations were noted during the study with either 0.06 mg/kg intravenous dosing or the 0.3 mg/kg subcutaneous dosing. These results demonstrate that PEG-IFNβ has a much greater half-life in comparison to Avonex®, indicating that the PEGylated interferon-β is cleared at a much slower rate.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

Those skilled in the art will recognize, or be able to ascertain using no more than routine experimentation, numerous equivalents to the specific method and reagents described herein, including alternatives, variants, additions, deletions, modifications and substitutions. Such equivalents are considered to be within the scope of this invention and are covered by the following claims.

The invention claimed is:

1. A method for producing a modified target polypeptide, wherein the modified target polypeptide includes at least one non-natural amino acid and retains the function of the corresponding wild-type target polypeptide, the method comprising:
providing a host cell comprising a heterologous polynucleotide that encodes the target polypeptide, wherein the polynucleotide has been mutated such that:
a region or location where a post-translational modification is desired in the target polypeptide comprises at least one codon for a selected amino acid; and
at least one codon for the selected amino acid is substituted with a codon for a different amino acid outside the region or location where a post-translational modification is desired, wherein the modified target polypeptide retains function; and
growing the host cell in a medium containing the non-natural amino acid under conditions sufficient for the host cell to incorporate the non-natural amino acid into at least one position of the selected amino acid in the region or location where a post-translational modification is desired in the target polypeptide,
thereby producing a modified target polypeptide that comprises a non-natural amino acid in the region or location where post-translational modification is desired.

2. The method according to claim 1, wherein the heterologous polynucleotide has been mutated to encode for substitution with the different amino acid residue at all positions that the wild-type heterologous polynucleotide encodes for the particular selected amino acid in the target polypeptide.

3. The method according to claim 2, wherein the heterologous polynucleotide has been mutated to encode for the selected amino acid at a single non-wild-type position in the region or location where a post-translational modification is desired in the target polypeptide and wherein the host cell incorporates the non-natural amino acid at that region or location in the target polypeptide.

4. The method according to claim 1, wherein the heterologous polynucleotide has been mutated to encode for substitution with the different amino acid at all positions except a single position of the wild-type polynucleotide encoding for the selected amino acid in the target polypeptide and wherein the host cell incorporates the non-natural amino acid at the position encoding the single remaining selected amino acid of the target polypeptide.

5. The method according to claim 1, wherein the heterologous polynucleotide has been mutated to encode for substitution at position 2 of the target polypeptide when position 1 of the target polypeptide is substituted with a non-natural amino acid.

6. The method according to claim 1, wherein the heterologous polynucleotide has been mutated to encode for substitution at position 2 of the target polypeptide when position 1 of the target polypeptide is not substituted with the non-natural amino acid.

7. The method according to claim 1, wherein the heterologous polynucleotide is mutated to encode for substitution at position 2 of the target polypeptide, wherein the host cell incorporates the non-natural amino acid at position 2 of the target polypeptide.

8. The method according to claim 1, wherein the heterologous polynucleotide has been mutated to encode for substitution of other amino acids of the target polypeptide that interact with the one or more selected amino acids that have been substituted.

9. The method according to claim 1, wherein the one or more residues of the non-natural amino acid contains an azide, alkene, alkyne, vinyl, or aryl halide group.

10. The method according to claim 1, wherein the non-natural amino acid is selected from azidohomoalanine, homoproparglyglycine, p-bromophenylalanine, p-iodophenylalanine, azidophenylalanine, acetylphenylalanine, or ethynylephenylalanine.

11. The method according to claim 1, further comprising attaching a chemical moiety to the one or more non-natural amino acid of the modified target polypeptide.

12. The method according to claim 11, wherein the chemical moiety is attached to the one or more residues of the non-natural amino acid by way of a chemical reaction selected from the group consisting of [3+2] cycloaddition, Suzuki coupling, Hiyama coupling, Kumada coupling, Heck reaction, Cadiot-Chodkiewicz coupling, and Sonogashira coupling.

13. The method according to claim 11, wherein the chemical moiety is polyethylene glycol (PEG).

14. The method according to claim 1, wherein the host cell is an auxotroph for the particular selected amino acid.

15. The method according to claim 14, wherein the medium containing the non-natural amino acid does not contain the selected amino acid.

16. The method according to claim 1, wherein the target polypeptide is selected from the group consisting of an antibody, antibody fragment, antibody derivative, Fab, Fab', F(ab)2, Fd, Fv, ScFv, diabody, tribody, tetrabody, dimer, trimer or minibody, a cytokine, a transcriptional modulator that modulates cell growth, differentiation or regulation, expression activator, inflammatory molecule, growth factor, growth factor receptor, and oncogene product.

17. The method of claim 16, wherein the target polypeptide is selected from the group consisting of an antibody, antibody fragment, antibody derivative, Fab, Fab', $F(ab)_2$, Fd, Fv, ScFv, diabody, tribody, tetrabody, dimer, trimer or minibody.

18. The method of claim 17, wherein the target polypeptide is a Fab variable region.

19. The method according to claim 1, wherein the target polypeptide is selected from the group consisting of Factor VII, Factor VIII, Factor IX, follitropin, thrombopoietin, erythropoietin, human growth hormone, G-CSF, GM-CSF, interferon-α, interferon-β, interferon-γ, interferon-ω, interferon-τ, and GLP-1.

20. The method of claim 1, wherein the target polypeptide is a Fc region.

21. The method according to claim 1, wherein the selected amino acid is methionine.

22. The method according to claim 21, wherein the heterologous polynucleotide has been mutated to encode for substitution of other amino acids that interact with the one or more selected amino acids that have been substituted.

23. The method according to claim 21, wherein the heterologous polynucleotide has not been mutated to encode for substitution of methionine at position 1 of the target polypeptide with a different amino acid.

24. The method according to claim 21, wherein the heterologous polynucleotide has been mutated to encode for substitution with the different amino acid at all positions that the wild-type polynucleotide encodes for methionine in the target polypeptide except position 1.

25. The method according to claim 21, wherein an optional substitution at position 2 of the target polypeptide is made when position 1 of the target polypeptide is substituted with the non-natural amino acid.

26. The method according to claim 21, wherein methionine at position 1 and each methionine residue in the one or more non-wild-type position in the region or location where a post-translational modification is desired is substituted with the non-natural amino acid.

27. The method according to claim 26, wherein the non-natural amino acid is a methionine analogue.

28. The method according to claim 26, wherein the non-natural amino acid at position 1 of the target polypeptide is removed during protein processing.

29. The method according to claim 28, wherein the heterologous polynucleotide has been mutated to encode for substitution at position 2 of the target polypeptide, wherein the host cell incorporates the non-natural amino acid at position 2 of the target polypeptide.

* * * * *

SEQUENCE LISTING

<160> NUMBER OF SEQ ID NOS: 22

<210> SEQ ID NO 1
<211> LENGTH: 564
<212> TYPE: DNA
<213> ORGANISM: Homo sapiens

<400> SEQUENCE: 1
atgaccaaca agtgtctcct ccaaattgct ctcctgttgt gcttctccac tacagctctt        60

| | | |
|---|---|---|
| tccatgagct acaacttgct tggattccta caaagaagca gcaattttca gtgtcagaag | 120 |
| ctcctgtggc aattgaatgg gaggcttgaa tactgcctca aggacaggat gaactttgac | 180 |
| atccctgagg agattaagca gctgcagcag ttccagaagg aggacgccgc attgaccatc | 240 |
| tatgagatgc tccagaacat ctttgctatt ttcagacaag attcatctag cactggctgg | 300 |
| aatgagacta ttgttgagaa cctcctggct aatgtctatc atcagataaa ccatctgaag | 360 |
| acagtcctgg aagaaaaact ggagaaagaa gatttcacca ggggaaaact catgagcagt | 420 |
| ctgcacctga aagatatta tgggaggatt ctgcattacc tgaaggccaa ggagtacagt | 480 |
| cactgtgcct ggaccatagt cagagtggaa atcctaagga actttactt cattaacaga | 540 |
| cttacaggtt acctccgaaa ctga | 564 |

<210> SEQ ID NO 2
<211> LENGTH: 187
<212> TYPE: PRT
<213> ORGANISM: Homo sapiens

<400> SEQUENCE: 2

```
Met Thr Asn Lys Cys Leu Leu Gln Ile Ala Leu Leu Cys Phe Ser
1               5                   10                  15

Thr Thr Ala Leu Ser Met Ser Tyr Asn Leu Leu Gly Phe Leu Gln Arg
            20                  25                  30

Ser Ser Asn Phe Gln Cys Gln Lys Leu Leu Trp Gln Leu Asn Gly Arg
        35                  40                  45

Leu Glu Tyr Cys Leu Lys Asp Arg Met Asn Phe Asp Ile Pro Glu Glu
    50                  55                  60

Ile Lys Gln Leu Gln Gln Phe Gln Lys Glu Asp Ala Ala Leu Thr Ile
65                  70                  75                  80

Tyr Glu Met Leu Gln Asn Ile Phe Ala Ile Phe Arg Gln Asp Ser Ser
                85                  90                  95

Ser Thr Gly Trp Asn Glu Thr Ile Val Glu Asn Leu Leu Ala Asn Val
            100                 105                 110

Tyr His Gln Ile Asn His Leu Lys Thr Val Leu Glu Glu Lys Leu Glu
        115                 120                 125

Lys Glu Asp Phe Thr Arg Gly Lys Leu Met Ser Ser Leu His Leu Lys
    130                 135                 140

Arg Tyr Tyr Gly Arg Ile Leu His Tyr Leu Lys Ala Lys Glu Tyr Ser
145                 150                 155                 160

His Cys Ala Trp Thr Ile Val Arg Val Glu Ile Leu Arg Asn Phe Tyr
                165                 170                 175

Phe Ile Asn Arg Leu Thr Gly Tyr Leu Arg Asn
            180                 185
```

<210> SEQ ID NO 3
<211> LENGTH: 501
<212> TYPE: DNA
<213> ORGANISM: Artificial Sequence
<220> FEATURE:
<223> OTHER INFORMATION: Modified human interferon (Synthetic sequence IFNb C17S)

<400> SEQUENCE: 3

| | | |
|---|---|---|
| atgagctata atctgttagg cttctgcaa cgtagcagca attttcagag ccagaaattg | 60 |
| ttatggcaac tgaatggtcg tcttgaatac tgtttgaagg accgcatgaa ctttgacatc | 120 |
| ccggaagaaa ttaagcaact gcaacagttc cagaagaag acgccgcact gaccatctat | 180 |

```
gagatgctcc agaacatctt tgctattttc cgtcaagatt catctagcac tggctggaat    240
gagactattg ttgagaattt actggcgaat gtctatcatc agatcaacca tctgaaaacc    300
gtgctggaag aaaaactgga gaagaagat ttcacccgtg gtaaactgat gagcagtctg    360
cacctgaaac gctattatgg ccgtattctg cattacctga aggcaaaaga atacagtcac    420
tgtgcctgga ccatcgtccg tgtggaaatc ctgcgcaact tttacttcat taaccgtctt    480
acgggttacc tgcgcaacta a                                              501
```

```
<210> SEQ ID NO 4
<211> LENGTH: 166
<212> TYPE: PRT
<213> ORGANISM: Artificial Sequence
<220> FEATURE:
<223> OTHER INFORMATION: Modified human interferon (Synthetic sequence
      IFNb C17S)

<400> SEQUENCE: 4
```

```
Met Ser Tyr Asn Leu Leu Gly Phe Leu Gln Arg Ser Ser Asn Phe Gln
1               5                   10                  15

Ser Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165
```

```
<210> SEQ ID NO 5
<211> LENGTH: 501
<212> TYPE: DNA
<213> ORGANISM: Artificial Sequence
<220> FEATURE:
<223> OTHER INFORMATION: Modified human interferon (Synthetic sequence
      IFNb TIS2E triple C17S)

<400> SEQUENCE: 5
atggagtata atctgttagg cttctgcaa cgtagcagca attttcagag ccagaaattg    60
ttatggcaac tgaatggtcg tcttgaatac tgtttgaagg accgcattaa ctttgacttc    120
ccggaagaac tgaagcaact gcaacagttc cagaaagaag acgccgcact gaccatctat    180
gagatcctcc agaacatctt tgctattttc cgtcaagatt catctagcac tggctggaat    240
gagactattg ttgagaattt actggcgaat gtctatcatc agatcaacca tctgaaaacc    300
gtgctggaag aaaaactgga gaagaagat ttcacccgtg gtaaactgac gagcagtctg    360
```

```
cacctgaaac gctattatgg ccgtattctg cattacctga aggcaaaaga atacagtcac    420
tgtgcctgga ccatcgtccg tgtggaaatc ctgcgcaact tttacttcat taaccgtctt    480
acgggttacc tgcgcaacta a                                              501
```

<210> SEQ ID NO 6
<211> LENGTH: 166
<212> TYPE: PRT
<213> ORGANISM: Artificial Sequence
<220> FEATURE:
<223> OTHER INFORMATION: Modified human interferon (Synthetic sequence
      IFNb TIS2E triple C17S)

<400> SEQUENCE: 6

```
Met Glu Tyr Asn Leu Leu Gly Phe Leu Gln Arg Ser Ser Asn Phe Gln
1               5                   10                  15

Ser Gln Lys Leu Leu Trp Gln Leu Asn Gly Arg Leu Glu Tyr Cys Leu
            20                  25                  30

Lys Asp Arg Ile Asn Phe Asp Phe Pro Glu Glu Leu Lys Gln Leu Gln
        35                  40                  45

Gln Phe Gln Lys Glu Asp Ala Ala Leu Thr Ile Tyr Glu Ile Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Thr Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165
```

<210> SEQ ID NO 7
<211> LENGTH: 33
<212> TYPE: DNA
<213> ORGANISM: Artificial Sequence
<220> FEATURE:
<223> OTHER INFORMATION: Oligonucleotide sequence encoding N-terminal
      tryptic peptide that was introduced in the mutein.

<400> SEQUENCE: 7

```
atggcgtata atctgttagg ctttctgcaa cgt                                 33
```

<210> SEQ ID NO 8
<211> LENGTH: 11
<212> TYPE: PRT
<213> ORGANISM: Artificial Sequence
<220> FEATURE:
<223> OTHER INFORMATION: Penultimate amino acid residue introduced to
      the mutein.
<220> FEATURE:
<221> NAME/KEY: VARIANT
<222> LOCATION: (1)..(1)
<223> OTHER INFORMATION: Xaa = Any Amino Acid

<400> SEQUENCE: 8

```
Xaa Gln Tyr Asn Leu Leu Gly Phe Leu Gln Arg
```

```
1               5                   10
```

<210> SEQ ID NO 9
<211> LENGTH: 33
<212> TYPE: DNA
<213> ORGANISM: Artificial Sequence
<220> FEATURE:
<223> OTHER INFORMATION: Oligonucleotide sequence encoding N-terminal
      tryptic peptide that was introduced in the mutein.

<400> SEQUENCE: 9
atgagctata atctgttagg ctttctgcaa cgt                                   33

<210> SEQ ID NO 10
<211> LENGTH: 11
<212> TYPE: PRT
<213> ORGANISM: Artificial Sequence
<220> FEATURE:
<223> OTHER INFORMATION: Penultimate amino acid residue introduced to
      the mutein.
<220> FEATURE:
<221> NAME/KEY: VARIANT
<222> LOCATION: (1)..(1)
<223> OTHER INFORMATION: Xaa = Any Amino Acid

<400> SEQUENCE: 10

Xaa Ser Tyr Asn Leu Leu Gly Phe Leu Gln Arg
1               5                   10

<210> SEQ ID NO 11
<211> LENGTH: 33
<212> TYPE: DNA
<213> ORGANISM: Artificial Sequence
<220> FEATURE:
<223> OTHER INFORMATION: Oligonucleotide sequence encoding N-terminal
      tryptic peptide that was introduced in the mutein.

<400> SEQUENCE: 11
atgggctata atctgttagg ctttctgcaa cgt                                   33

<210> SEQ ID NO 12
<211> LENGTH: 11
<212> TYPE: PRT
<213> ORGANISM: Artificial Sequence
<220> FEATURE:
<223> OTHER INFORMATION: Penultimate amino acid residue introduced to
      the mutein.
<220> FEATURE:
<221> NAME/KEY: VARIANT
<222> LOCATION: (1)..(1)
<223> OTHER INFORMATION: Xaa = Any Amino Acid

<400> SEQUENCE: 12

Xaa Gly Tyr Asn Leu Leu Gly Phe Leu Gln Arg
1               5                   10

<210> SEQ ID NO 13
<211> LENGTH: 33
<212> TYPE: DNA
<213> ORGANISM: Artificial Sequence
<220> FEATURE:
<223> OTHER INFORMATION: Oligonucleotide sequence encoding N-terminal
      tryptic peptide that was introduced in the mutein.

<400> SEQUENCE: 13
atgcactata atctgttagg ctttctgcaa cgt                                   33

<210> SEQ ID NO 14

```
<211> LENGTH: 11
<212> TYPE: PRT
<213> ORGANISM: Artificial Sequence
<220> FEATURE:
<223> OTHER INFORMATION: Penultimate amino acid residue introduced to
      the mutein.
<220> FEATURE:
<221> NAME/KEY: VARIANT
<222> LOCATION: (1)..(1)
<223> OTHER INFORMATION: Xaa = Any Amino Acid

<400> SEQUENCE: 14

Xaa His Tyr Asn Leu Leu Gly Phe Leu Gln Arg
1               5                   10

<210> SEQ ID NO 15
<211> LENGTH: 33
<212> TYPE: DNA
<213> ORGANISM: Artificial Sequence
<220> FEATURE:
<223> OTHER INFORMATION: Oligonucleotide sequence encoding N-terminal
      tryptic peptide that was introduced in the mutein.

<400> SEQUENCE: 15
atgcagtata atctgttagg ctttctgcaa cgt                                33

<210> SEQ ID NO 16
<211> LENGTH: 11
<212> TYPE: PRT
<213> ORGANISM: Artificial Sequence
<220> FEATURE:
<223> OTHER INFORMATION: Penultimate amino acid residue introduced to
      the mutein.
<220> FEATURE:
<221> NAME/KEY: VARIANT
<222> LOCATION: (1)..(1)
<223> OTHER INFORMATION: Xaa = Any Amino Acid

<400> SEQUENCE: 16

Xaa Gln Tyr Asn Leu Leu Gly Phe Leu Gln Arg
1               5                   10

<210> SEQ ID NO 17
<211> LENGTH: 33
<212> TYPE: DNA
<213> ORGANISM: Artificial Sequence
<220> FEATURE:
<223> OTHER INFORMATION: Oligonucleotide sequence encoding N-terminal
      tryptic peptide that was introduced in the mutein.

<400> SEQUENCE: 17
atggagtata atctgttagg ctttctgcaa cgt                                33

<210> SEQ ID NO 18
<211> LENGTH: 11
<212> TYPE: PRT
<213> ORGANISM: Artificial Sequence
<220> FEATURE:
<223> OTHER INFORMATION: Penultimate amino acid residue introduced to
      the mutein.
<220> FEATURE:
<221> NAME/KEY: VARIANT
<222> LOCATION: (1)..(1)
<223> OTHER INFORMATION: Xaa = Any Amino Acid

<400> SEQUENCE: 18

Xaa Glu Tyr Asn Leu Leu Gly Phe Leu Gln Arg
1               5                   10
```

-continued

```
<210> SEQ ID NO 19
<211> LENGTH: 166
<212> TYPE: PRT
<213> ORGANISM: Homo sapiens

<400> SEQUENCE: 19

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 20
<211> LENGTH: 166
<212> TYPE: PRT
<213> ORGANISM: Artificial Sequence
<220> FEATURE:
<223> OTHER INFORMATION: Modified human interferon beta

<400> SEQUENCE: 20

Met Glu Tyr Asn Leu Leu Gly Phe Leu Gln Arg Ser Ser Asn Phe Gln
1               5                   10                  15

Ser Gln Lys Leu Leu Trp Gln Leu Asn Gly Arg Leu Glu Tyr Cys Leu
            20                  25                  30

Lys Asp Arg Ile Asn Phe Asp Phe Pro Glu Glu Leu Lys Gln Leu Gln
        35                  40                  45

Gln Phe Gln Lys Glu Asp Ala Ala Leu Thr Ile Tyr Glu Ile Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Thr Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160
```

```
Thr Gly Tyr Leu Arg Asn
            165

<210> SEQ ID NO 21
<211> LENGTH: 166
<212> TYPE: PRT
<213> ORGANISM: Artificial Sequence
<220> FEATURE:
<223> OTHER INFORMATION: Modified human interferon beta
<220> FEATURE:
<221> NAME/KEY: MOD_RES
<222> LOCATION: (1)..(1)
<223> OTHER INFORMATION: Xaa - Azidohomoalanine

<400> SEQUENCE: 21

Xaa Glu Tyr Asn Leu Leu Gly Phe Leu Gln Arg Ser Ser Asn Phe Gln
1               5                   10                  15

Ser Gln Lys Leu Leu Trp Gln Leu Asn Gly Arg Leu Glu Tyr Cys Leu
            20                  25                  30

Lys Asp Arg Ile Asn Phe Asp Phe Pro Glu Glu Leu Lys Gln Leu Gln
        35                  40                  45

Gln Phe Gln Lys Glu Asp Ala Ala Leu Thr Ile Tyr Glu Ile Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Thr Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
            165

<210> SEQ ID NO 22
<211> LENGTH: 7
<212> TYPE: PRT
<213> ORGANISM: Escherichia coli
<220> FEATURE:
<221> NAME/KEY: MISC_FEATURE
<222> LOCATION: (1)..(1)
<223> OTHER INFORMATION: X = AHA

<400> SEQUENCE: 22

Xaa Ser Tyr Asn Leu Leu Gly
1               5
```